(12) United States Patent
Kawamura et al.

(10) Patent No.: US 9,997,717 B2
(45) Date of Patent: Jun. 12, 2018

(54) ORGANIC ELECTROLUMINESCENCE DEVICE AND ELECTRONIC DEVICE

(71) Applicant: IDEMITSU KOSAN CO., LTD., Chiyoda-ku (JP)

(72) Inventors: Yuichiro Kawamura, Sodegaura (JP); Toshinari Ogiwara, Sodegaura (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 152 days.

(21) Appl. No.: 14/966,201

(22) Filed: Dec. 11, 2015

(65) Prior Publication Data

US 2016/0172601 A1 Jun. 16, 2016

(30) Foreign Application Priority Data

Dec. 12, 2014 (JP) .................................. 2014-252216

(51) Int. Cl.
*C09K 11/00* (2006.01)
*H01L 51/00* (2006.01)
(Continued)

(52) U.S. Cl.
CPC ........ *H01L 51/0067* (2013.01); *C07C 13/567* (2013.01); *C07C 13/62* (2013.01);
(Continued)

(58) Field of Classification Search
CPC .............. C07D 491/147; C07D 495/14; C07D 209/82; C09K 11/06; H01L 51/5012; H05B 33/14; C07C 13/62; C07C 13/567
(Continued)

(56) References Cited

U.S. PATENT DOCUMENTS

2009/0295279 A1* 12/2009 Igawa ..................... C07C 13/62
313/504
2012/0119197 A1* 5/2012 Nishimura ........... C07D 209/86
257/40
(Continued)

FOREIGN PATENT DOCUMENTS

JP 2008-255095 10/2008
JP 2008-285450 11/2008
(Continued)

OTHER PUBLICATIONS

Hajime Nakanotani, et al., "High-efficiency organic light-emitting diodes with fluorescent emitters", Nature Communications, 5:4016, 2014, 7 pgs.
(Continued)

*Primary Examiner* — Amanda C Walke
(74) *Attorney, Agent, or Firm* — Oblon, McClelland, Maier & Neustadt, L.L.P.

(57) ABSTRACT

An object of the invention is to provide a high-performance organic electroluminescence device and an electronic device including the organic electroluminescence device. An
(Continued)

organic electroluminescence device includes an anode, a cathode and an emitting layer, in which the emitting layer includes a first compound and a second compound, the first compound is a delayed fluorescent compound, and the second compound is represented by a formula (2) below.

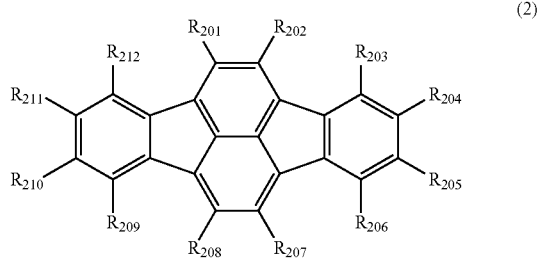

(2)

37 Claims, 5 Drawing Sheets

(51) Int. Cl.
C09K 11/02 (2006.01)
C09K 11/06 (2006.01)
H05B 33/14 (2006.01)
C07C 13/567 (2006.01)
C07C 13/62 (2006.01)
C07D 491/147 (2006.01)
C07D 209/82 (2006.01)
C07D 495/14 (2006.01)
H01L 51/50 (2006.01)

(52) U.S. Cl.
CPC ....... *C07D 209/82* (2013.01); *C07D 491/147* (2013.01); *C07D 495/14* (2013.01); *C09K 11/025* (2013.01); *C09K 11/06* (2013.01); *H01L 51/006* (2013.01); *H01L 51/0056* (2013.01); *H01L 51/0071* (2013.01); *H01L 51/0072* (2013.01); *H01L 51/0073* (2013.01); *H05B 33/14* (2013.01); *C09K 2211/1007* (2013.01); *C09K 2211/1011* (2013.01); *C09K 2211/1059* (2013.01); *H01L 51/5012* (2013.01); *H01L 2251/5384* (2013.01)

(58) Field of Classification Search
USPC ............ 428/690; 257/E51.024, 40; 548/416
See application file for complete search history.

(56) References Cited

U.S. PATENT DOCUMENTS

| 2012/0168734 | A1* | 7/2012 | Park | C07D 491/147 257/40 |
| 2012/0175598 | A1* | 7/2012 | Balaganesan | C07D 209/88 257/40 |
| 2015/0214483 | A1* | 7/2015 | Kamatani | H01L 51/009 257/40 |
| 2016/0164004 | A1* | 6/2016 | Seo | H01L 51/0072 257/40 |

FOREIGN PATENT DOCUMENTS

| JP | 2010-263065 | 11/2010 |
| WO | WO 2008/111540 A1 | 9/2008 |
| WO | WO 2008/111543 A1 | 9/2008 |
| WO | WO 2012/153780 A1 | 11/2012 |
| WO | WO 2013/038650 A1 | 3/2013 |
| WO | WO 2013/180241 A1 | 12/2013 |
| WO | WO 2014/092083 A1 | 6/2014 |
| WO | WO 2014/104346 A1 | 7/2014 |
| WO | WO 2015/135624 A1 | 9/2015 |

OTHER PUBLICATIONS

Chihaya Adachi, "Device Physics of Organic Semiconductors", Yuki Hando-tai no Debaisu Bussei, 2012, 5 pgs.(with English translation).
Hiroki Uoyama, et al., "Highly efficient organic light-emitting diodes from delayed fluorescence", Nature 492, 2012, 7 pgs.

* cited by examiner

ORGANIC ELECTROLUMINESCENCE DEVICE AND ELECTRONIC DEVICE

The entire disclosure of Japanese Patent Application No. 2014-252216, filed Dec. 12, 2014, is expressly incorporated by reference herein.

TECHNICAL FIELD

The present invention relates to an organic electroluminescence device and an electronic device.

BACKGROUND ART

When a voltage is applied to an organic electroluminescence device (hereinafter, occasionally referred to as an "organic EL device"), holes are injected from an anode into an emitting layer and electrons are injected from a cathode into the emitting layer. The injected electrons and holes are recombined in an emitting layer to form excitons. Here, according to the electron spin statistics theory, singlet excitons and triplet excitons are generated at a ratio of 25%:75%.

A fluorescent organic EL device, which employs emission caused by singlet excitons, has been applied to a full-color display of a mobile phone, TV and the like. A study for further improving a device performance of the fluorescent organic EL device has been conducted (e.g., Document 1 (JP-A-2008-255095), Document 2 (JP-A-2008-285450), Document 3 (International Publication No. WO2008/111540), Document 4 (International Publication No. WO2008/111543), and Document 5 (JP-A-2010-263065)).

Moreover, an organic EL device employing delayed fluorescence has been proposed and studied. For instance, a thermally activated delayed fluorescence (TADF) mechanism has been studied. The TADF mechanism uses such a phenomenon that inverse intersystem crossing from triplet excitons to singlet excitons thermally occurs when a material having a small energy difference ($\Delta ST$) between singlet energy level and triplet energy level is used. As for thermally activated delayed fluorescence, refer to, for instance, ADACHI, Chihaya, ed. (Mar. 22, 2012), "Yuki Hando-tai no Debaisu Bussei (Device Physics of Organic Semiconductors)", Kodansha, pp. 261-262. An organic EL device using the TADF mechanism is disclosed in, for instance, Document 6 (H. Nakanotani, Nat. Commun., 5, 4016, 2014).

SUMMARY OF THE INVENTION

An object of the invention is to provide a high-performance organic electroluminescence device. Another object of the invention is to provide an electronic device including the organic electroluminescence device.

According to an aspect of the invention, an organic electroluminescence device includes an anode, a cathode and an emitting layer, in which the emitting layer includes a first compound and a second compound, the first compound is a delayed fluorescent compound, and the second compound is represented by a formula (2) below.

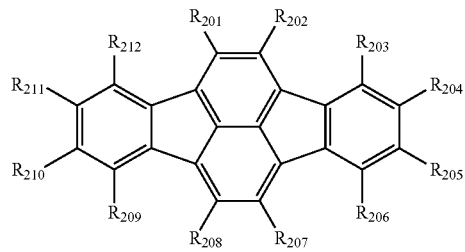

(2)

In the formula (2), $R_{201}$ to $R_{212}$ are each independently a hydrogen atom or a substituent. When $R_{201}$ to $R_{212}$ are a substituent, the substituent is selected from the group consisting of a substituted or unsubstituted alkyl group having 1 to 30 carbon atoms, a substituted or unsubstituted aryl group having 6 to 30 ring carbon atoms, a substituted or unsubstituted heterocyclic group having 5 to 30 ring atoms, a substituted or unsubstituted alkoxy group having 1 to 30 carbon atoms, a substituted or unsubstituted aryloxy group having 6 to 30 ring carbon atoms, a substituted or unsubstituted aralkyl group having 6 to 30 ring carbon atoms, a substituted amino group, a cyano group and a halogen atom. The substituents of $R_{201}$ to $R_{212}$ may be mutually bonded to form a cyclic structure.

According to another aspect of the invention, an electronic device including the organic electroluminescence device according to the above aspect is provided.

With the above arrangement, a high-performance organic electroluminescence device can be provided. Moreover, with the above arrangement, an electronic device including the above-described organic electroluminescence device can be provided.

BRIEF DESCRIPTION OF DRAWING(S)

FIG. 1 schematically shows an exemplary arrangement of an organic electroluminescence device according to a first exemplary embodiment.

DESCRIPTION OF EMBODIMENT(S)

First Exemplary Embodiment

An arrangement of an organic EL device according to a first exemplary embodiment will be described below.

The organic EL device includes an anode, a cathode (electrodes) and an organic layer therebetween. The organic layer includes at least one layer formed of an organic compound. The organic layer may further include an inorganic compound. The organic EL device in the exemplary embodiment includes at least one emitting layer as the organic layer. The organic layer may consist solely of the emitting layer, or may include any layer(s) usable in a typical organic EL device, such as a hole injecting layer, a hole transporting layer, an electron injecting layer, an electron transporting layer and a blocking layer.

Figure 1:
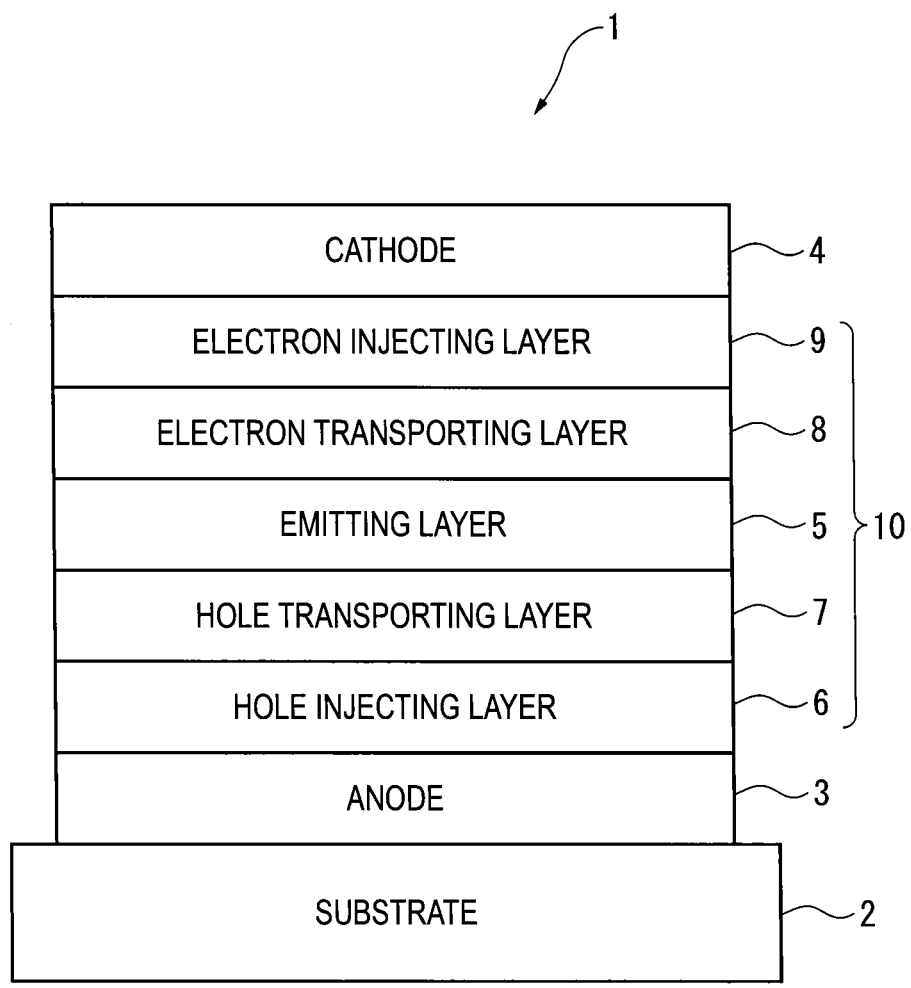

FIG. 1 schematically shows an arrangement of an exemplary organic EL device according to the exemplary embodiment. An organic EL device 1 includes a light-transmissive substrate 2, an anode 3, a cathode 4 and an organic layer 10 disposed between the anode 3 and the cathode 4. The organic layer 10 includes a hole injecting layer 6, a hole transporting layer 7, an emitting layer 5, an electron transporting layer 8, and an electron injecting layer 9, which are sequentially laminated from the anode 3.

Emitting Layer

The emitting layer includes a first compound and a second compound. The emitting layer may include a metal complex. However, in the exemplary embodiment, the emitting layer preferably contains no phosphorescent metal complex, more preferably contains no other metal complex in addition to the phosphorescent metal complex.

First Compound

The first compound in the exemplary embodiment is a delayed fluorescent compound. The first compound of the exemplary embodiment is not a metal complex. The first compound is preferably represented by a formula (1) below.

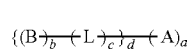

(1)

In the formula (1), A is an acceptor moiety that is a group having a partial structure selected from partial structures represented by formulae (a-1) to (a-7) below. When a plurality of A are present, the plurality of A are mutually the same or different and are optionally mutually bonded to form a saturated or unsaturated ring. B is a donor moiety and has a partial structure selected from partial structures represented by formulae (b-1) to (b-6) below. When a plurality of B are present, the plurality of B are mutually the same or different and are optionally mutually bonded to form a saturated or unsaturated ring. a, b and d are each independently an integer of 1 to 5. c is an integer of 0 to 5. When c is 0, A is bonded to B by a single bond or a Spiro bond. When c is an integer of 1 to 5, L is a linking group selected from the group consisting of a substituted or unsubstituted aromatic hydrocarbon group having 6 to 30 ring carbon atoms and a substituted or unsubstituted heterocyclic group having 5 to 30 ring atoms. When a plurality of L are present, the plurality of L are mutually the same or different and are optionally mutually bonded to form a saturated or unsaturated ring.

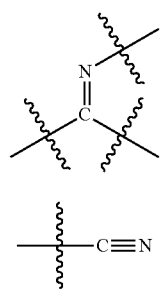

(a-1)

(a-2)

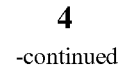

(a-3)

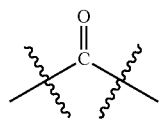

(a-4)

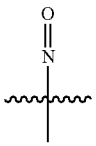

(a-5)

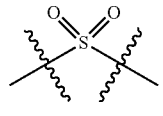

(a-6)

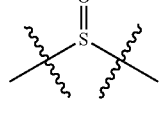

(a-7)

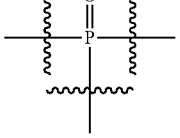

(b-1)

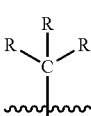

(b-2)

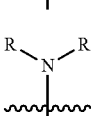

(b-3)

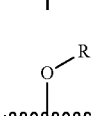

(b-4)

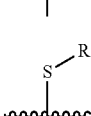

(b-5)

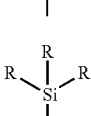

(b-6)

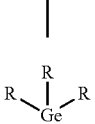

In the formulae (b-1) to (b-6), R is each independently a hydrogen atom or a substituent. When R is a substituent, the substituent is selected from the group consisting of a substituted or unsubstituted aromatic hydrocarbon group having 6 to 30 ring carbon atoms, a substituted or unsubstituted heterocyclic group having 5 to 30 ring atoms, and a substituted or unsubstituted alkyl group having 1 to 30 carbon atoms. When a plurality of R are present, the plurality of R are mutually the same or different and are optionally mutually bonded to form a saturated or unsaturated ring. A bonding pattern of the compound represented by the formula (1) is exemplified by bonding patterns shown in Table 1 below.

TABLE 1

| No. | a | b | c | d | Bonding Pattern |
|---|---|---|---|---|---|
| (1A) | 1 | 1 | 0 | 1 | B—A |
| (1B) | 1 | 1 | 1 | 1 | B—L—A |
| (1C) | 2 | 1 | 0 | 1 | B—A—A, <br> B—A / \ A |
| (1D) | 1 | 2 | 0 | 1 | B—B—A, <br> B \ A / B |
| (1E) | 2 | 1 | 1 | 1 | B—L—A—A, <br> B—L / \ A |
| (1F) | 1 | 2 | 1 | 1 | B—B—L—A, <br> B \ L—A / B |
| (1G) | 1 | 1 | 2 | 1 | B—L—L—A |
| (1H) | 1 | 1 | 1 | 2 | B—L \ A, <br> B—L / <br> B—L—B—L—A |

The first compound is preferably represented by a formula (1A) below.

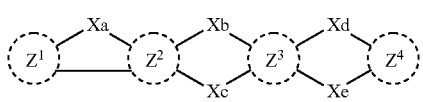

(1A)

In the formula (1A): Xa is an oxygen atom, a sulfur atom, $NR^1$ or $CR^3R^4$.

Xb, Xc, Xd and Xe are each independently a single bond, an oxygen atom, a sulfur atom, $NR^1$ or $CR^3R^4$.

However, at least one of Xa, Xb, Xc, Xd, and Xe is $NR^1$. Xb and Xc are not single bonds at the same time. Xd and Xe are not single bonds at the same time.

$R^1$ is a hydrogen atom or a substituent. $R^1$ as the substituent is selected from the group consisting of a substituted or unsubstituted alkyl group having 1 to 30 carbon atoms, a substituted or unsubstituted cycloalkyl group having 3 to 30 ring carbon atoms, a substituted or unsubstituted aromatic hydrocarbon group having 6 to 30 ring carbon atoms, a substituted or unsubstituted heterocyclic group having 5 to 30 ring atoms, and a group represented by $-L^1-R^2$.

$L^1$ is a single bond or a linking group. $L^1$ as the linking group is selected from the group consisting of a substituted or unsubstituted aromatic hydrocarbon group having 6 to 30 ring carbon atoms and a substituted or unsubstituted heterocyclic group having 5 to 30 ring atoms.

$R^2$ to $R^4$ are each independently a hydrogen atom or a substituent. $R^2$ to $R^4$ as the substituent are each independently selected from the group consisting of a substituted or unsubstituted alkyl group having 1 to 30 carbon atoms, a substituted or unsubstituted cycloalkyl group having 3 to 30 ring carbon atoms, a substituted or unsubstituted aromatic hydrocarbon group having 6 to 30 ring carbon atoms and a substituted or unsubstituted heterocyclic group having 5 to 30 ring atoms.

$Z^1$, $Z^2$, $Z^3$ and $Z^4$ each independently represent a cyclic structure selected from the group consisting of a substituted or unsubstituted aromatic hydrocarbon ring having 6 to 30 ring carbon atoms and a substituted or unsubstituted heterocyclic ring having 5 to 30 ring atoms.

It is preferable that $Z^1$, $Z^2$, $Z^3$ and $Z^4$ are each independently a substituted or unsubstituted aromatic hydrocarbon ring having 6 to 30 ring carbon atoms in the formula (1A).

It is preferable that two or more of Xa, Xb, Xc, Xd and Xe are each independently $NR^1$ in the formula (1A).

It is also preferable that at least one of $R^1$ is the group represented by $-L^1-R^2$ in the formula (1A).

It is also preferable that the first compound represented by the formula (1A) is represented by a formula (10) below.

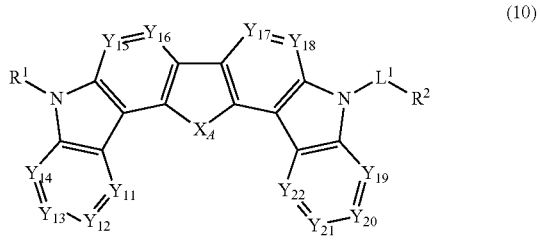

(10)

In the formula (10), $R^1$, $R^2$ and $L^1$ represent the same as $R^1$, $R^2$ and $L^1$ in the formula (1A).

$X_A$ is an oxygen atom, a sulfur atom, $NR_{10}$ or $CR_{11}R_{12}$.

$Y_{11}$ to $Y_{22}$ are each independently a nitrogen atom or $CR_{13}$.

$R_{10}$ to $R_{13}$ are each independently a hydrogen atom or a substituent. $R_{10}$ to $R_{13}$ as the substituent are each independently selected from the group consisting of a substituted or unsubstituted alkyl group having 1 to 30 carbon atoms, a substituted or unsubstituted cycloalkyl group having 3 to 30 carbon atoms, a substituted or unsubstituted aromatic hydrocarbon group having 6 to 30 ring carbon atoms and a substituted or unsubstituted heterocyclic group having 5 to 30 ring atoms.

A plurality of $R_{13}$ are optionally mutually the same or different. When at least two of the plurality of $R_{13}$ are substituents, the substituents $R_{13}$ are optionally mutually bonded to form a cyclic structure.

In the formula (10), $R^1$ and $R^2$ are each independently preferably a substituent selected from the group consisting of a substituted or unsubstituted aromatic hydrocarbon group having 6 to 30 ring carbon atoms and a substituted or unsubstituted heterocyclic group having 5 to 30 ring atoms.

In the formula (10), $R^1$ is preferably different from the group represented by -$L^1$-$R^2$.

In the formula (10), it is preferable that $R^1$ is a substituent selected from the group consisting of an unsubstituted aromatic hydrocarbon group having 6 to 30 ring carbon atoms and an unsubstituted heterocyclic group having 5 to 30 ring atoms, and $L^1$ is a linking group.

The first compound represented by the formula (1A) is preferably represented by a formula (10A) below.

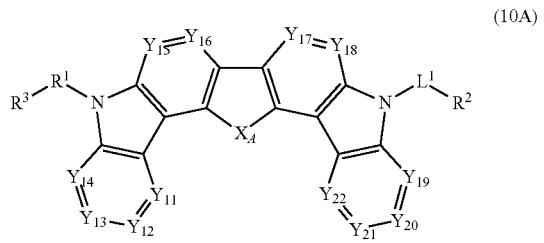

(10A)

In the formula (10): $X_1$, $Y_{11}$ to $Y_{22}$, $L^1$, $R^1$ and $R^2$ each represent the same as $X_1$, $Y_{11}$ to $Y_{12}$, $L^1$, $R^1$ and $R^2$ in the formula (10); and $R^3$ is a substituent and is selected from the group consisting of a substituted or unsubstituted aromatic hydrocarbon group having 6 to 30 ring carbon atoms and a substituted or unsubstituted heterocyclic group having 5 to 30 ring atoms.

In the formula (10A), it is preferable that $R^1$ and $L^1$ are the same and $R^3$ and $R^2$ are the same.

$X_A$ is preferably an oxygen atom or sulfur atom in the formulae (10) and (10A).

$Y_{11}$ to $Y_{22}$ are each independently $CR_{13}$, in which $R_{13}$ is preferably a hydrogen atom.

$R^2$ in the formulae (10) and (10A) is preferably a group represented by a formula (11) below.

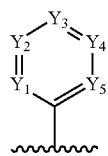

(11)

In the formula (11), $Y_1$ to $Y_5$ are each independently a nitrogen atom or $CR_{14}$.

$R_{14}$ is a hydrogen atom or a substituent. $R_{14}$ as the substituent is selected from the group consisting of a fluorine atom, a cyano group, a substituted or unsubstituted alkyl group having 1 to 30 carbon atoms, a substituted or unsubstituted cycloalkyl group having 3 to 30 carbon atoms, a substituted silyl group, a substituted phosphine oxide group, a substituted or unsubstituted aromatic hydrocarbon group having 6 to 30 ring carbon atoms and a substituted or unsubstituted heterocyclic group having 5 to 30 ring atoms.

A plurality of $R_{14}$ are optionally mutually the same or different. When at least two of the plurality of $R_{14}$ are substituents, the substituents $R_{14}$ are optionally mutually bonded to form a cyclic structure.

In the formula (11), $Y_1$ to $Y_5$ are preferably each independently $CR_{14}$. In the formula (11), it is also preferable that $Y_1$ to $Y_5$ are each independently $CR_{14}$, in which $R_{14}$ is a hydrogen atom.

In the formula (11), it is also preferable that at least one of $Y_1$ to $Y_5$ are a nitrogen atom.

It is also preferable that at least one of $Y_1$ to $Y_5$ is $CR_{14}$ in the formula (11), in which at least one of $R_{14}$ is a cyano group.

In the formulae (10) and (10A), $R^2$ is preferably a group represented by a formula (11a) below, a group represented by a formula (11b) below, a group represented by a formula (11c) below, a group represented by a formula (11d) below, or a group represented by a formula (11e) below.

(11a)

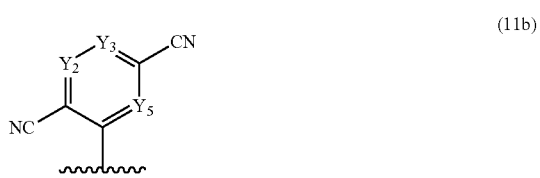

(11b)

(11c)

(11d)

(11e)

In the formulae (11a) to (11e), $Y_1$ to $Y_5$ represent the same as $Y_1$ to $Y_5$ in the formula (11).

$R^2$ in the formulae (10) and (10A) is also preferably a group represented by a formula (11f) below or a group represented by a formula (11h) below.

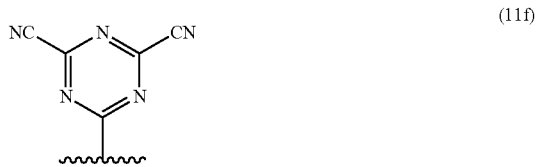

(11f)

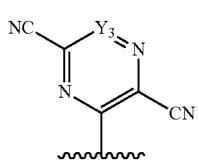 (11g)

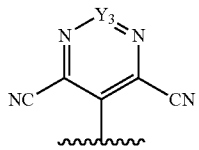 (11h)

In the formulae (11g) to (11h), $Y_3$ represents the same as $Y_3$ in the formula (11).

The first compound is also preferably represented by a formula (100) below.

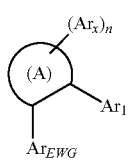 (100)

In the formula (100), $Ar_1$ is any group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group and groups represented by formulae (12a) to (12j) below.

$Ar_{EWG}$ is preferably a substituted or unsubstituted heteroaryl group having 5 to 30 ring atoms including at least one nitrogen atom in the ring or a substituted or unsubstituted aryl group having 6 to 30 ring carbon atoms and substituted by at least one cyano group.

$Ar_X$ is each independently a hydrogen atom or a substituent. $Ar_X$ as the substituent is any group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group and groups represented by the formulae (12a) to (12j) below.

n is an integer of 0 to 5.

When n is 2 or more, a plurality of $Ar_X$ are optionally mutually the same or different.

A ring (A) is a five-membered ring, a six-membered ring, or a seven-membered ring.

At least one of $Ar_1$ and $Ar_X$ is any group selected from the group consisting of the groups represented by the formulae (12a) to (12j) below.

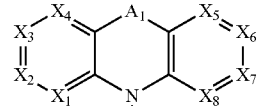 (12a)

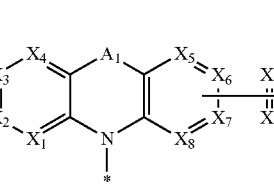 (12b)

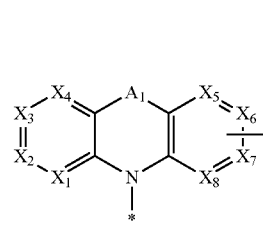 (12c)

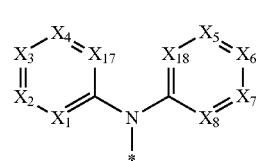 (12d)

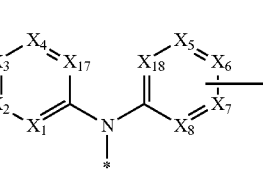 (12e)

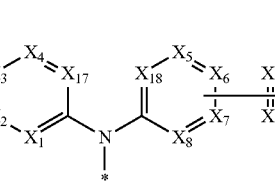 (12f)

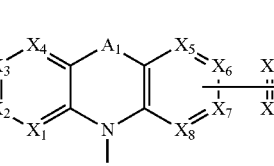 (12g)

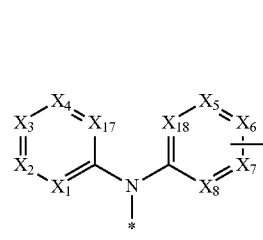 (12h)

-continued

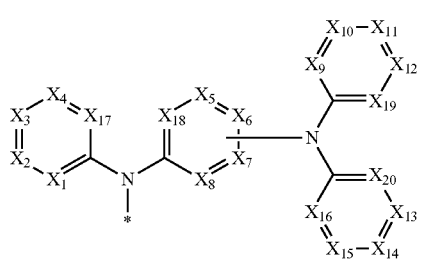

(12i)

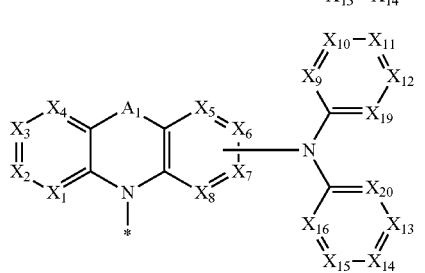

(12j)

In the formulae (12a) to (12j), $X_1$ to $X_{20}$ are each independently N or C-Rx.

In the formula (12b), any one of $X_5$ to $X_8$ is a carbon atom to be bonded to any one of $X_9$ to $X_{12}$. Any one of $X_9$ to $X_{12}$ is a carbon atom bonded to any one of $X_5$ to $X_8$.

In the formula (12c), any one of $X_5$ to $X_8$ is a carbon atom bonded to a nitrogen atom of a five-membered ring in a fused ring including $X_9$ to $X_{12}$ and $X_{13}$ to $X_{16}$.

In the formula (12e), any one of $X_5$ to $X_8$ and $X_{18}$ is a carbon atom bonded to any one of $X_9$ to $X_{12}$. Any one of $X_9$ to $X_{12}$ is a carbon atom bonded to any one of $X_5$ to $X_8$ and $X_{18}$.

In the formula (12f), any one of $X_5$ to $X_8$ and $X_{18}$ is a carbon atom bonded to any one of $X_9$ to $X_{12}$ and $X_{19}$. Any one of $X_9$ to $X_{12}$ and $X_{19}$ is a carbon atom bonded to any one of $X_5$ to $X_8$ and $X_{18}$.

In the formula (12g), any one of $X_5$ to $X_8$ is a carbon atom bonded to any one of $X_9$ to $X_{12}$ and $X_{19}$. Any one of $X_9$ to $X_{12}$ and $X_{19}$ is a carbon atom bonded to any one of $X_5$ to $X_8$.

In the formula (12h), any one of $X_5$ to $X_8$ and $X_{18}$ is a carbon atom bonded to a nitrogen atom of a six-membered ring in a fused ring including $X_9$ to $X_{12}$, $X_{13}$ to $X_{16}$ and $A_2$.

In the formula (12i), any one of $X_5$ to $X_8$ and $X_{18}$ is a carbon atom bonded to a nitrogen atom linking a ring including $X_9$ to $X_{12}$ and $X_{19}$ to a ring including $X_{13}$ to $X_{16}$ and $X_{20}$.

In the formula (12j), any one of $X_5$ to $X_8$ is a carbon atom bonded to a nitrogen atom linking a ring including $X_9$ to $X_{12}$ and $X_{19}$ to a ring including $X_{13}$ to $X_{16}$ and $X_{20}$.

Rx is each independently a hydrogen atom or a substituent.

Rx as the substituent is any group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group.

A plurality of Rx as the substituent are optionally mutually the same or different.

The plurality of Rx as the substituent are optionally directly bonded to each other to form a ring, or are optionally bonded to each other by a hetero atom to form a ring.

$A_1$ and $A_2$ are each independently a single bond, O, S, $C(R_{101})(R_{102})$, $Si(R_{103})(R_{104})$, C(=O), S(=O), $SO_2$ or $N(R_{105})$.

$R_{101}$ to $R_{105}$ are each independently a hydrogen atom or a substituent. $R_{101}$ to $R_{105}$ as the substituent is any group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group.

Ara is any group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, and a substituted silyl group.

The first compound represented by the formula (100) is also preferably represented by a formula (101) below.

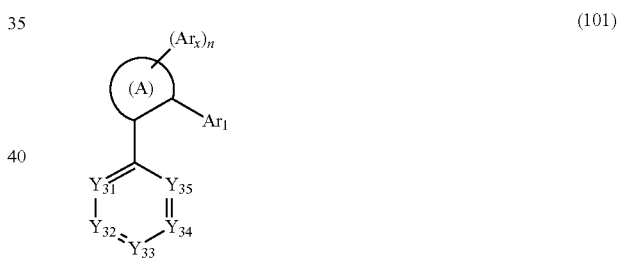

(101)

In the formula (101), $Y_{31}$ to $Y_{35}$ are each independently N, C—CN or C-Ry.

At least one of $Y_{31}$ to $Y_{35}$ is N or C—CN.

Ry is each independently a hydrogen atom or a substituent. Ry as the substituent is any group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group.

$Ar_1$ is any group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group and groups represented by formulae (1a) to (1c) below.

$Ar_X$ is each independently a hydrogen atom or a substituent. $Ar_X$ as the substituent is any group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group and groups represented by the formulae (12a) to (12c).

n is an integer of 0 to 5.

When n is 2 or more, a plurality of $Ar_X$ are optionally mutually the same or different.

A ring (A) is a five-membered ring, a six-membered ring, or a seven-membered ring.

At least one of $Ar_1$ and $Ar_X$ is any group selected from the group consisting of the groups represented by the formulae (12a) to (12c).

The first compound represented by the formula (100) is also preferably represented by a formula (102) below.

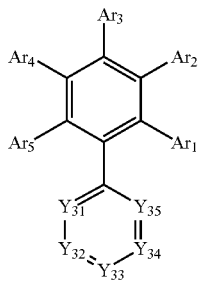

(102)

In the formula (102), $Y_{31}$ to $Y_{35}$ are each independently N, C—CN or C-Ry.

At least one of $Y_{31}$ to $Y_{35}$ is N or C—CN.

Ry is each independently a hydrogen atom or a substituent. Ry as the substituent is any group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group.

$Ar_1$ is any group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group and groups represented by the formulae (12a) to (12c).

$Ar_2$ to $Ar_5$ are each independently a hydrogen atom or a substituent. $Ar_2$ to $Ar_5$ as the substituent is any group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group and groups represented by the formulae (12a) to (12c).

At least one of $Ar_1$ and $Ar_5$ is any group selected from the group consisting of the groups represented by the formulae (12a) to (12c).

The first compound represented by the formula (100) is also preferably a compound represented by a formula (103), (104) or (105) below.

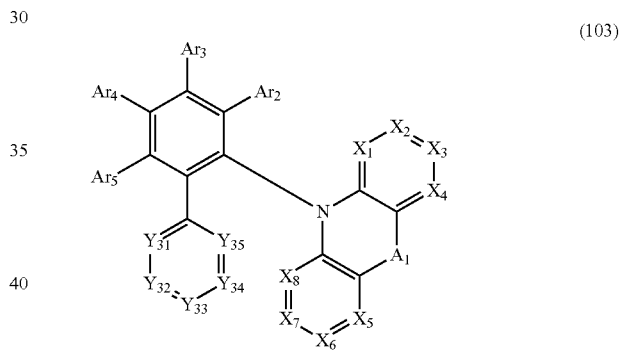

(103)

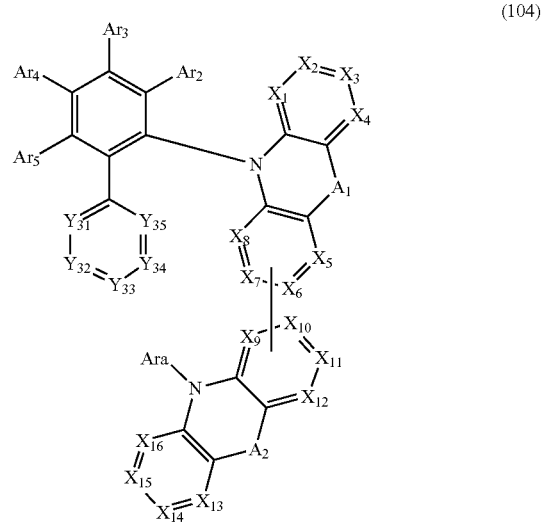

(104)

(105)

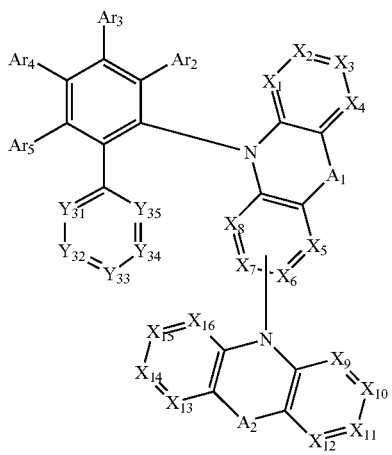

In the formulae (103) to (105), $Y_{31}$ to $Y_{35}$, Ry, $Ar_2$ to $Ar_5$, $X_1$ to $X_{16}$, Rx, $A_1$, $A_2$, $R_{101}$ to $R_{105}$ and Ara represent the same as $Y_{31}$ to $Y_{35}$, Ry, $Ar_2$ to $Ar_5$, $X_1$ to $X_{16}$, Rx, $A_1$, $A_2$, $R_{101}$ to $R_{105}$ and Ara described above.

The first compound represented by the formula (100) is also preferably a compound represented by a formula (106), (107) or (108) below.

(106)

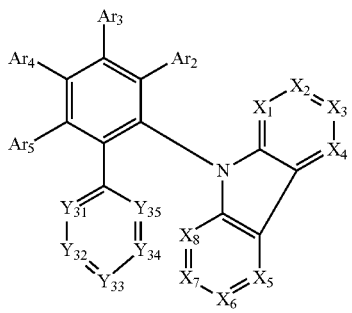

(107)

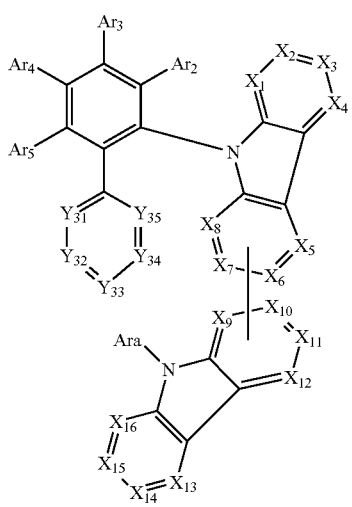

(108)

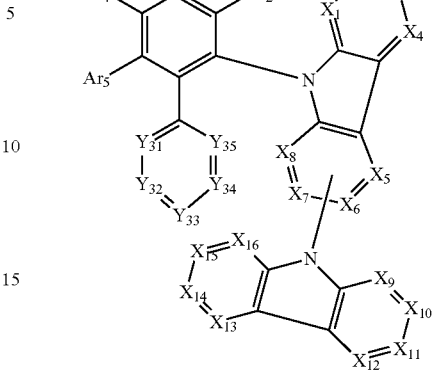

In the formulae (106) to (108), $Y_{31}$ to $Y_{35}$, Ry, $Ar_2$ to $Ar_5$, $X_1$ to $X_{16}$, Rx and Ara represent the same as $Y_{31}$ to $Y_{35}$, Ry, $Ar_2$ to $Ar_5$, $X_1$ to $X_{16}$, Rx and Ara described above.

It is also preferable that $Ar_1$ and $Ar_e$ each are any group selected from the group consisting of the groups represented by the formulae (12a) to (12j), or $Ar_e$ and $Ar_3$ each are any group selected from the group consisting of the groups represented by the formulae (12a) to (12j).

It is also preferable that $Ar_1$, $Ar_2$ and $Ar_3$ each are any group selected from the group consisting of the groups represented by the formulae (12a) to (12j) below.

It is also preferable that at least one of $Y_{31}$, $Y_{33}$ and $Y_{35}$ is N.

It is also preferable that $Y_{31}$, $Y_{33}$ and $Y_{35}$ are N, and $Y_{32}$ and $Y_{34}$ are C-Ry.

It is also preferable that $Y_{31}$ and $Y_{33}$ are N, and $Y_{32}$, $Y_{34}$ and $Y_{35}$ are C-Ry.

It is also preferable that $Y_{31}$ and $Y_{35}$ are N, and $Y_{32}$, $Y_{33}$ and $Y_{34}$ are C-Ry.

The first compound is also preferably represented by a formula (150) below.

(150)

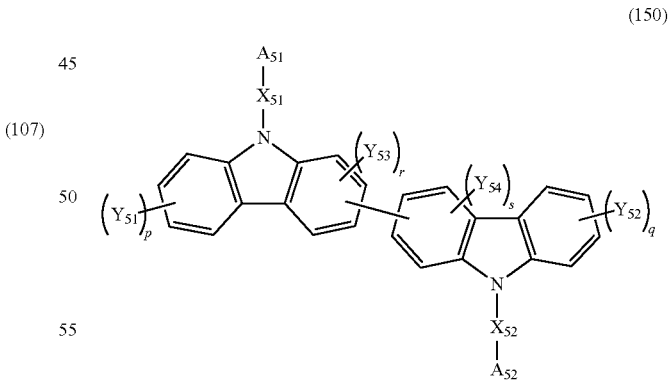

In the formula (150), $A_{51}$ is a substituted or unsubstituted nitrogen-containing heterocyclic group having 1 to 30 ring carbon atoms.

$A_{52}$ is a substituted or unsubstituted aromatic hydrocarbon group having 6 to 30 ring carbon atoms or a substituted or unsubstituted nitrogen-containing heterocyclic group having 1 to 30 ring carbon atoms.

$X_{51}$ and $X_{52}$ are each independently a single bond or a linking group. $X_{51}$ and $X_{52}$ as the linking group are each independently selected from the group consisting of a substituted or unsubstituted aromatic hydrocarbon group having 6 to 30 ring carbon atoms, a substituted or unsubstituted fused aromatic hydrocarbon group having 10 to 30 ring carbon atoms, a substituted or unsubstituted aromatic heterocyclic group having 2 to 30 ring carbon atoms, and a substituted or unsubstituted fused aromatic heterocyclic group having 2 to 30 ring carbon atoms.

$Y_{51}$ to $Y_{54}$ are each independently a hydrogen atom or a substituent. $Y_{51}$ to $Y_{54}$ as the substituent is each independently selected from the group consisting of a fluorine atom, a cyano group, a substituted or unsubstituted alkyl group having 1 to 20 carbon atoms, a substituted or unsubstituted alkoxy group having 1 to 20 carbon atoms, a substituted or unsubstituted haloalkyl group having 1 to 20 carbon atoms, a substituted or unsubstituted haloalkoxy group having 1 to 20 carbon atoms, a substituted or unsubstituted alkylsilyl group having 1 to 10 carbon atoms, a substituted or unsubstituted arylsilyl group having 6 to 30 carbon atoms, a substituted or unsubstituted aromatic hydrocarbon group having 6 to 30 ring carbon atoms, and a substituted or unsubstituted heterocyclic group having 5 to 30 ring atoms.

p is an integer of 1 to 4. q is an integer of 1 to 4. r is an integer of 1 to 3. s is an integer of 1 to 3.

A plurality of $Y_{51}$ are mutually the same or different and are optionally bonded to each other to form a cyclic structure.

A plurality of $Y_{52}$ are mutually the same or different and are optionally bonded to each other to form a cyclic structure.

A plurality of $Y_{53}$ are mutually the same or different and are optionally bonded to each other to form a cyclic structure.

A plurality of $Y_{54}$ are mutually the same or different and are optionally bonded to each other to form a cyclic structure.

The first compound represented by the formula (150) is also preferably represented by a formula (151) below.

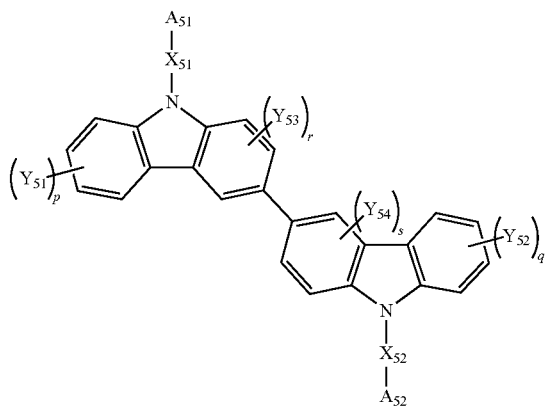

(151)

In the formula (151), $A_{51}$, $A_{52}$, $X_{51}$, $X_{52}$, $Y_{51}$ to $Y_{54}$, p, q, r and s represent the same as $A_{51}$, $A_{52}$, $X_{51}$, $X_{52}$, $Y_{51}$ to $Y_{54}$, p, q, r and s in the formula (150).

$A_{51}$ is more preferably selected from a substituted or unsubstituted pyridine ring, substituted or unsubstituted pyrimidine ring, and substituted or unsubstituted triazine ring, more preferably selected from a substituted or unsubstituted pyrimidine ring and substituted or unsubstituted triazine ring.

$A_{51}$ is also preferably a substituted or unsubstituted pyrimidine ring.

The first compound represented by the formula (150) is also preferably represented by a formula (152) below.

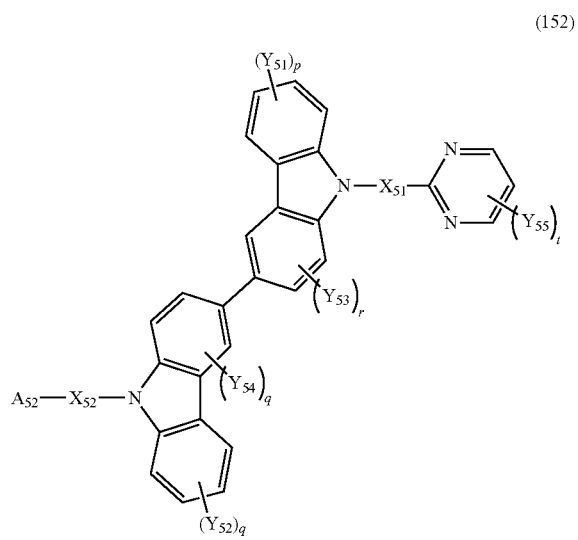

(152)

In the formula (152), $A_{52}$, $X_{51}$, $Y_{51}$ to $Y_{54}$, p, q, r and s represent the same as $A_{52}$, $X_{51}$, $Y_{51}$ to $Y_{54}$, p, q, r and s in the formula (151).

$Y_{55}$ represents the same as $Y_{51}$ to $Y_{54}$ in the formula (151).

t is an integer of 1 to 3. A plurality of $Y_{55}$ are mutually the same or different.

In the formulae (150) and (151), $A_{51}$ is also preferably a substituted or unsubstituted quinazoline ring.

Specific examples of the first compound are shown below. It should be noted that the first compound according to the invention is not limited to these specific examples.

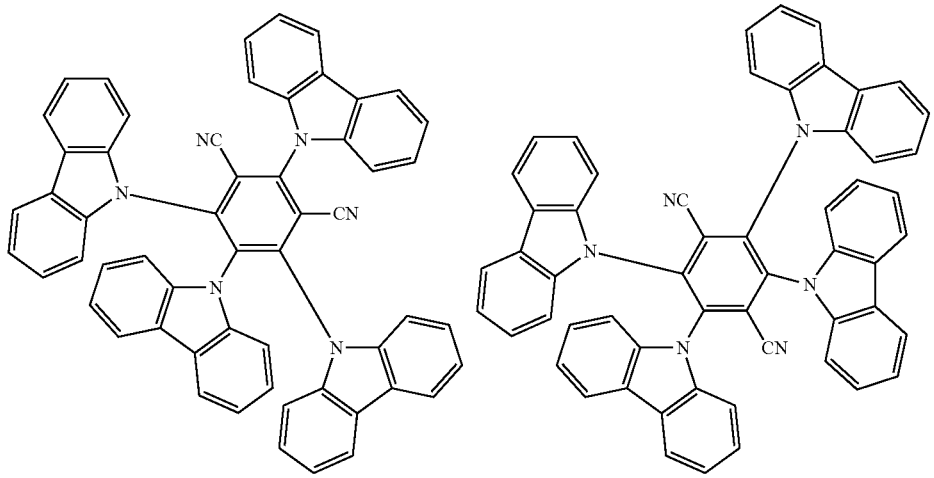
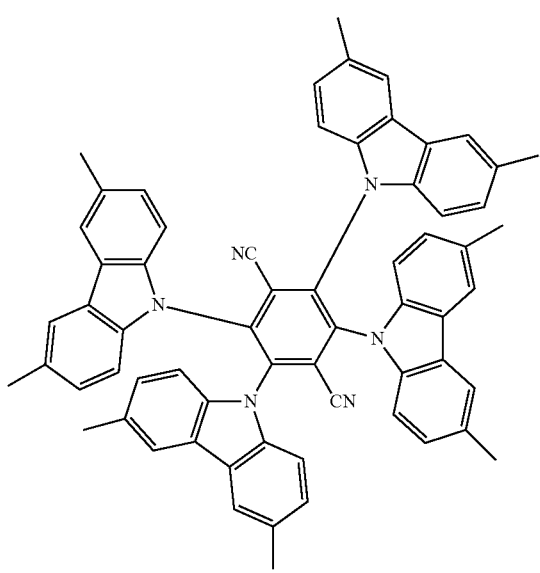

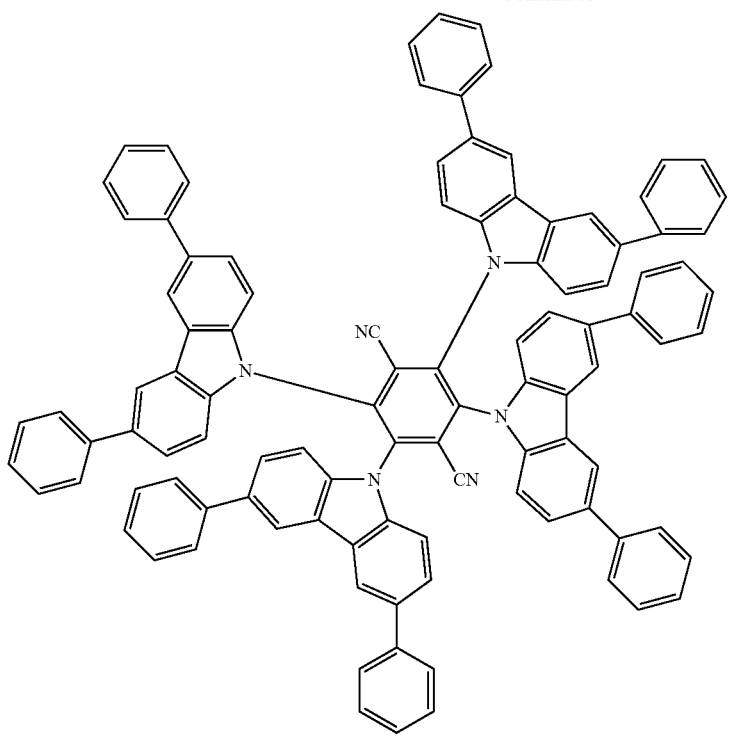
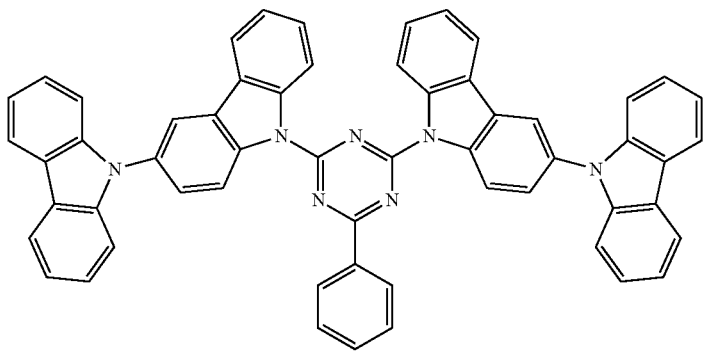
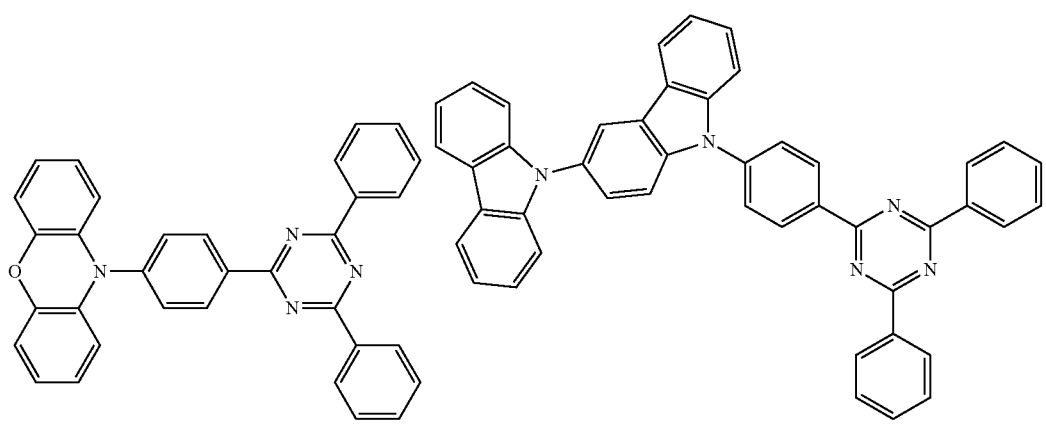

-continued
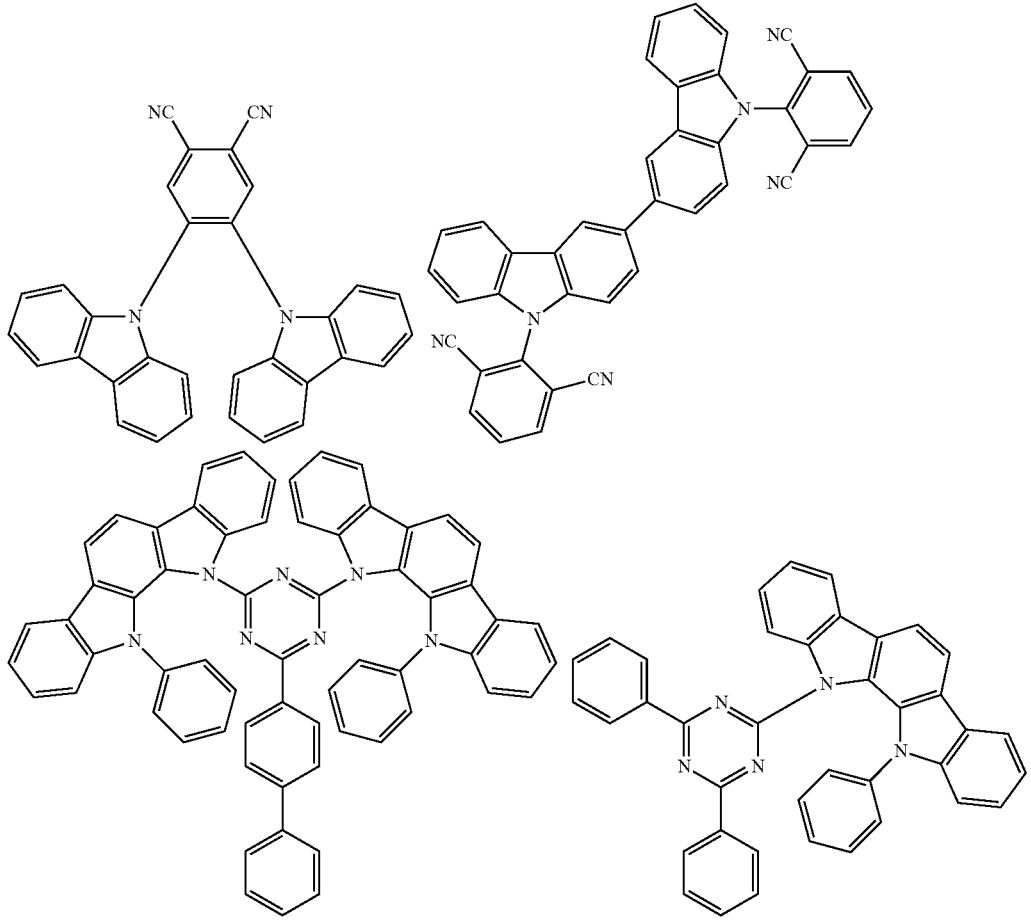
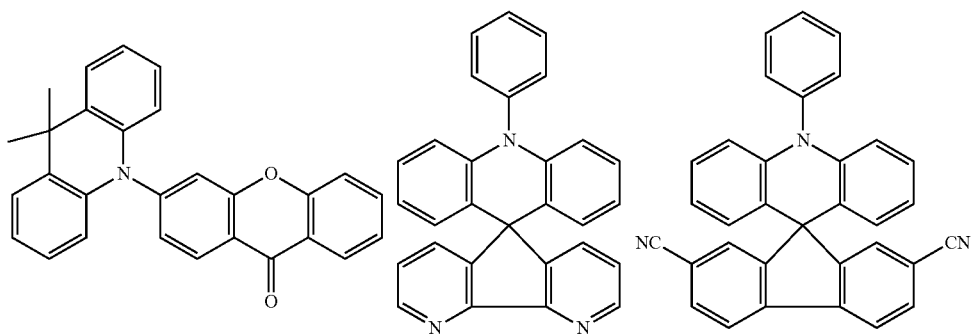
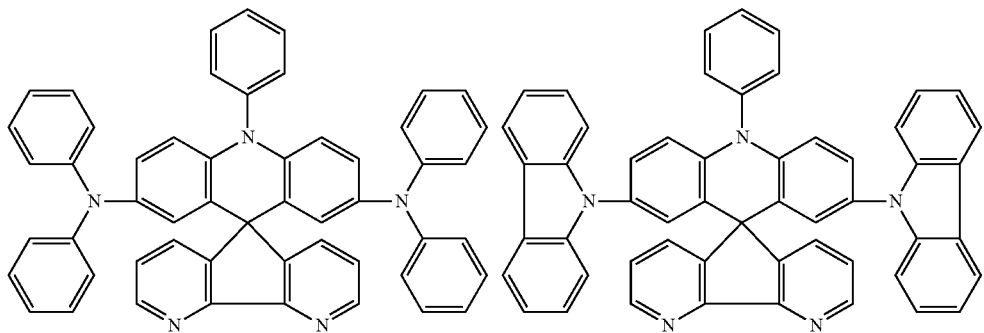

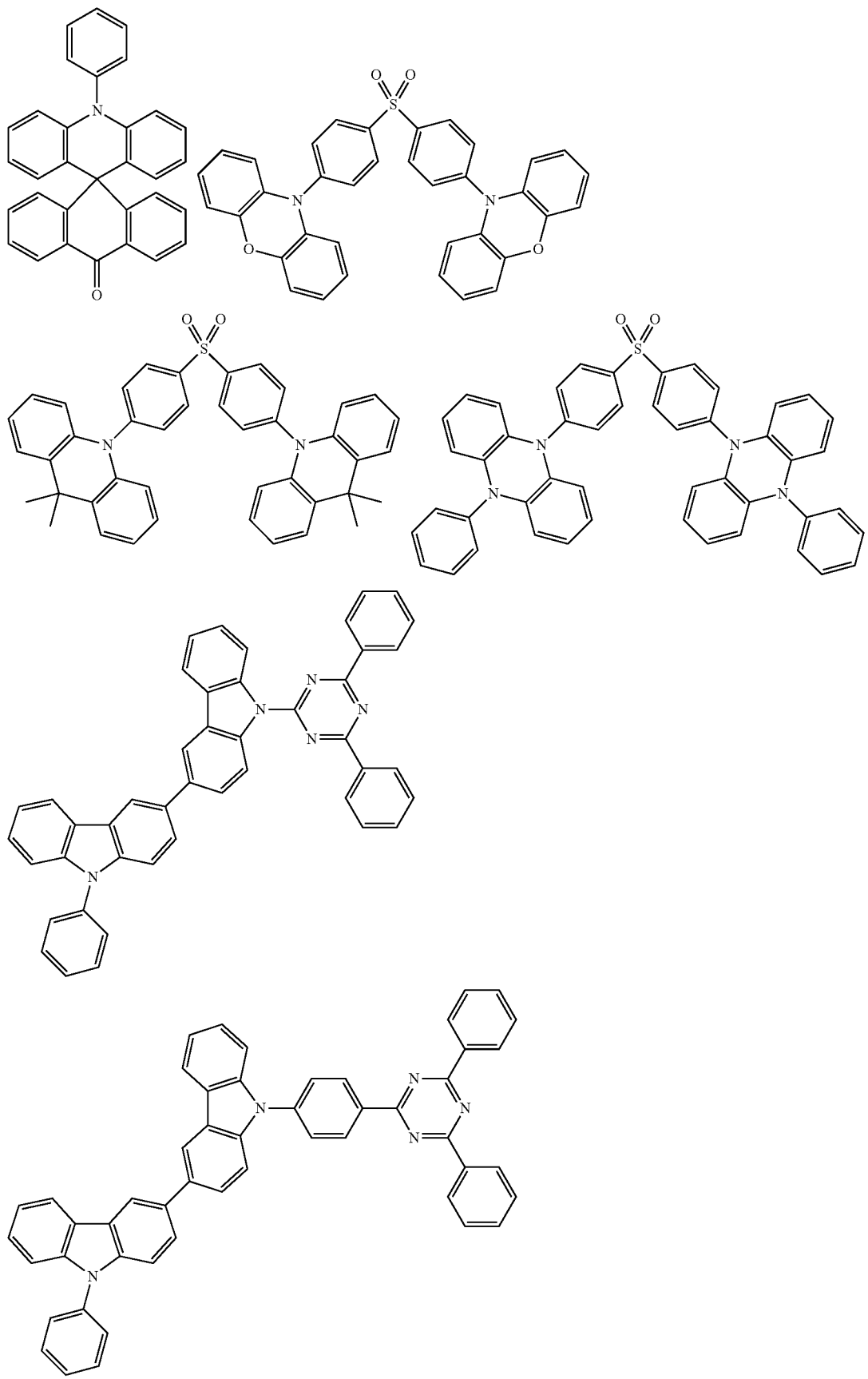

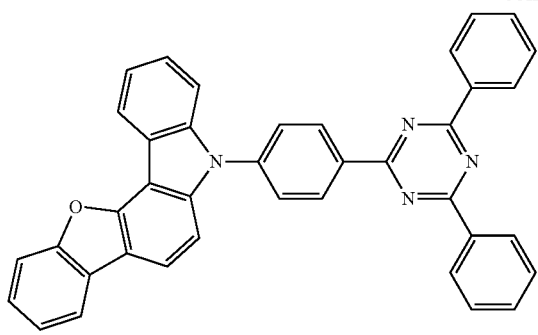
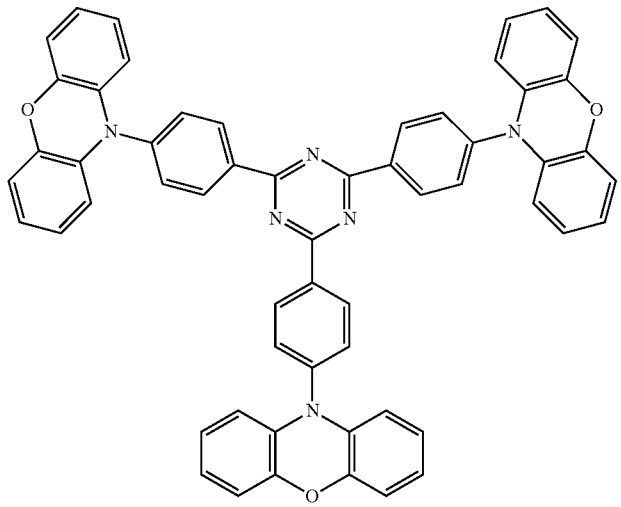
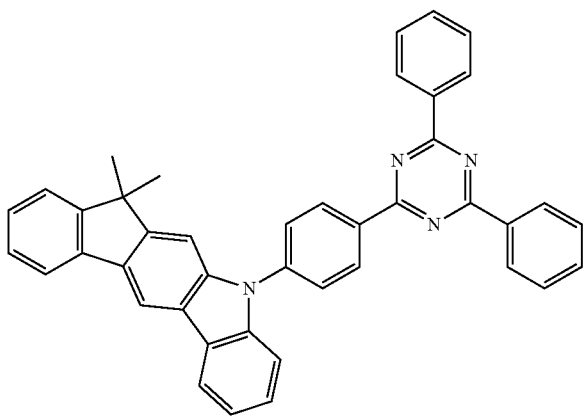
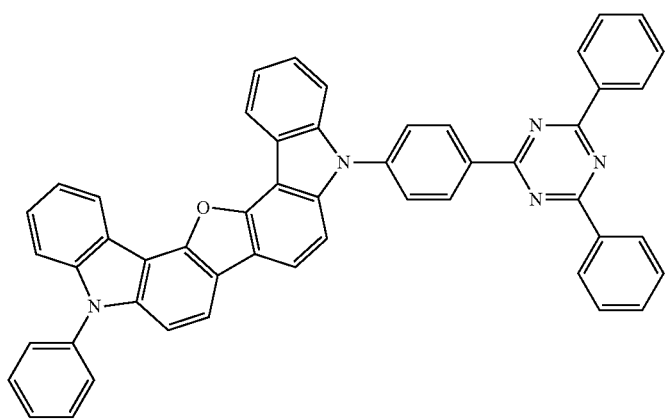

-continued
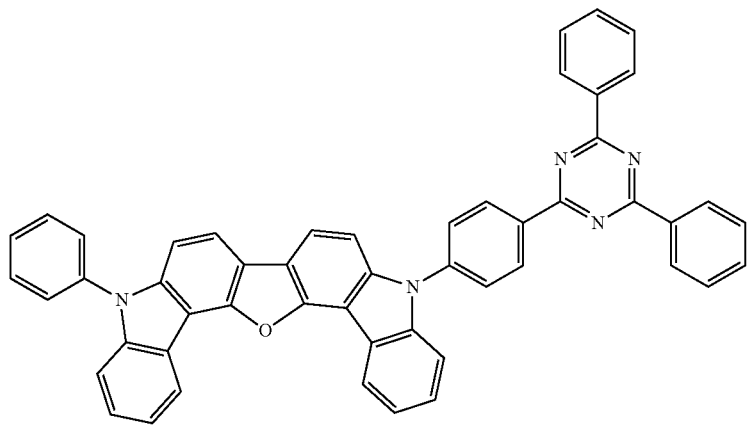
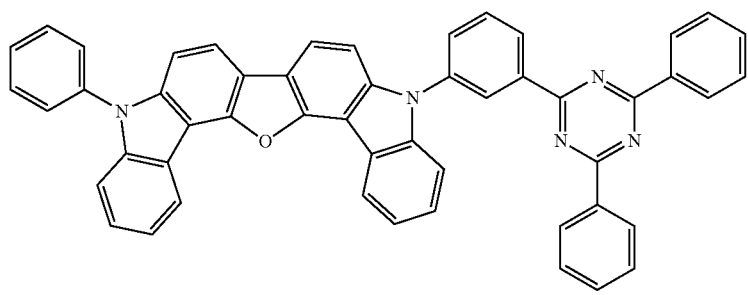
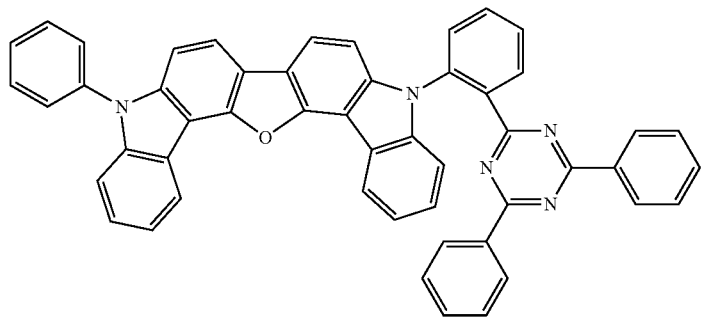
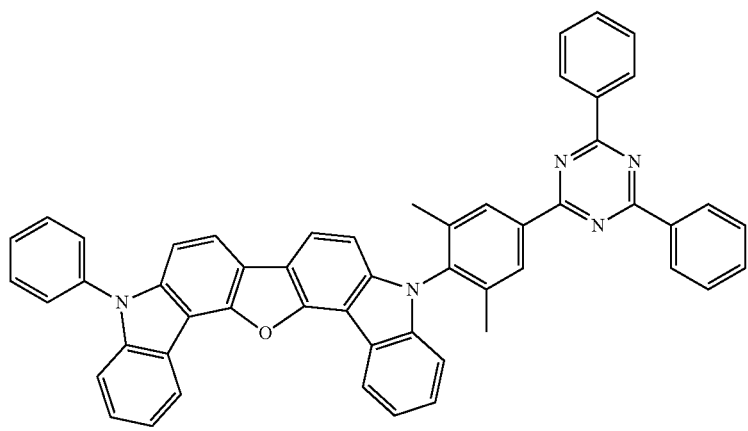

-continued
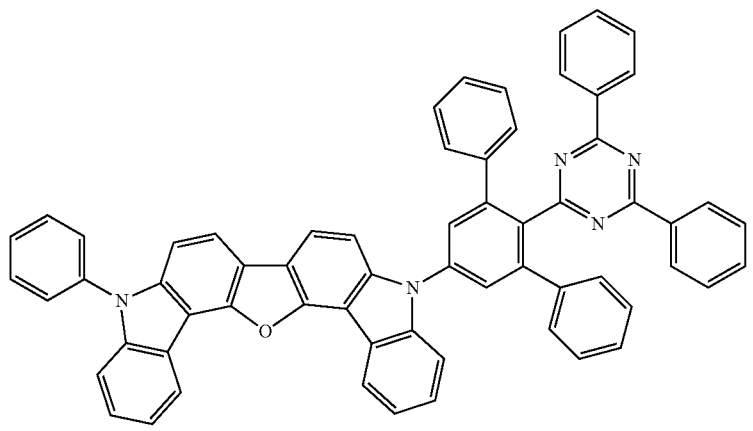
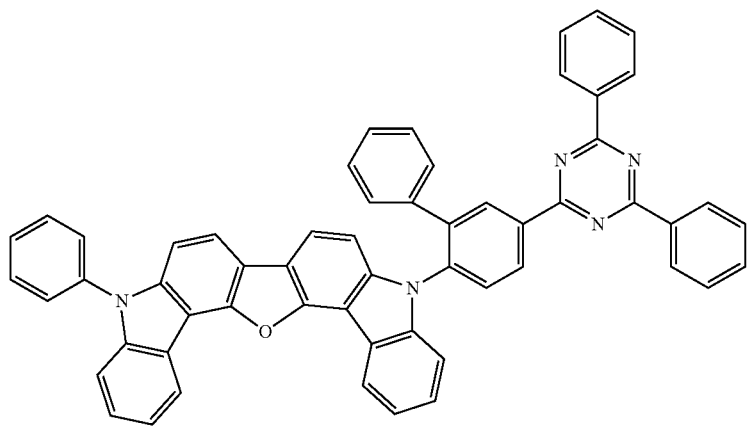
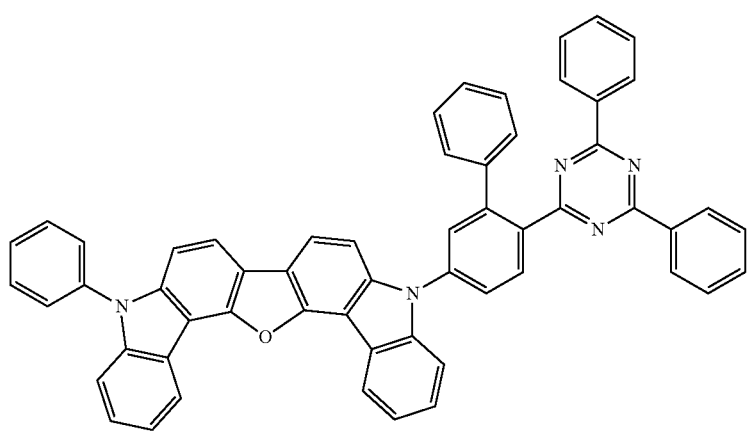

-continued
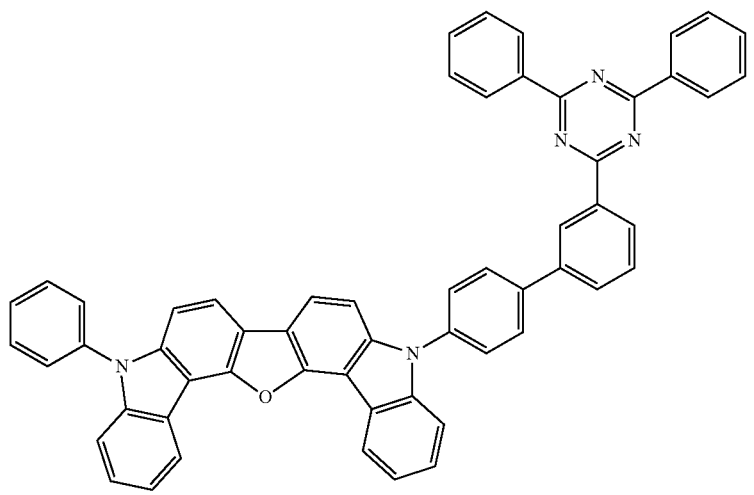
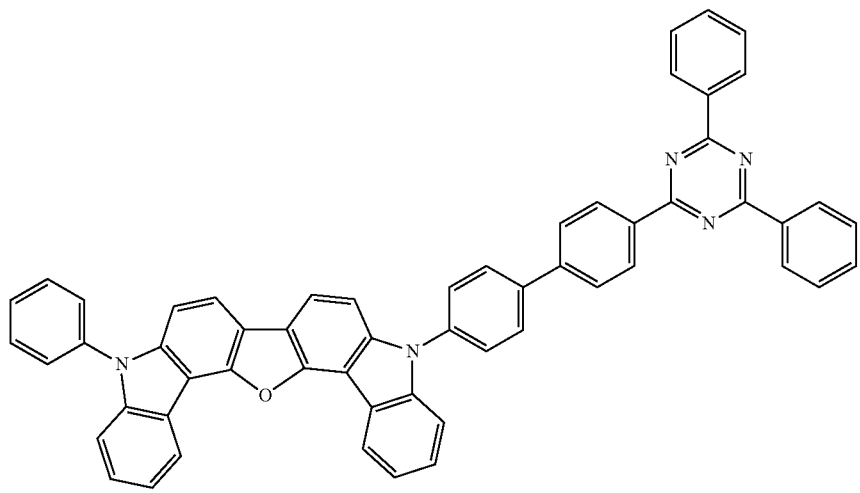
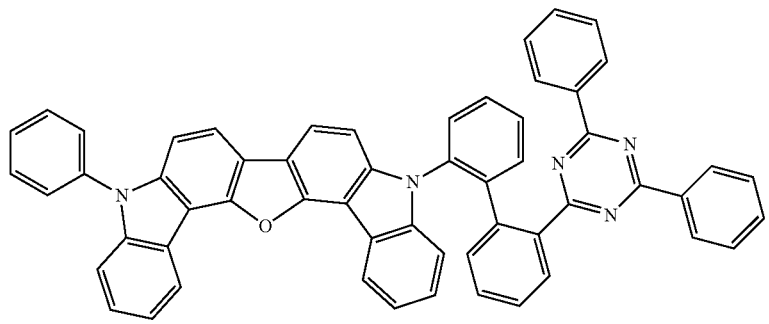

-continued
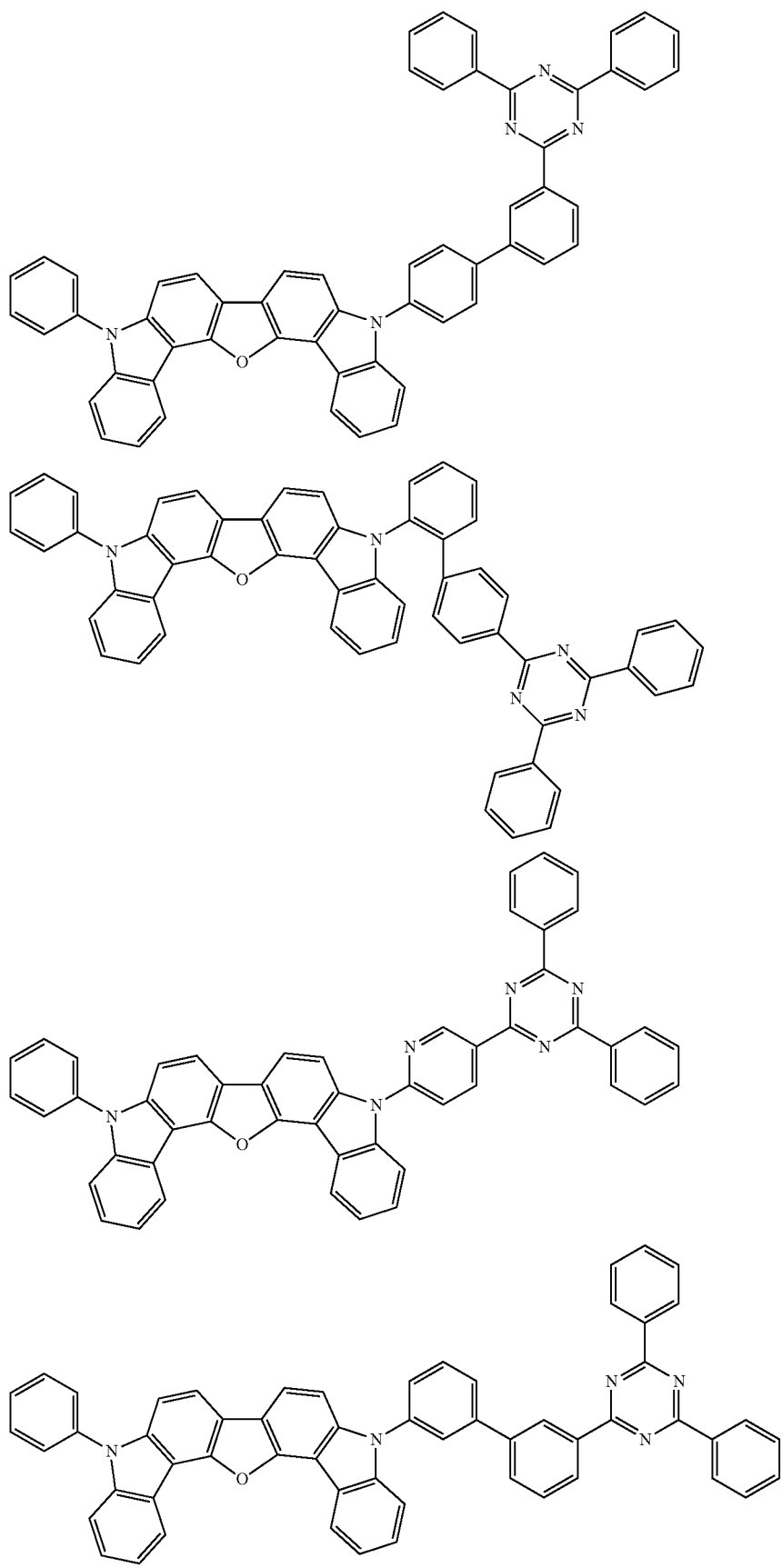

-continued
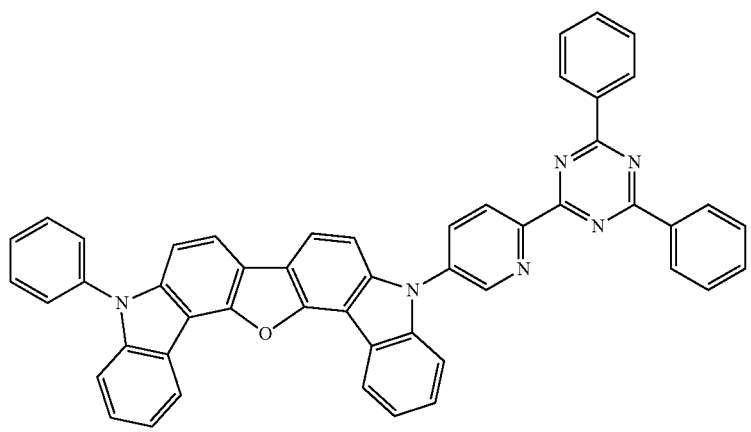
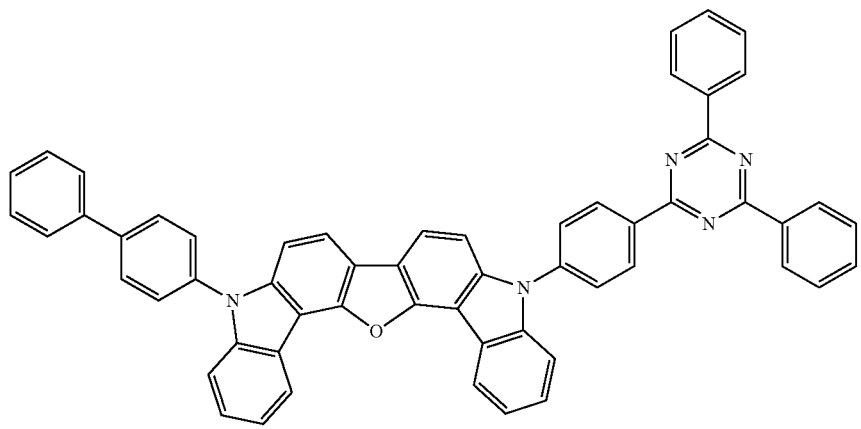
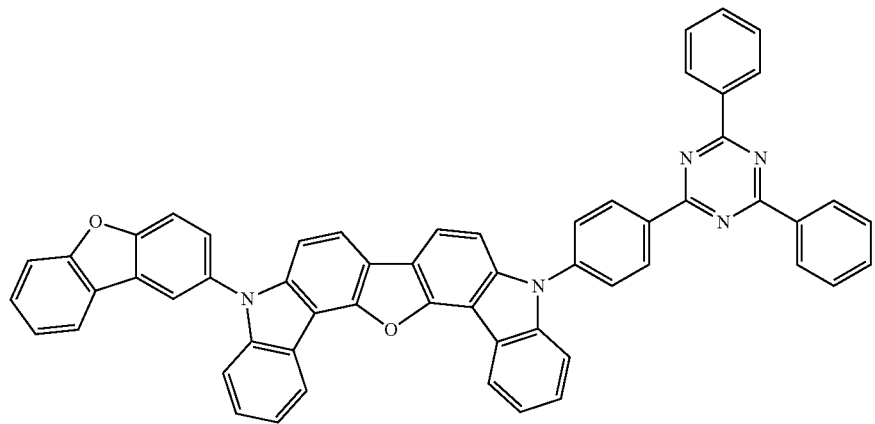
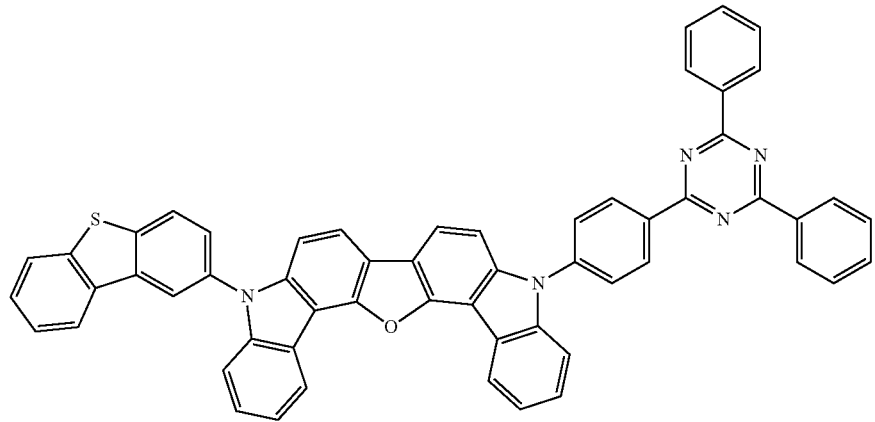

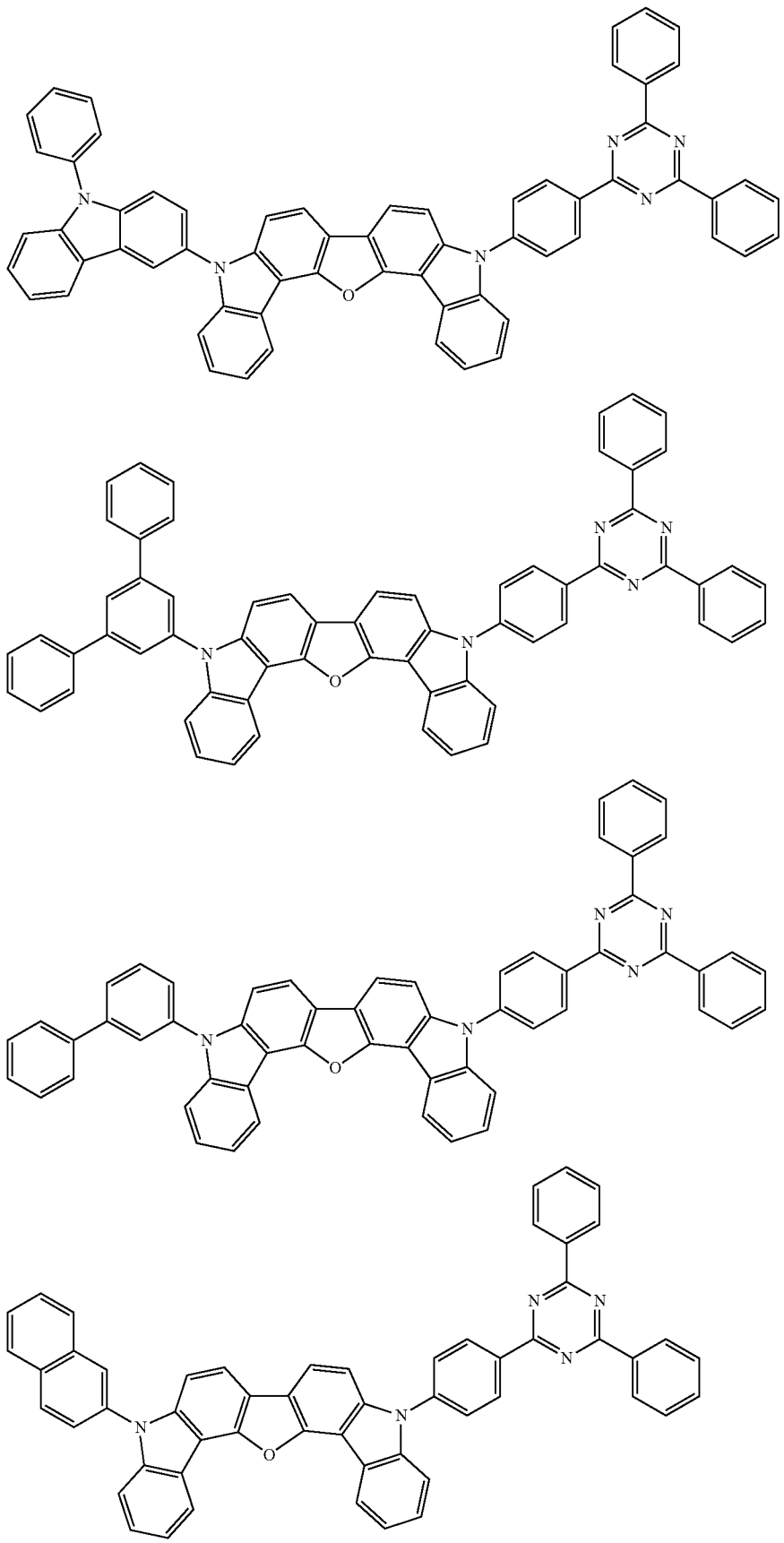 [SMILES: c1ccc(-c2nc(-c3ccccc3)nc(-c3ccc(-n4c5ccccc5c5c6oc7c(ccc8c7c7ccccc7n8-c7ccc8c(c7)c7ccccc7n8-c7ccccc7)c6ccc54)cc3)n2)cc1 ; c1ccc(-c2cc(-c3ccccc3)cc(-n3c4ccccc4c4c5oc6c(ccc7c6c6ccccc6n7-c6ccc(-c7nc(-c8ccccc8)nc(-c8ccccc8)n7)cc6)c5ccc43)c2)cc1 ; c1ccc(-c2cccc(-n3c4ccccc4c4c5oc6c(ccc7c6c6ccccc6n7-c6ccc(-c7nc(-c8ccccc8)nc(-c8ccccc8)n7)cc6)c5ccc43)c2)cc1 ; c1ccc(-c2nc(-c3ccccc3)nc(-c3ccc(-n4c5ccccc5c5c6oc7c(ccc8c7c7ccccc7n8-c7ccc8ccccc8c7)c6ccc54)cc3)n2)cc1]

-continued
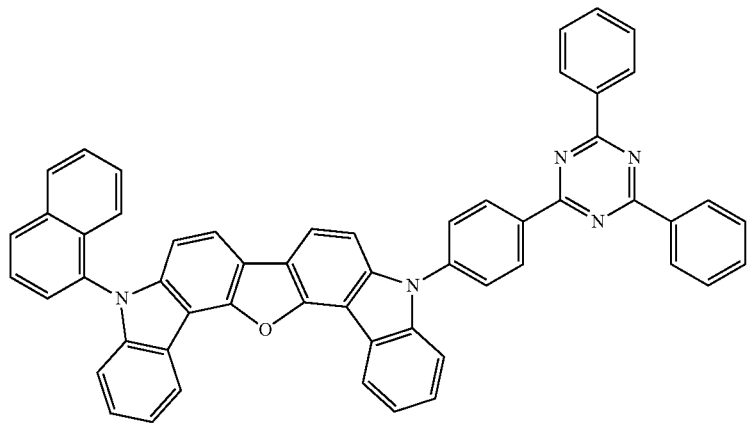 [SMILES: c1ccc(-c2nc(-c3ccccc3)nc(-c3ccc(-n4c5ccccc5c5c6oc7c(ccc8c7c7ccccc7n8-c7cccc8ccccc78)c6ccc54)cc3)n2)cc1]
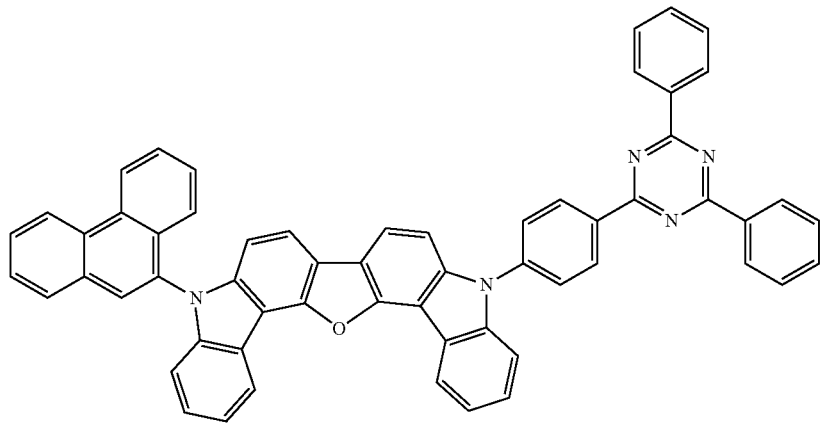
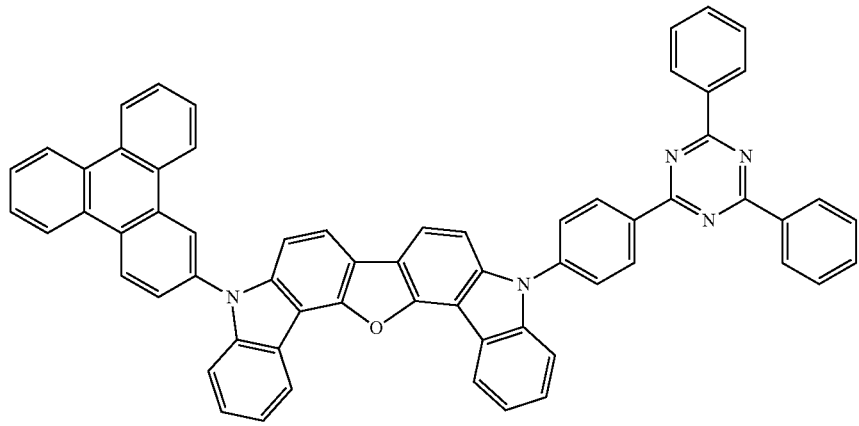
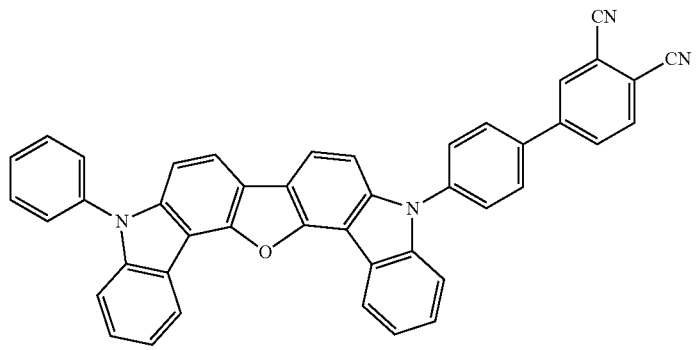

-continued
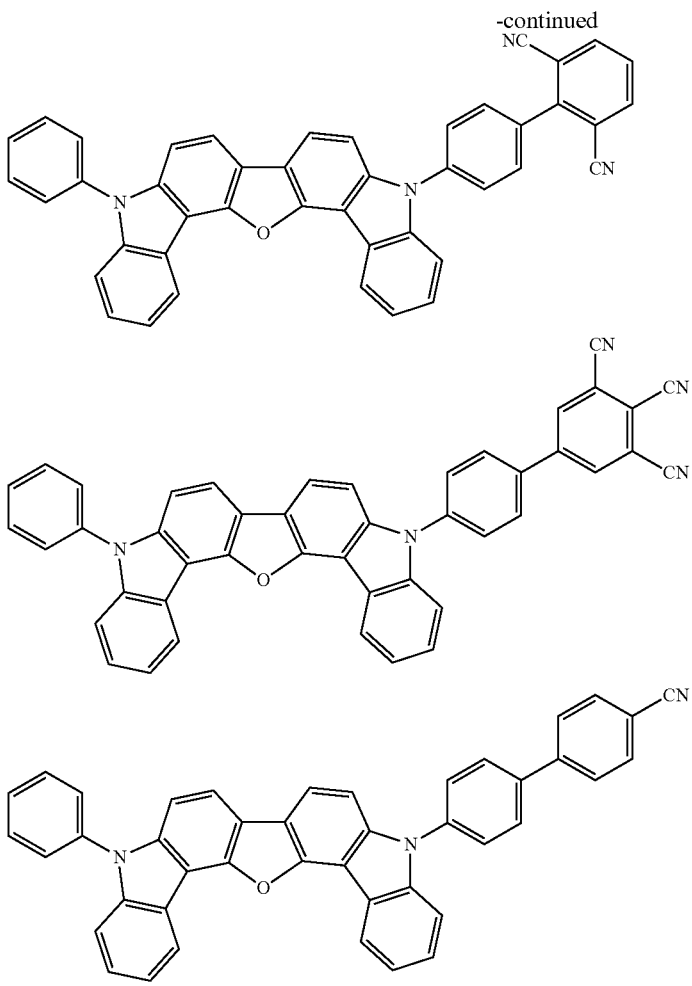
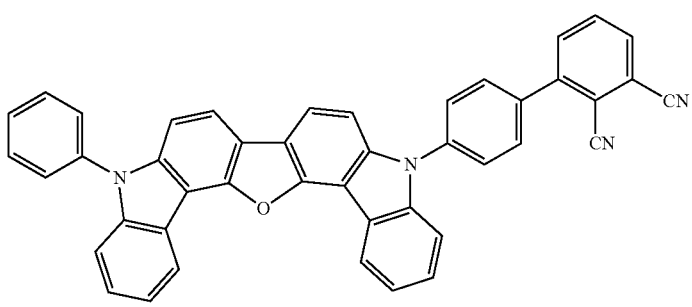
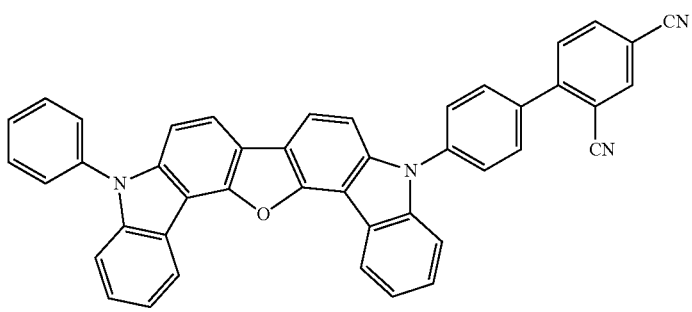

-continued
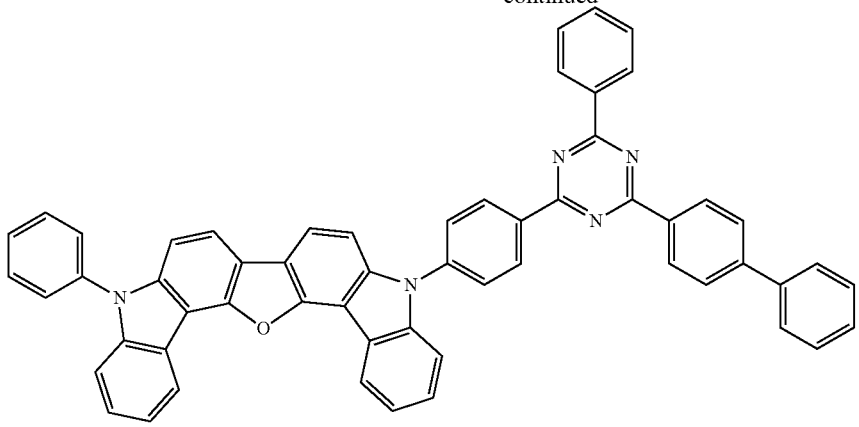
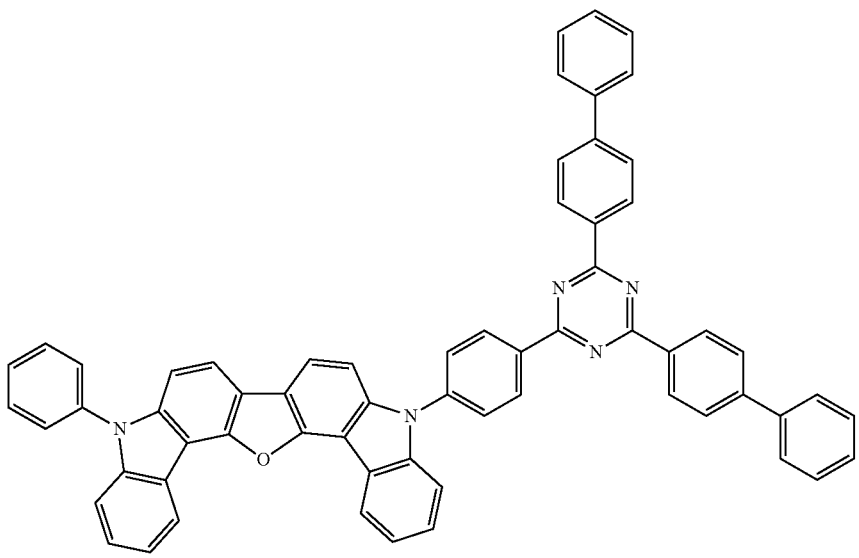
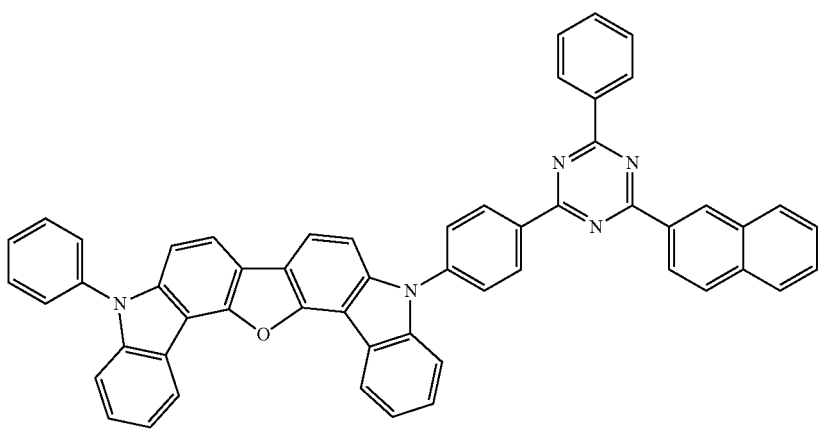

-continued
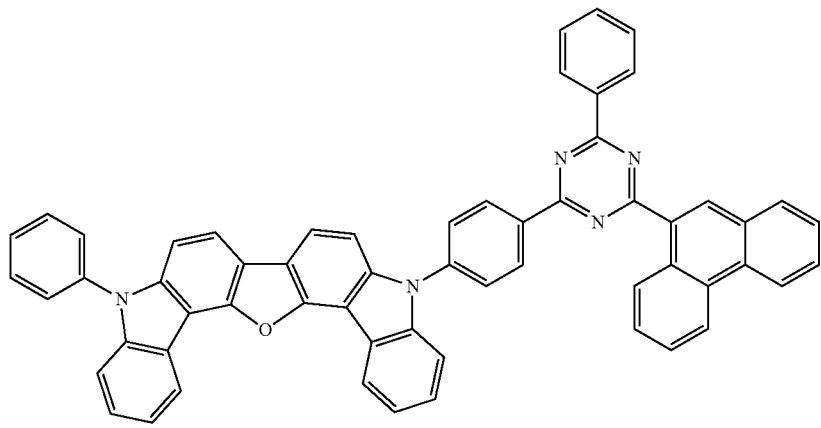
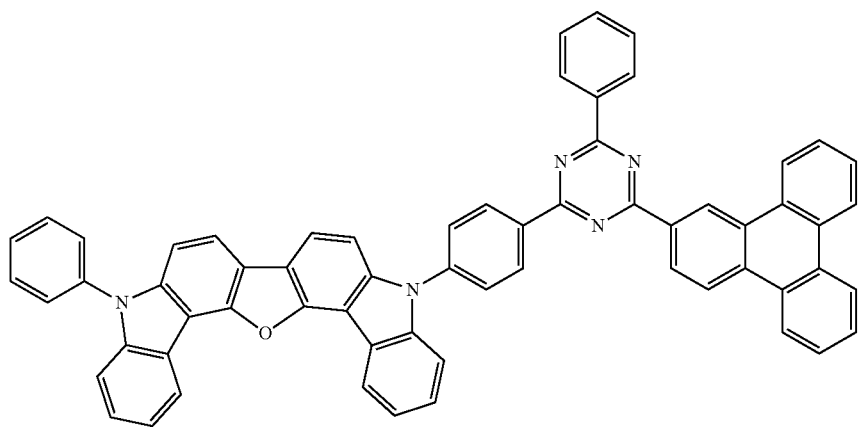
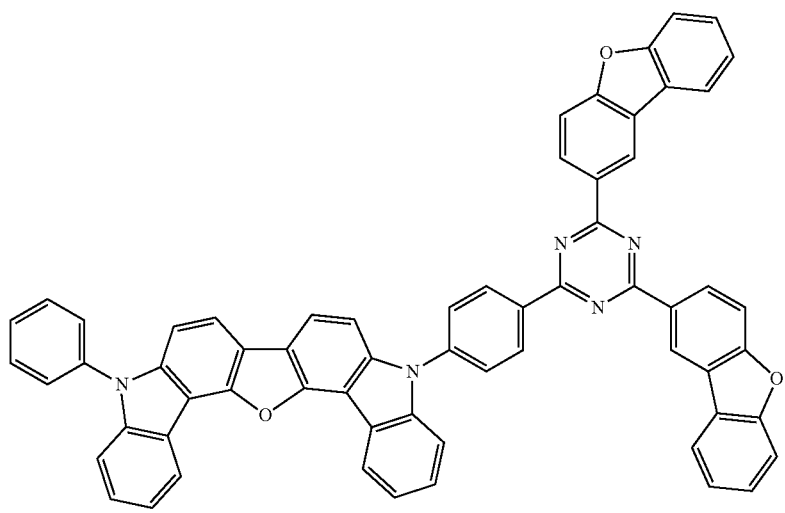

-continued
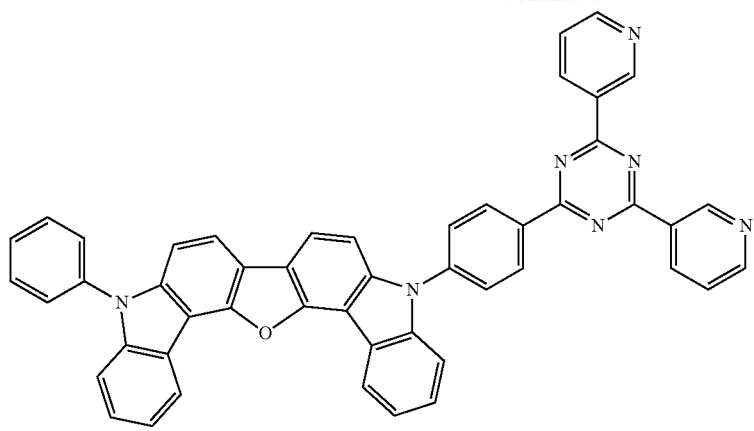
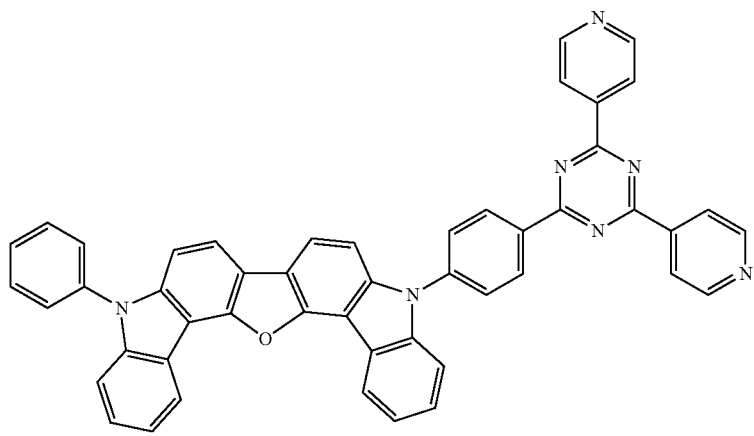
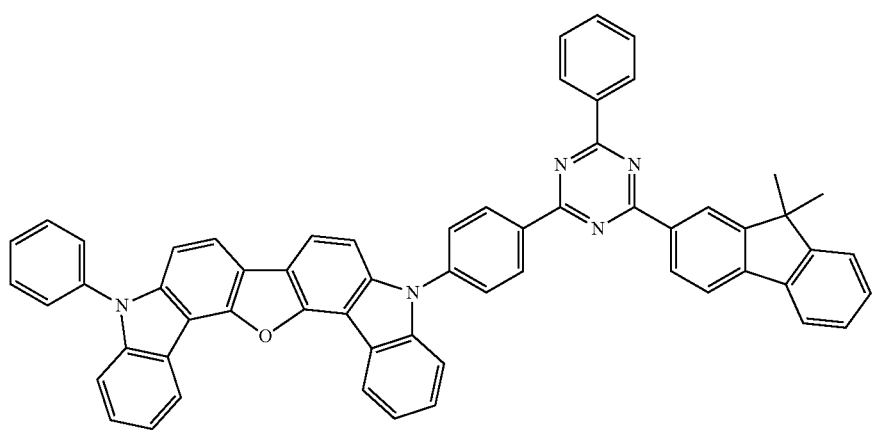
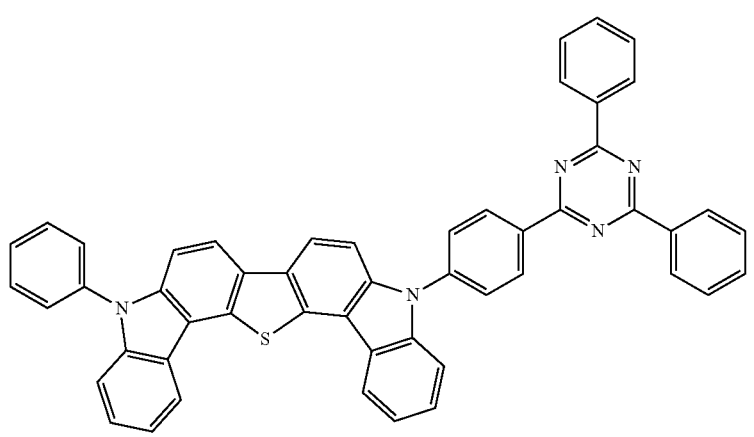

-continued
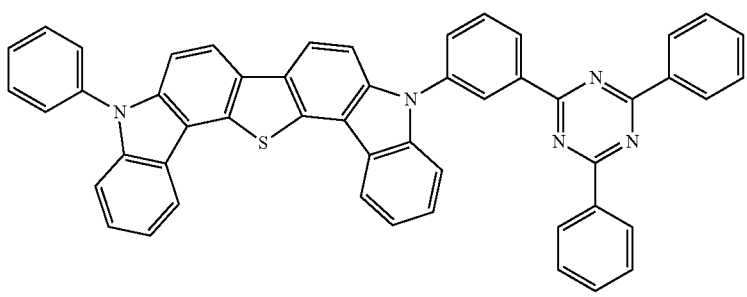
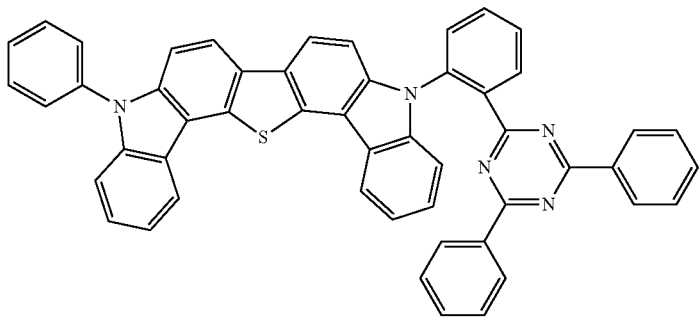
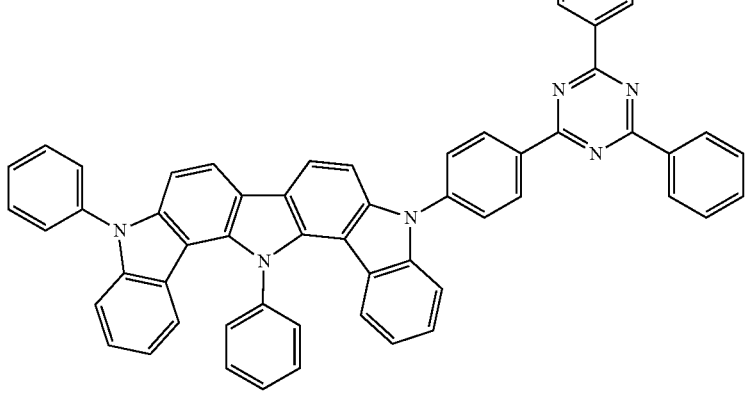
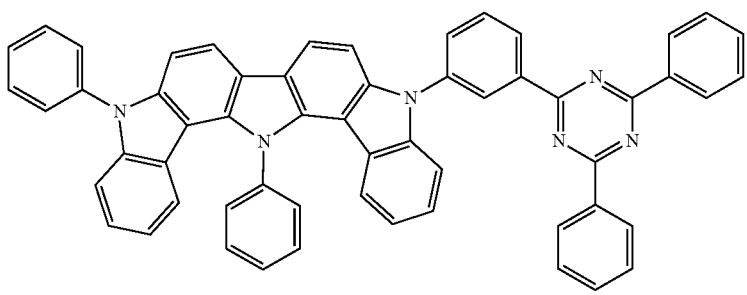
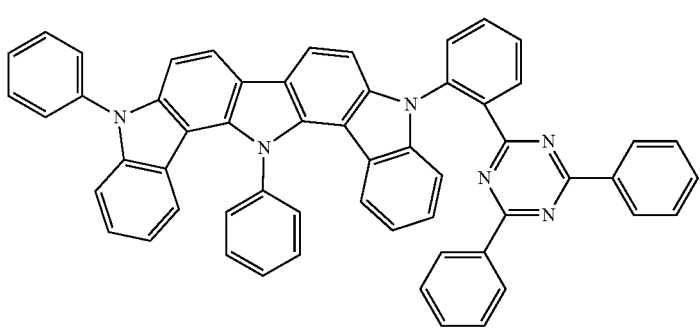

-continued
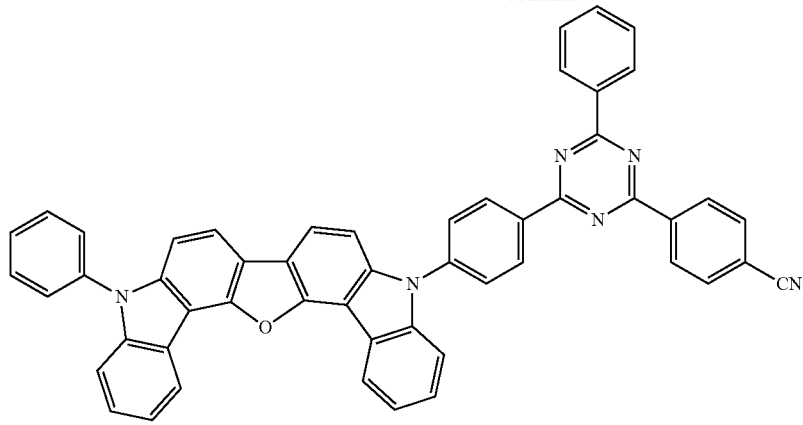
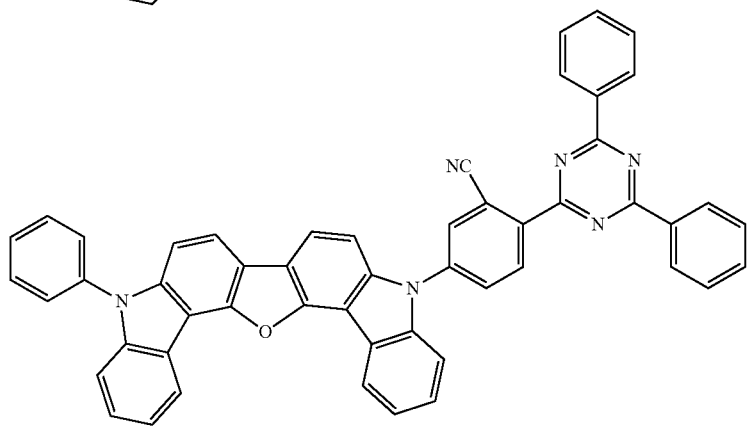
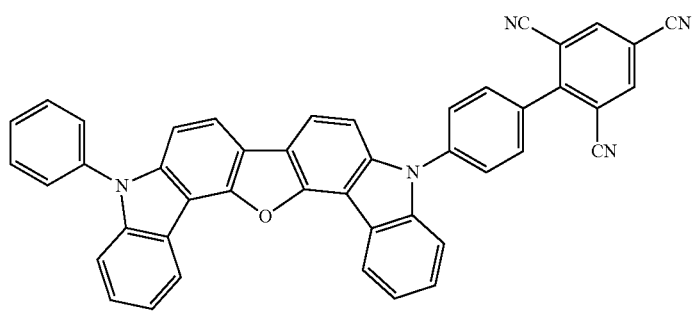
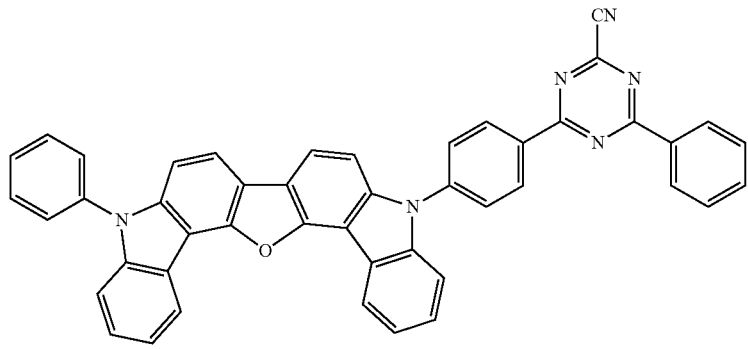

-continued
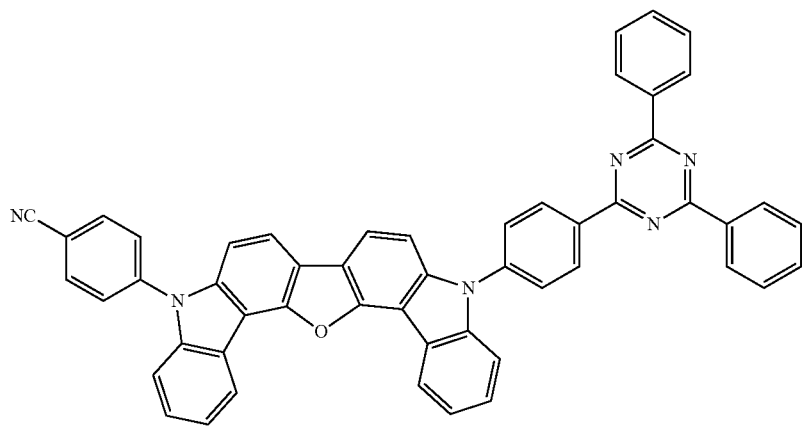
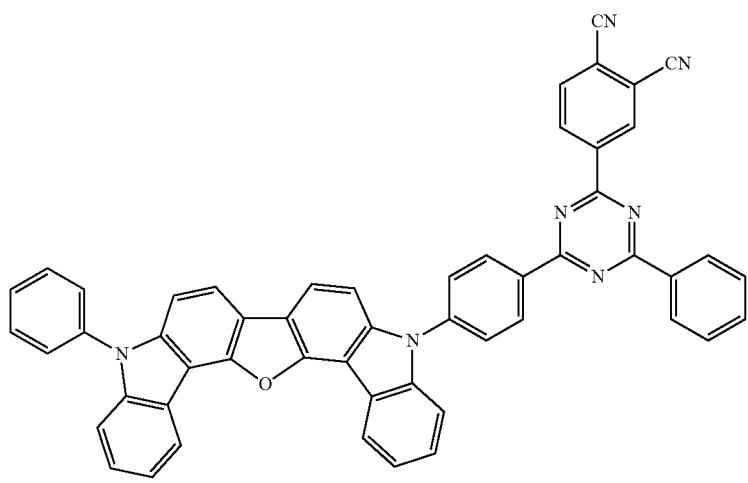
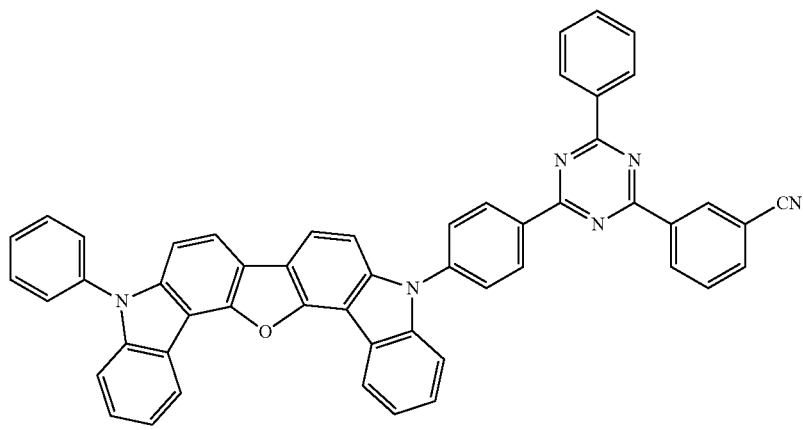

-continued
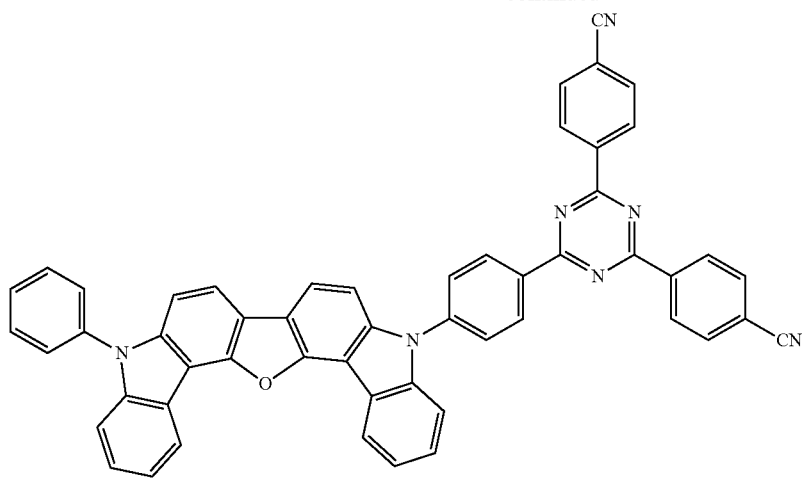
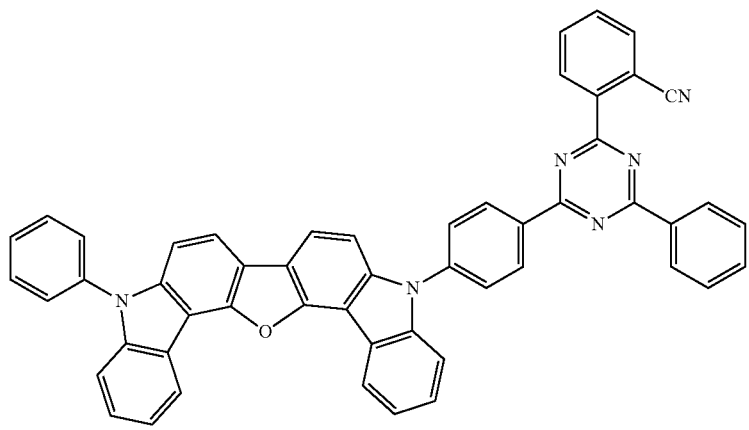
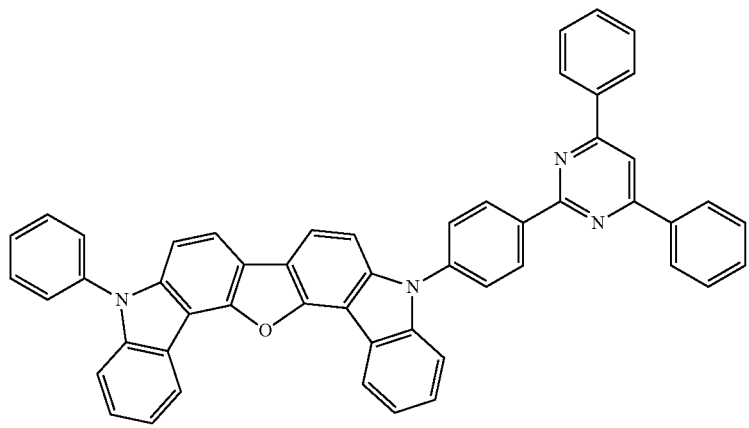

-continued
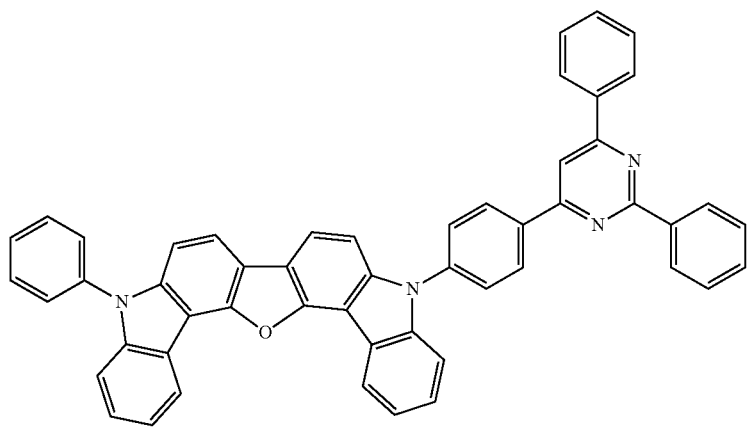
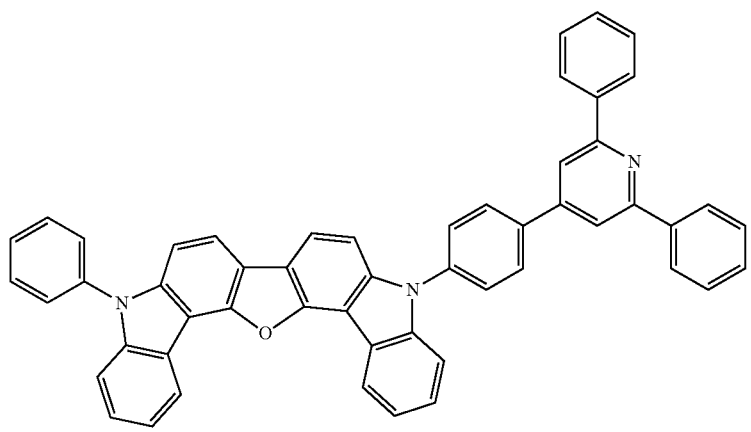
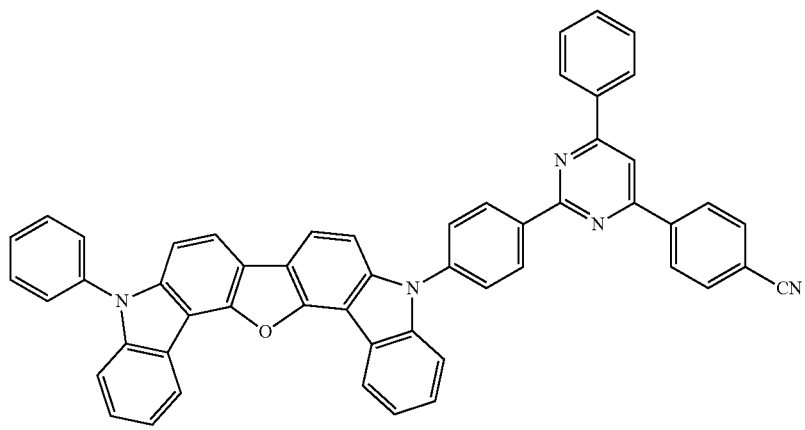
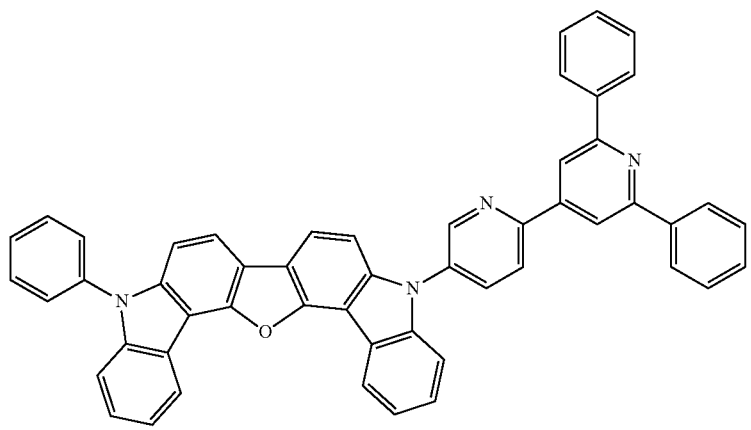

-continued
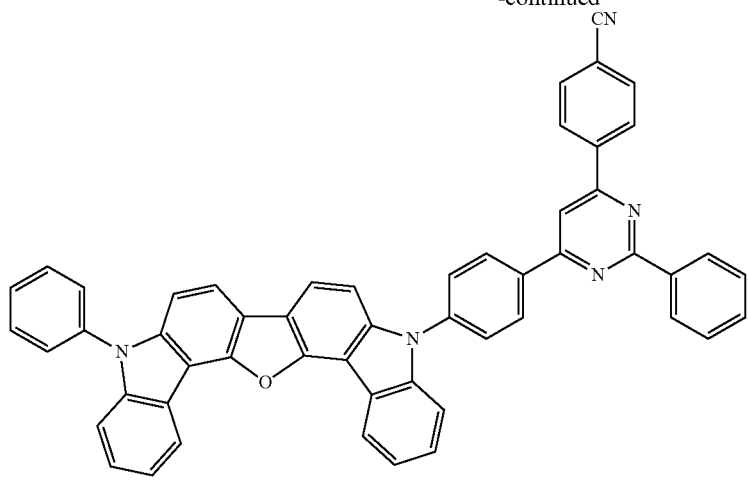
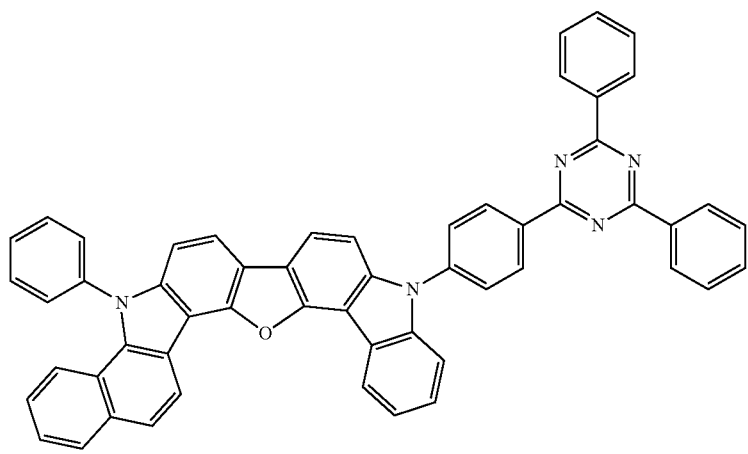
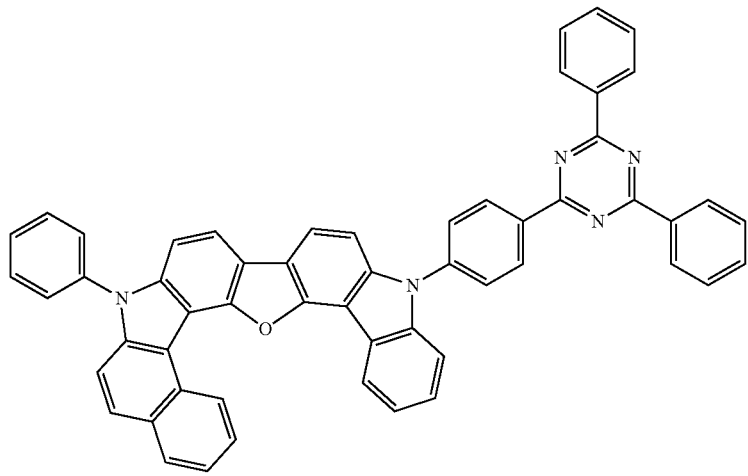

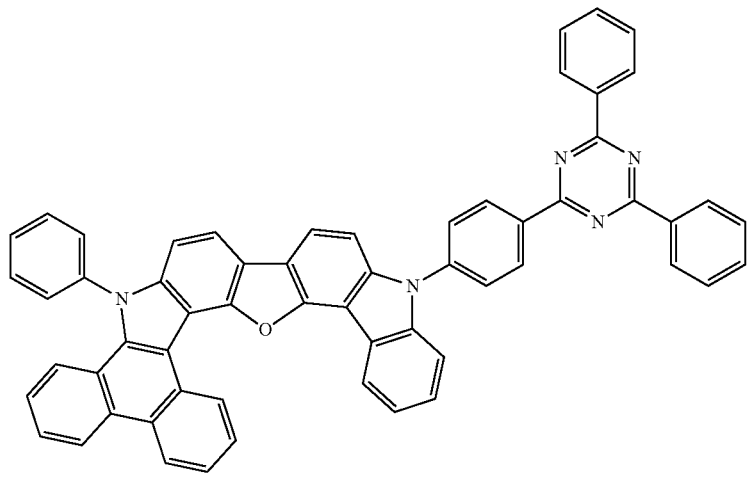
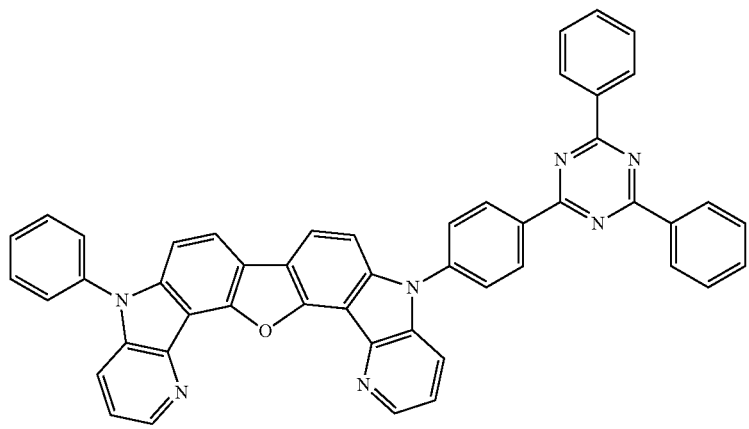
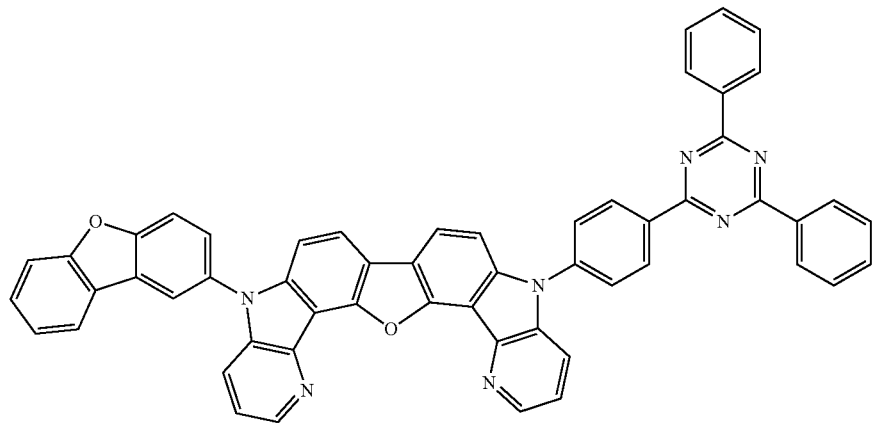

-continued
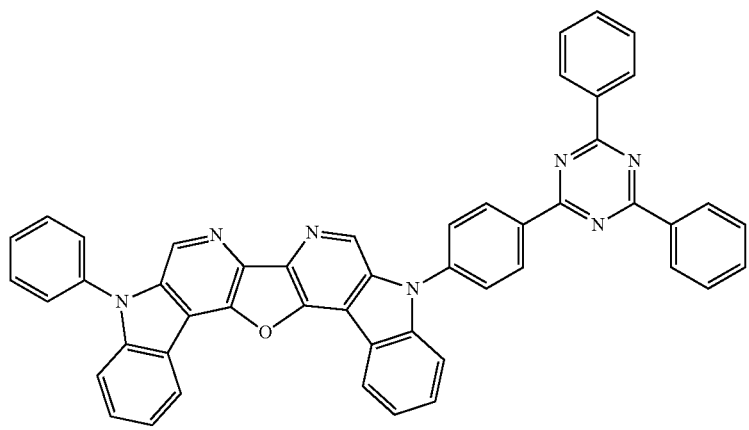
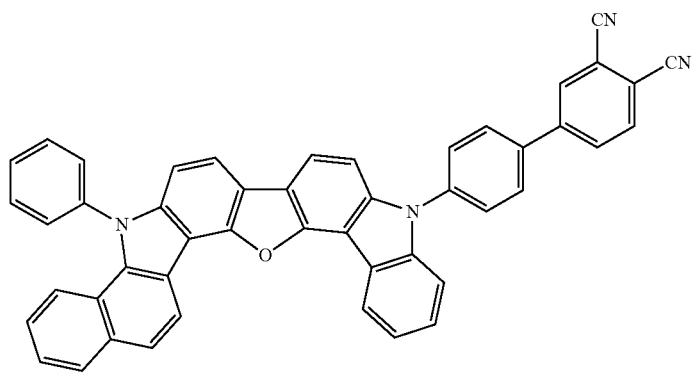
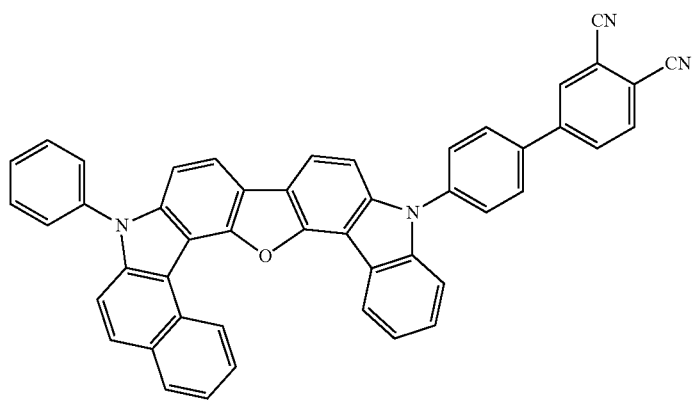
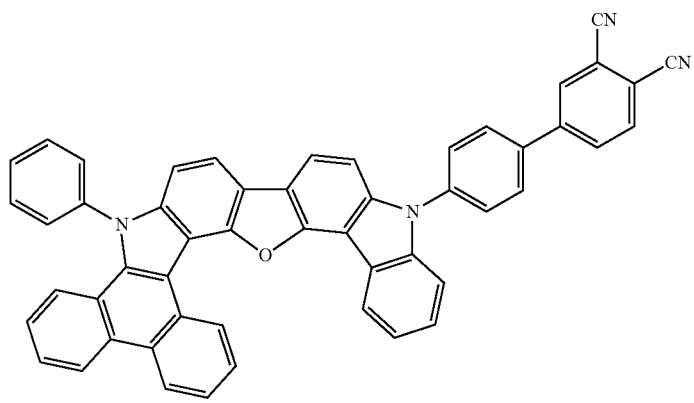

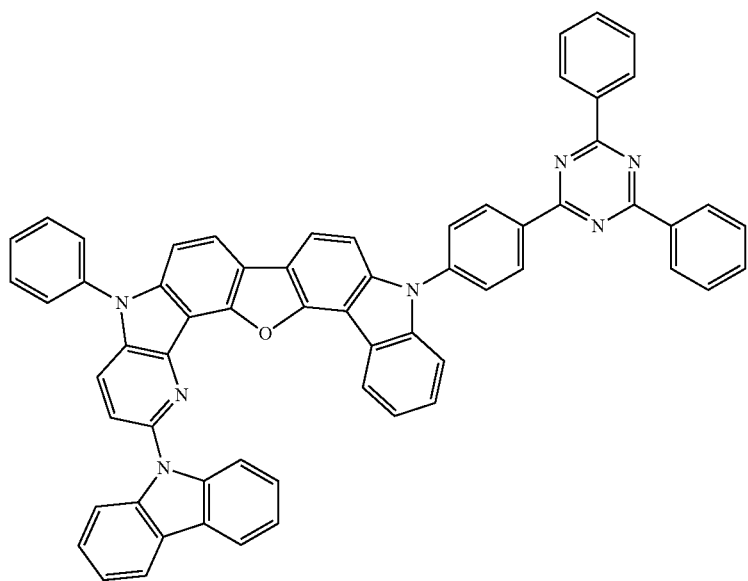
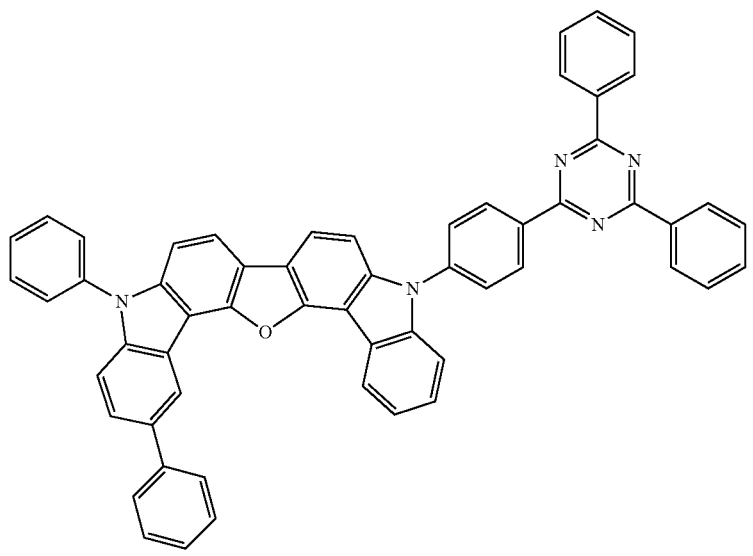
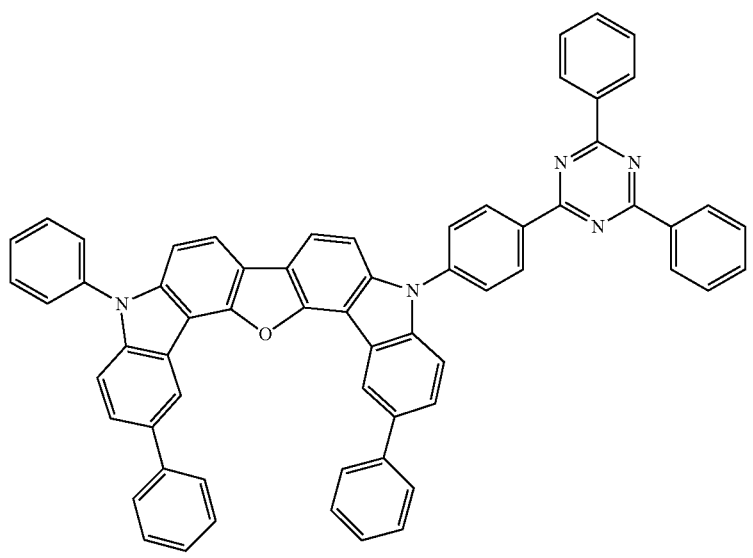

-continued
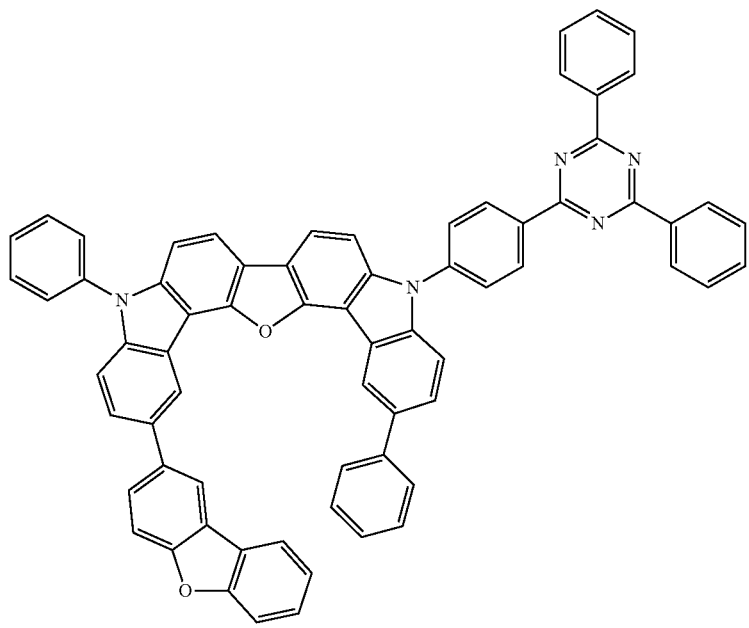
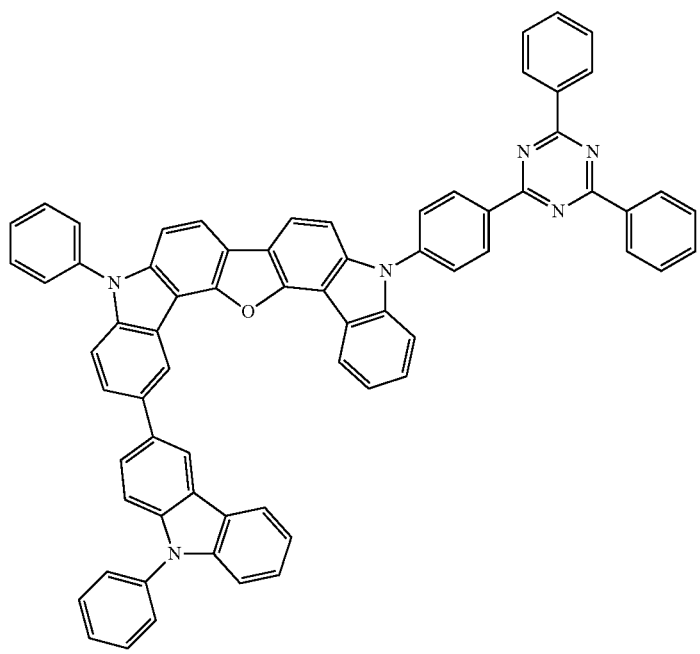

-continued
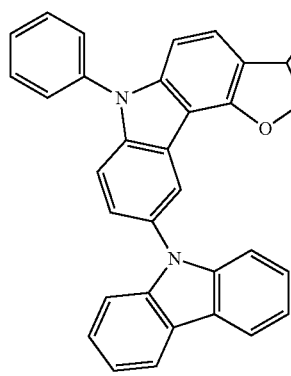
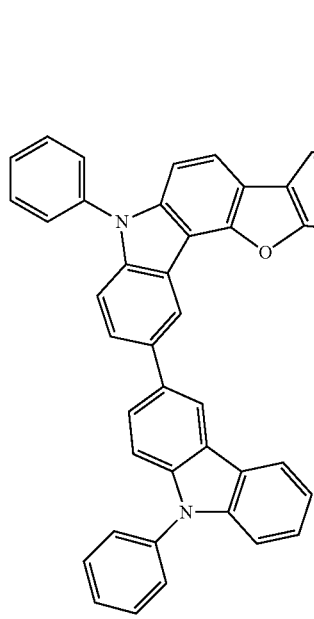
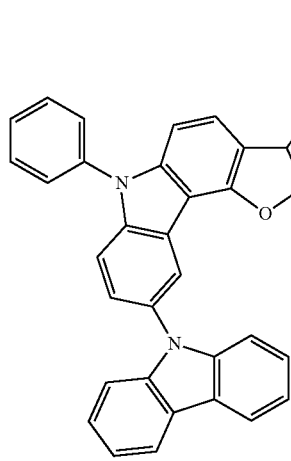

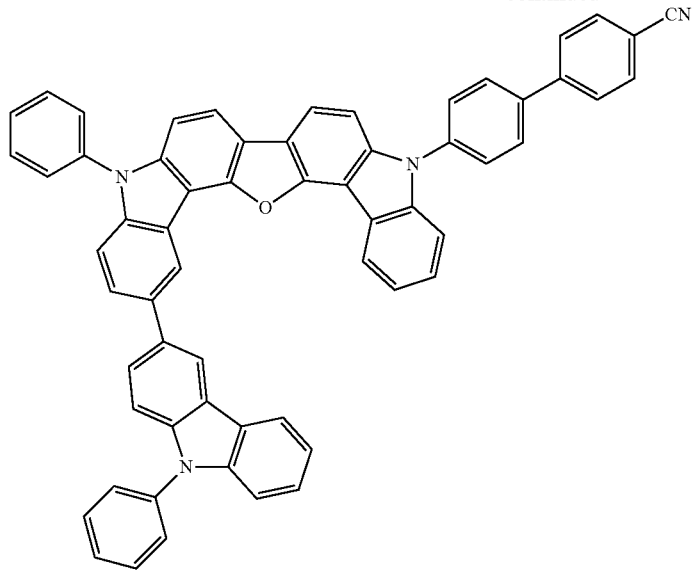

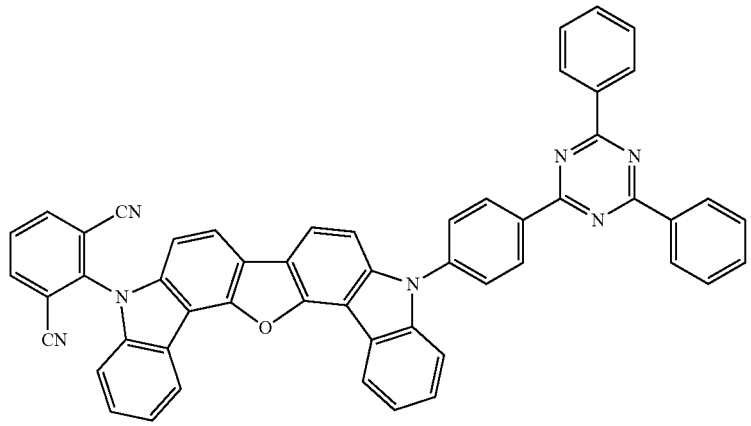
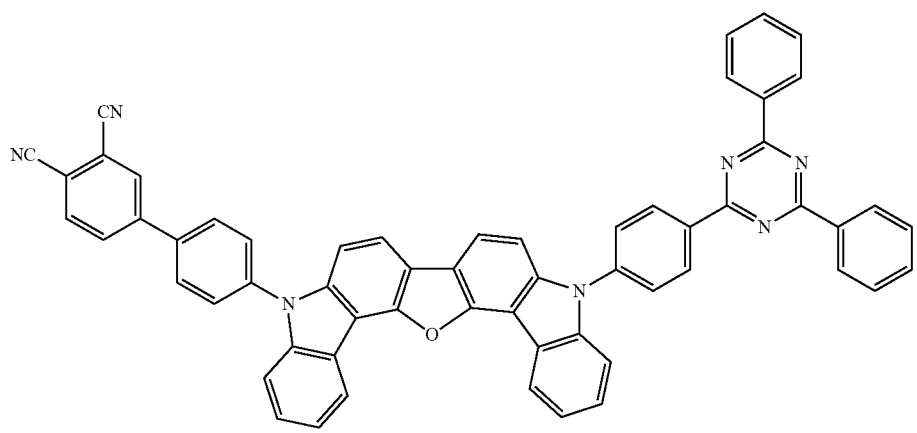
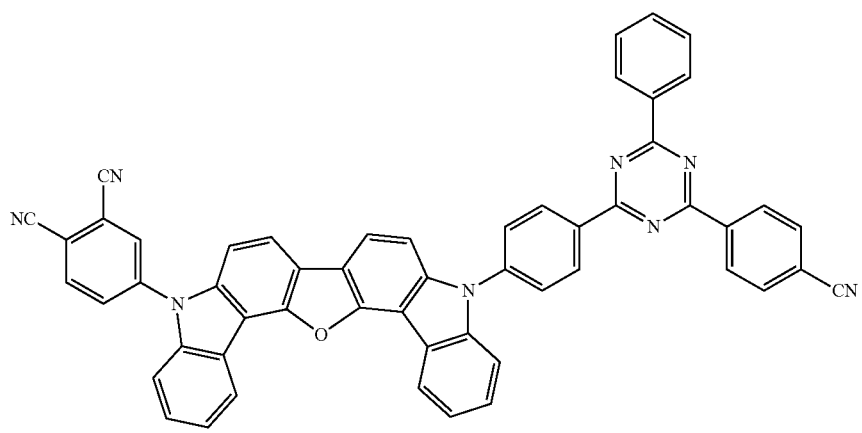
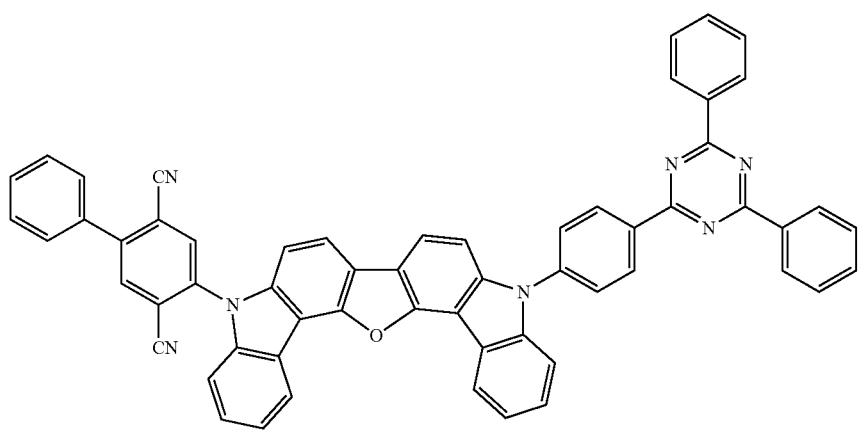

-continued
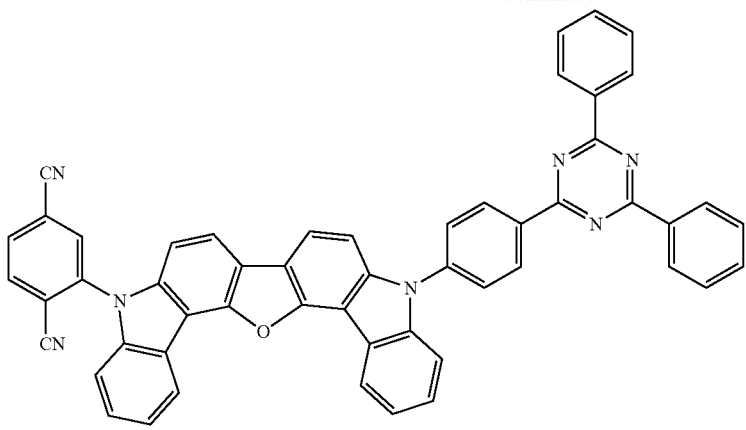
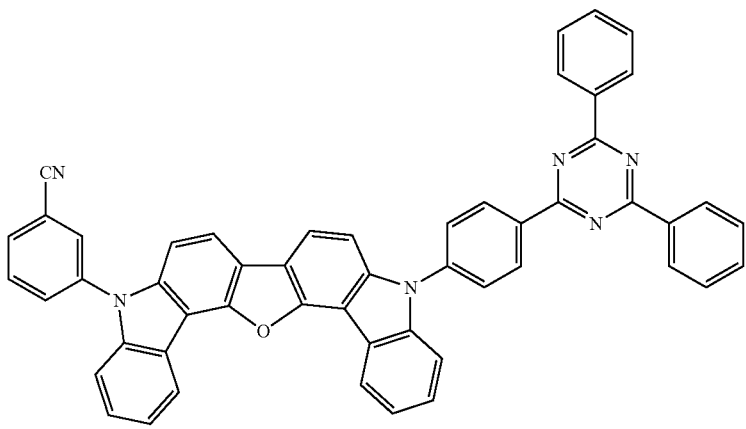
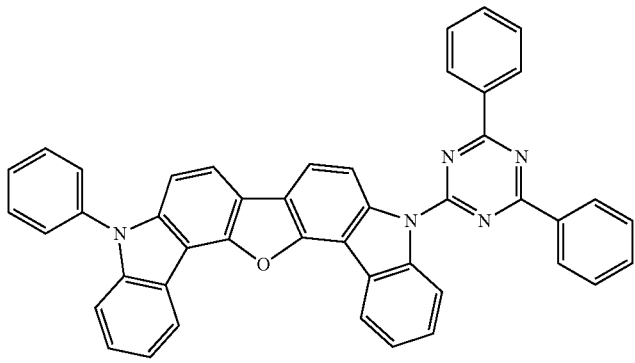
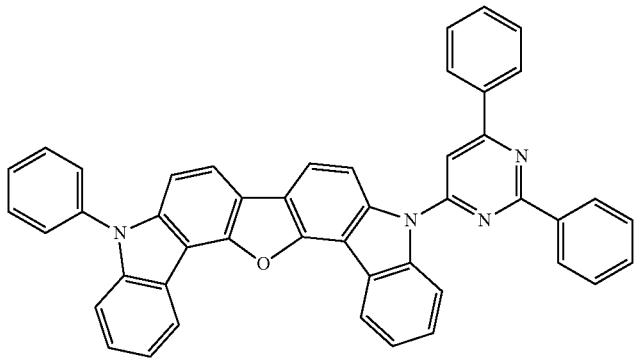

-continued
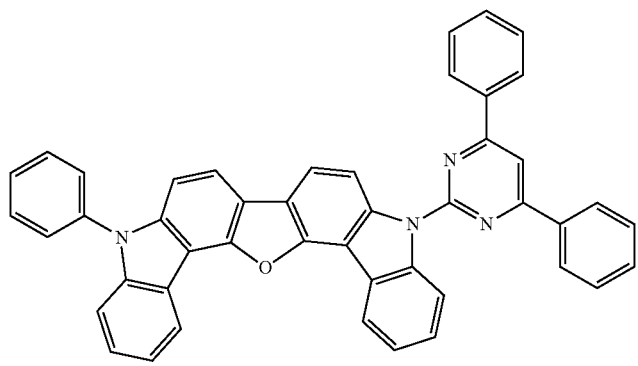
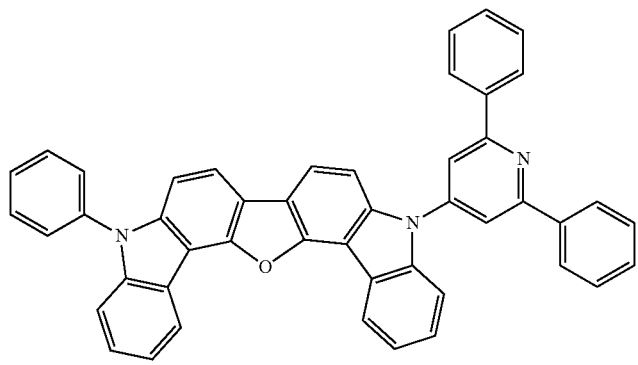
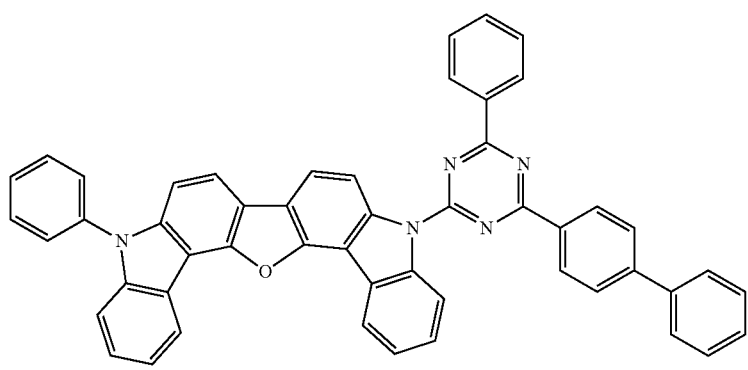
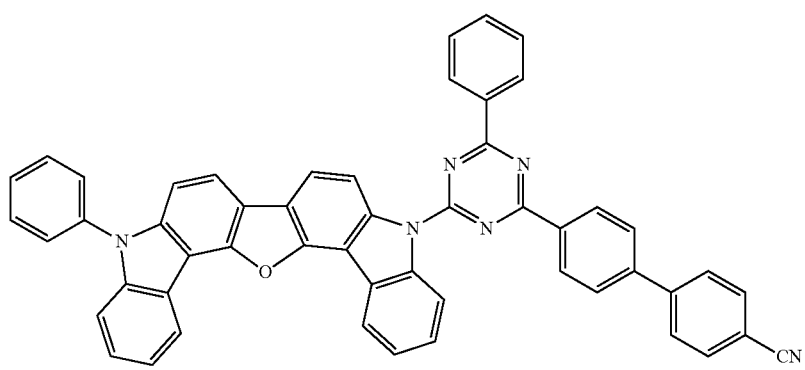

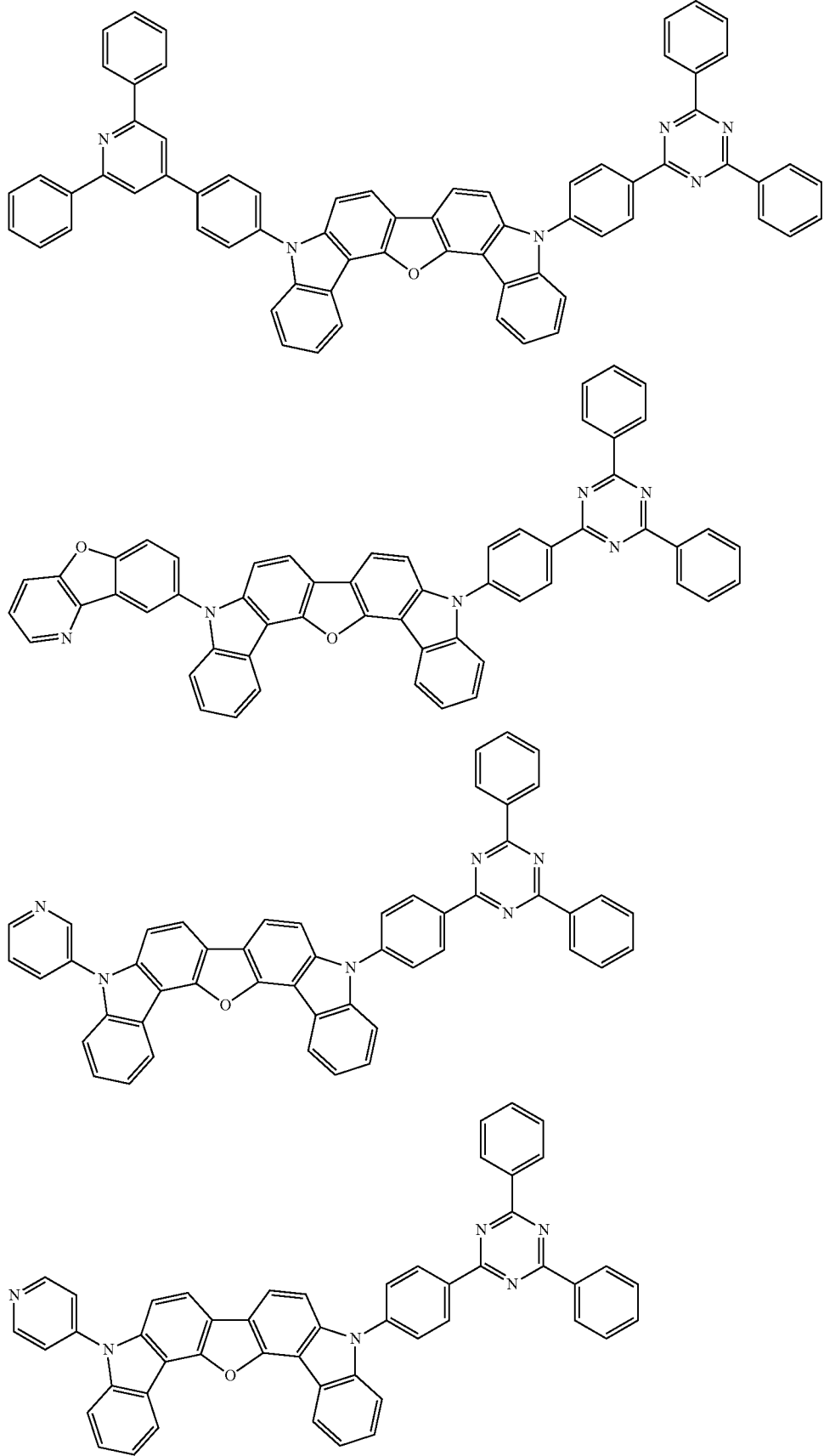

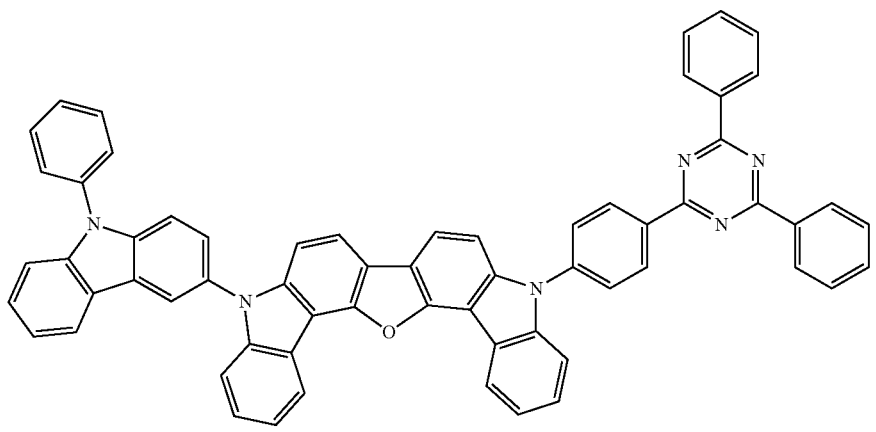
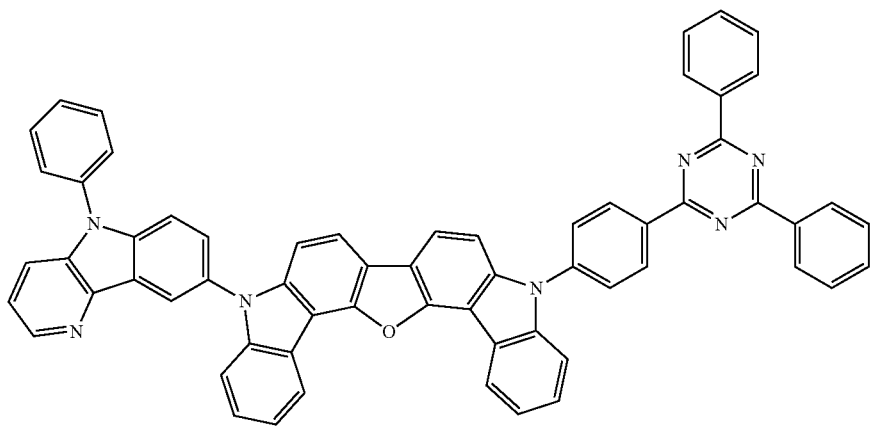
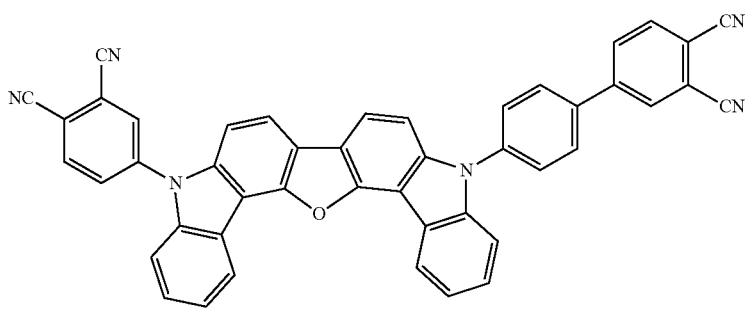
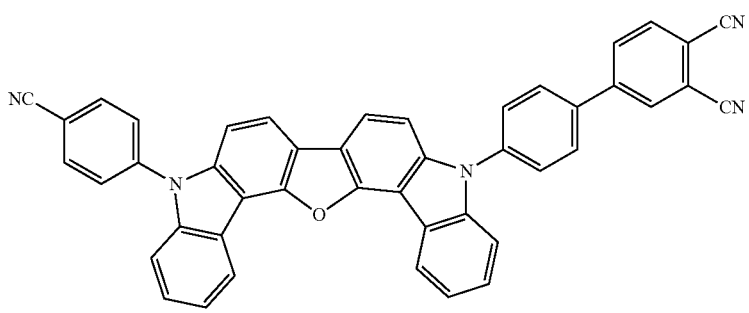

-continued
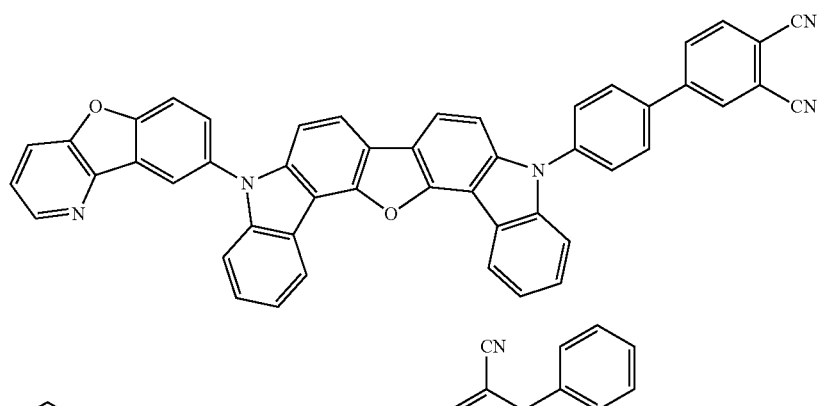
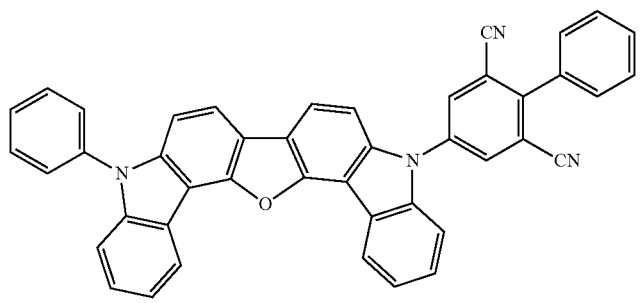
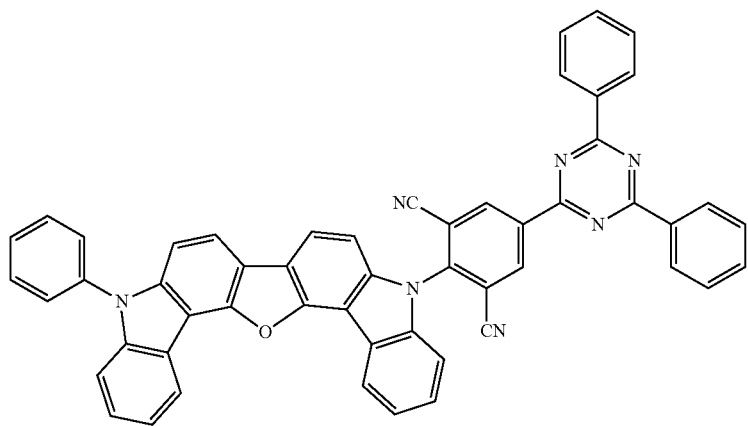
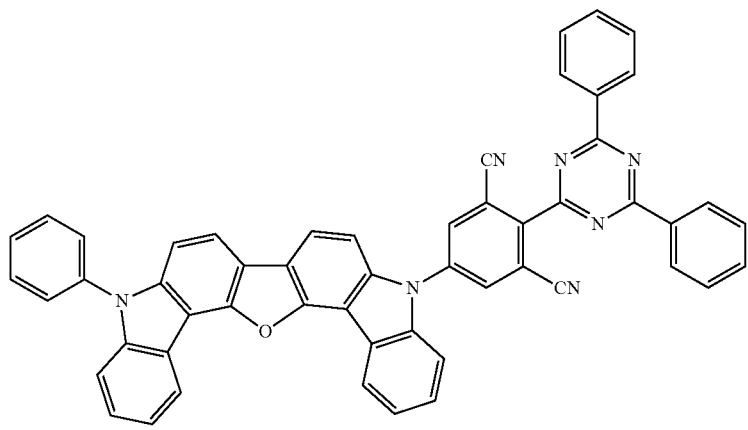

-continued
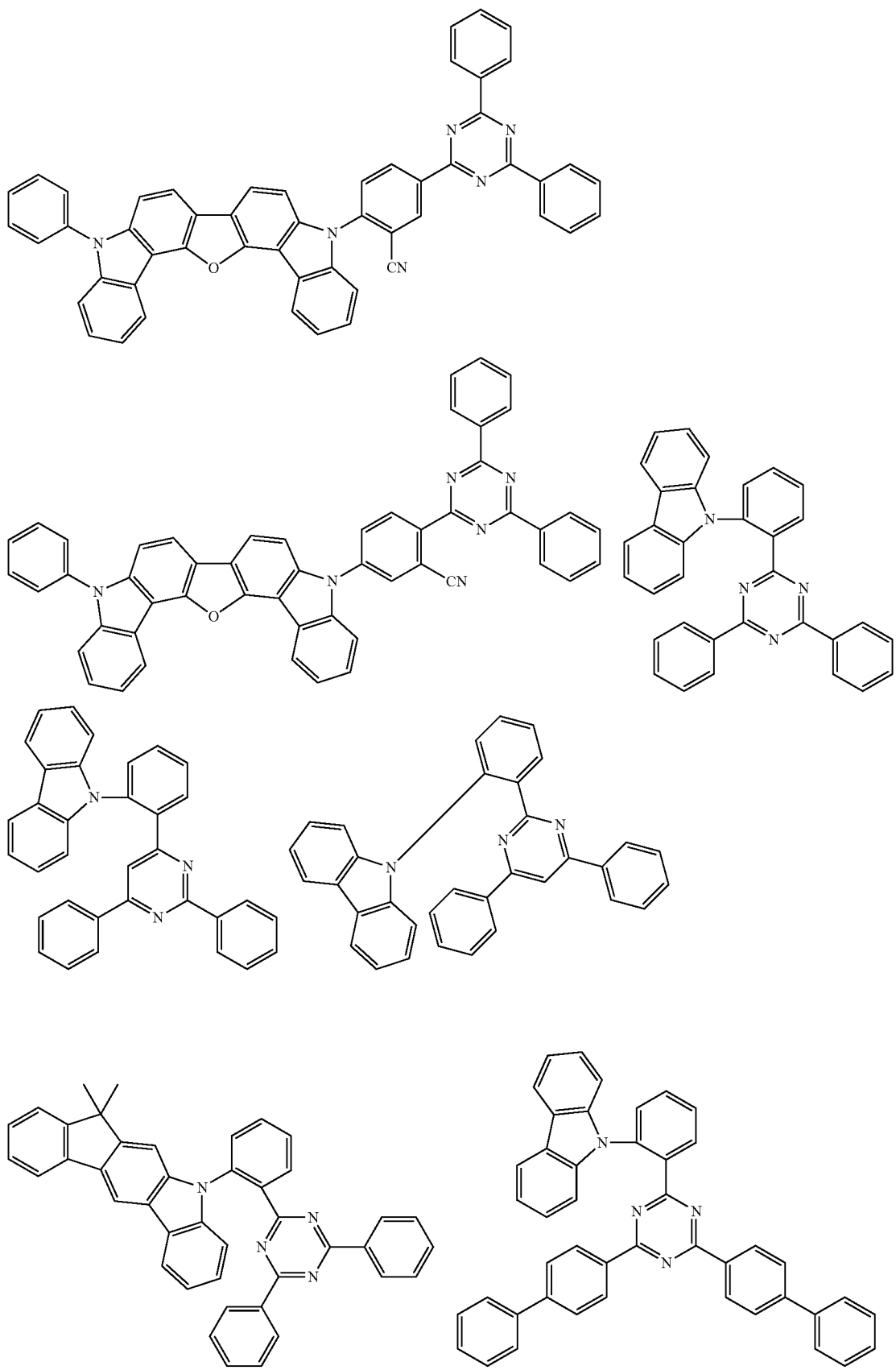

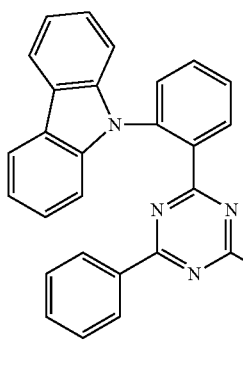
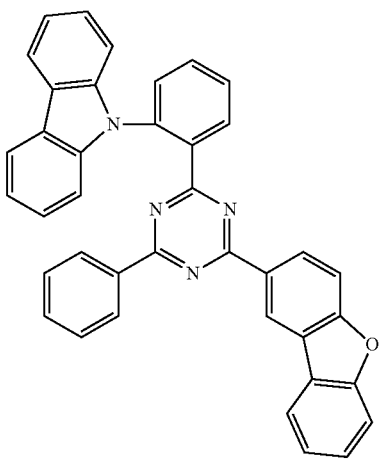
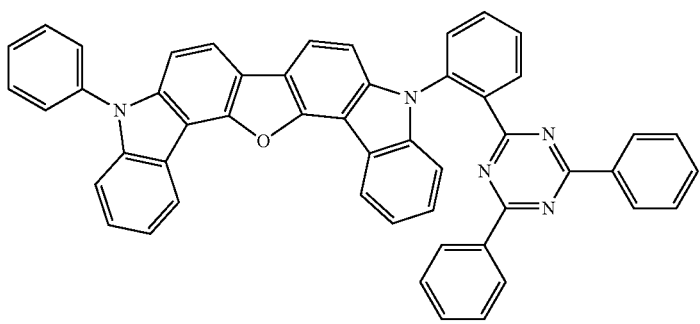
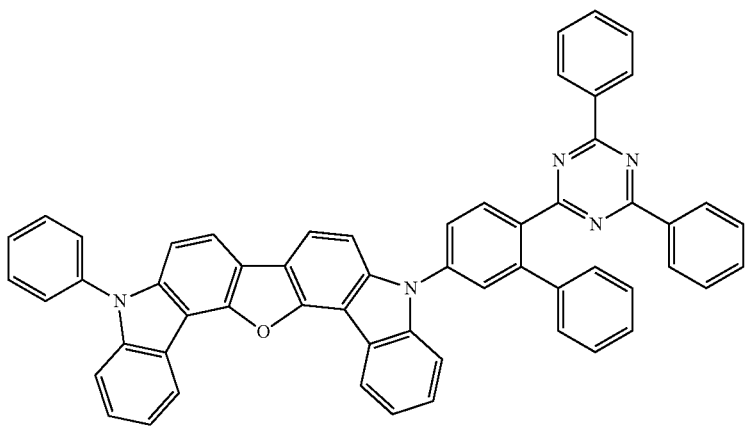
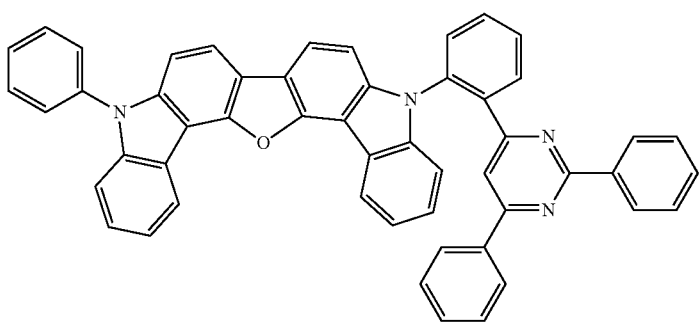

-continued
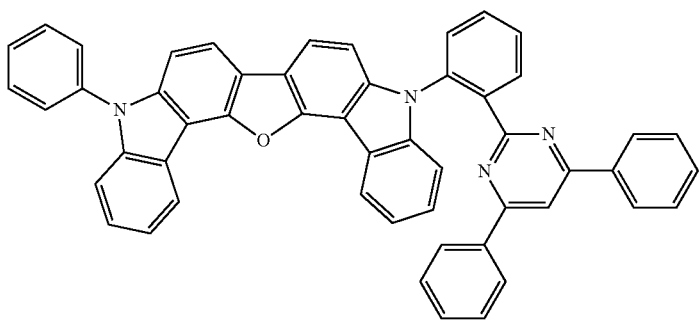
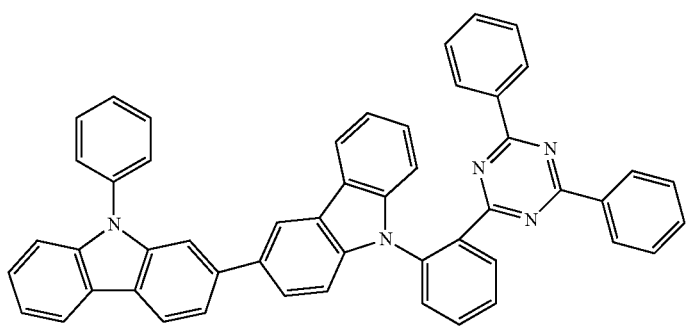 [SMILES: c1ccc(-c2nc(-c3ccccc3)nc(-c3ccccc3-n3c4ccccc4c4cc(-c5ccc6c7ccccc7n(-c7ccccc7)c6c5)ccc43)n2)cc1]
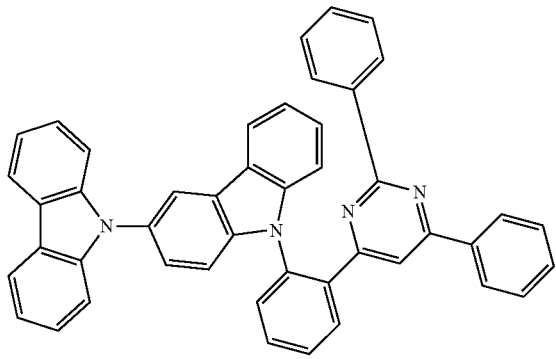
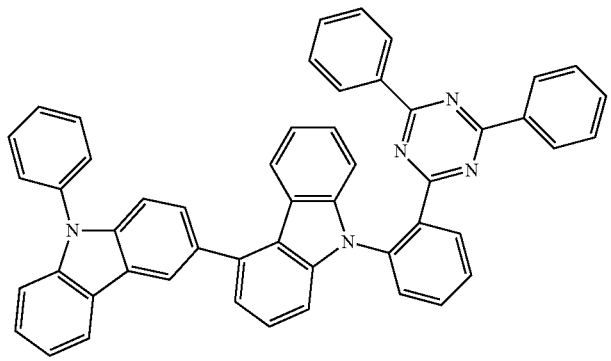
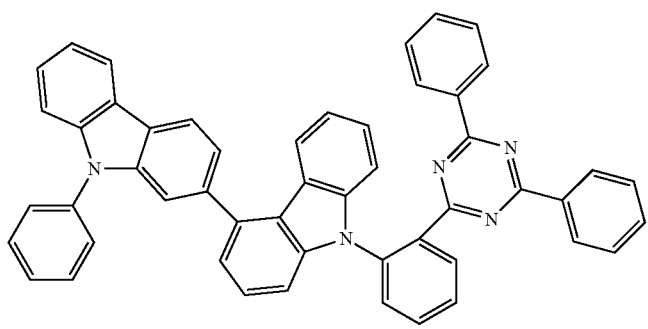

-continued
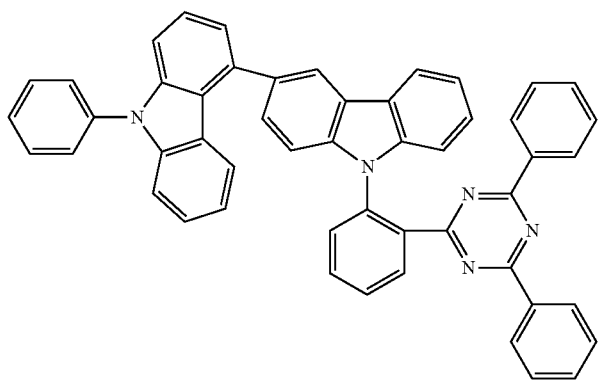
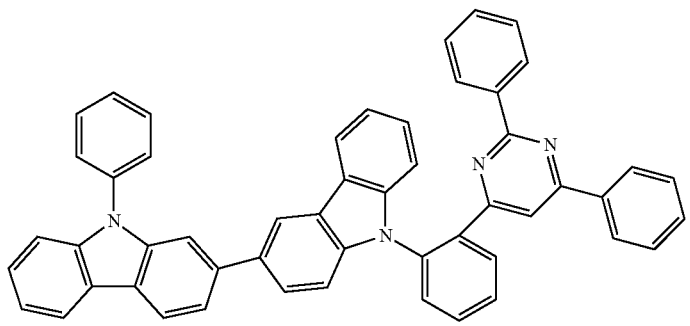
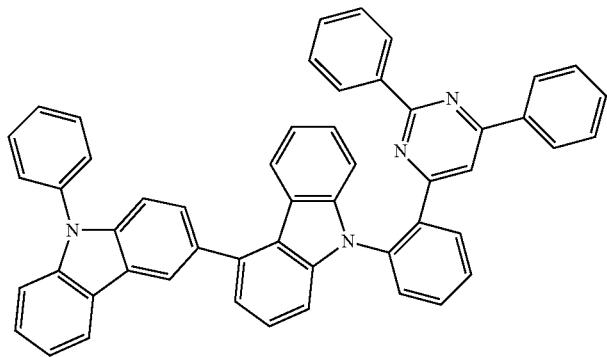
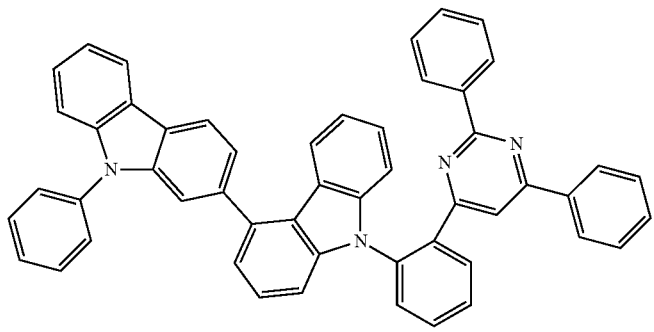

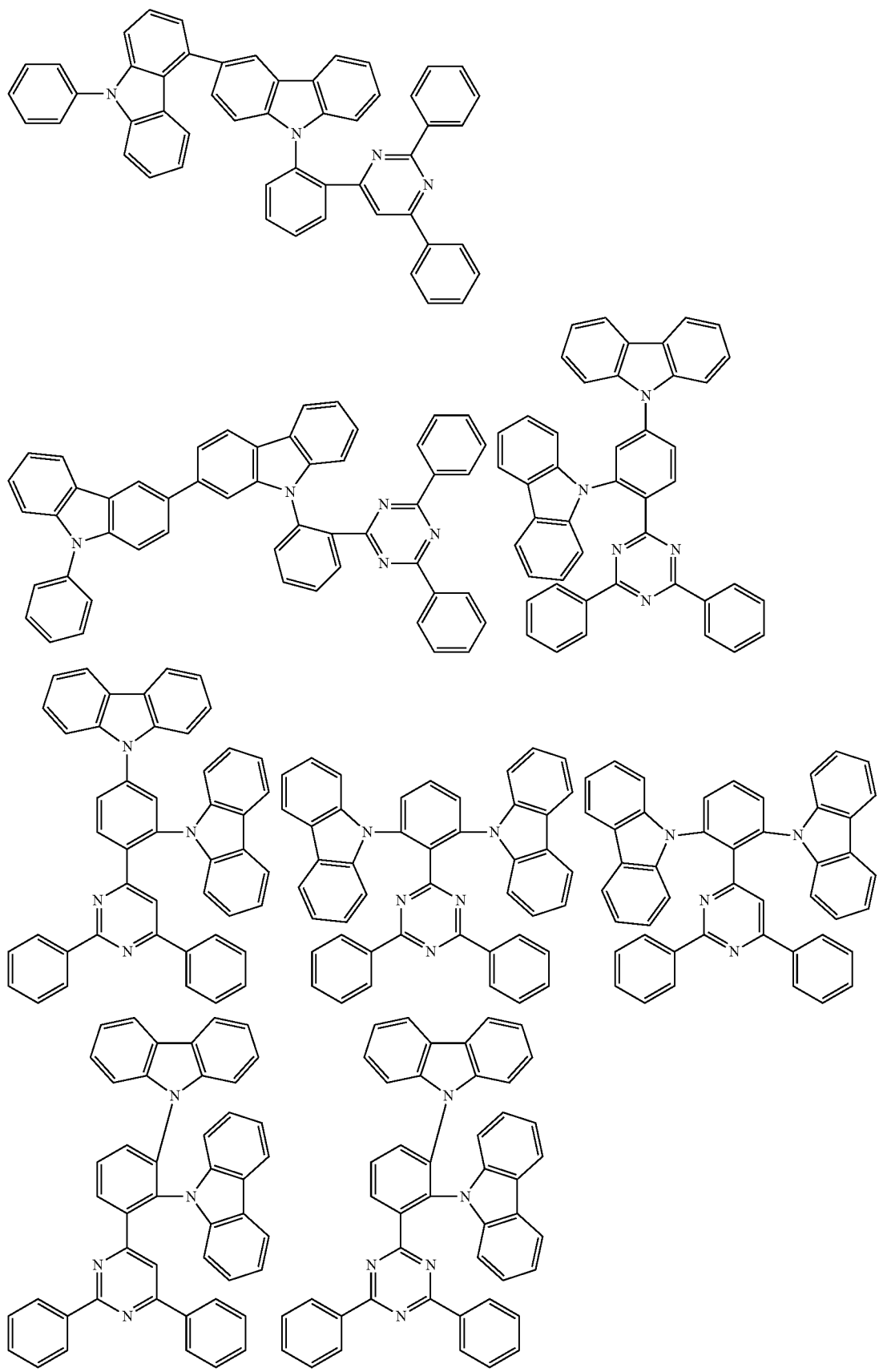

-continued
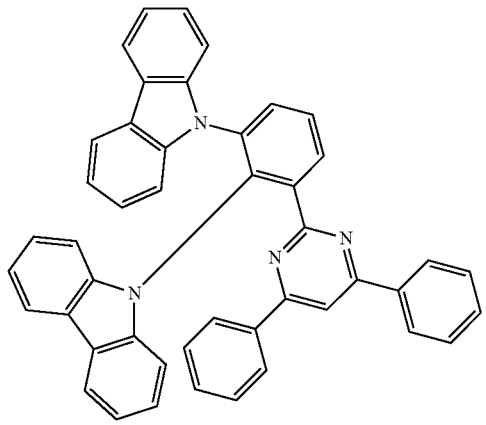
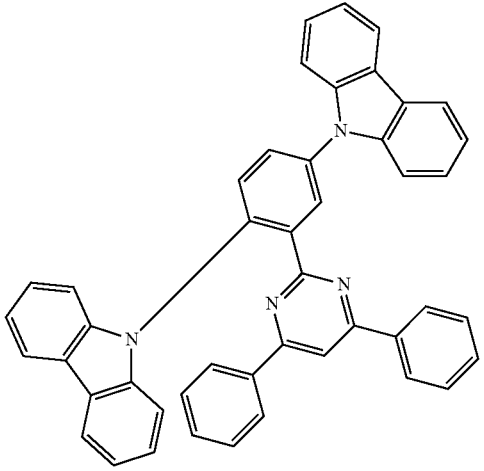
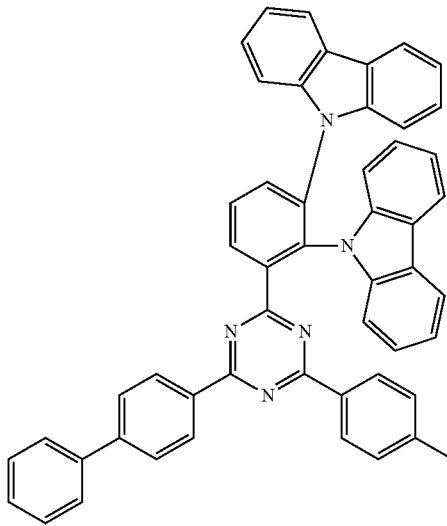
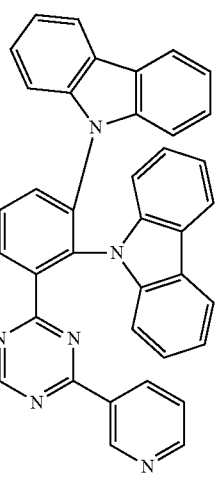
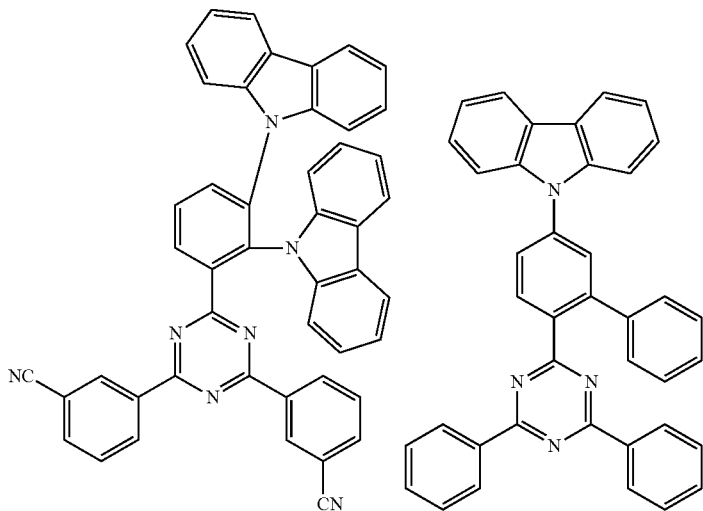
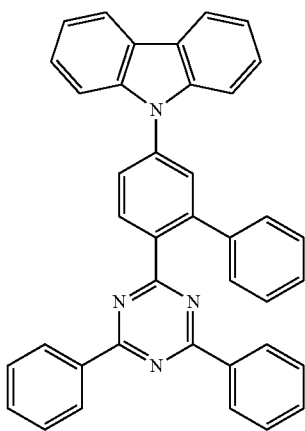

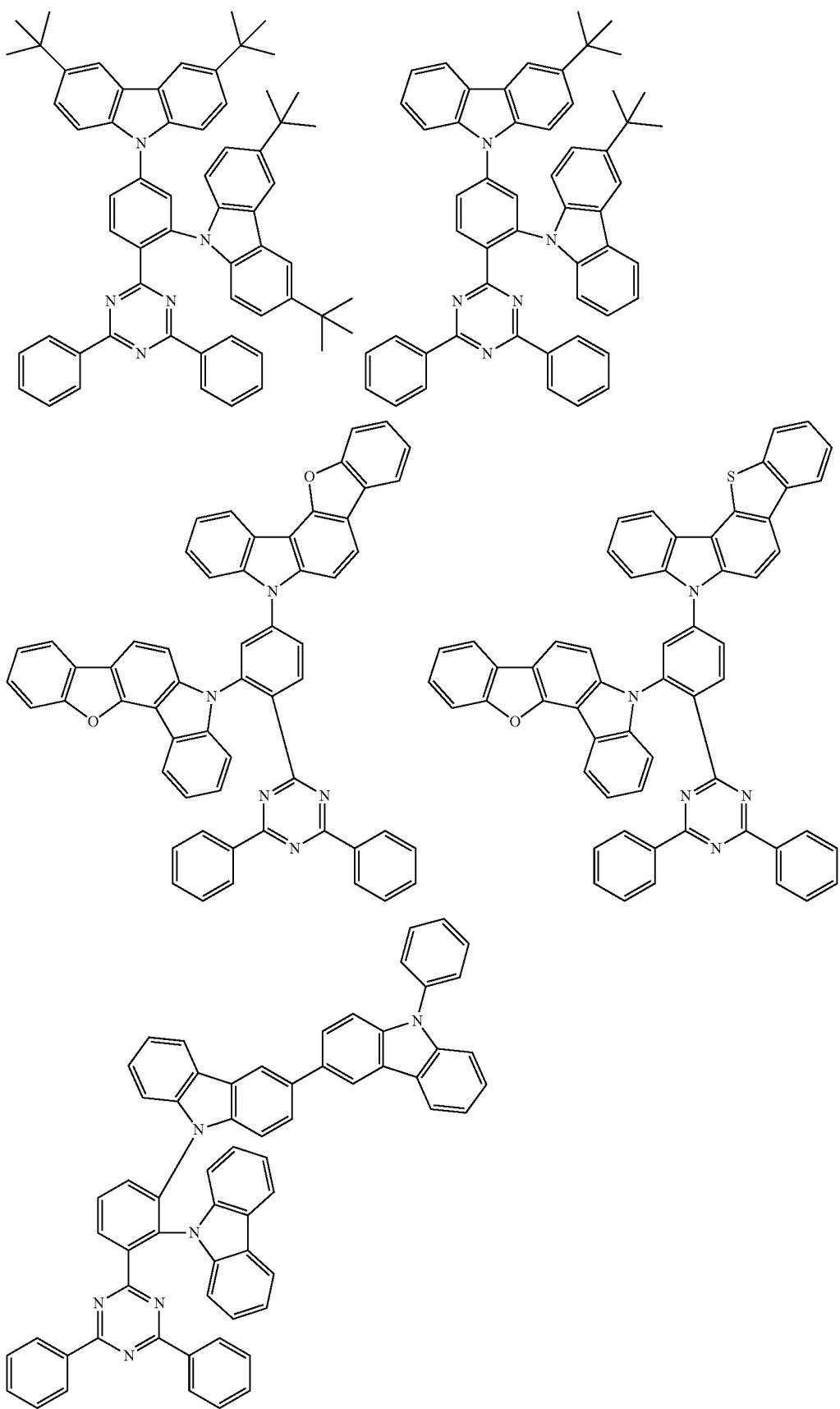

-continued
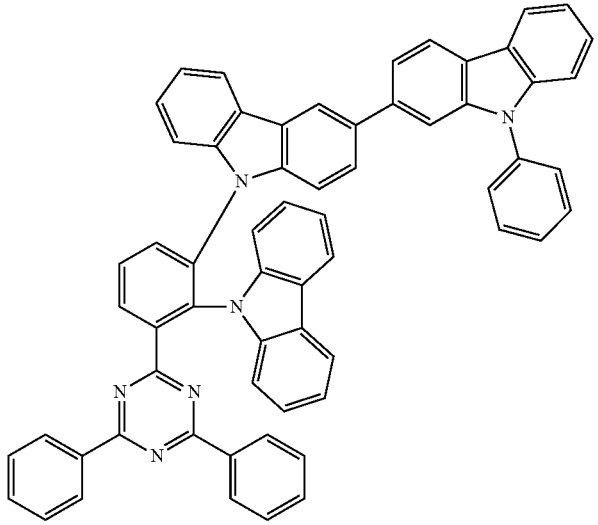
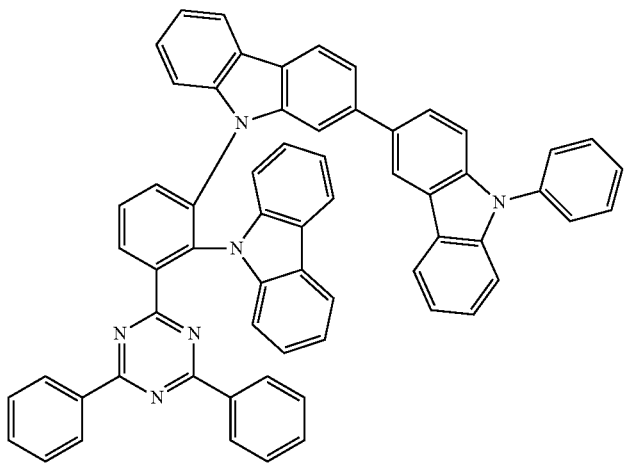
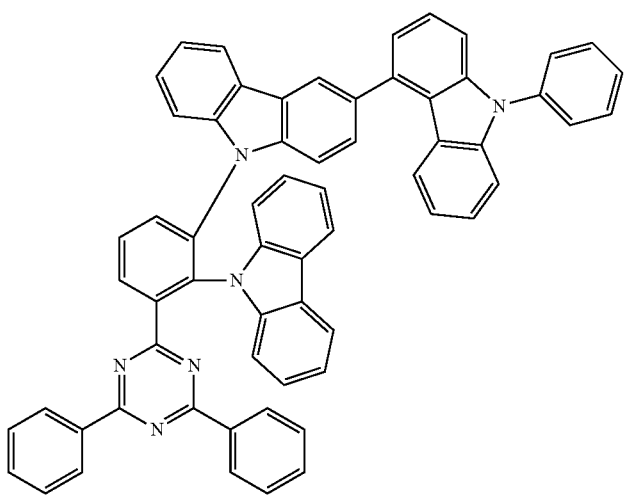 [SMILES: c1ccc(-c2nc(-c3ccccc3)nc(-c3cccc(-n4c5ccccc5c5cc(-c6cccc7c6c6ccccc6n7-c6ccccc6)ccc54)c3-n3c4ccccc4c4ccccc43)n2)cc1]

103
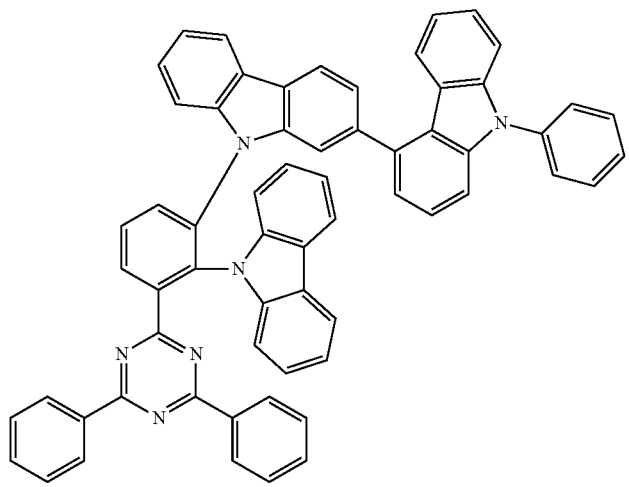
104
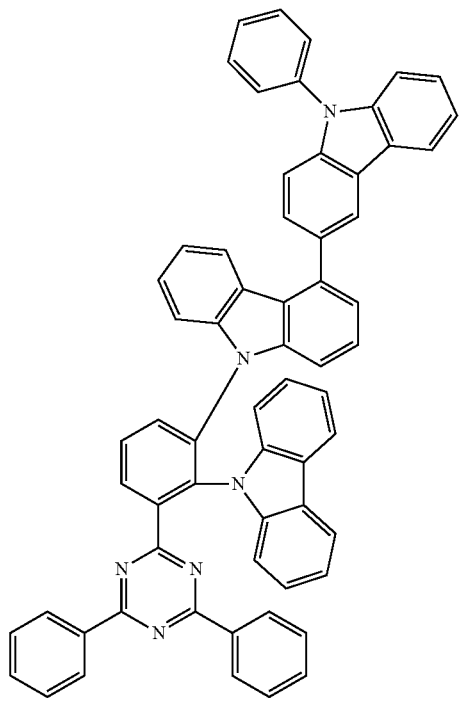
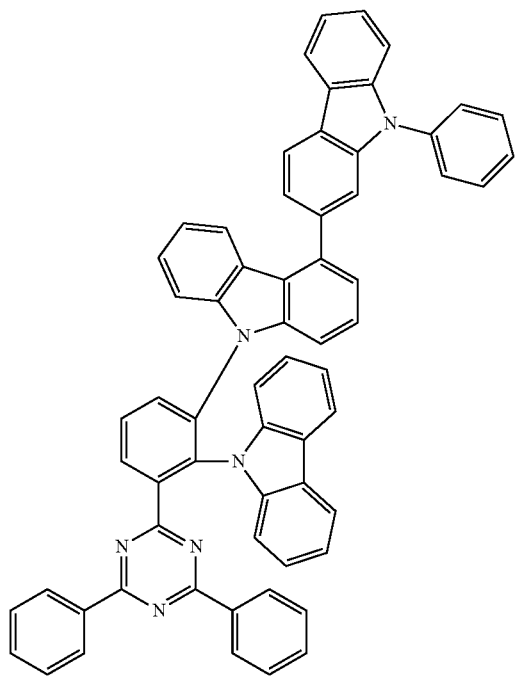
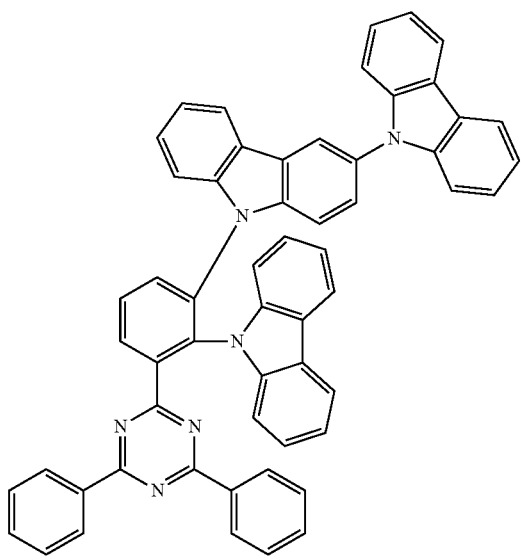

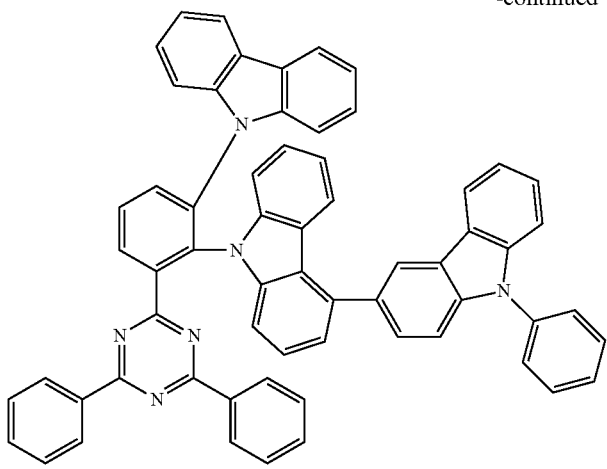
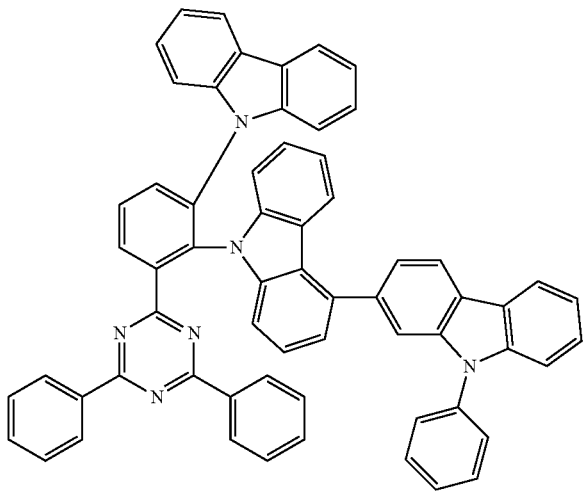
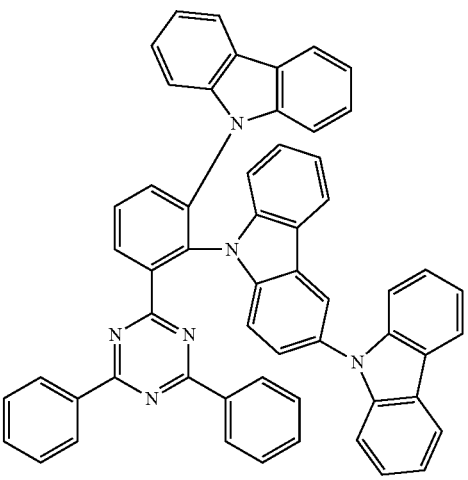
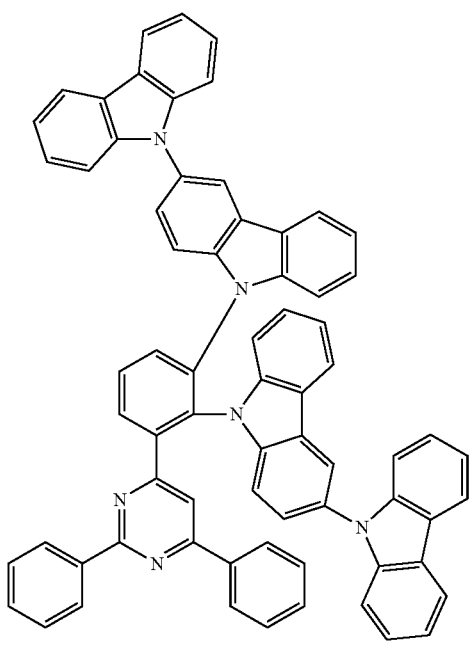
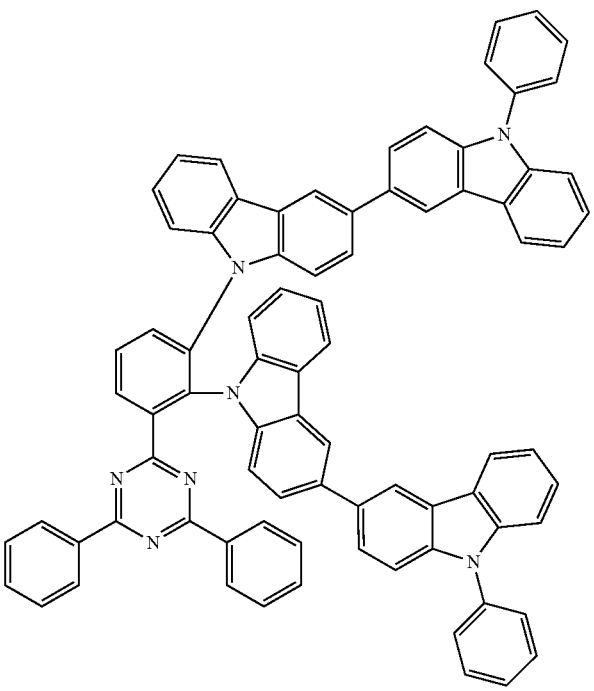

107
108
-continued
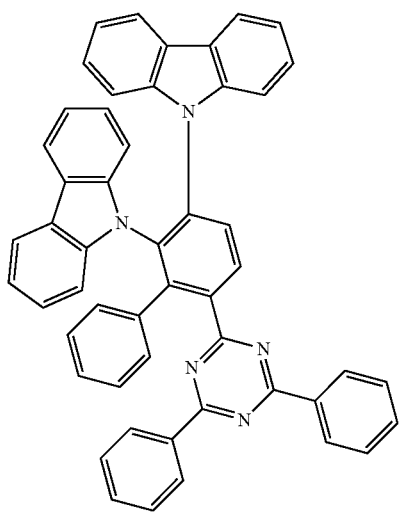
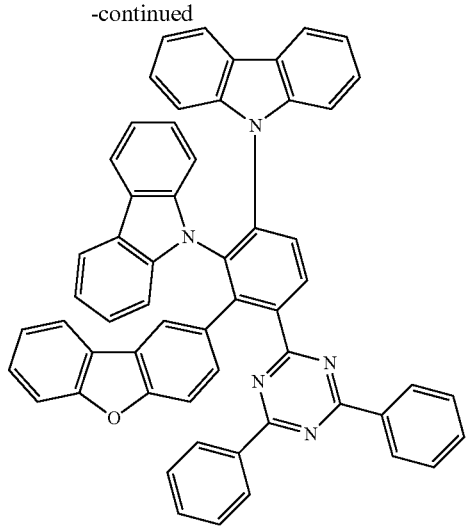
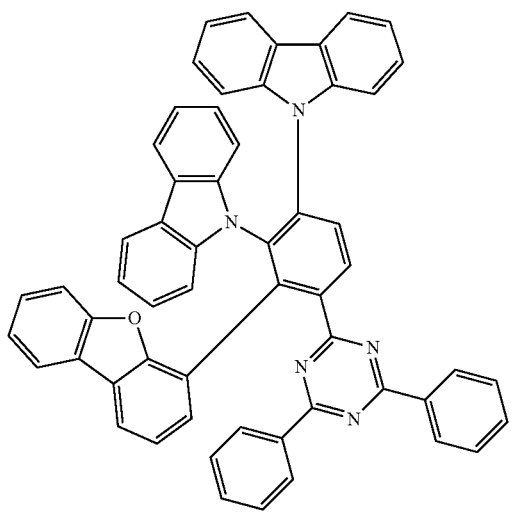
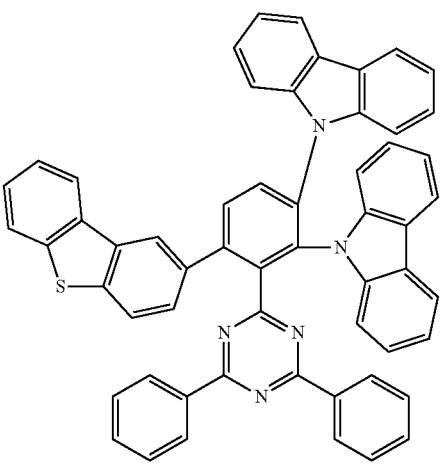
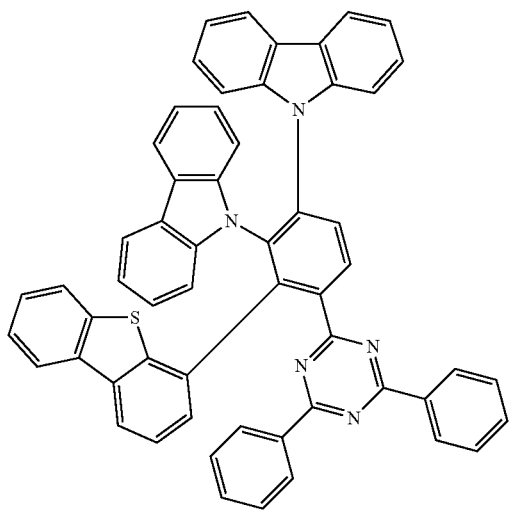
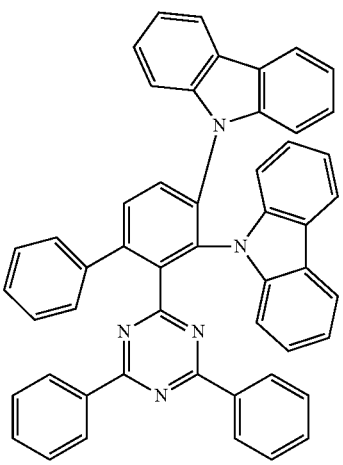

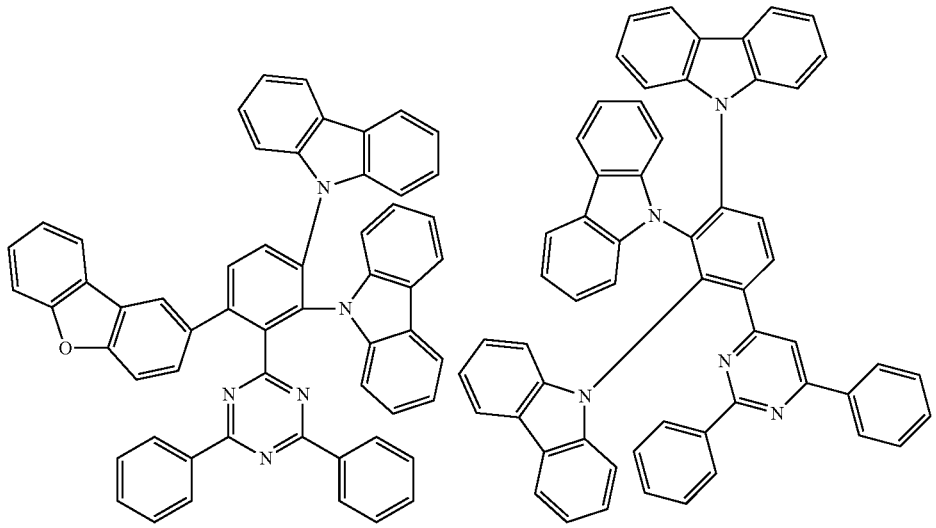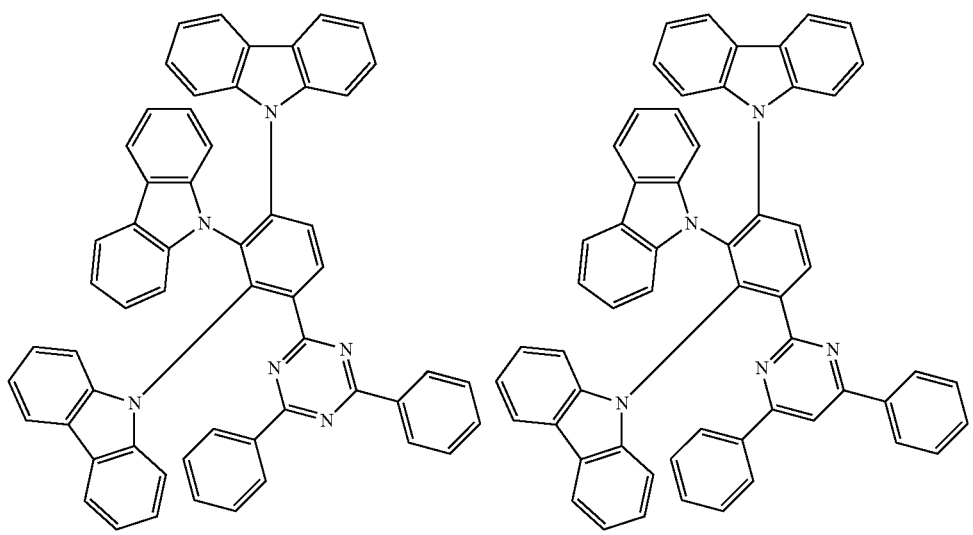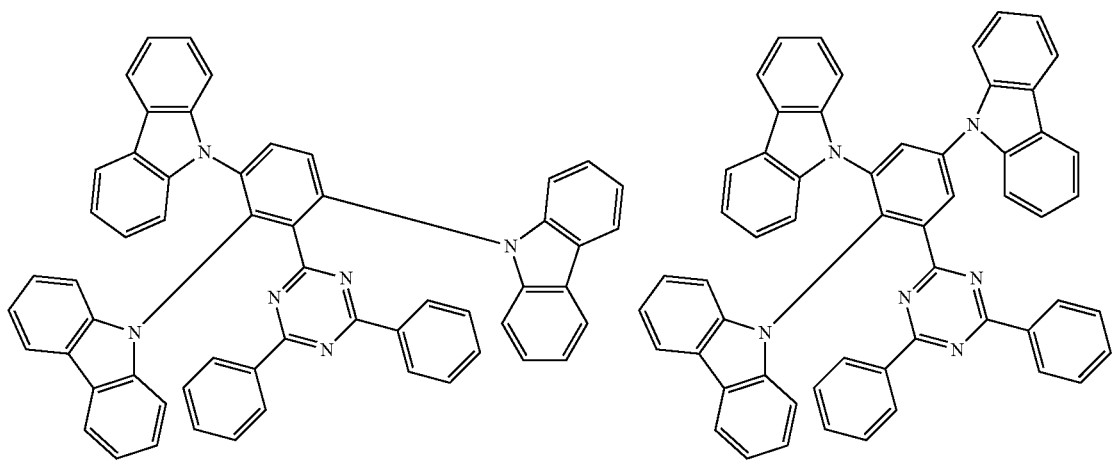

-continued
111 112
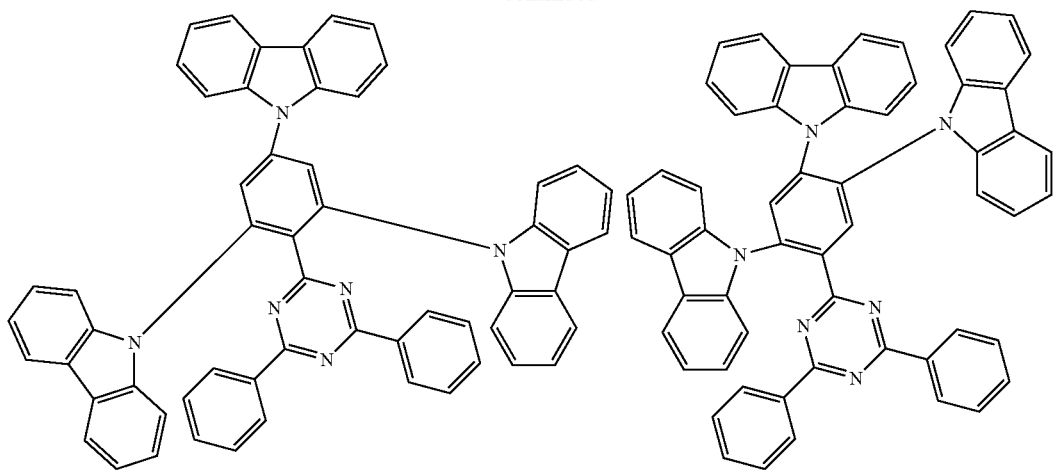
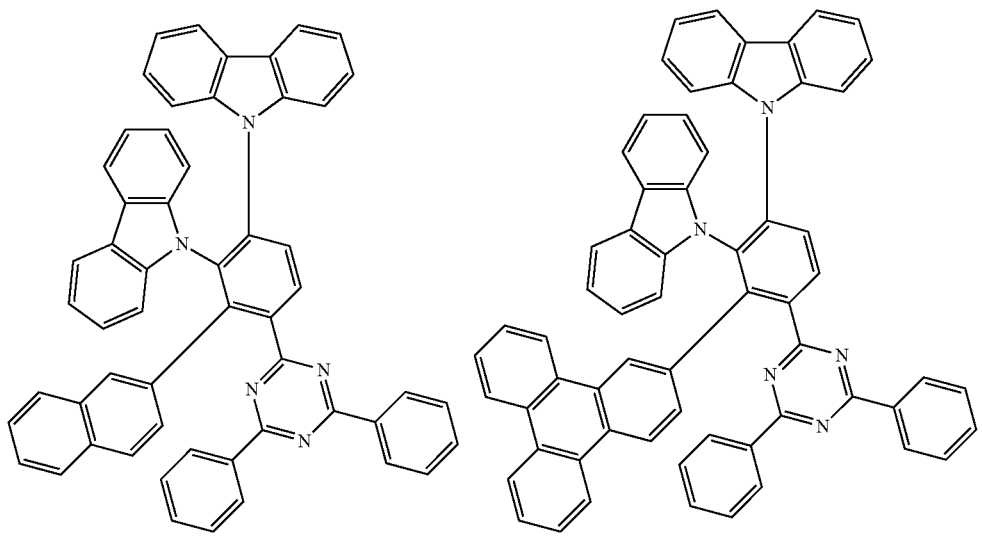
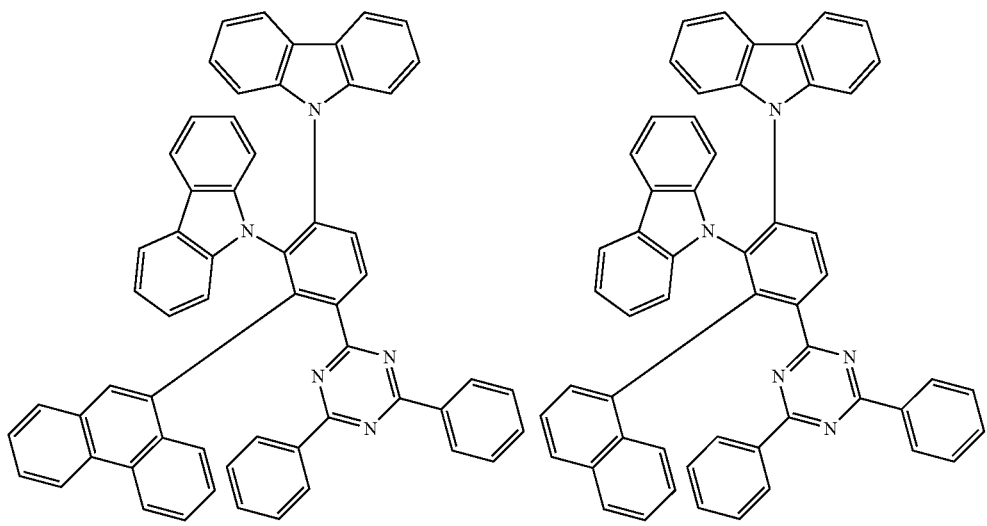

113
114
-continued
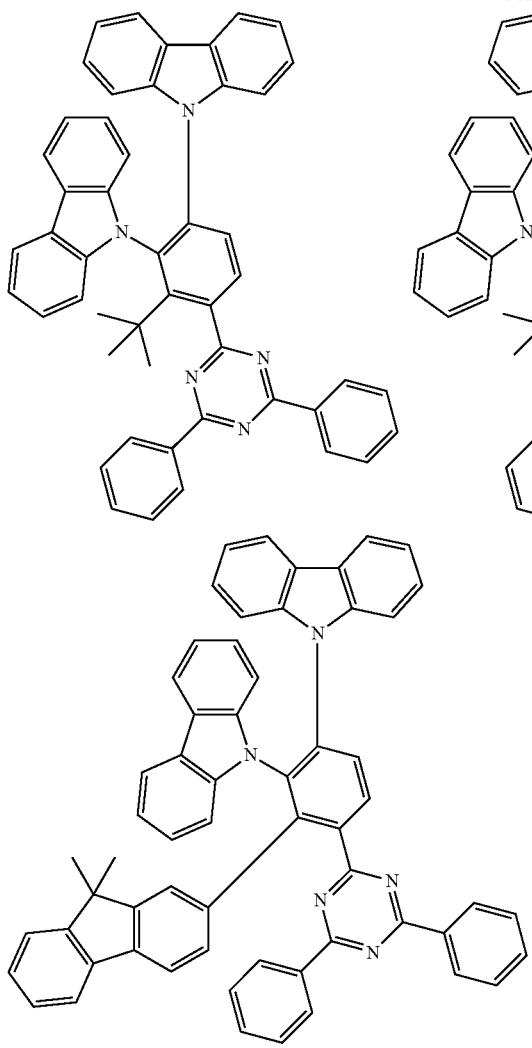
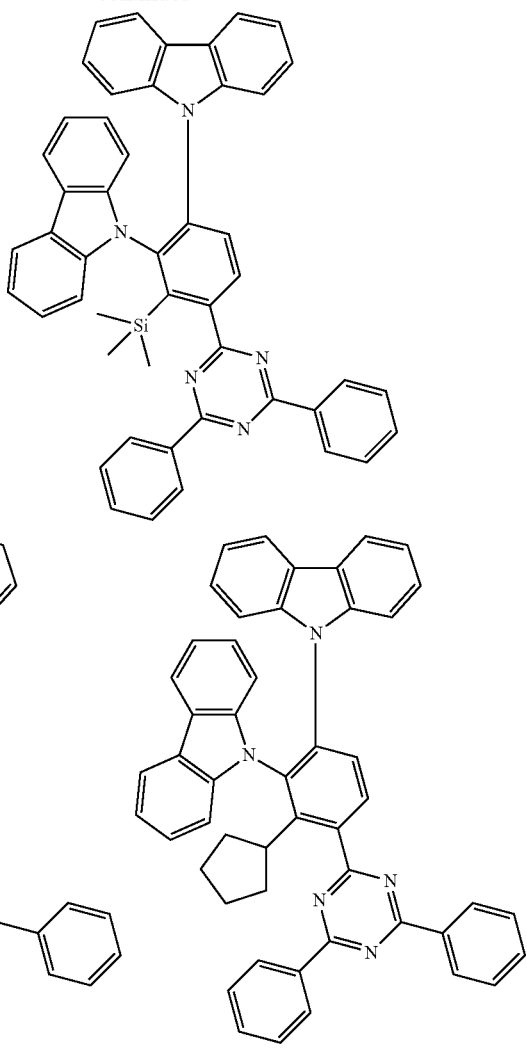
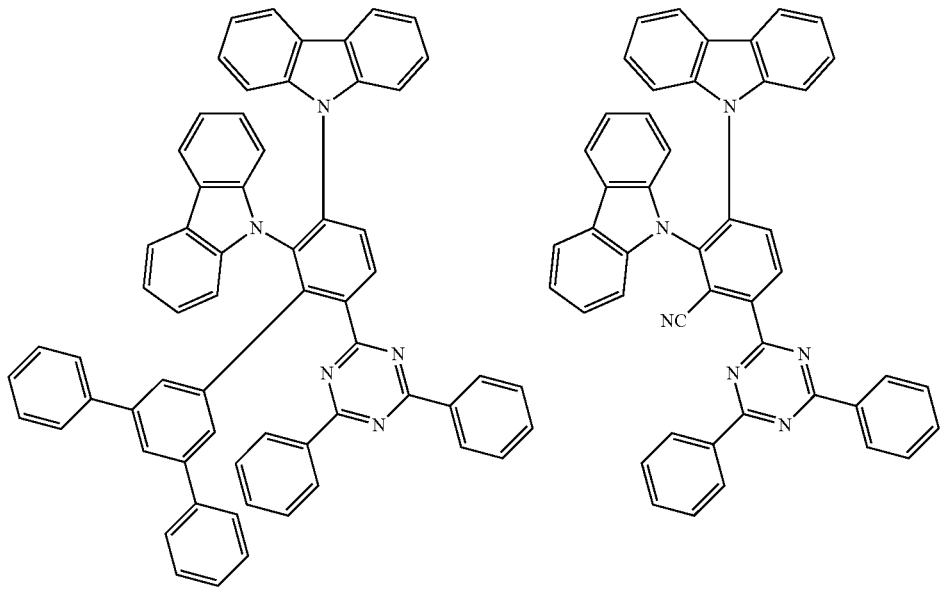

-continued
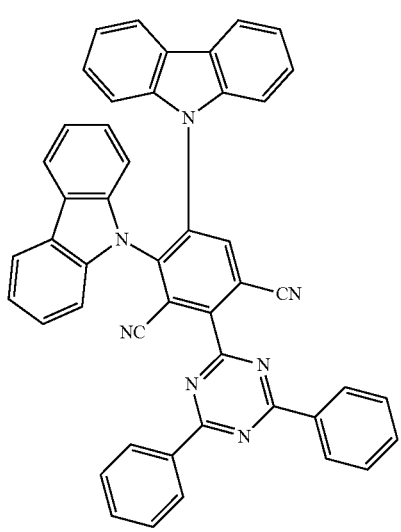
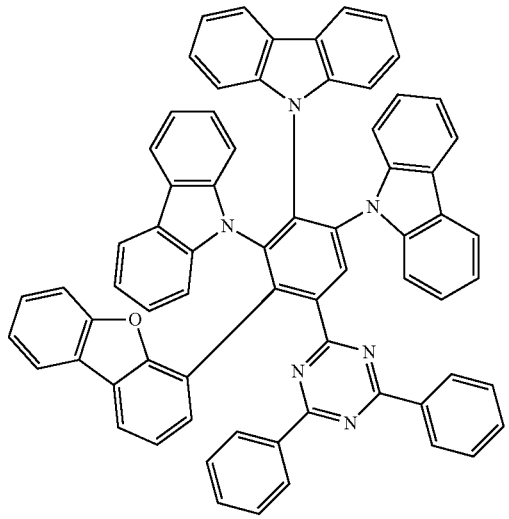
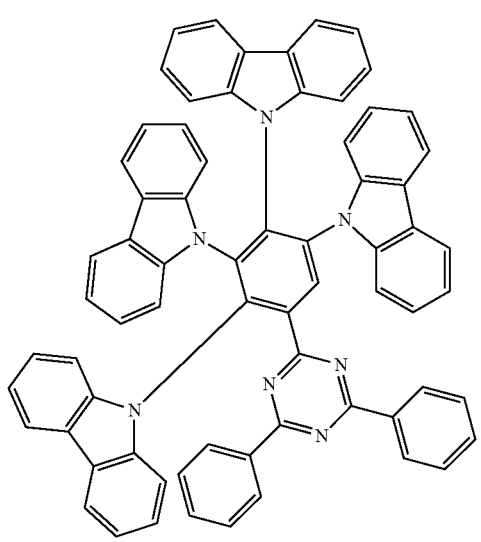
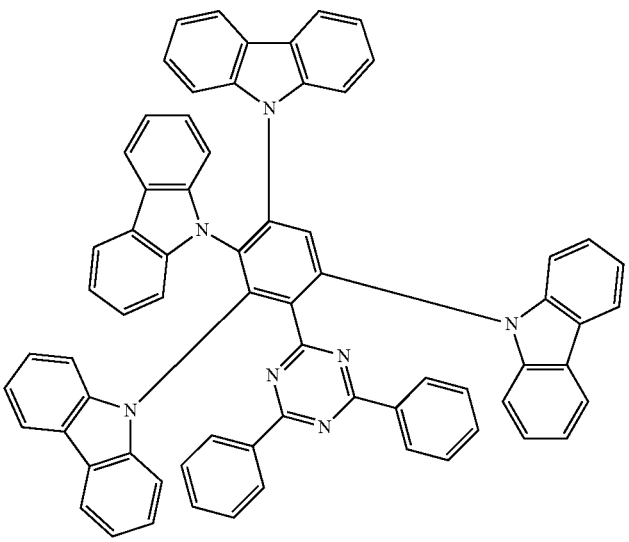
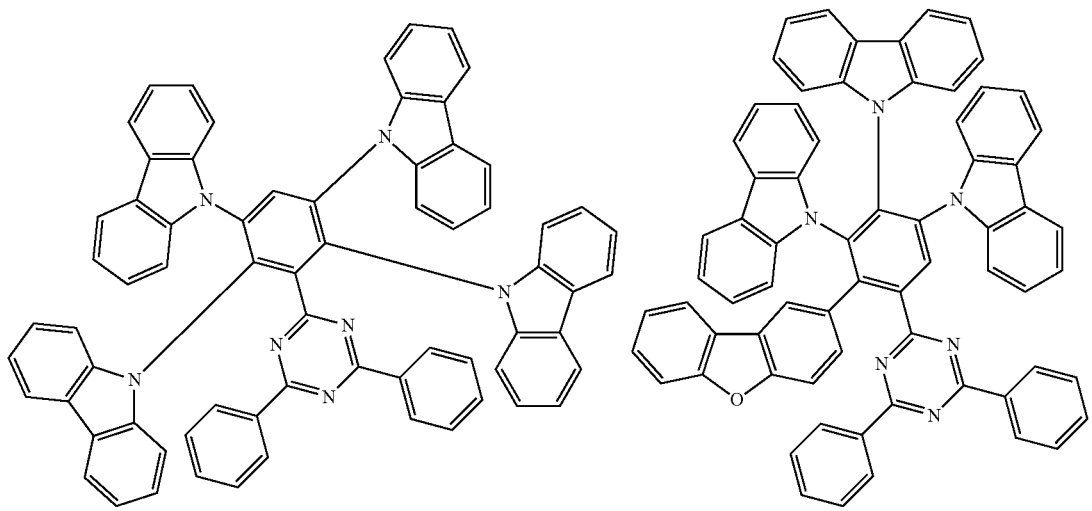

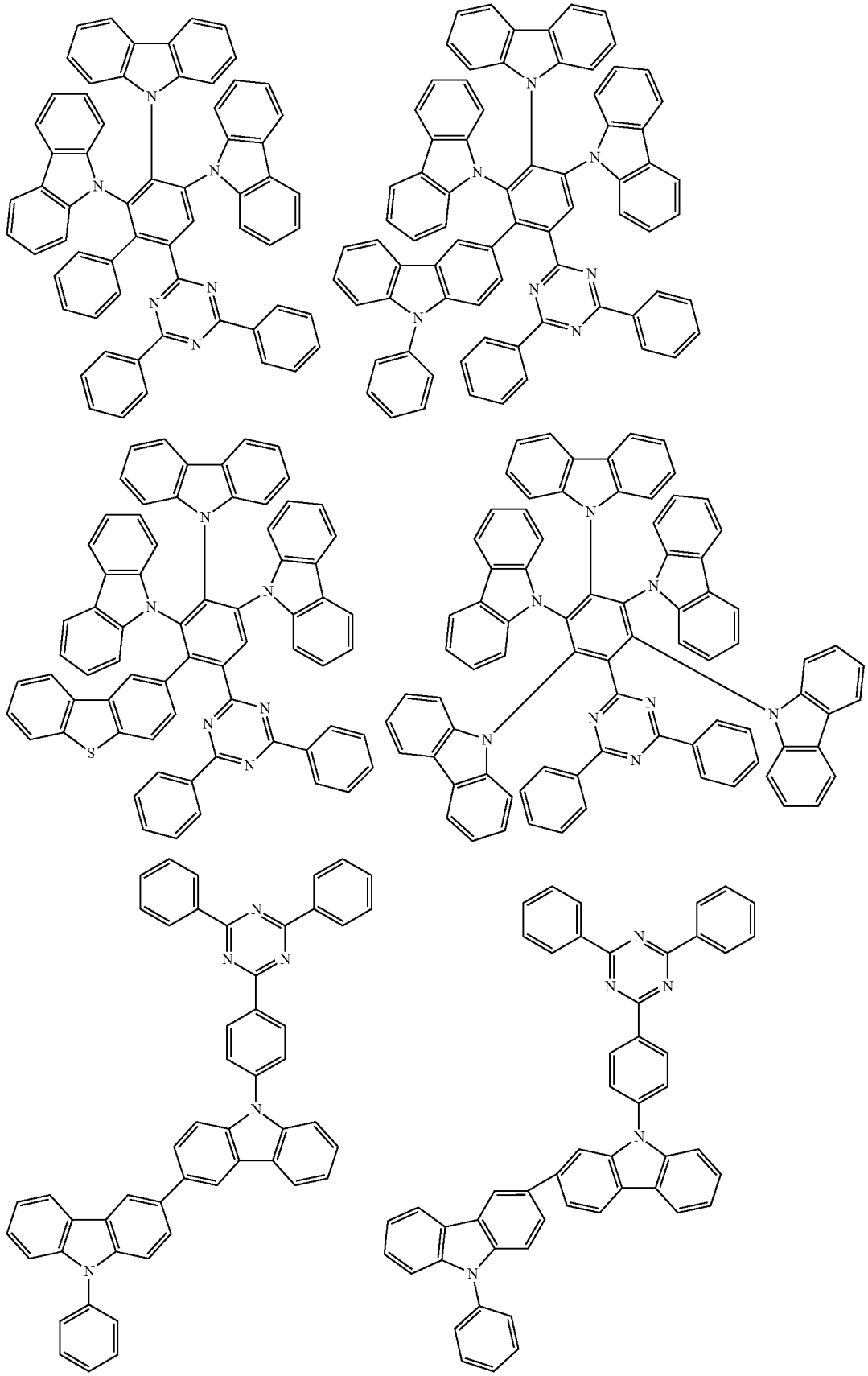
-continued

-continued
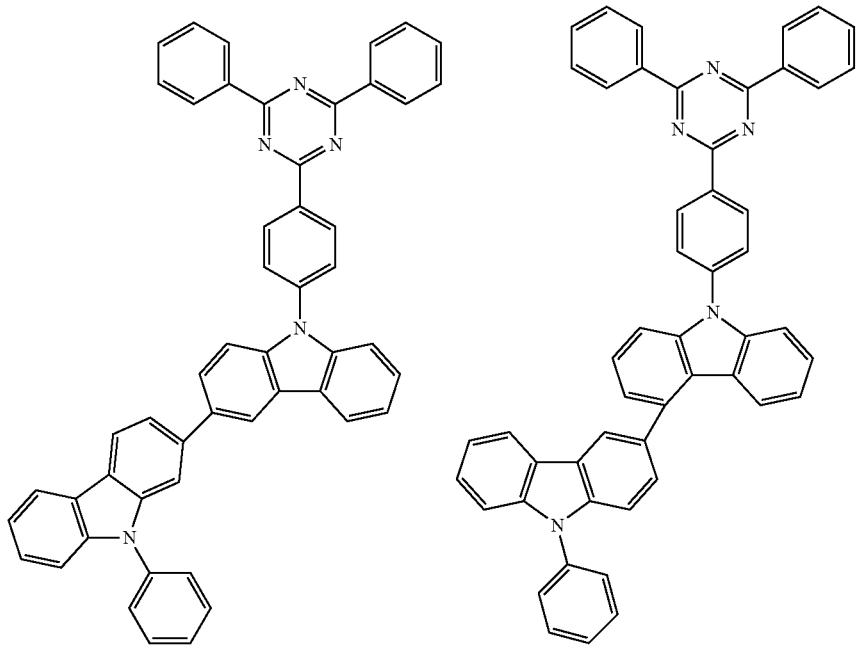
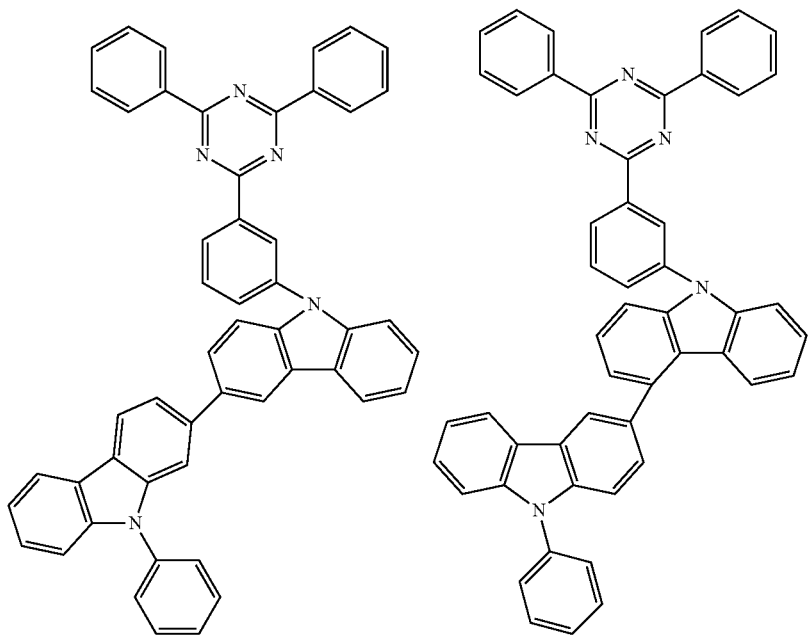

-continued
121
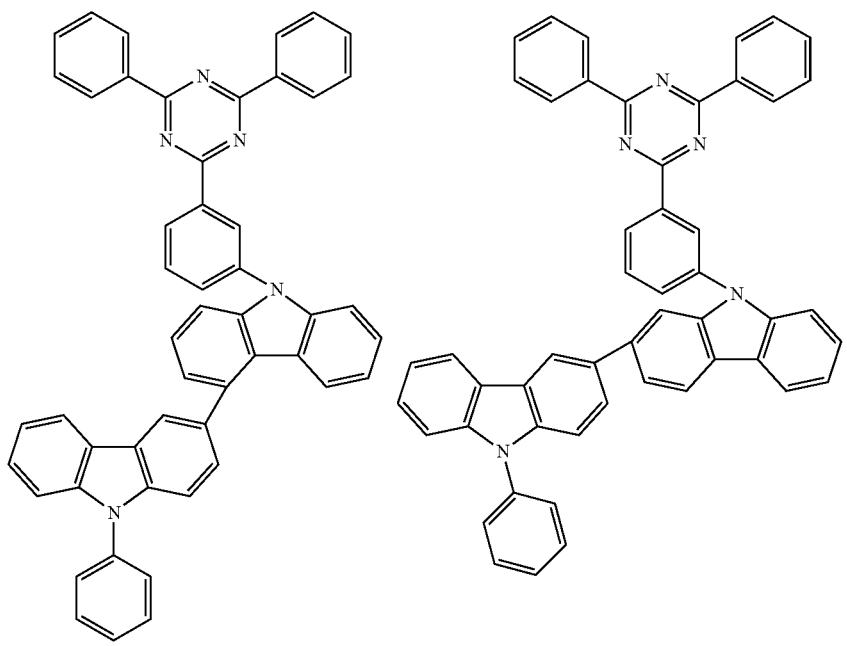
122
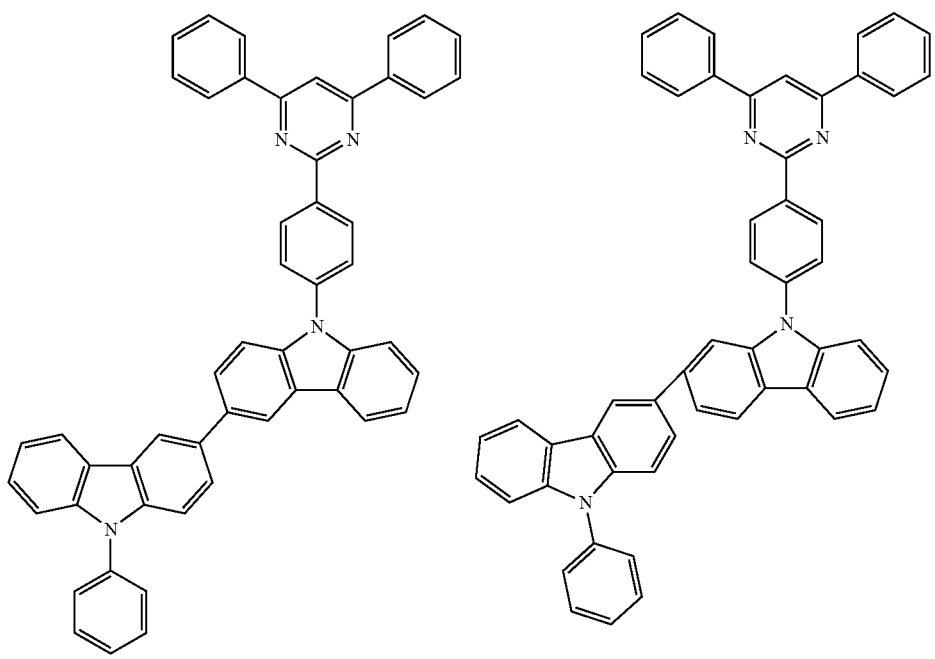

-continued
123
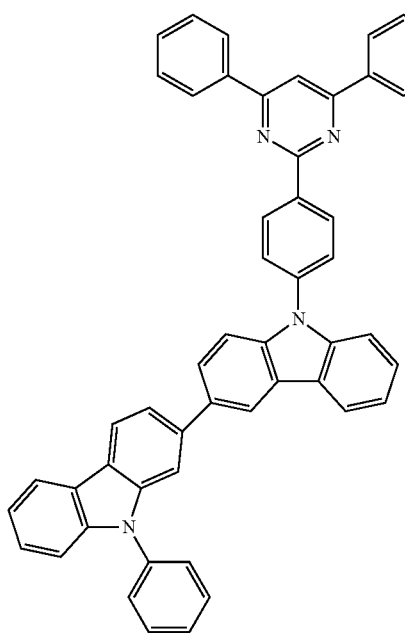
124
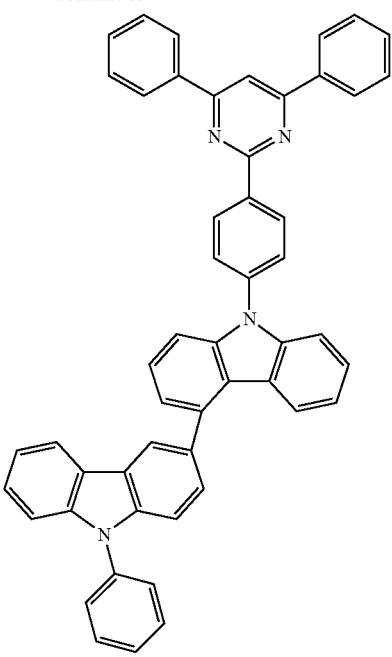
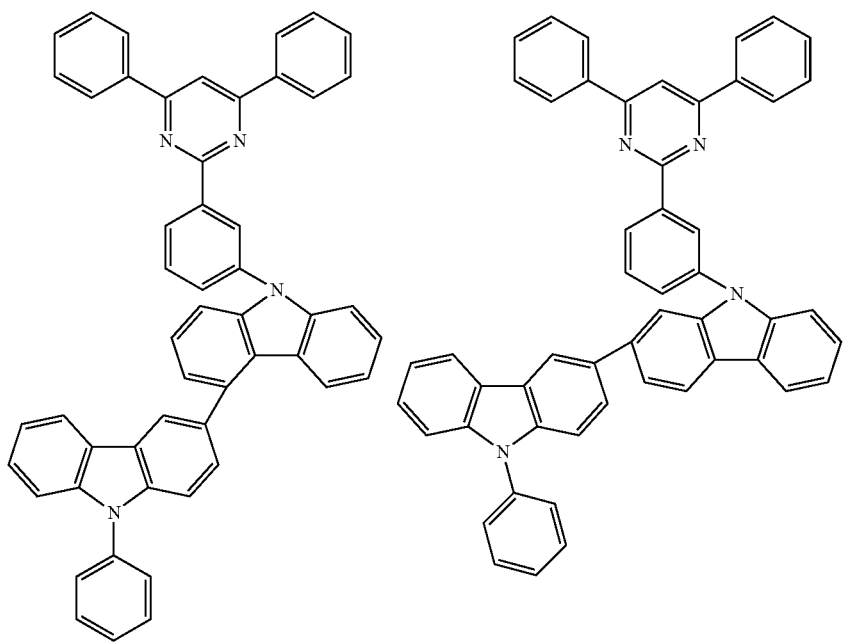

-continued
125
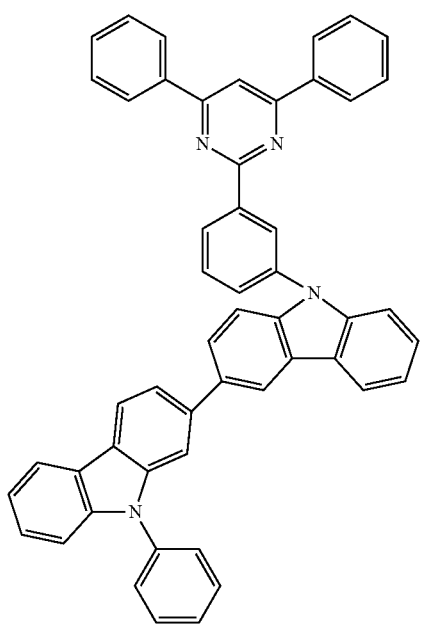
126
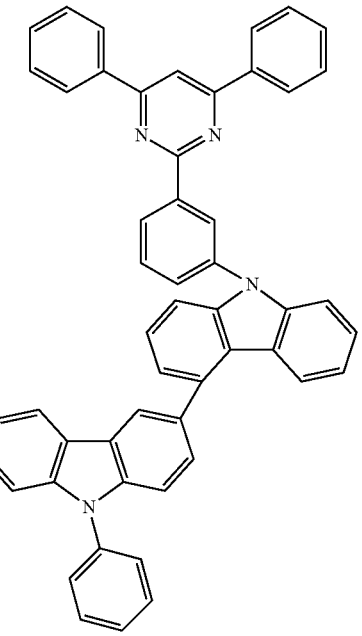
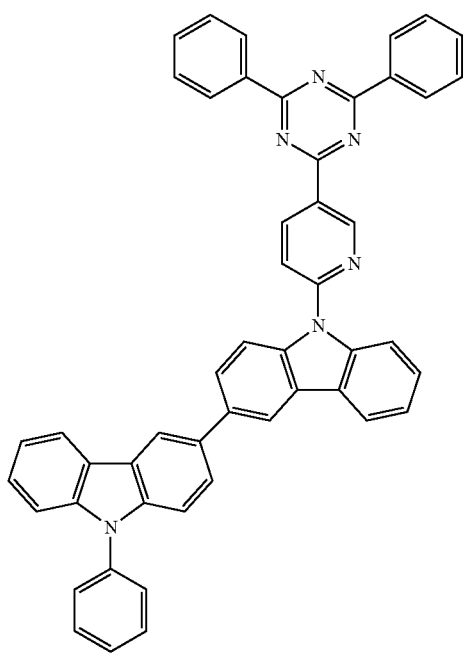
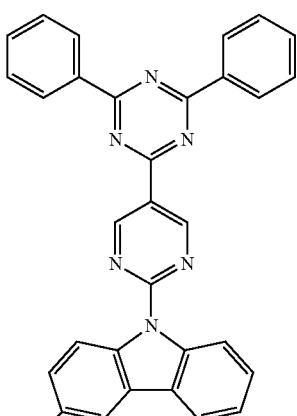
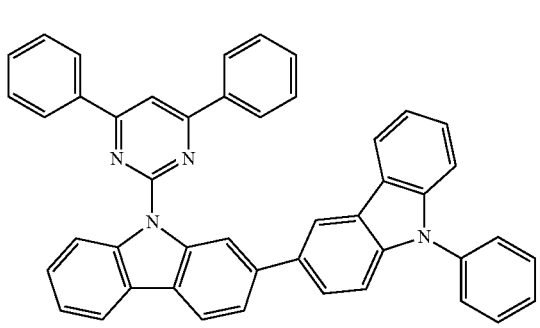
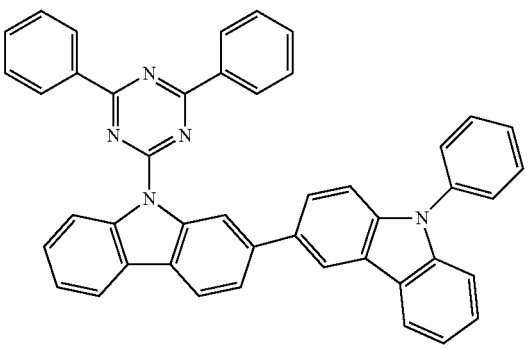

127
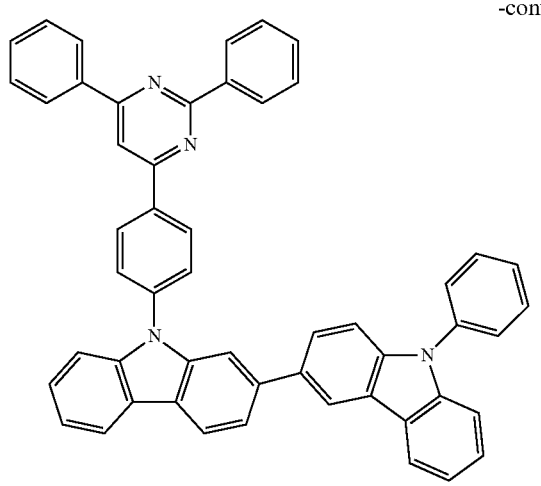
128
-continued
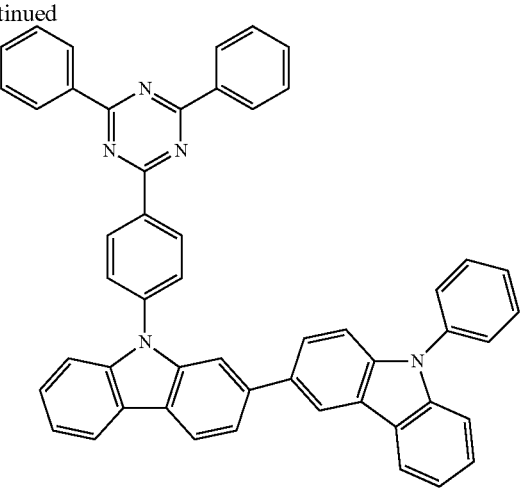
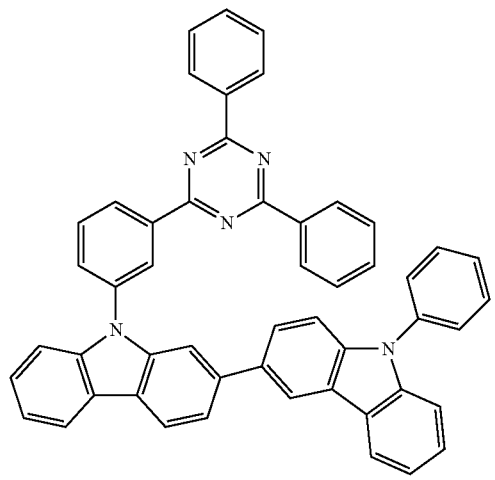
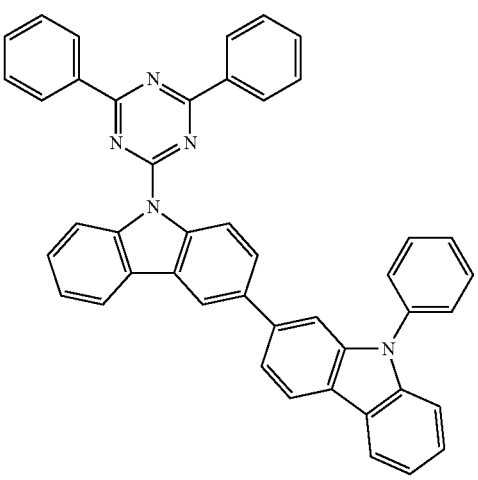
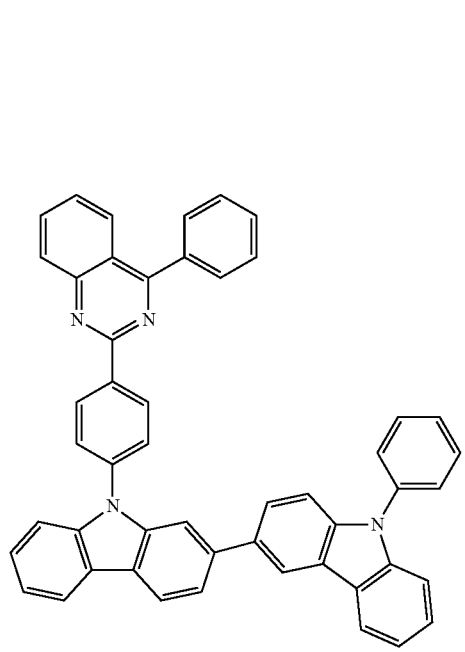
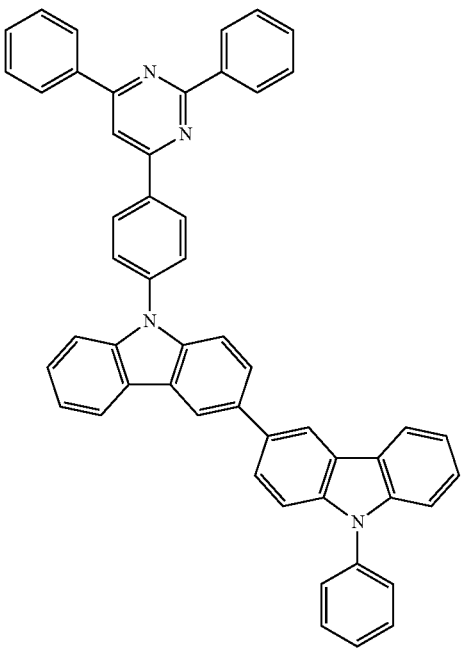

-continued
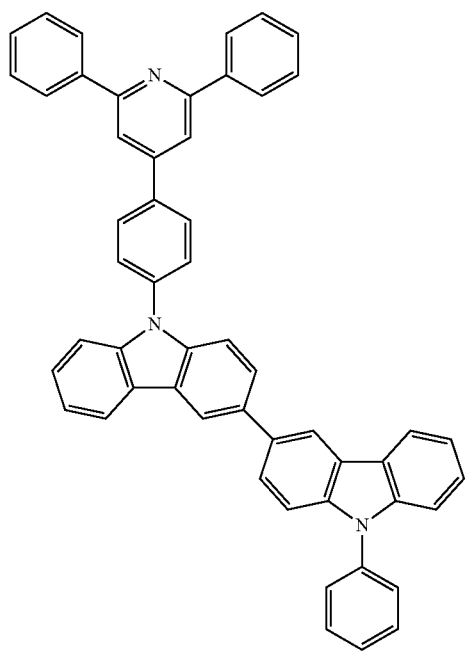
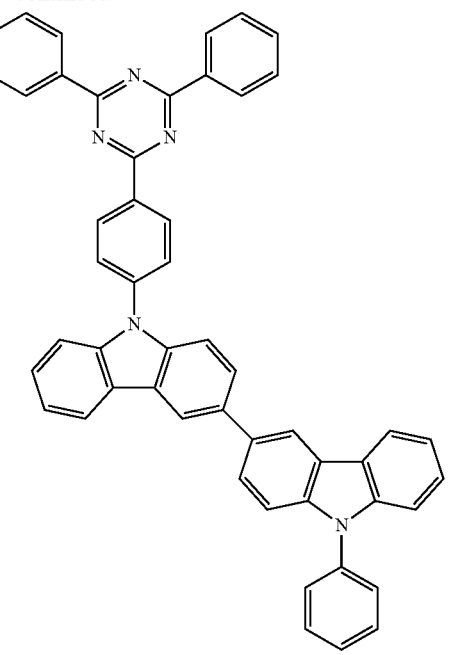
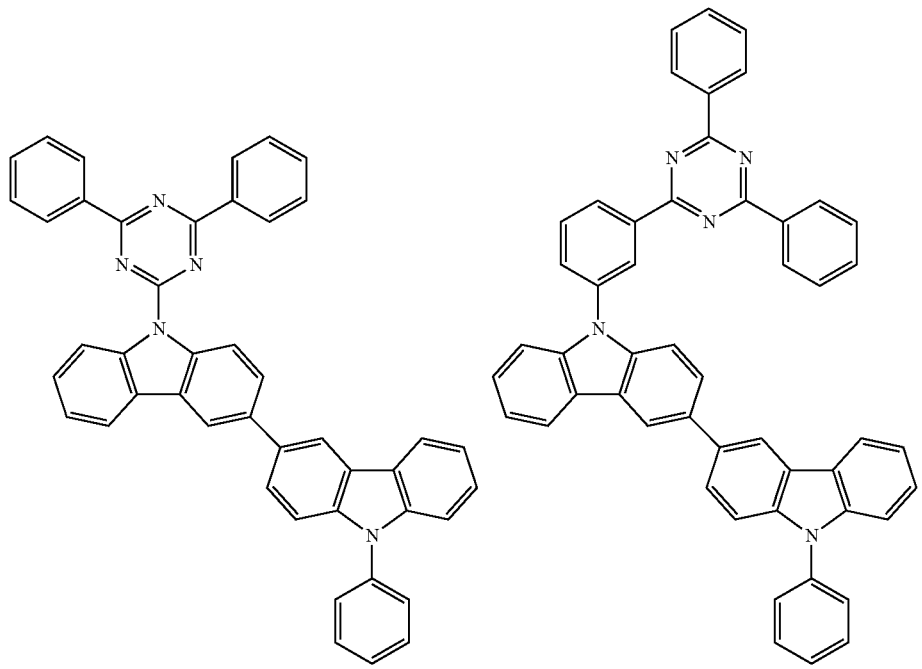

131

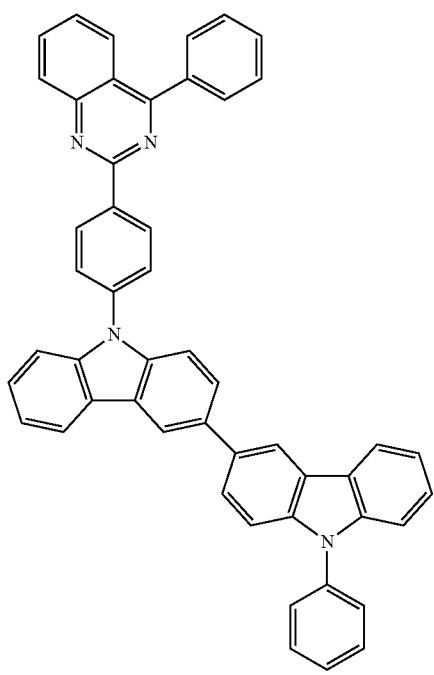

-continued

132

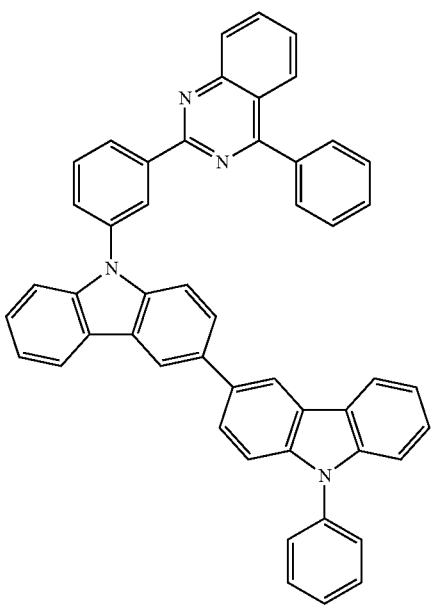

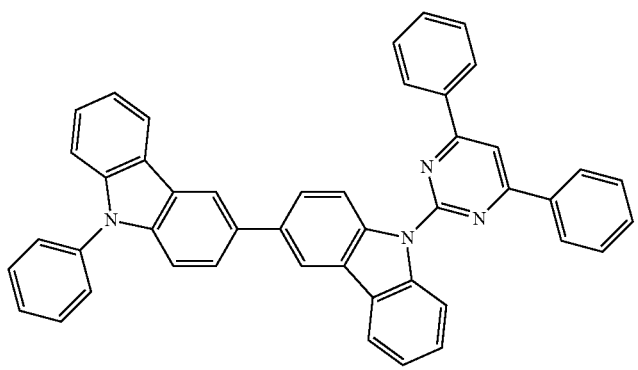

Method of Preparing First Compound

The first compound can be prepared by methods disclosed in International Publication Nos. WO2013/180241, WO2014/0920831, WO2014/104346 and the like.

Delayed Fluorescence

Thermally activated delayed fluorescence is described in "Yuki Hando-tai no Debaisu Bussei (Device Physics of Organic Semiconductor)" edited by Chihaya Adachi, published by Kodansha Company Ltd, pages 261 to 268. This document describes that, when an energy gap $\Delta E_{13}$ between a singlet state and a triplet state of a fluorescent material can be decreased, in spite of a typical low transition probability, inverse energy transfer from the triplet state to the singlet state occurs at a high probability to express thermally stimulated delayed fluorescence (TADF). Further, a generating mechanism of delayed fluorescence is described in FIG. 10.38 in this document. The first compound in the exemplary embodiment is a compound emitting thermally activated delayed fluorescence to be generated by such a mechanism. Delayed fluorescence can be observed by measuring transient PL (Photo Luminescence).

Behavior of delayed fluorescence can also be analyzed based on the decay curve obtained by measuring the transient PL. The transient PL measurement is a method for measuring reduction behavior (transitional property) of PL emission obtained after irradiating pulse laser on a sample to excite the sample and stopping irradiating the pulse laser. PL emission using a TADF material is divided into an emission component from singlet excitons generated by the first PL excitation and an emission component from singlet excitons generated via triplet excitons. Lifetime of the singlet excitons initially generated in the PL excitation is very short at a nano-second order. Accordingly, the emission from the singlet excitons is rapidly reduced after pulse laser radiation.

On the other hand, since delayed fluorescence provides emission from singlet excitons generated through long-life triplet excitons, emission is gradually reduced. Thus, there is a large difference in time between the emission from the singlet excitons initially generated in the PL excitation and the emission from the singlet excitons derived from the triplet excitons. Accordingly, a luminous intensity derived from delayed fluorescence is obtainable.

Figure 2:
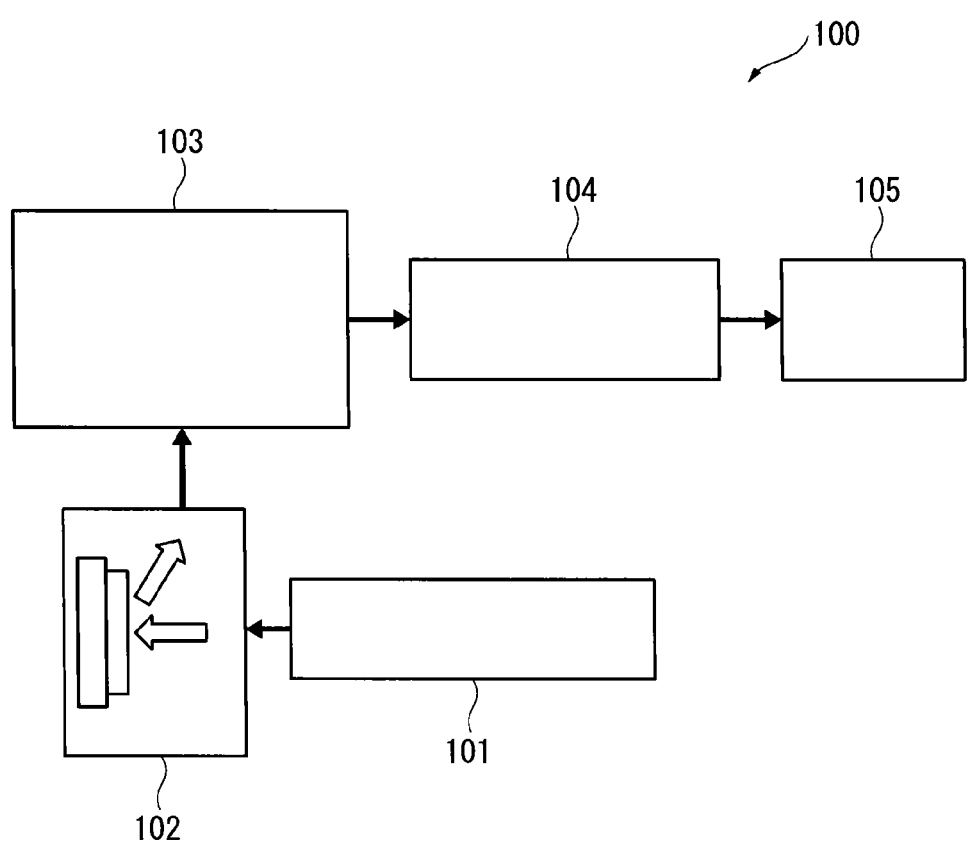
FIG. 2 is a schematic illustration of a measuring device of transient PL.

FIG. 2 is a schematic illustration of an exemplary device for measuring the transient PL.

In the exemplary embodiment, a transient PL measuring device 100 includes a pulse laser 101 configured to irradiate light having a predetermined wavelength, a sample chamber 102 configured to house a measurement sample, a spectrometer 103 configured to disperse the light irradiated from the measurement sample, a streak camera 104 configured to produce a two-dimensional image, and a personal computer 105 configured to import and analyze the two-dimensional image. A device usable for the measurement of the transient PL is not limited to the device described in the first exemplary embodiment.

The sample housed in the sample chamber 102 is obtained by forming a thin film, in which a doping material is doped to a matrix material at a concentration of 12 mass %, on the quartz substrate.

The thin film sample housed in the sample chamber 102 is irradiated with pulse laser from the pulse laser 101 to excite the doping material. Emission is extracted at 90 degrees angle relative to an irradiation direction of the excited light. The extracted emission is dispersed with the spectrometer 103 to form a two-dimensional image in the streak camera 104. As a result, the two-dimensional image expressed in coordinates of which ordinate axis indicates time and of which abscissa axis indicates a wavelength, in which a luminous point indicates a luminous intensity, can be obtained. If the two-dimensional image is cut out along a predetermined time axis, emission spectrum expressed in coordinates of which ordinate axis indicates a luminous intensity and of which abscissa axis indicates the wavelength can be obtained. If the two-dimensional image is cut out along a wavelength axis, a decay curve (transient PL) expressed in coordinates of which ordinate axis indicates a logarithm of the luminous intensity and of which abscissa axis indicates time can be obtained.

For instance, using a reference compound H1 below as the matrix material and a reference compound D1 as the doping material, a thin film sample A was prepared as described above and the transient PL was measured.

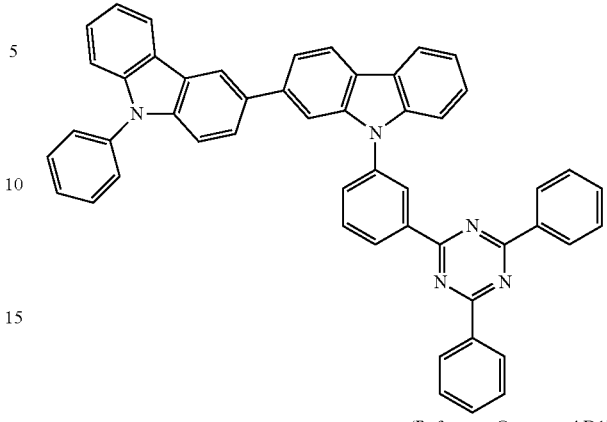
(Reference Compound H1)

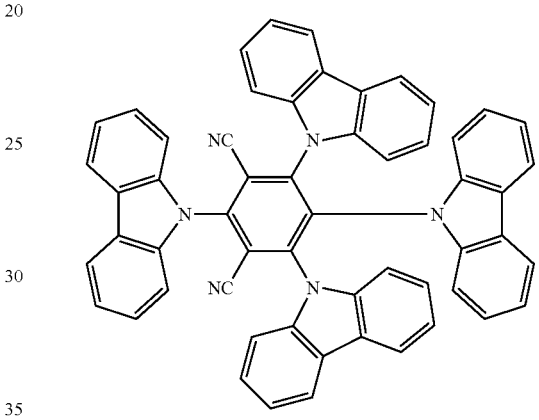
(Reference Compound D1)

Herein, the decay curve was analyzed using the above-described thin film sample A and a thin film sample B. The thin film sample B was prepared as described above, using a reference compound H2 below as the matrix material and the reference compound D1 as the doping material.

Figure 3:
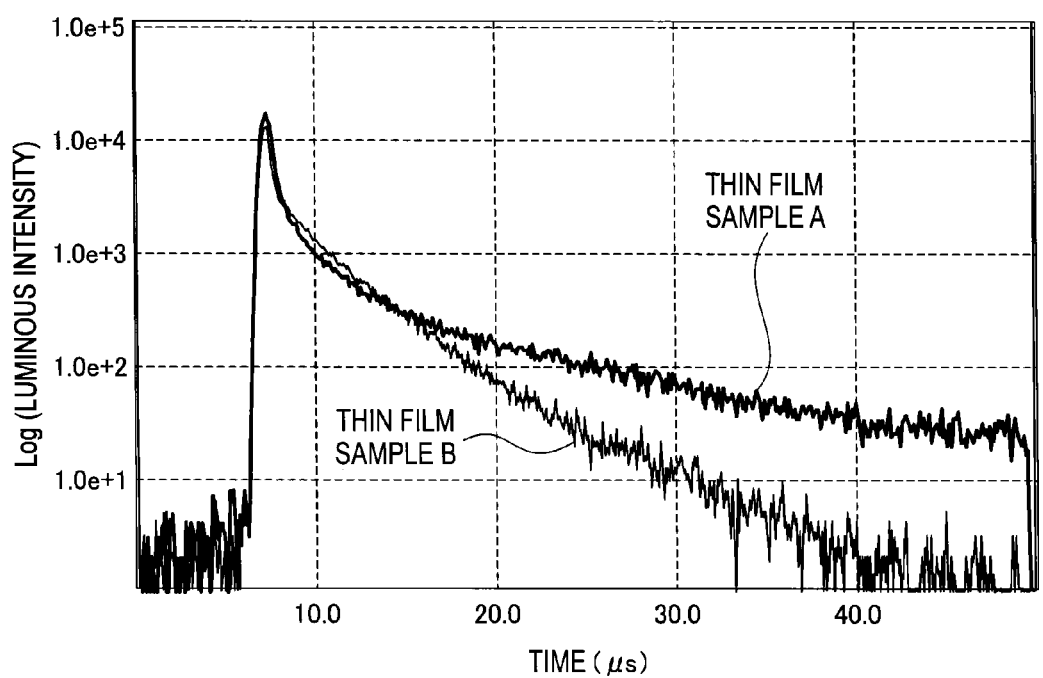
FIG. 3 shows an example of a decay curve of the transient PL.

FIG. 3 shows a decay curve obtained from the measured transient PL of the thin film sample A and the thin film sample B.

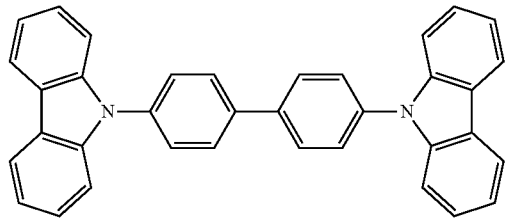
(Reference Compound H2)

An emission decay curve expressed in coordinates of which ordinate axis indicates a luminous intensity and of which abscissa axis indicates time can be obtained by measuring the transient PL as described above. Based on the emission decay curve, a fluorescence intensity ratio between fluorescence in the single state generated by light excitation and the delayed fluorescence in the singlet state generated by the inverse energy transfer through the triplet state can be estimated. In the delayed fluorescence material, a ratio of the delayed fluorescence intensity to be gradually reduced is larger to some extent than a ratio of the fluorescence intensity to be rapidly reduced.

In the first exemplary embodiment, an amount of the delayed fluorescence can be calculated using the device of FIG. 2. In the first compound after excited with pulse light (light irradiated from the pulse laser) having a wavelength to be absorbed in the first compound, Prompt Emission that is immediately observed in the excited state and Delay Emission that is not observed immediately after the excitation but is later observed are present. In the first exemplary embodiment, an amount of Delay Emission is preferably 5% or more based on an amount of Prompt Emission.

The amount of Prompt Emission and the amount of Delay Emission can be obtained according to the method as a method described in "Nature 492, 234-238, 2012." The amount of Prompt emission and the amount of Delay emission may be calculated using a device different from one described in the above Reference Documents.

A sample usable for measuring delayed fluorescence is obtained, for instance, by co-depositing the first compound and a compound TH-2 described later on a quartz substrate so that a ratio of the first compound is 12 mass %, thereby forming a 100-nm-thick thin film.

Second Compound

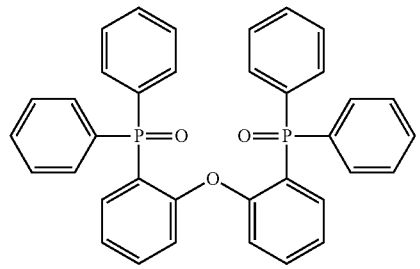

TH-2

A second compound is represented by a formula (2) below.

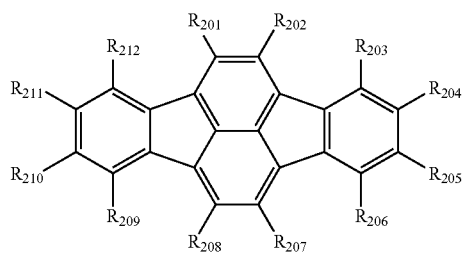

(2)

In the formula (2), $R_{201}$ to $R_{212}$ are each independently a hydrogen atom or a substituent.

When $R_{201}$ to $R_{212}$ are a substituent, the substituent is selected from the group consisting of a substituted or unsubstituted alkyl group having 1 to 30 carbon atoms, a substituted or unsubstituted aryl group having 6 to 30 ring carbon atoms, a substituted or unsubstituted heterocyclic group having 5 to 30 ring atoms, a substituted or unsubstituted alkoxy group having 1 to 30 carbon atoms, a substituted or unsubstituted aryloxy group having 6 to 30 ring carbon atoms, a substituted or unsubstituted aralkyl group having 6 to 30 ring carbon atoms, a substituted amino group, a cyano group and a halogen atom. The substituents of $R_{201}$ to $R_{212}$ may be mutually bonded to form a cyclic structure.

The second compound is also preferably represented by a formula (21) below.

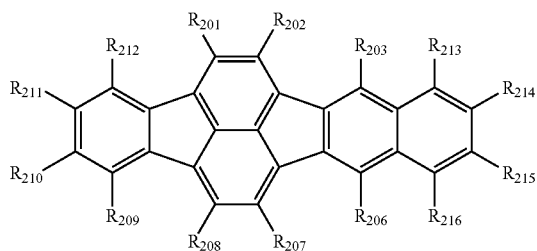

(21)

In the formula (21), $R_{201}$ to $R_{203}$ and $R_{206}$ to $R_{216}$ are each independently a hydrogen atom or a substituent. When $R_{201}$ to $R_{203}$ and $R_{206}$ to $R_{216}$ each are a substituent, the substituent is selected from the group consisting of a substituted or unsubstituted alkyl group having 1 to 30 carbon atoms, a substituted or unsubstituted aryl group having 6 to 30 ring carbon atoms, a substituted or unsubstituted heterocyclic group having 5 to 30 ring atoms, a substituted or unsubstituted alkoxy group having 1 to 30 carbon atoms, a substituted or unsubstituted aryloxy group having 6 to 30 ring carbon atoms, a substituted or unsubstituted aralkyl group having 6 to 30 ring carbon atoms, a substituted amino group, a cyano group and a halogen atom. The substituents of $R_{201}$ to $R_{203}$ and $R_{206}$ to $R_{216}$ may be mutually bonded to form a cyclic structure.

The second compound is more preferably represented by a formula (211) below.

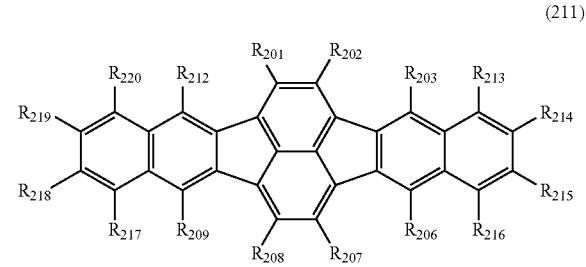

(211)

In the formula (211), $R_{201}$ to $R_{203}$, $R_{206}$ to $R_{209}$ and $R_{212}$ to $R_{220}$ are each independently a hydrogen atom or a substituent. When $R_{201}$ to $R_{203}$, $R_{206}$ to $R_{209}$ and $R_{212}$ to $R_{220}$ are a substituent, the substituent is selected from the group consisting of a substituted or unsubstituted alkyl group having 1 to 30 carbon atoms, a substituted or unsubstituted aryl group having 6 to 30 ring carbon atoms, a substituted or unsubstituted heterocyclic group having 5 to 30 ring atoms, a substituted or unsubstituted alkoxy group having 1 to 30 carbon atoms, a substituted or unsubstituted aryloxy group having 6 to 30 ring carbon atoms, a substituted or unsubstituted aralkyl group having 6 to 30 ring carbon atoms, a substituted amino group, a cyano group and a halogen atom. The substituents of $R_{201}$ to $R_{203}$, $R_{206}$ to $R_{209}$ and $R_{212}$ to $R_{220}$ may be mutually bonded to form a cyclic structure.

In the formula (211), it is also preferable that $R_{201}$ and $R_{207}$ are the same, $R_{202}$ and $R_{208}$ are the same, $R_{203}$ and $R_{209}$ are the same, $R_{213}$ and $R_{217}$ are the same, $R_{214}$ and $R_{218}$ are the same, $R_{215}$ and $R_{219}$ are the same, $R_{216}$ and $R_{220}$ are the same, and $R_{206}$ and $R_{212}$ are the same.

In the formula (211), it is also preferable that at least one of a combination of $R_{201}$ and $R_{207}$, a combination of $R_{202}$ and $R_{208}$, a combination of $R_{203}$ and $R_{209}$, a combination of $R_{213}$ and $R_{217}$, a combination of $R_{214}$ and $R_{218}$, a combination of $R_{215}$ and $R_{219}$, a combination of $R_{216}$ and $R_{220}$, and a combination of $R_{206}$ and $R_{212}$ includes mutually different groups.

In the formula (211), $R_{203}$, $R_{206}$, $R_{209}$ and $R_{212}$ are each independently preferably a substituted or unsubstituted aryl group having 6 to 30 ring carbon atoms, more preferably a substituted or unsubstituted aryl group having 6 to 18 ring carbon atoms, for instance, one selected from the group consisting of a phenyl group, biphenyl group, terphenyl group, naphthyl group, fluorenyl group, phenanthrenyl group, fluoranthenyl group, anthryl group, pyrenyl group, and chrysenyl group, further preferably a substituted or unsubstituted aryl group having 6 to 12 ring carbon atoms, for instance, one selected from the group consisting of a phenyl group, biphenyl group, naphthyl group, and fluorenyl group.

The second compound is further preferably represented by a formula (214) below.

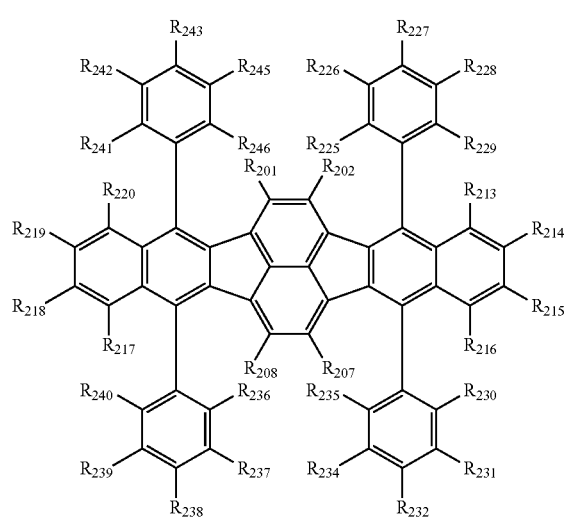

(214)

In the formula (214), $R_{201}$, $R_{202}$, $R_{207}$, $R_{208}$, $R_{213}$ to $R_{220}$ and $R_{225}$ to $R_{246}$ are each independently a hydrogen atom or a substituent. When $R_{201}$, $R_{202}$, $R_{207}$, $R_{208}$, $R_{213}$ to $R_{220}$ and $R_{225}$ to $R_{246}$ are a substituent, the substituent is selected from the group consisting of a substituted or unsubstituted alkyl group having 1 to 30 carbon atoms, a substituted or unsubstituted aryl group having 6 to 30 ring carbon atoms, a substituted or unsubstituted heterocyclic group having 5 to 30 ring atoms, a substituted or unsubstituted alkoxy group having 1 to 30 carbon atoms, a substituted or unsubstituted aryloxy group having 6 to 30 ring carbon atoms, a substituted or unsubstituted aralkyl group having 6 to 30 ring carbon atoms, a substituted amino group, a cyano group and a halogen atom. The substituents of $R_{201}$, $R_{202}$, $R_{207}$, $R_{208}$, and $R_{213}$ to $R_{220}$ may be mutually bonded to form a cyclic structure.

The second compound is also preferably represented by a formula (25) below.

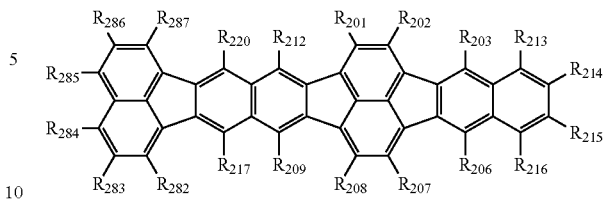

(25)

In the formula (25), $R_{201}$ to $R_{203}$, $R_{206}$ to $R_{209}$ and $R_{212}$ to $R_{217}$, $R_{220}$ and $R_{282}$ to $R_{287}$ are each independently a hydrogen atom or a substituent. When $R_{201}$ to $R_{203}$, $R_{206}$ to $R_{209}$ and $R_{212}$ to $R_{217}$, $R_{220}$ and $R_{282}$ to $R_{287}$ are a substituent, the substituent is selected from the group consisting of a substituted or unsubstituted alkyl group having 1 to 30 carbon atoms, a substituted or unsubstituted aryl group having 6 to 30 ring carbon atoms, a substituted or unsubstituted heterocyclic group having 5 to 30 ring atoms, a substituted or unsubstituted alkoxy group having 1 to 30 carbon atoms, a substituted or unsubstituted aryloxy group having 6 to 30 ring carbon atoms, a substituted or unsubstituted aralkyl group having 6 to 30 ring carbon atoms, a substituted amino group, a cyano group and a halogen atom. The substituents of $R_{201}$ to $R_{203}$, $R_{206}$ to $R_{209}$ and $R_{212}$ to $R_{217}$, $R_{220}$ and $R_{282}$ to $R_{287}$ may be mutually bonded to form a cyclic structure.)

The second compound is also preferably represented by a formula (212) below.

(212)

In the formula (212), $R_{201}$ to $R_{203}$, $R_{206}$ to $R_{213}$, $R_{216}$ and $R_{221}$ to $R_{224}$ are each independently a hydrogen atom or a substituent. When $R_{201}$ to $R_{203}$, $R_{206}$ to $R_{213}$, $R_{216}$ and $R_{221}$ to $R_{224}$ are a substituent, the substituent is selected from the group consisting of a substituted or unsubstituted alkyl group having 1 to 30 carbon atoms, a substituted or unsubstituted aryl group having 6 to 30 ring carbon atoms, a substituted or unsubstituted heterocyclic group having 5 to 30 ring atoms, a substituted or unsubstituted alkoxy group having 1 to 30 carbon atoms, a substituted or unsubstituted aryloxy group having 6 to 30 ring carbon atoms, a substituted or unsubstituted aralkyl group having 6 to 30 ring carbon atoms, a substituted amino group, a cyano group and a halogen atom. The substituents of $R_{201}$ to $R_{203}$, $R_{206}$ to $R_{213}$, $R_{216}$ and $R_{221}$ to $R_{224}$ may be mutually bonded to form a cyclic structure.

The second compound is also preferably represented by a formula (213) below.

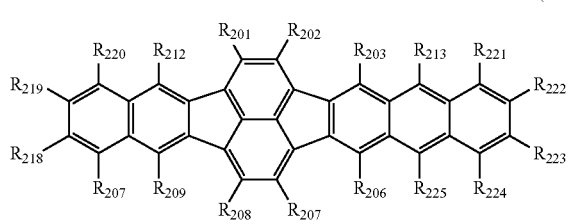

(213)

In the formula (213), $R_{201}$ to $R_{203}$, $R_{206}$ to $R_{209}$, $R_{212}$, $R_{213}$ and $R_{216}$ to $R_{224}$ are each independently a hydrogen atom or a substituent. When $R_{201}$ to $R_{203}$, $R_{206}$ to $R_{209}$, $R_{212}$, $R_{213}$ and $R_{216}$ to $R_{224}$ are a substituent, the substituent is selected from the group consisting of a substituted or unsubstituted alkyl group having 1 to 30 carbon atoms, a substituted or unsubstituted aryl group having 6 to 30 ring carbon atoms, a substituted or unsubstituted heterocyclic group having 5 to 30 ring atoms, a substituted or unsubstituted alkoxy group having 1 to 30 carbon atoms, a substituted or unsubstituted aryloxy group having 6 to 30 ring carbon atoms, a substituted or unsubstituted aralkyl group having 6 to 30 ring carbon atoms, a substituted amino group, a cyano group and a halogen atom. The substituents of $R_{201}$ to $R_{203}$, $R_{206}$ to $R_{209}$, $R_{212}$, $R_{213}$ and $R_{216}$ to $R_{224}$ may be mutually bonded to form a cyclic structure.

The second compound is also preferably represented by a formula (26) below.

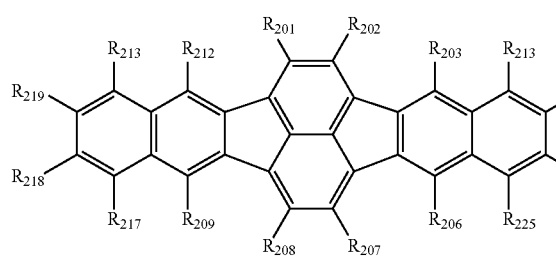

(26)

In the formula (26), $R_{201}$ to $R_{203}$, $R_{206}$ to $R_{209}$, $R_{212}$, $R_{213}$ and $R_{216}$ to $R_{221}$, $R_{224}$ and $R_{288}$ to $R_{297}$ are each independently a hydrogen atom or a substituent. When $R_{201}$ to $R_{203}$, $R_{206}$ to $R_{209}$, $R_{212}$, $R_{213}$ and $R_{216}$ to $R_{221}$, $R_{224}$ and $R_{288}$ to $R_{297}$ are a substituent, the substituent is selected from the group consisting of a substituted or unsubstituted alkyl group having 1 to 30 carbon atoms, a substituted or unsubstituted aryl group having 6 to 30 ring carbon atoms, a substituted or unsubstituted heterocyclic group having 5 to 30 ring atoms, a substituted or unsubstituted alkoxy group having 1 to 30 carbon atoms, a substituted or unsubstituted aryloxy group having 6 to 30 ring carbon atoms, a substituted or unsubstituted aralkyl group having 6 to 30 ring carbon atoms, a substituted amino group, a cyano group and a halogen atom. The substituents of $R_{201}$ to $R_{203}$, $R_{206}$ to $R_{209}$, $R_{212}$, $R_{213}$ and $R_{216}$ to $R_{221}$, $R_{224}$ and $R_{288}$ to $R_{297}$ may be mutually bonded to form a cyclic structure.

The second compound is also preferably represented by a formula (24) below.

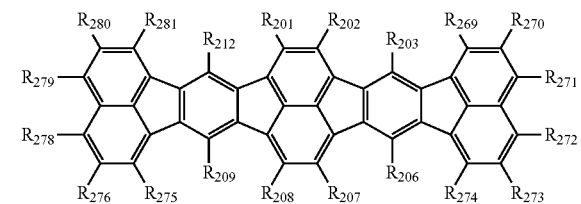

(24)

In the formula (24), $R_{201}$ to $R_{203}$, $R_{206}$ to $R_{209}$, $R_{212}$ and $R_{269}$ to $R_{281}$ are each independently a hydrogen atom or a substituent. When $R_{201}$ to $R_{203}$, $R_{206}$ to $R_{209}$, $R_{212}$ and $R_{269}$ to $R_{281}$ are a substituent, the substituent is selected from the group consisting of a substituted or unsubstituted alkyl group having 1 to 30 carbon atoms, a substituted or unsubstituted aryl group having 6 to 30 ring carbon atoms, a substituted or unsubstituted heterocyclic group having 5 to 30 ring atoms, a substituted or unsubstituted alkoxy group having 1 to 30 carbon atoms, a substituted or unsubstituted aryloxy group having 6 to 30 ring carbon atoms, a substituted or unsubstituted aralkyl group having 6 to 30 ring carbon atoms, a substituted amino group, a cyano group and a halogen atom. The substituents of $R_{201}$ to $R_{203}$, $R_{206}$ to $R_{209}$, $R_{212}$ and $R_{269}$ to $R_{281}$ may be mutually bonded to form a cyclic structure.

The second compound is also preferably represented by a formula (22) below.

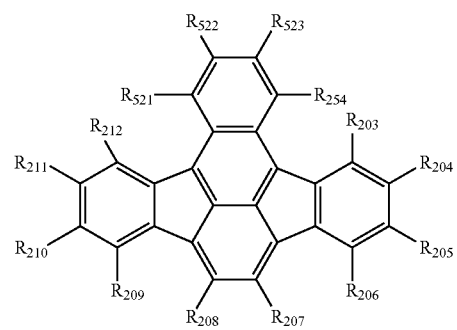

(22)

In the formula (22), $R_{203}$ to $R_{212}$ and $R_{251}$ to $R_{254}$ are each independently a hydrogen atom or a substituent. When $R_{203}$ to $R_{212}$ and $R_{251}$ to $R_{254}$ are a substituent, the substituent is selected from the group consisting of a substituted or unsubstituted alkyl group having 1 to 30 carbon atoms, a substituted or unsubstituted aryl group having 6 to 30 ring carbon atoms, a substituted or unsubstituted heterocyclic group having 5 to 30 ring atoms, a substituted or unsubstituted alkoxy group having 1 to 30 carbon atoms, a substituted or unsubstituted aryloxy group having 6 to 30 ring carbon atoms, a substituted or unsubstituted aralkyl group having 6 to 30 ring carbon atoms, a substituted amino group, a cyano group and a halogen atom. The substituents of $R_{203}$ to $R_{212}$ and $R_{251}$ to $R_{254}$ may be mutually bonded to form a cyclic structure.

The second compound is also preferably represented by a formula (27) below.

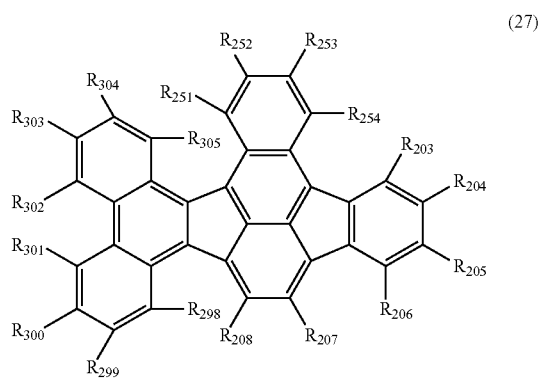

(27)

In the formula (27), $R_{203}$ to $R_{208}$, $R_{251}$ to $R_{254}$ and $R_{298}$ to $R_{305}$ are each independently a hydrogen atom or a substituent. When $R_{203}$ to $R_{208}$, $R_{251}$ to $R_{254}$ and $R_{298}$ to $R_{305}$ are a substituent, the substituent is selected from the group consisting of a substituted or unsubstituted alkyl group having 1 to 30 carbon atoms, a substituted or unsubstituted aryl group having 6 to 30 ring carbon atoms, a substituted or unsubstituted heterocyclic group having 5 to 30 ring atoms, a substituted or unsubstituted alkoxy group having 1 to 30 carbon atoms, a substituted or unsubstituted aryloxy group having 6 to 30 ring carbon atoms, a substituted or unsubstituted aralkyl group having 6 to 30 ring carbon atoms, a substituted amino group, a cyano group and a halogen atom. The substituents of $R_{203}$ to $R_{208}$, $R_{251}$ to $R_{254}$ and $R_{298}$ to $R_{305}$ may be mutually bonded to form a cyclic structure.

The second compound is also preferably represented by a formula (221) below.

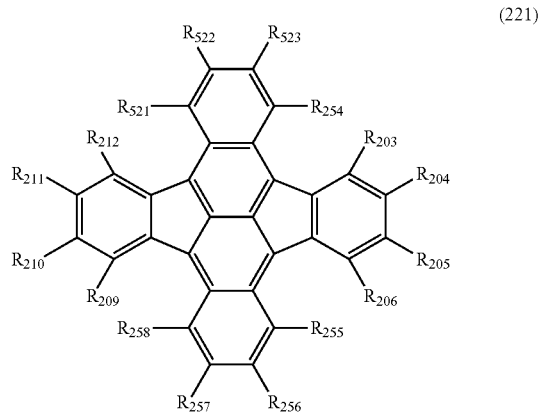

(221)

In the formula (221), $R_{203}$ to $R_{206}$, $R_{209}$ to $R_{212}$ and $R_{251}$ to $R_{258}$ are each independently a hydrogen atom or a substituent. When $R_{203}$ to $R_{206}$, $R_{209}$ to $R_{212}$ and $R_{251}$ to $R_{258}$ are a substituent, the substituent is selected from the group consisting of a substituted or unsubstituted alkyl group having 1 to 30 carbon atoms, a substituted or unsubstituted aryl group having 6 to 30 ring carbon atoms, a substituted or unsubstituted heterocyclic group having 5 to 30 ring atoms, a substituted or unsubstituted alkoxy group having 1 to 30 carbon atoms, a substituted or unsubstituted aryloxy group having 6 to 30 ring carbon atoms, a substituted or unsubstituted aralkyl group having 6 to 30 ring carbon atoms, a substituted amino group, a cyano group and a halogen atom. The substituents of $R_{203}$ to $R_{206}$, $R_{209}$ to $R_{212}$ and $R_{251}$ to $R_{258}$ may be mutually bonded to form a cyclic structure.

The second compound is also preferably represented by a formula (23) below.

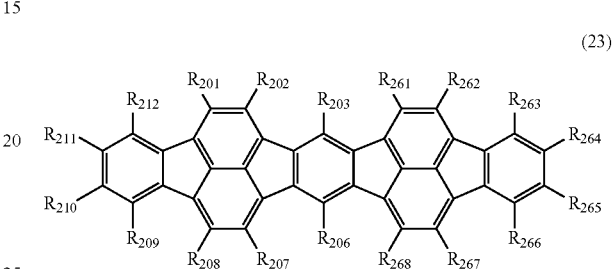

(23)

In the formula (23), $R_{201}$ to $R_{203}$, $R_{206}$ to $R_{212}$ and $R_{261}$ to $R_{268}$ are each independently a hydrogen atom or a substituent. When $R_{201}$ to $R_{203}$, $R_{206}$ to $R_{212}$ and $R_{261}$ to $R_{268}$ are a substituent, the substituent is selected from the group consisting of a substituted or unsubstituted alkyl group having 1 to 30 carbon atoms, a substituted or unsubstituted aryl group having 6 to 30 ring carbon atoms, a substituted or unsubstituted heterocyclic group having 5 to 30 ring atoms, a substituted or unsubstituted alkoxy group having 1 to 30 carbon atoms, a substituted or unsubstituted aryloxy group having 6 to 30 ring carbon atoms, a substituted or unsubstituted aralkyl group having 6 to 30 ring carbon atoms, a substituted amino group, a cyano group and a halogen atom. The substituents of $R_{201}$ to $R_{203}$, $R_{206}$ to $R_{212}$ and $R_{261}$ to $R_{268}$ may be mutually bonded to form a cyclic structure.

$R_{201}$ to $R_{305}$ are preferably each independently any one selected from the group consisting of a hydrogen atom, biphenyl group, terphenyl group, naphthyl group, fluorenyl group, phenanthrenyl group, fluoranthenyl group, anthryl group, pyrenyl group, and chrysenyl group, more preferably any one selected from the group consisting of a hydrogen atom, biphenyl group, terphenyl group, naphthyl group, and fluorenyl group, further preferably any one selected from the group consisting of a hydrogen atom, biphenyl group, and naphthyl group.

All of $R_{201}$ to $R_{305}$ are also preferably hydrogen atoms.

The second compound is preferably a fluorescent compound, more preferably a fluorescent compound having the emission peak in a wavelength range from 480 nm to 560 nm. The performance of the organic EL device is improved by using the second fluorescent compound together with the first compound in the emitting layer. The wavelength range of the emission peak of the second compound is more preferably from 500 nm to 550 nm. The wavelength of the emission peak means a peak wavelength of luminescence spectrum exhibiting a maximum luminous intensity among luminous spectra measured in a toluene solution in which a measurement target compound is dissolved at a concentration from $10^{-6}$ mol/l to $10^{-5}$ mol/l.

The second compound is also preferably a green fluorescent compound.

Specific examples of the second compound of the exemplary embodiment are shown below. It should be noted that the second compound according to the invention is not limited to these specific examples.
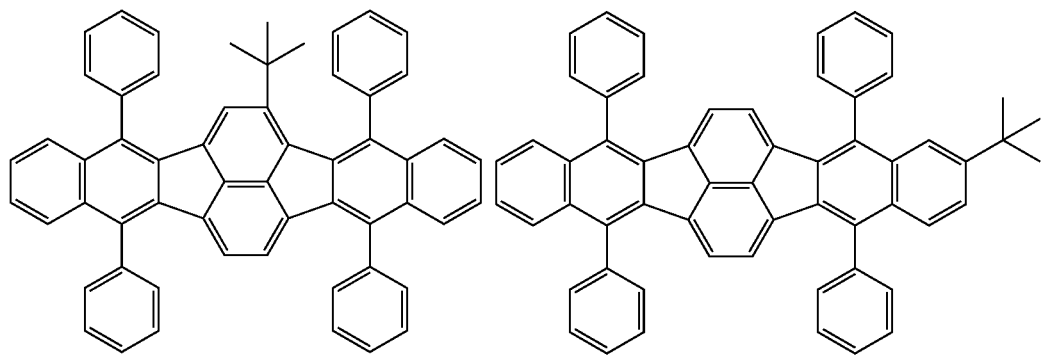
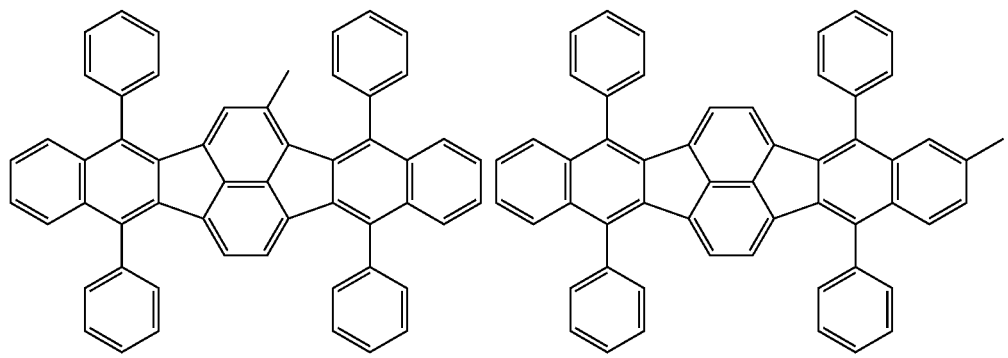
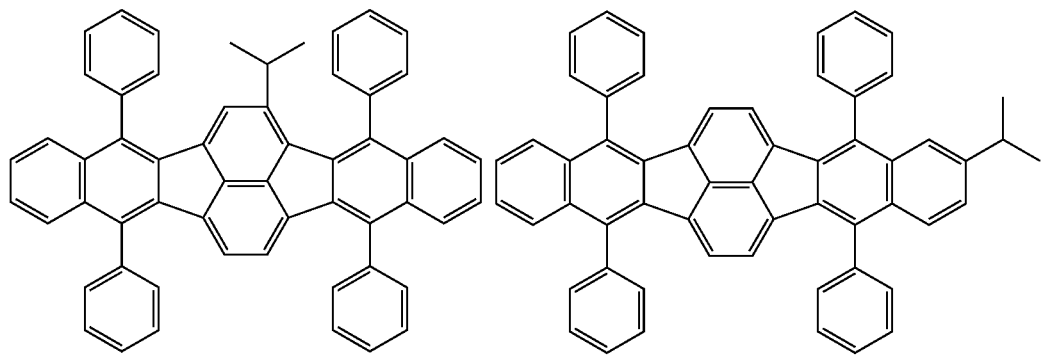
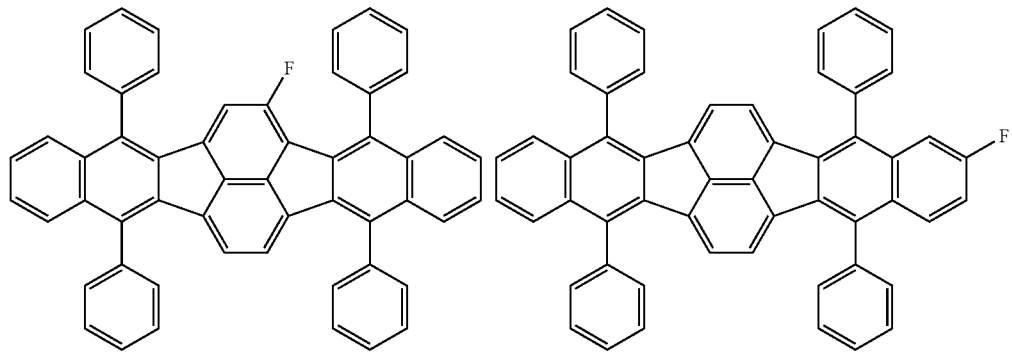

145 146
-continued
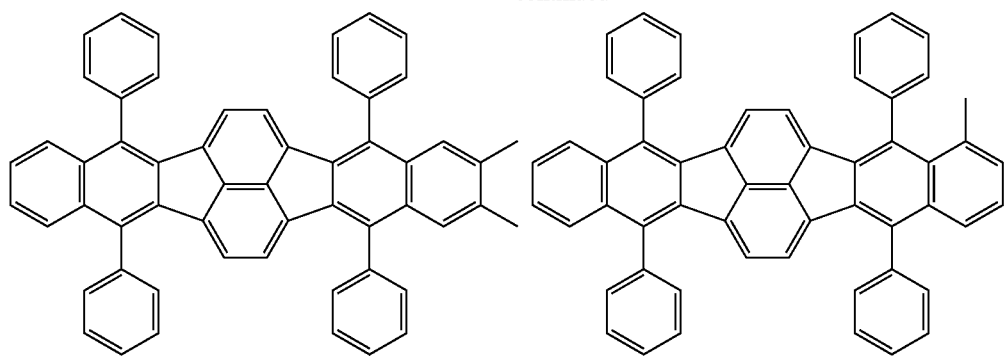
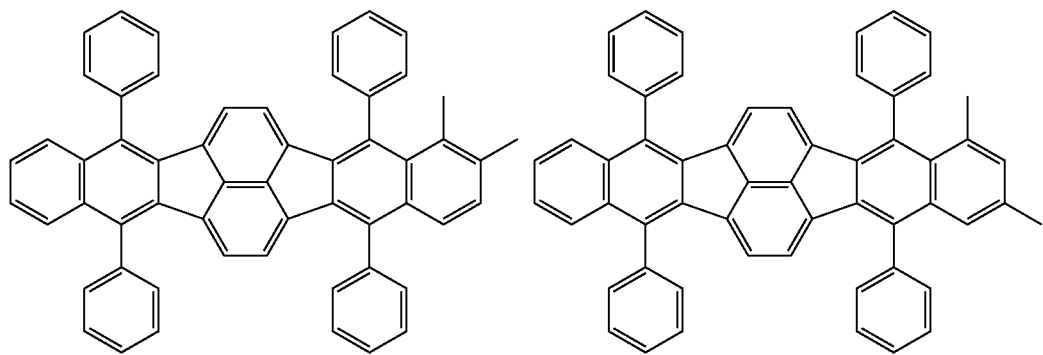
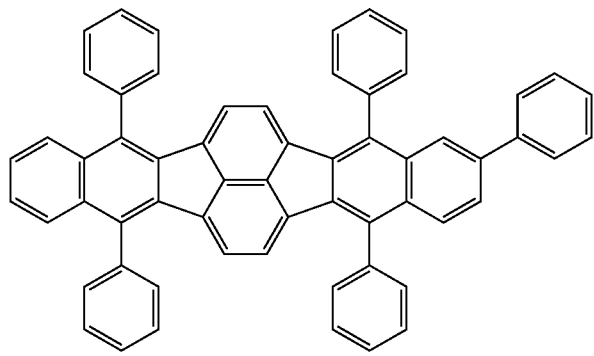
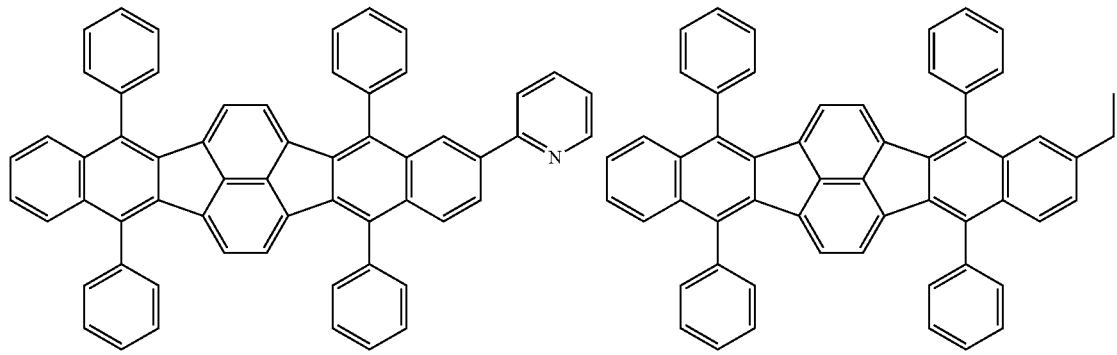

-continued
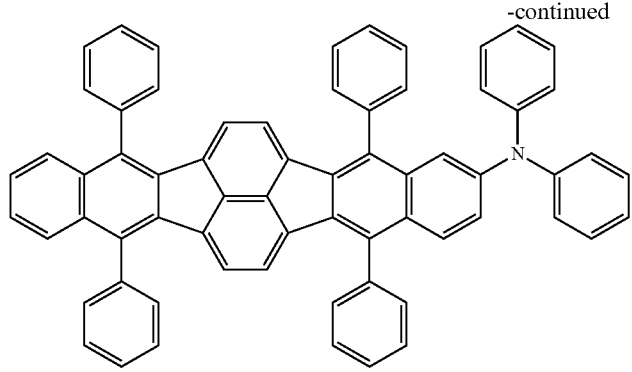
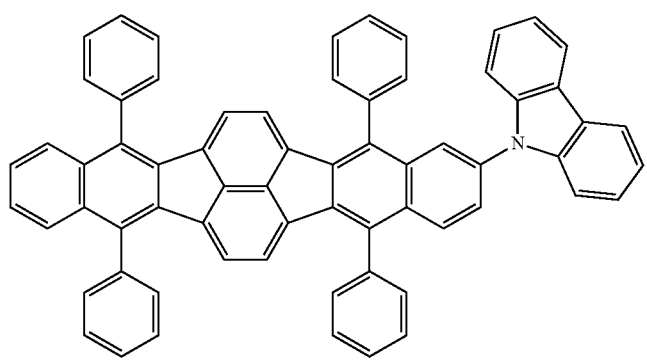
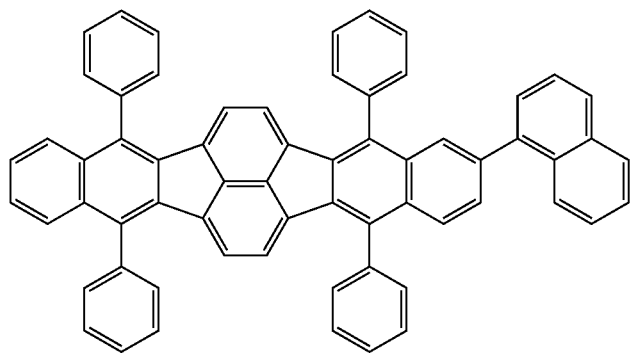
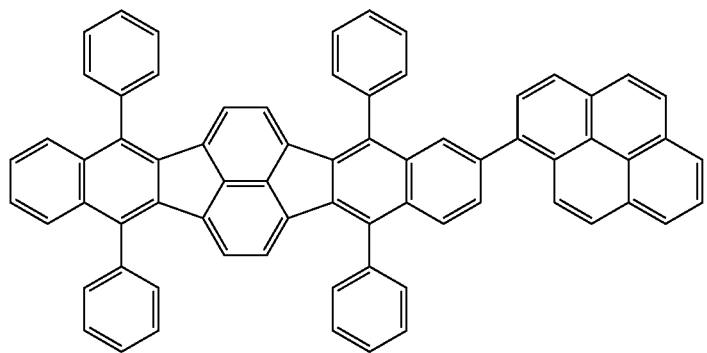

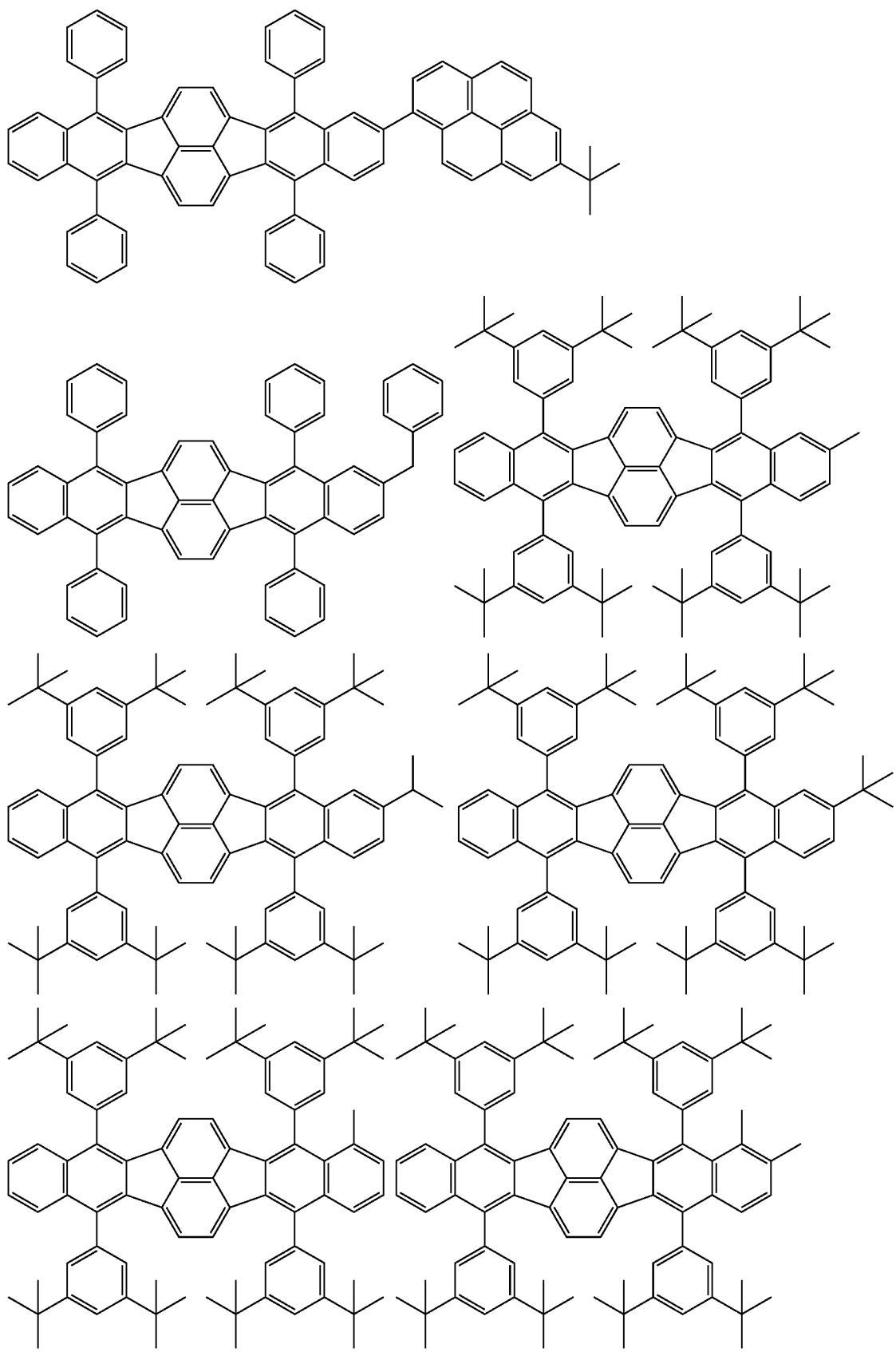

151 152
-continued
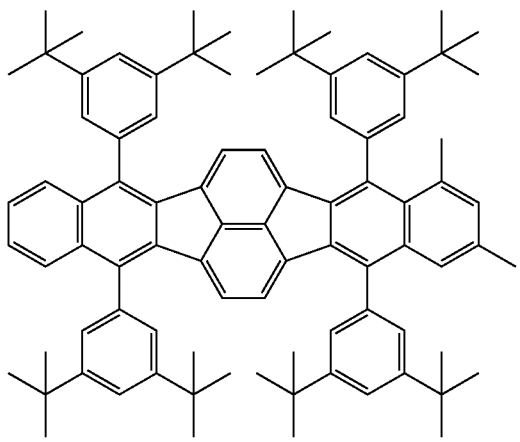 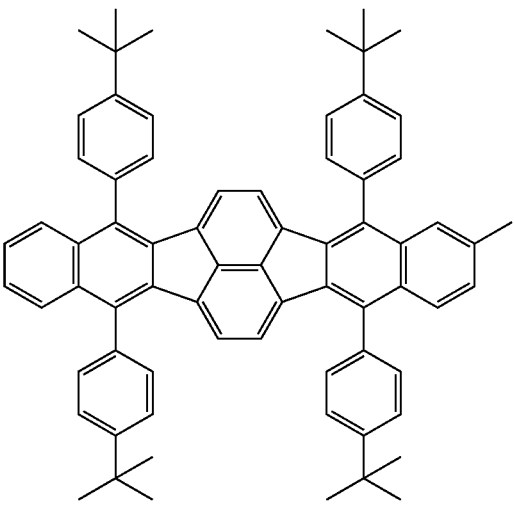
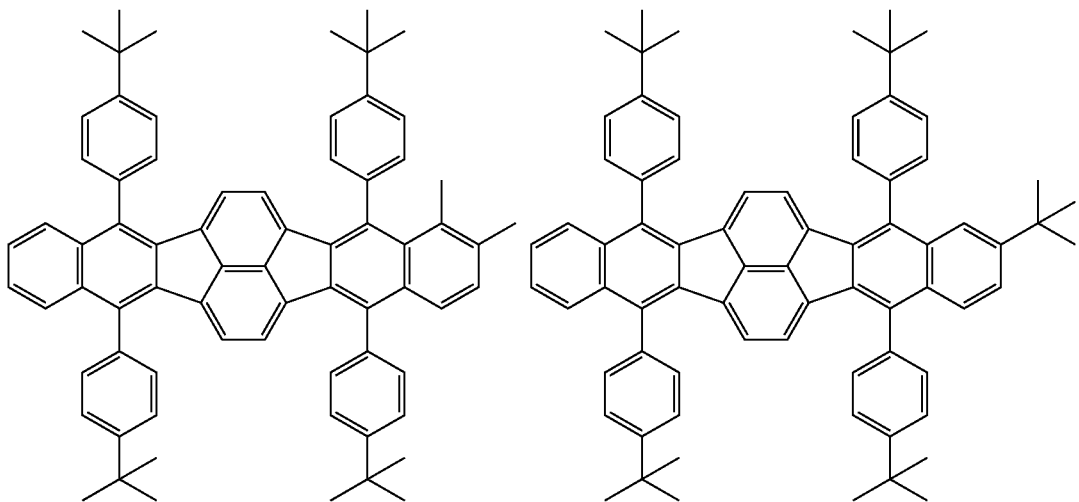
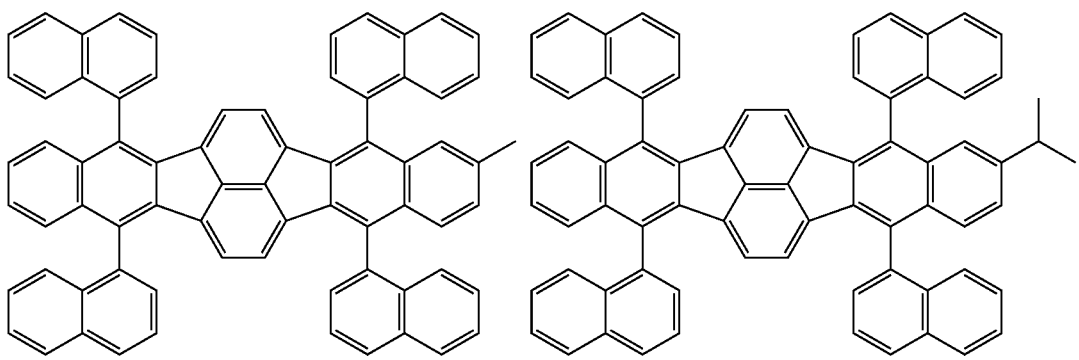

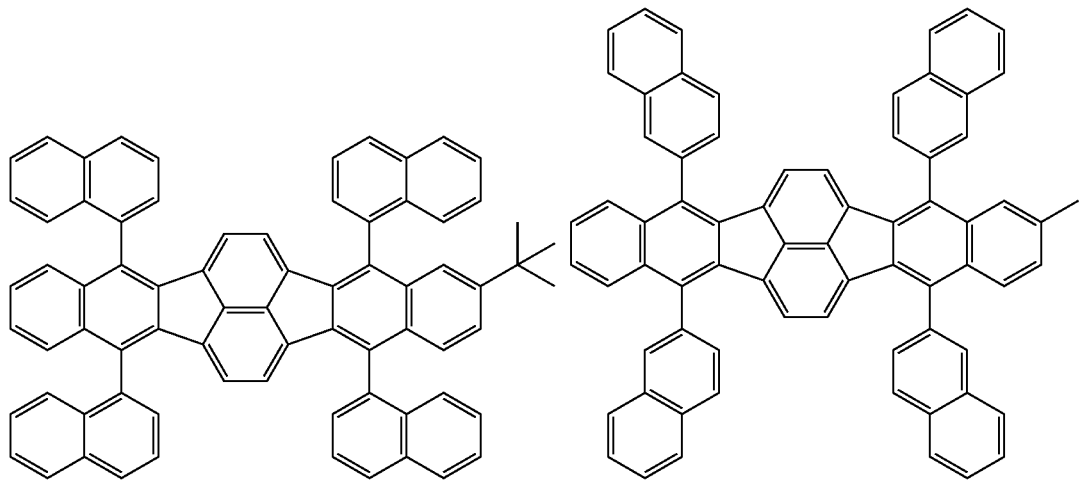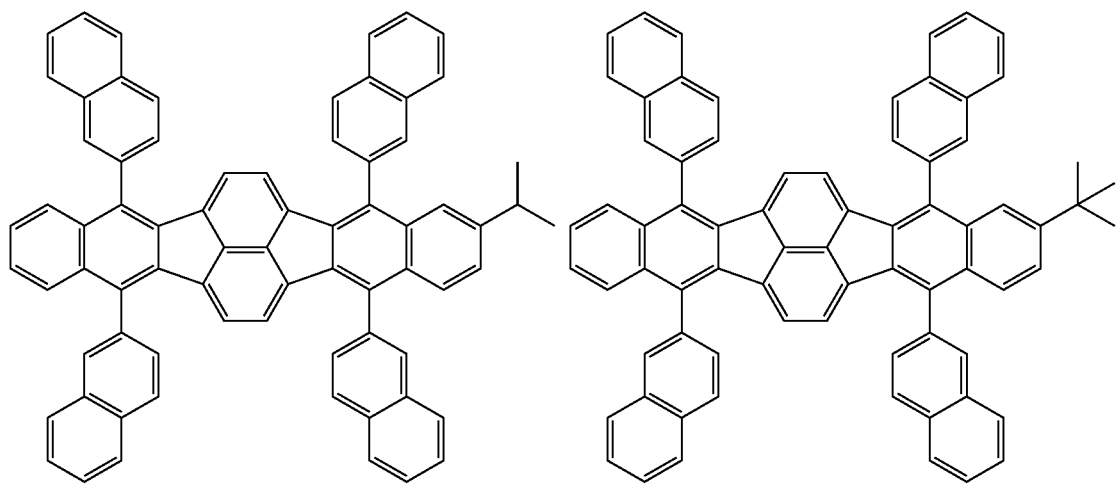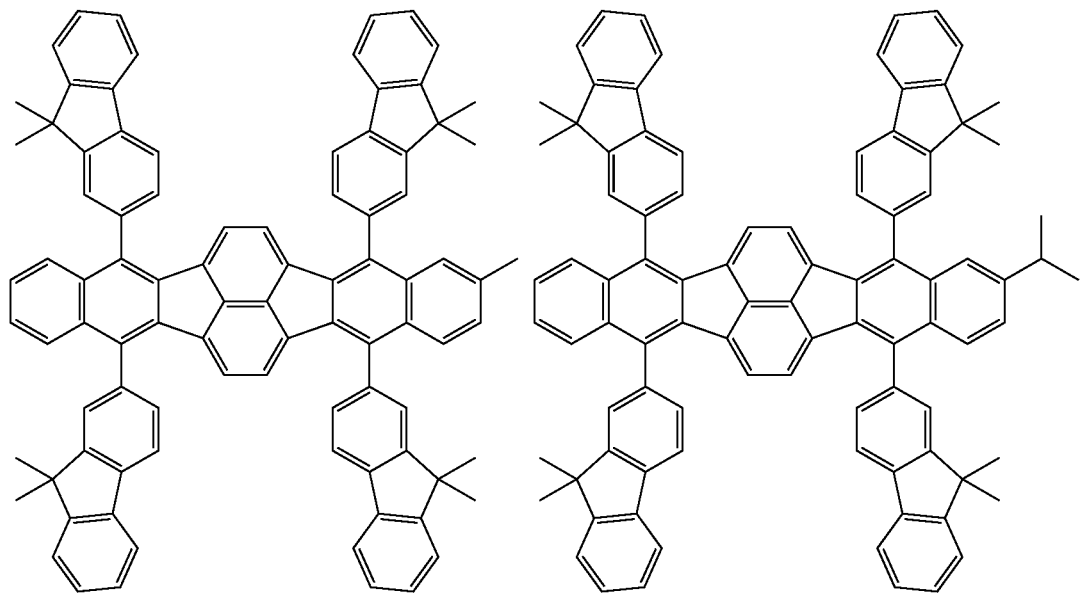

-continued
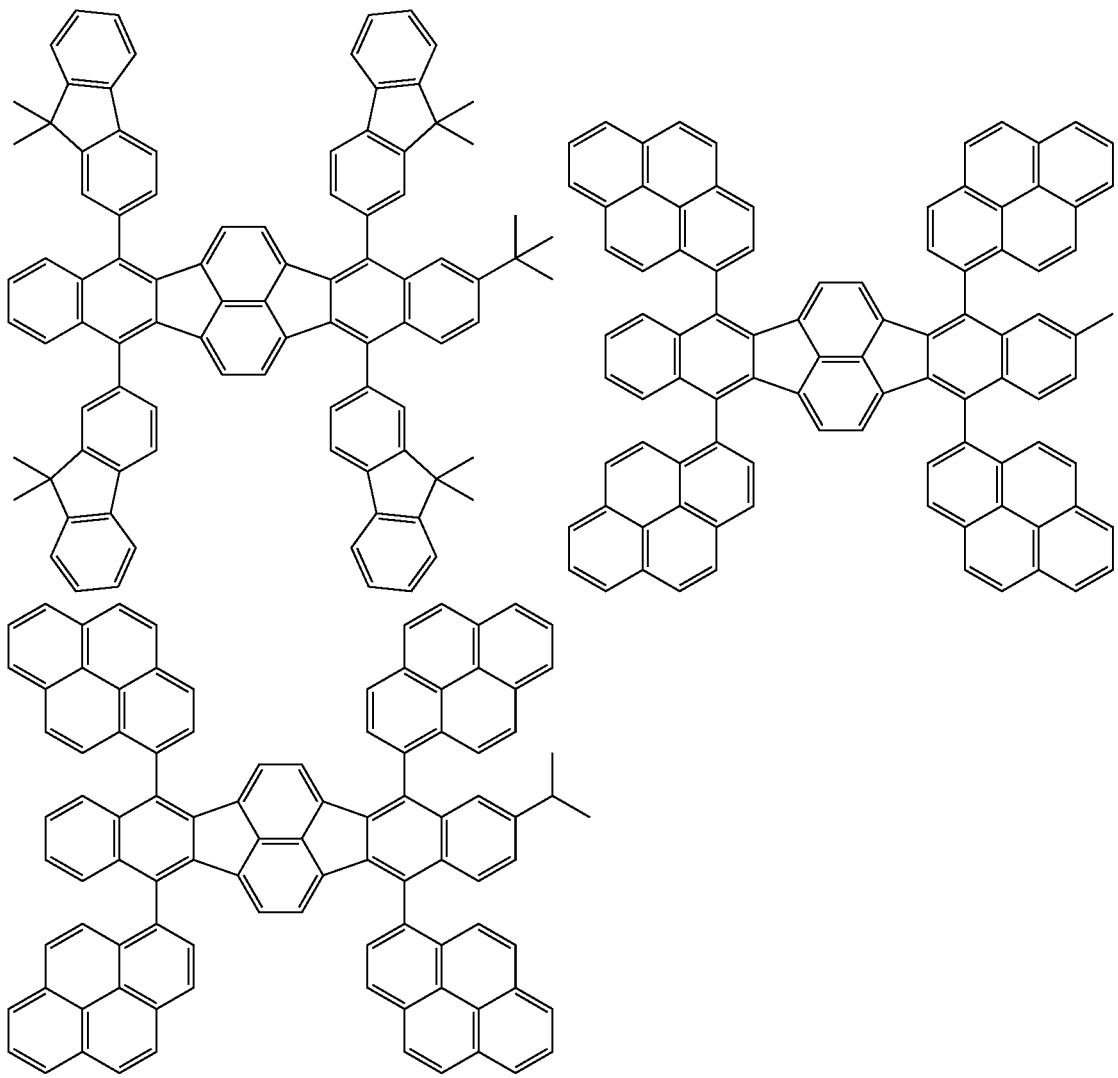
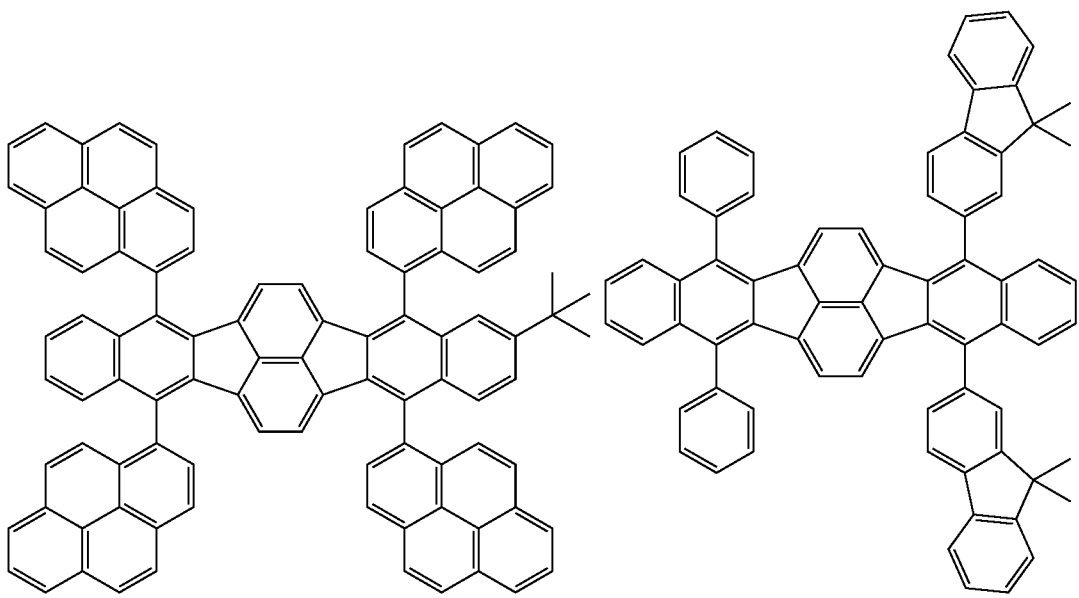

157 158
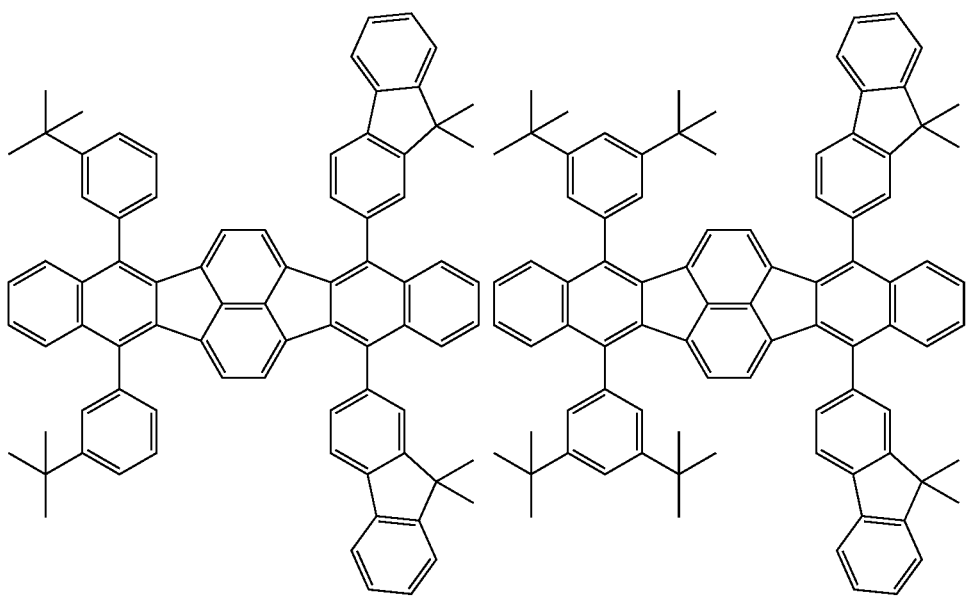
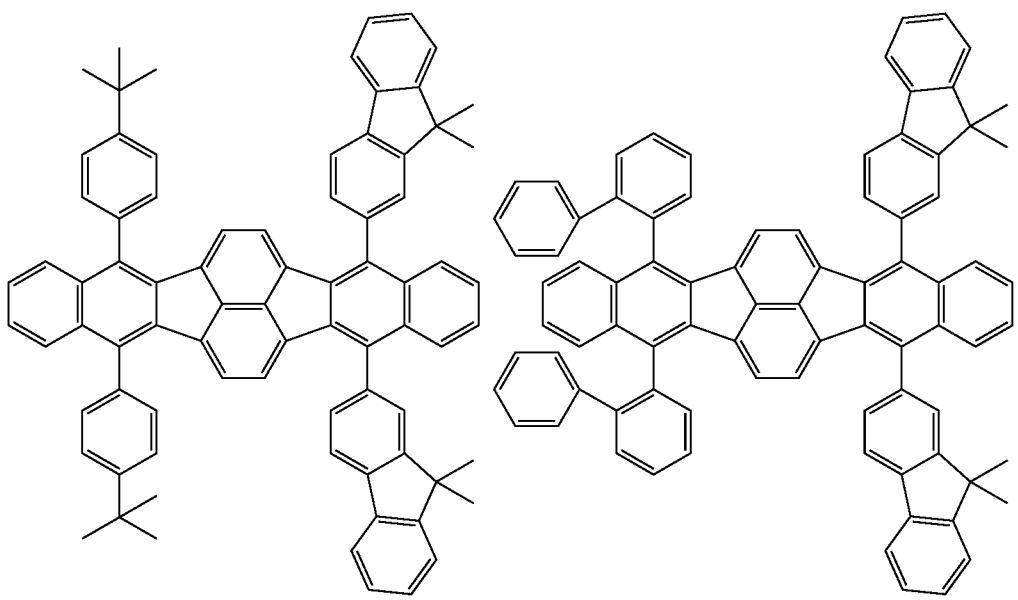

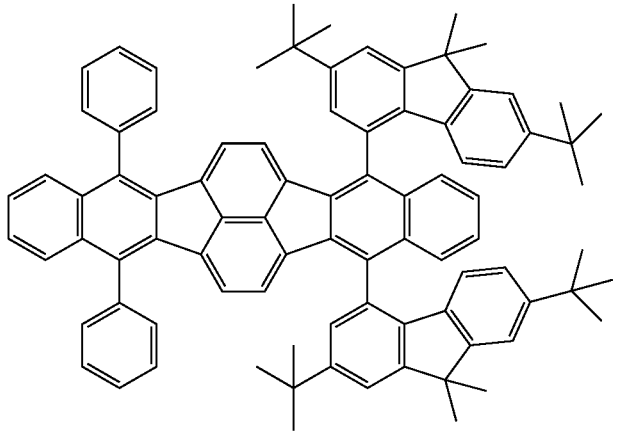
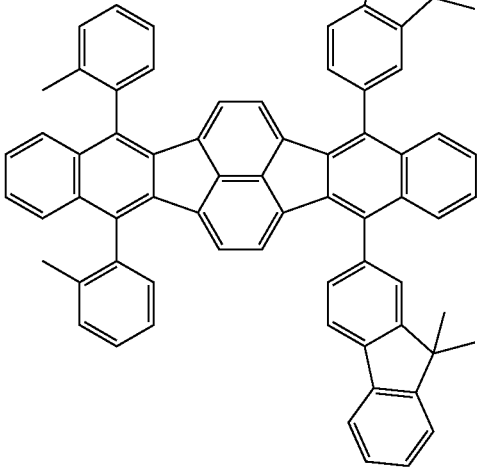
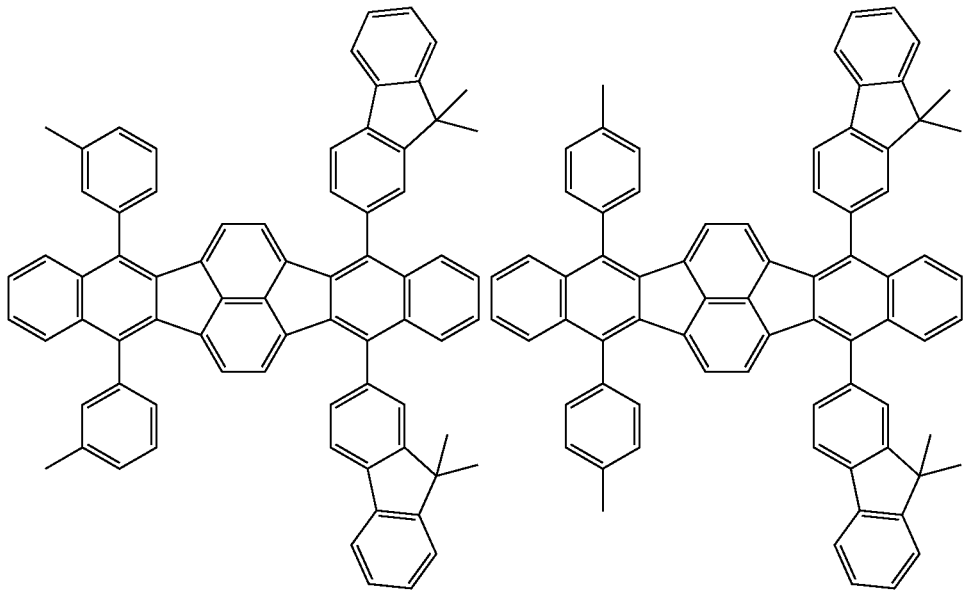
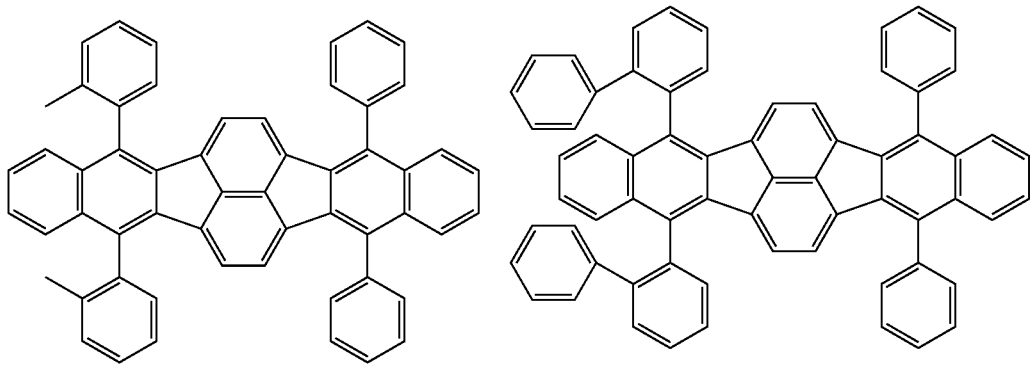

161
162
-continued
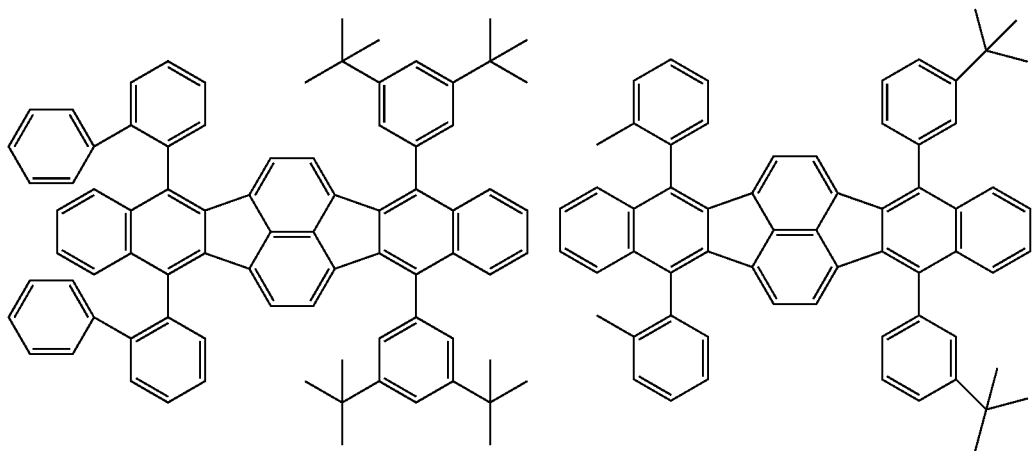
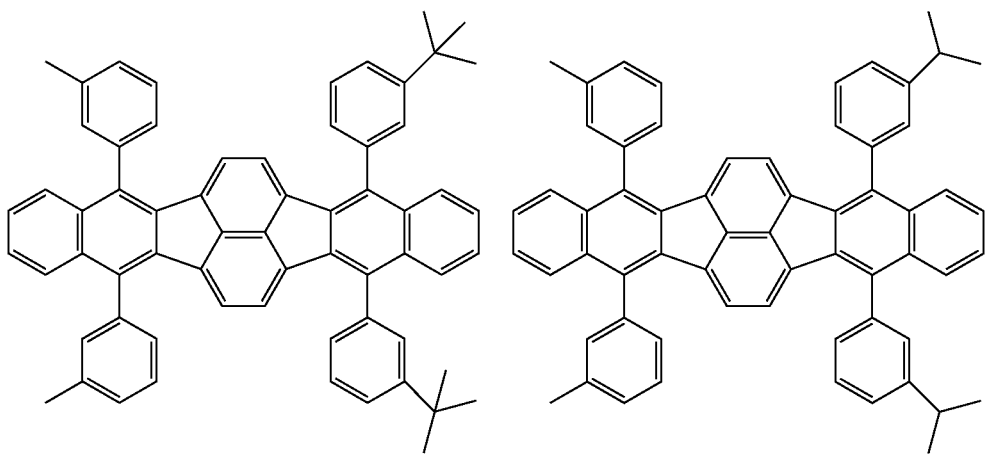
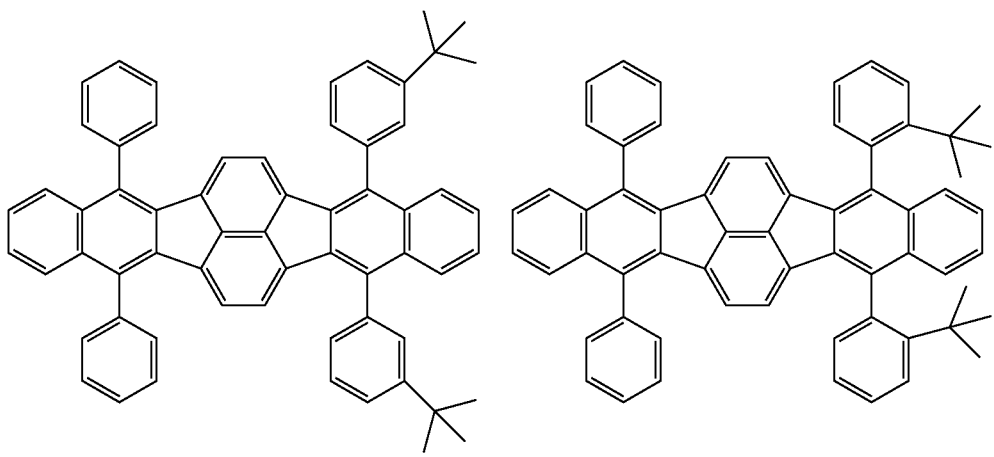

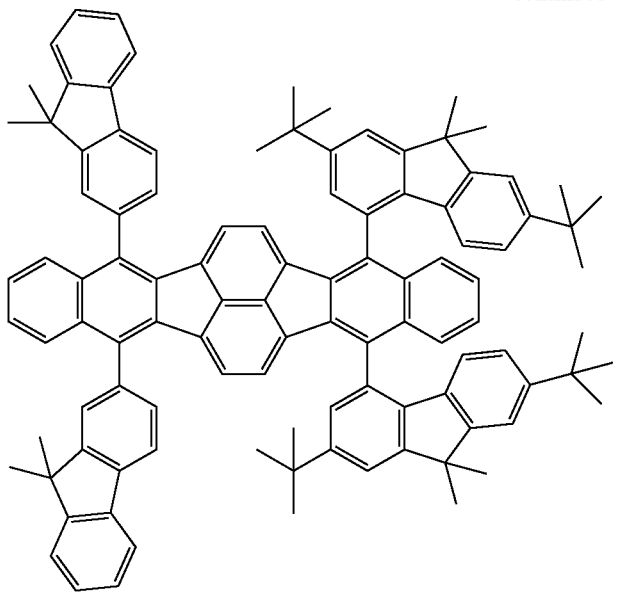
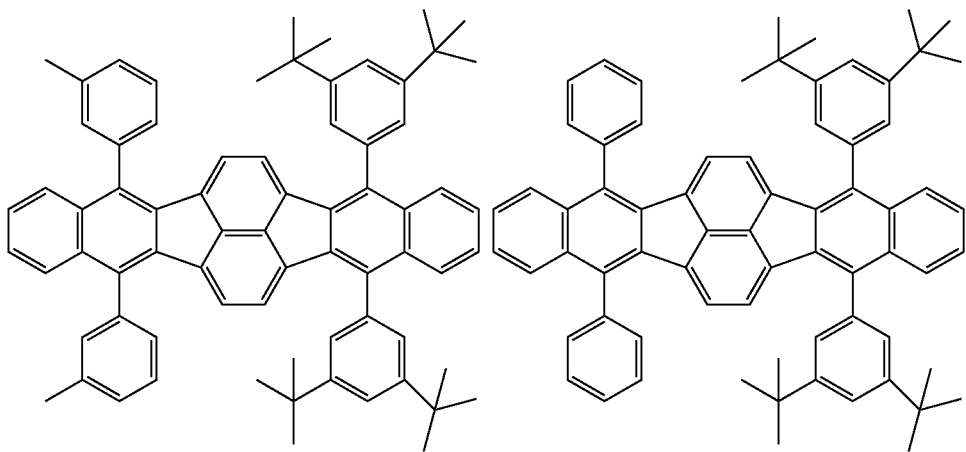
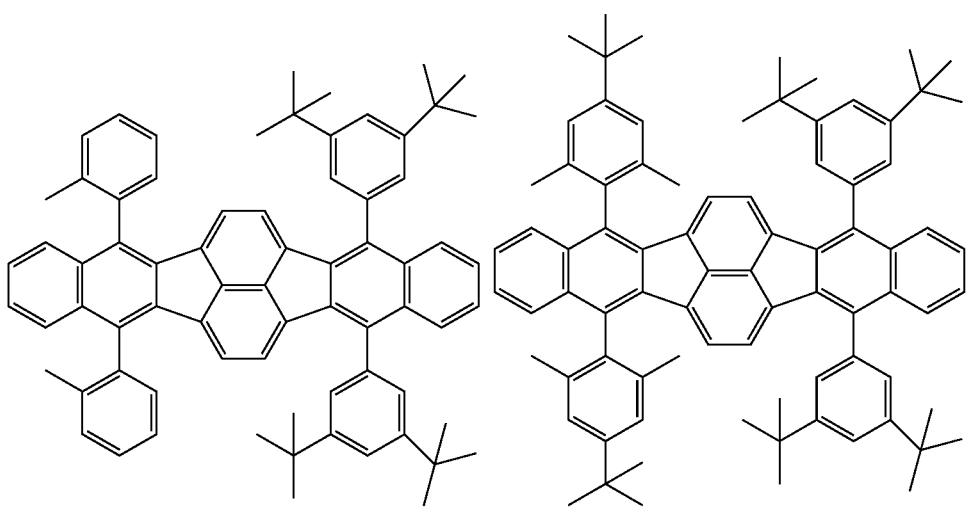

165
166
-continued
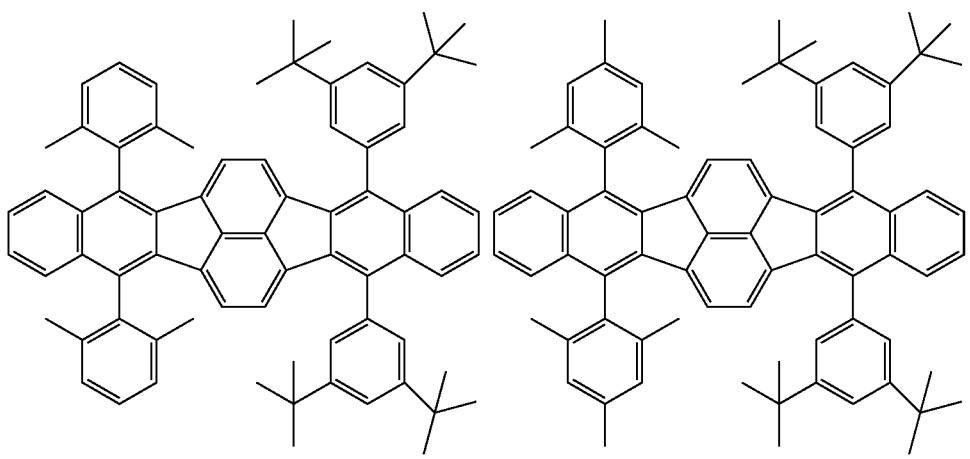
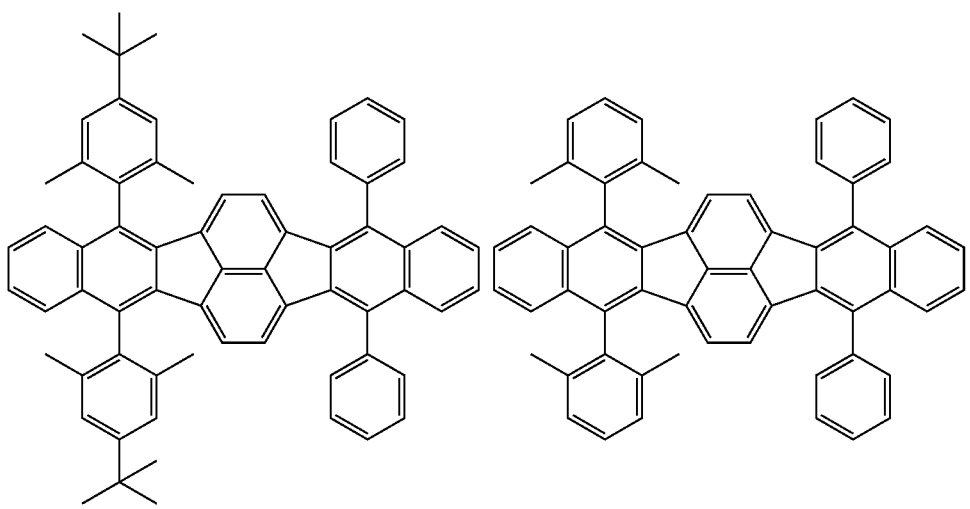
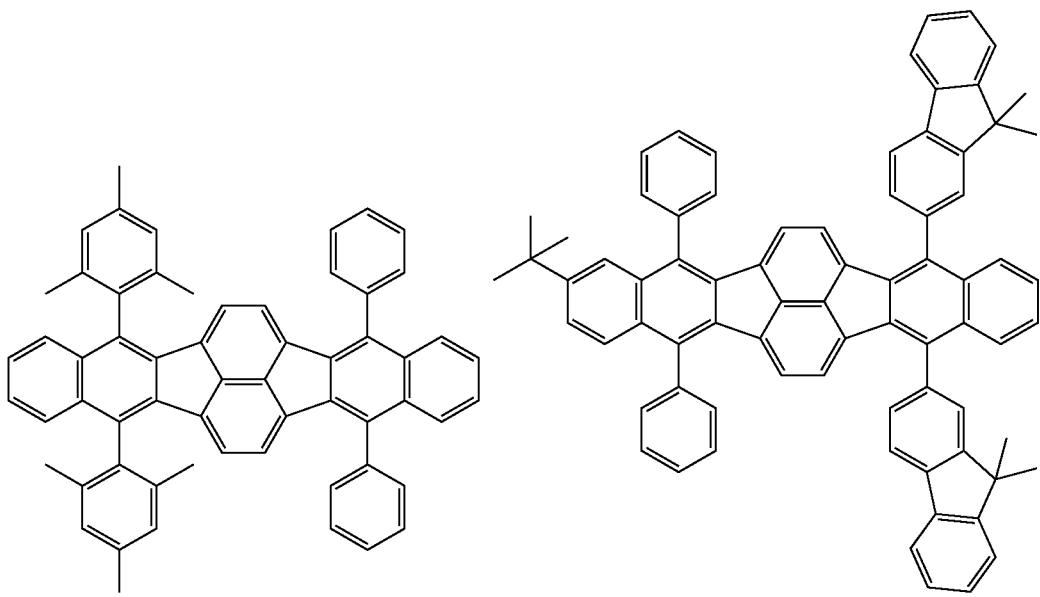

-continued
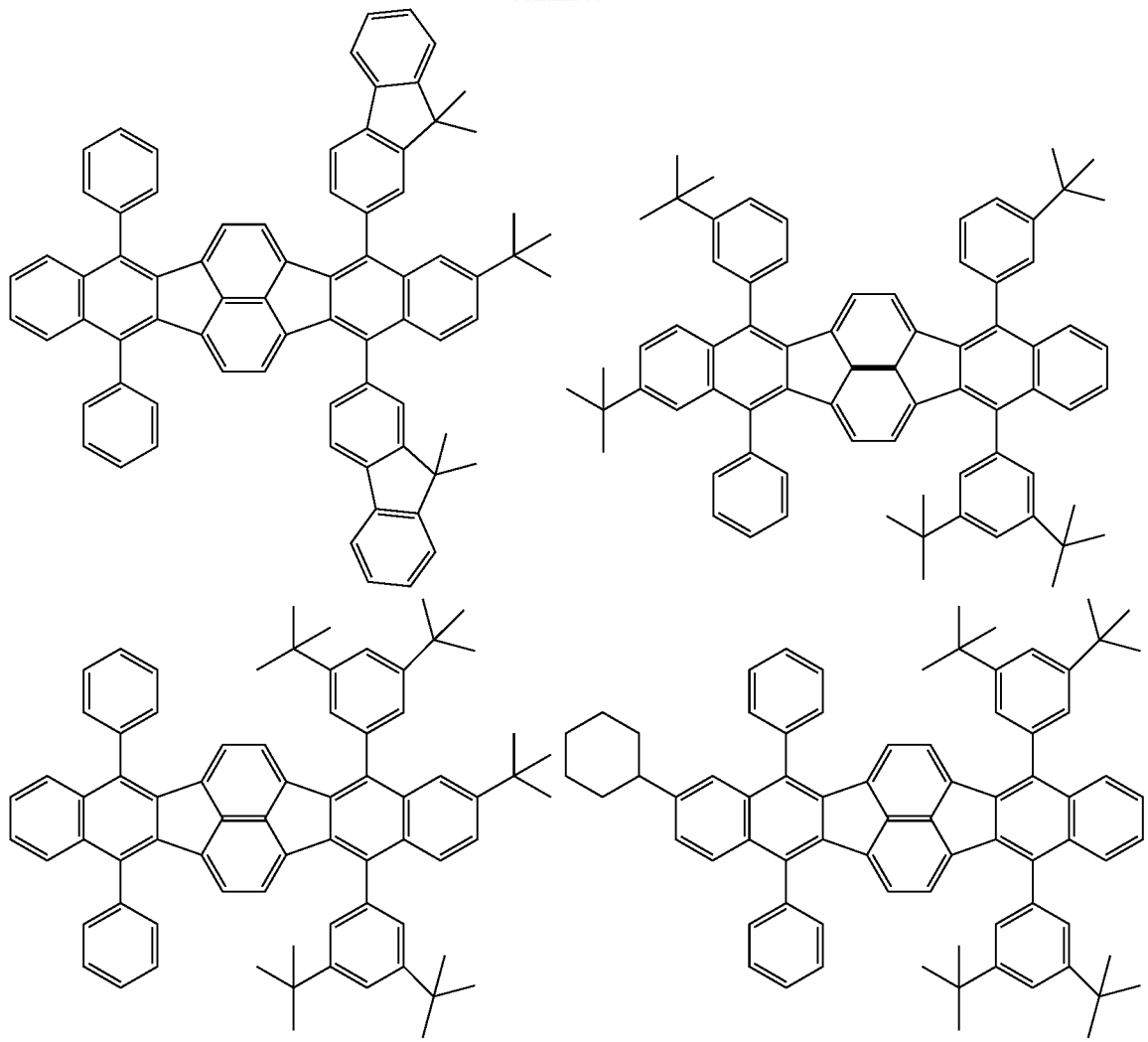
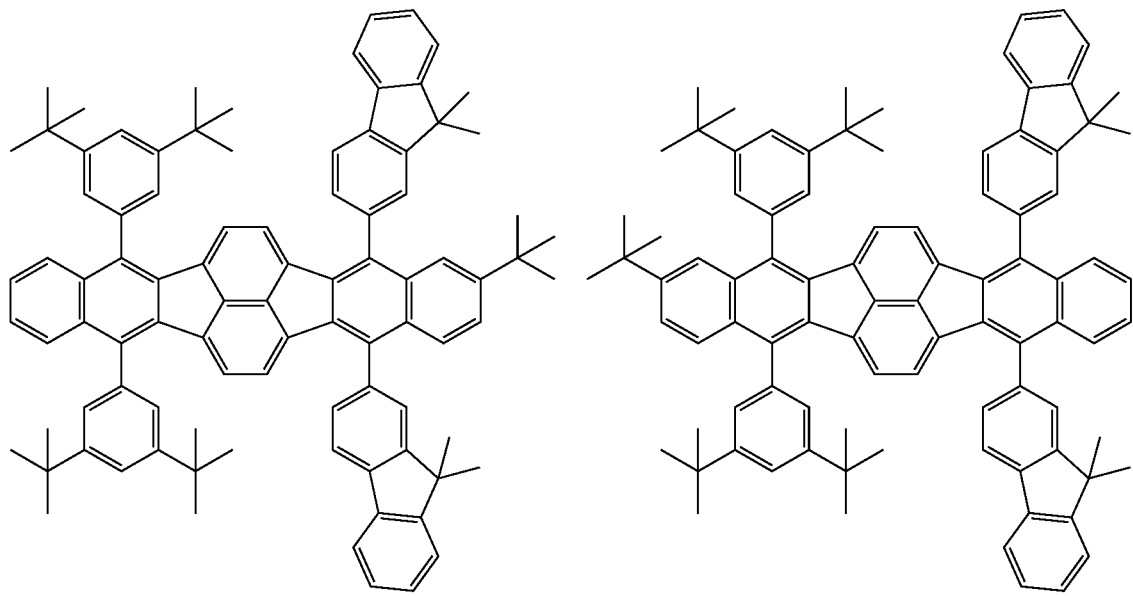

169 170
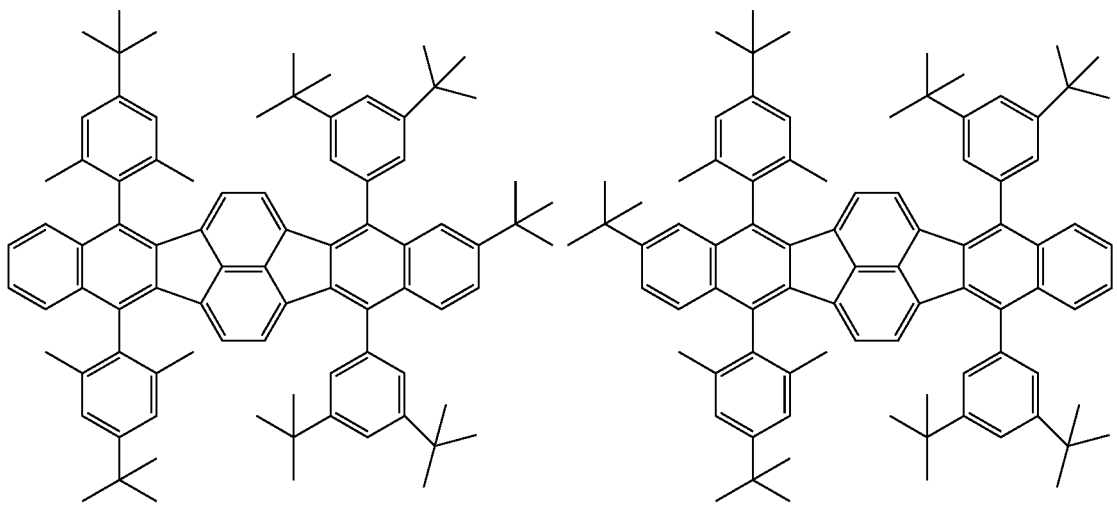
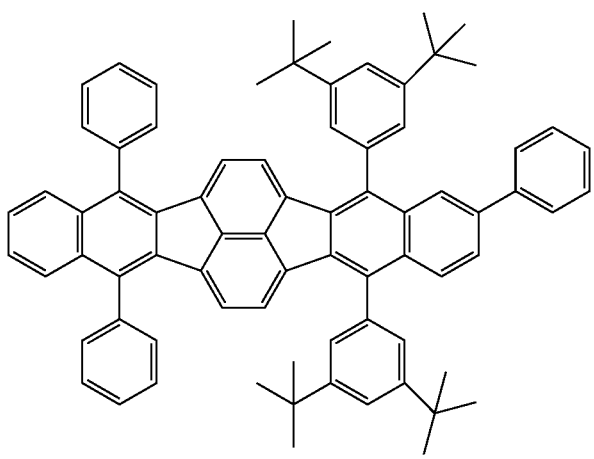
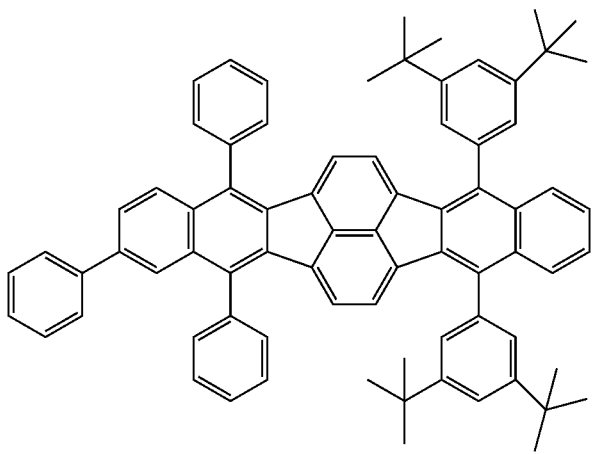

-continued
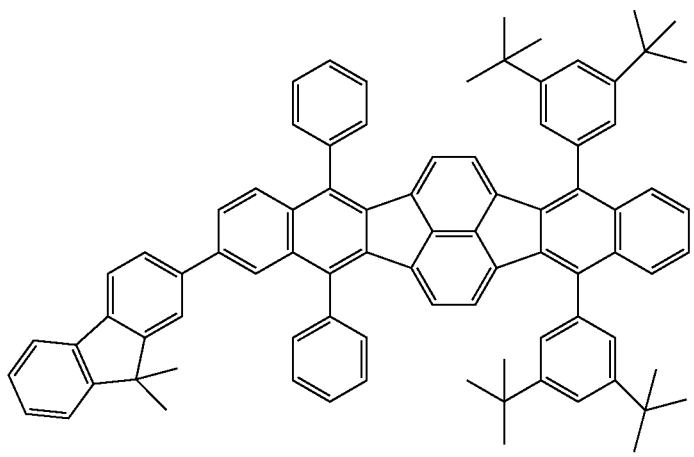
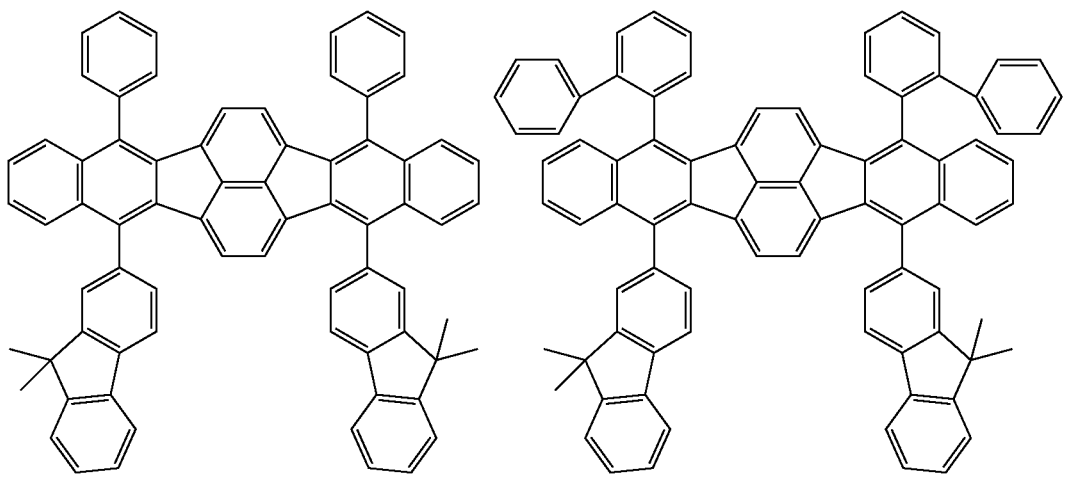
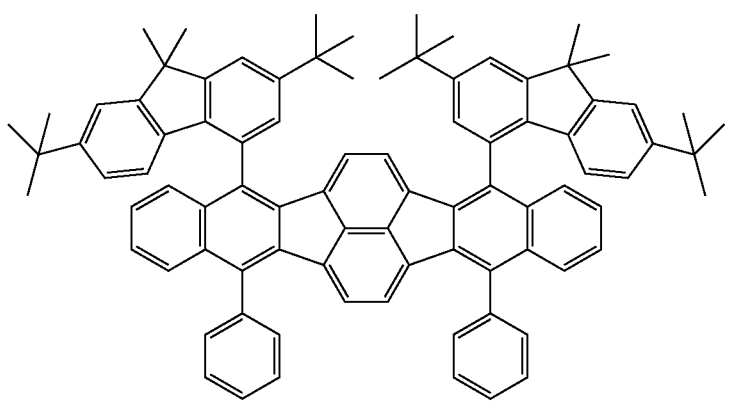

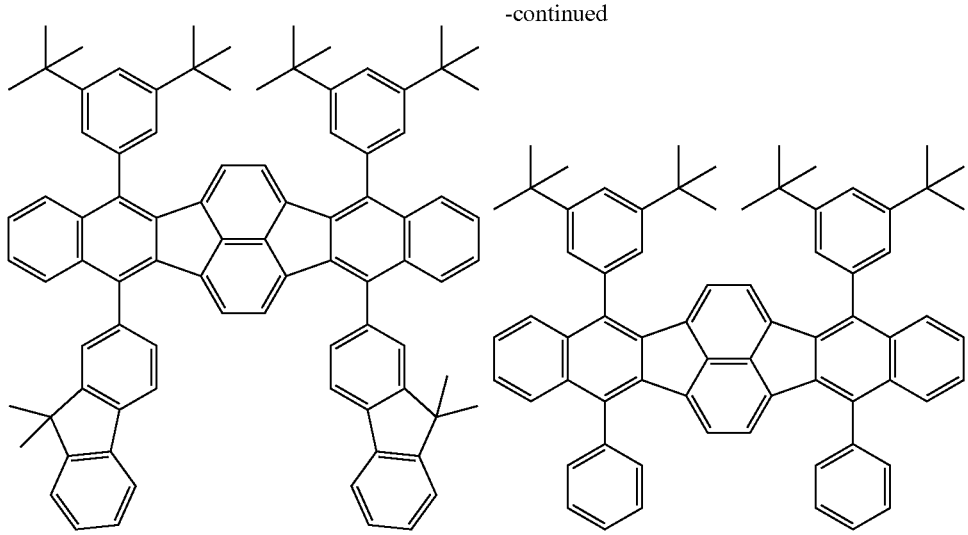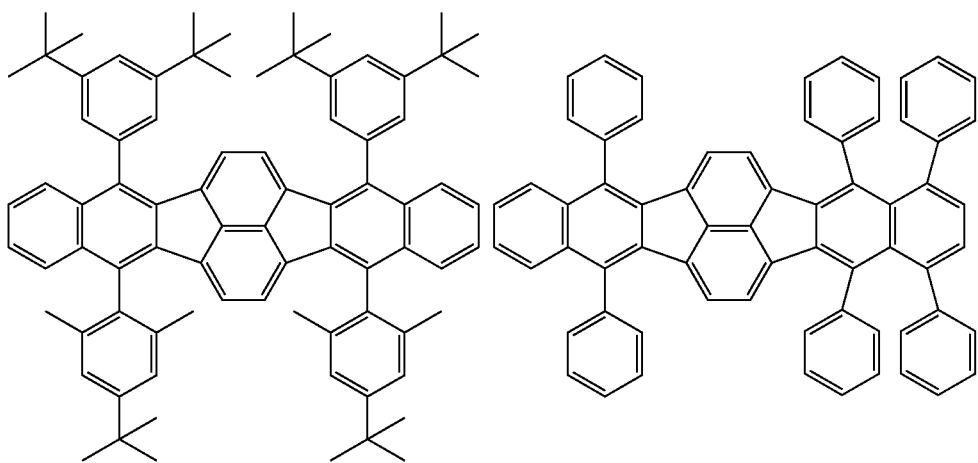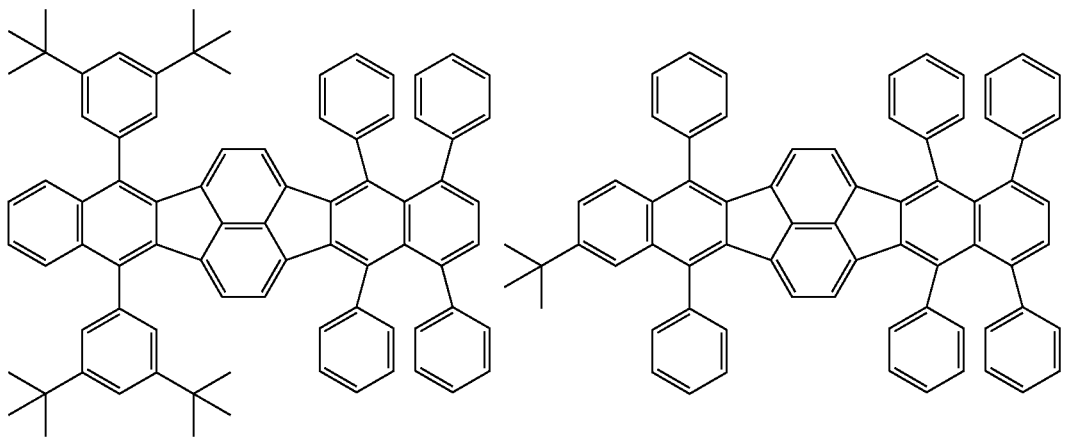

-continued
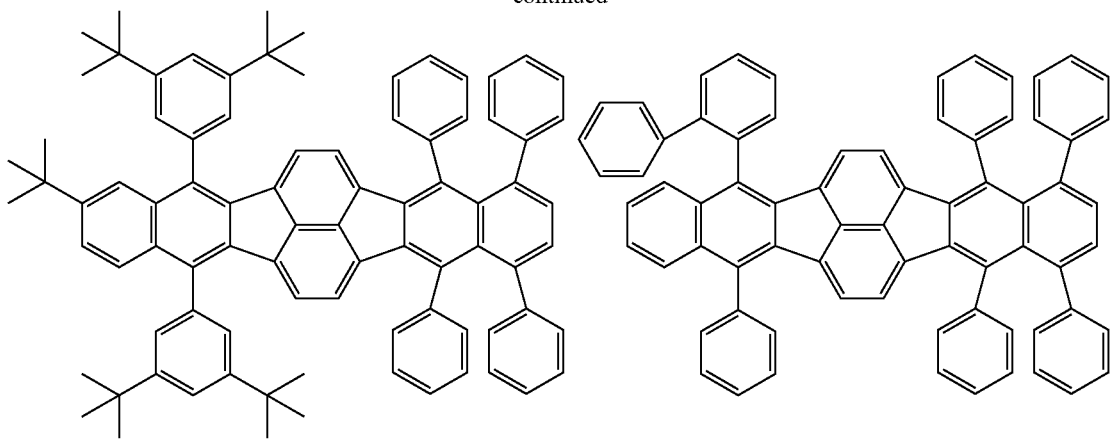
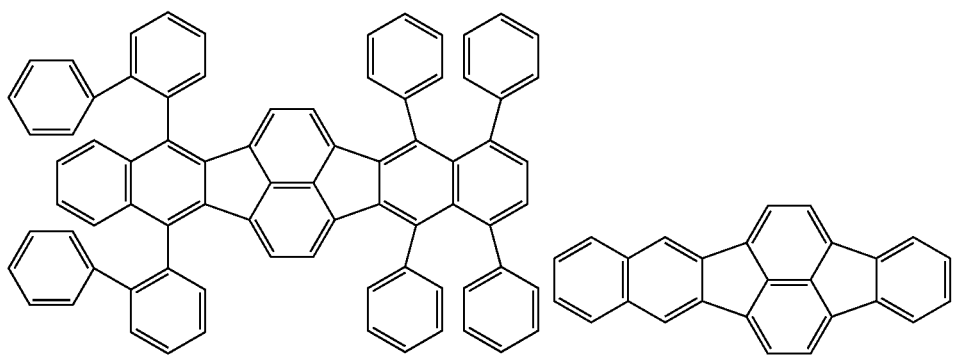
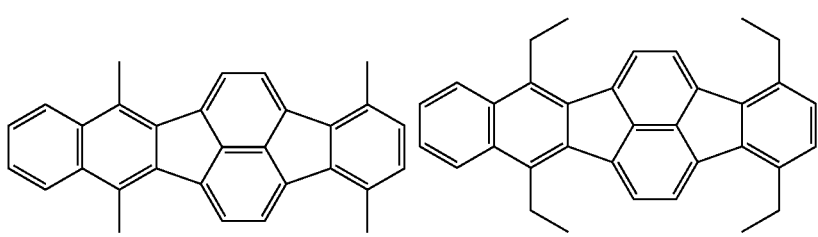
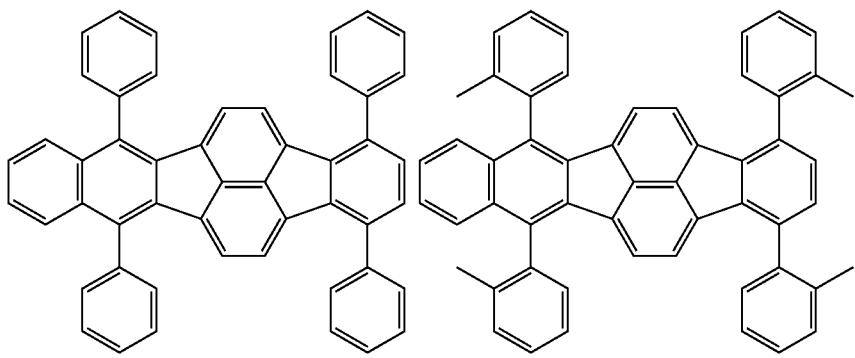

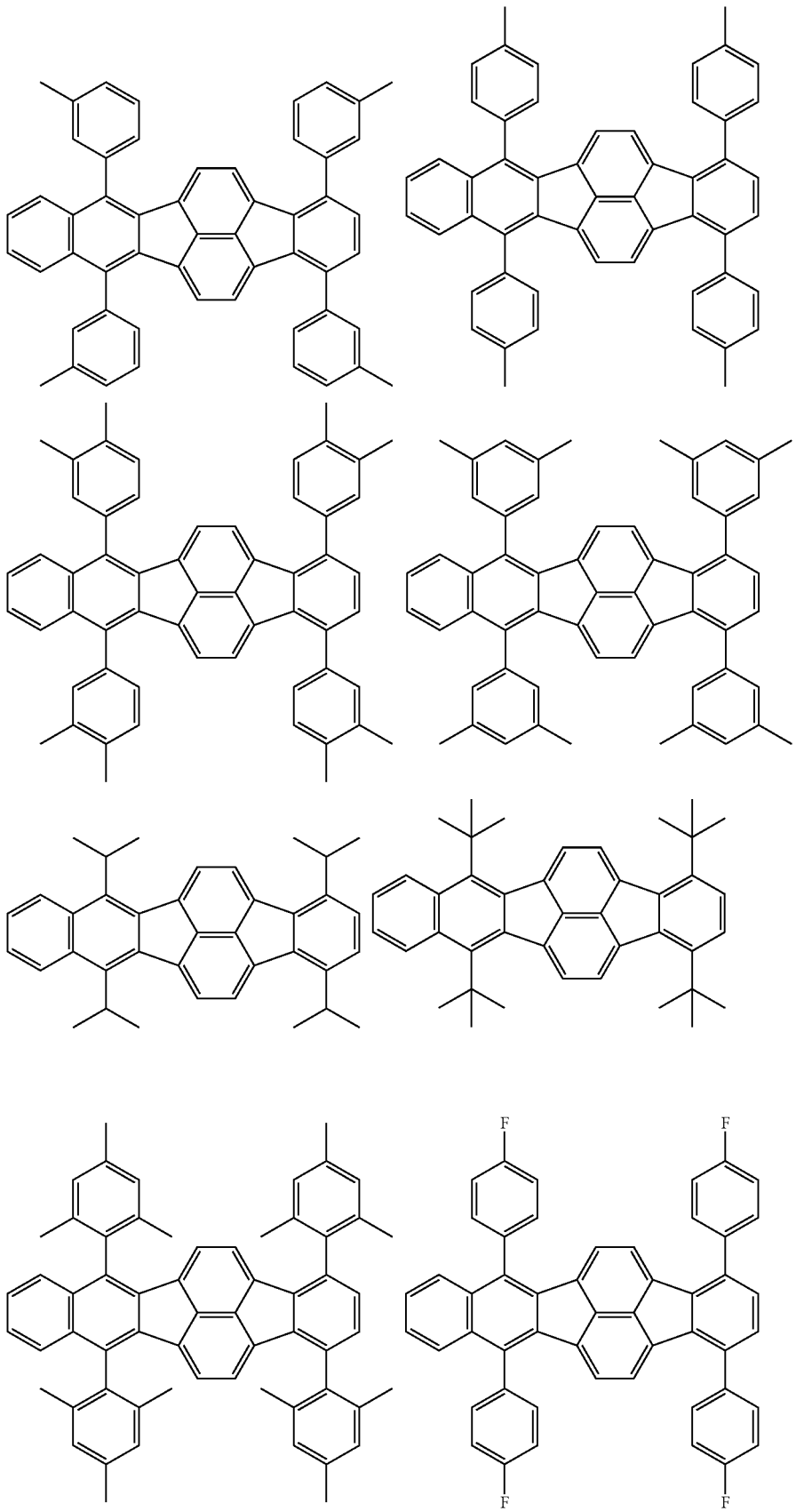

-continued
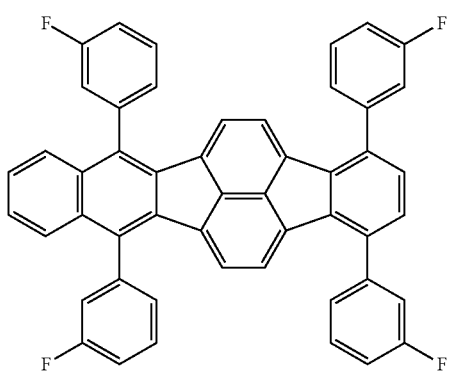
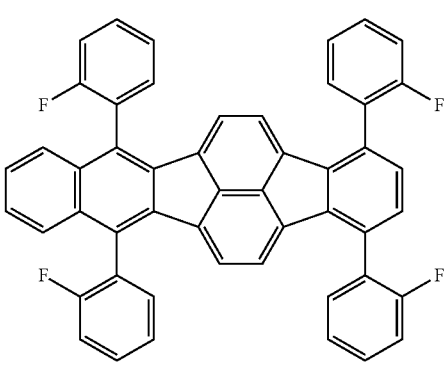
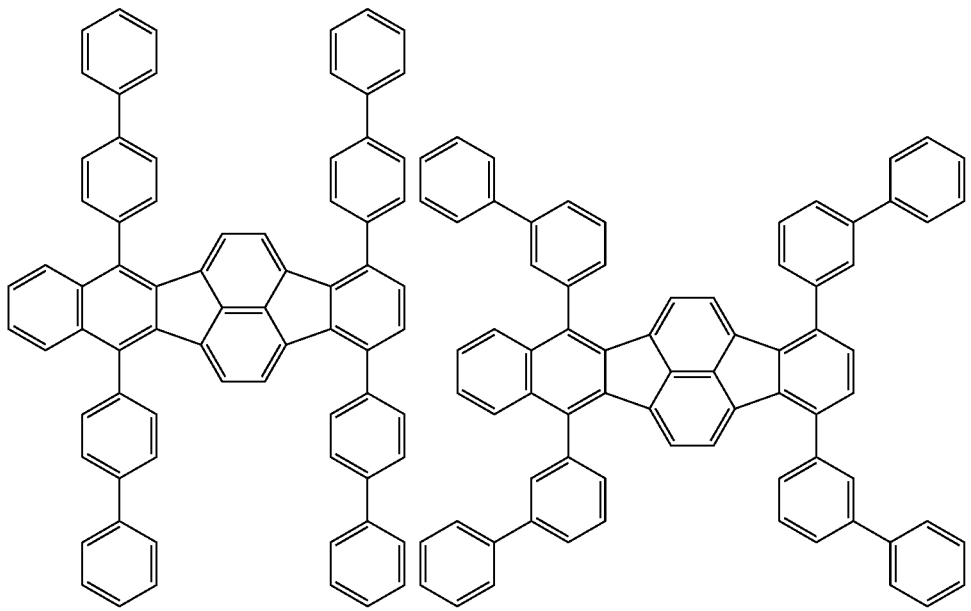
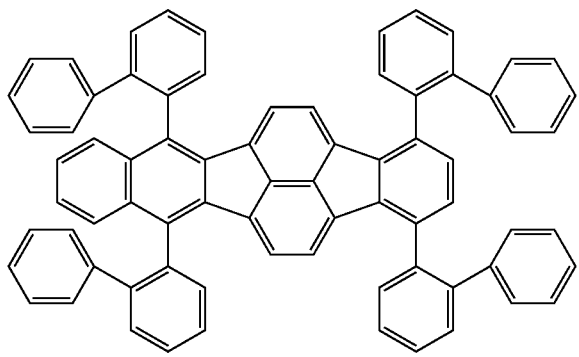

181 182
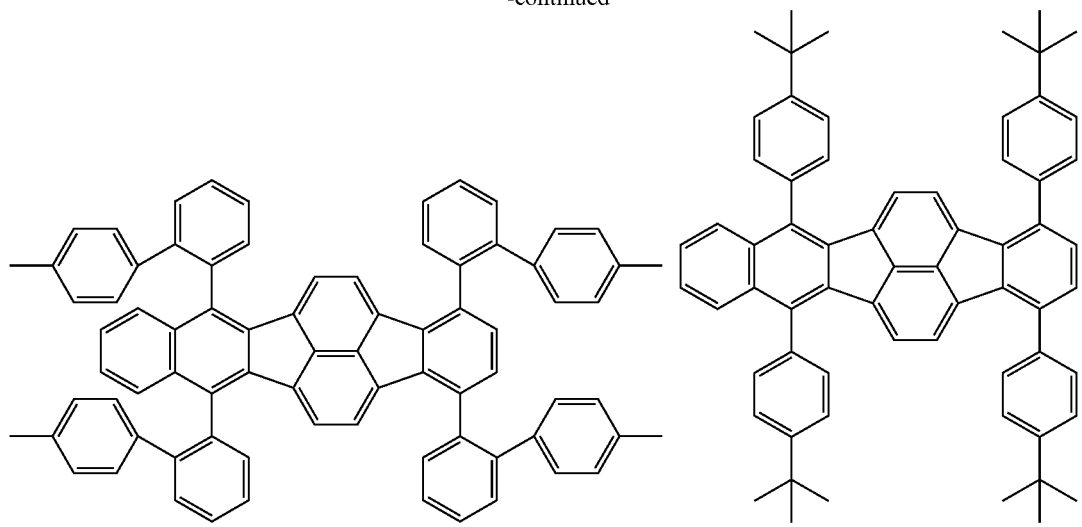
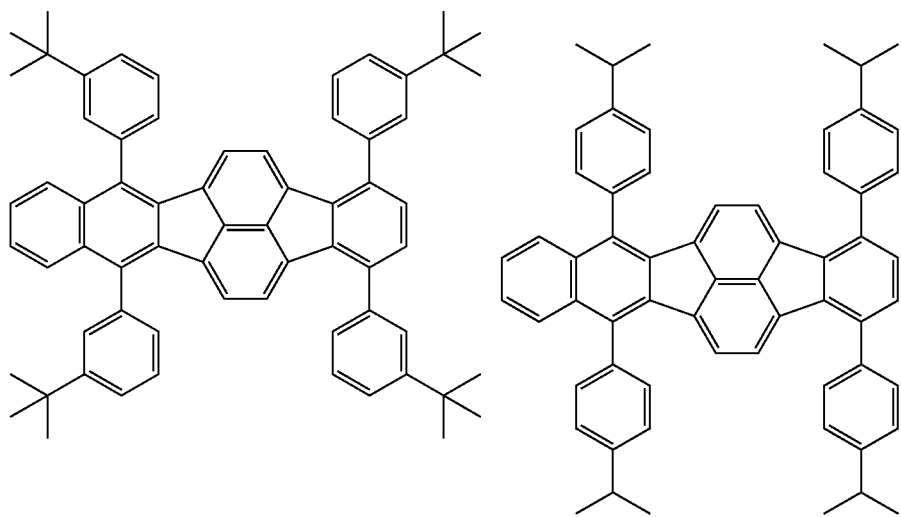
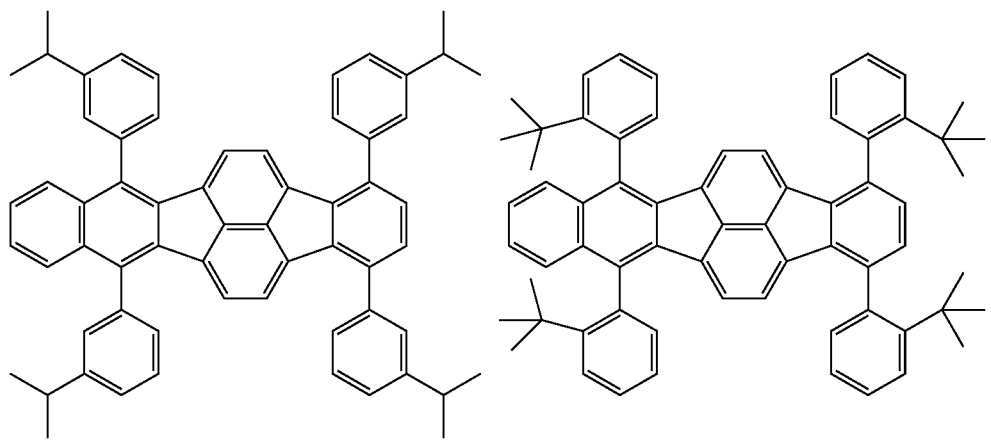

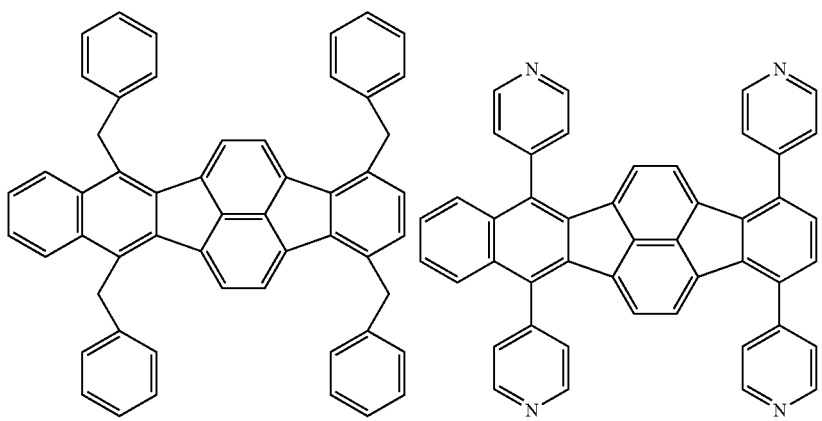
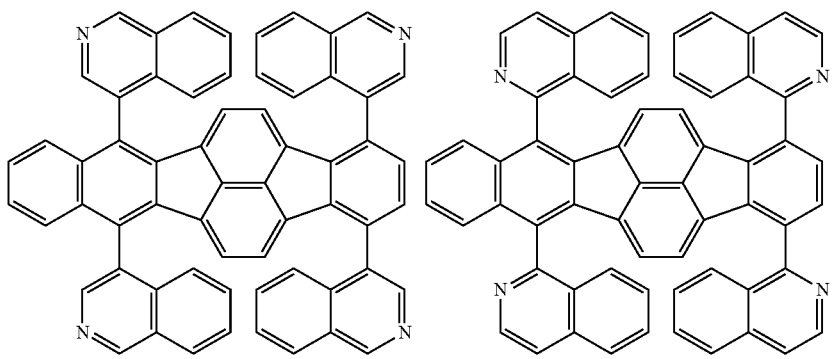
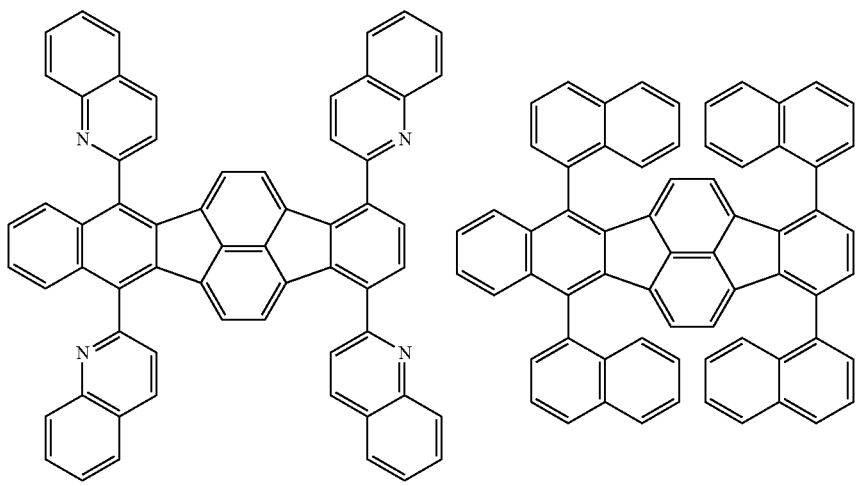

-continued
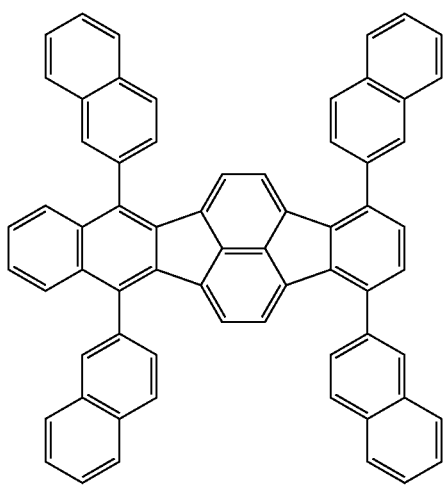
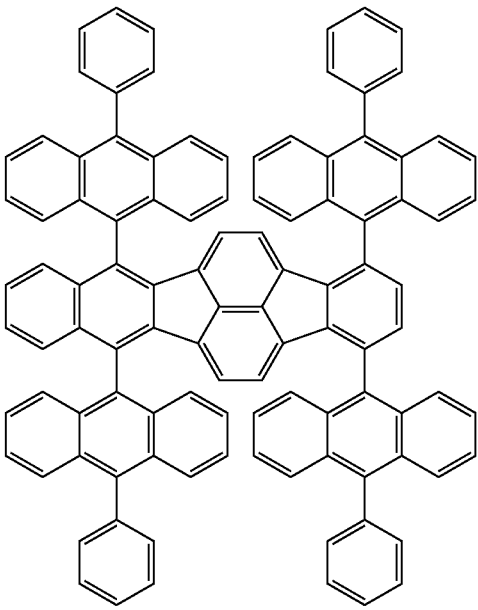
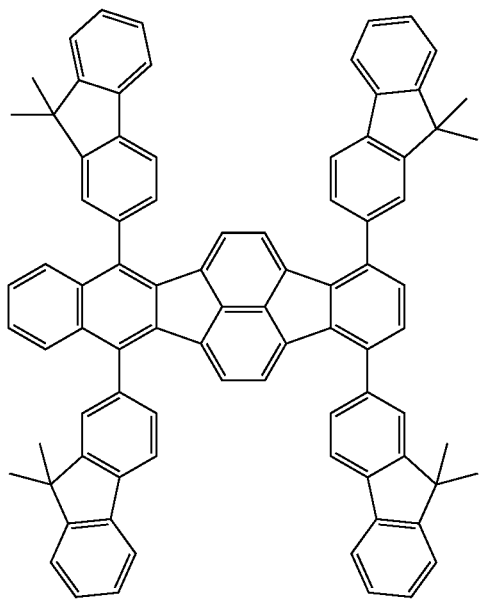
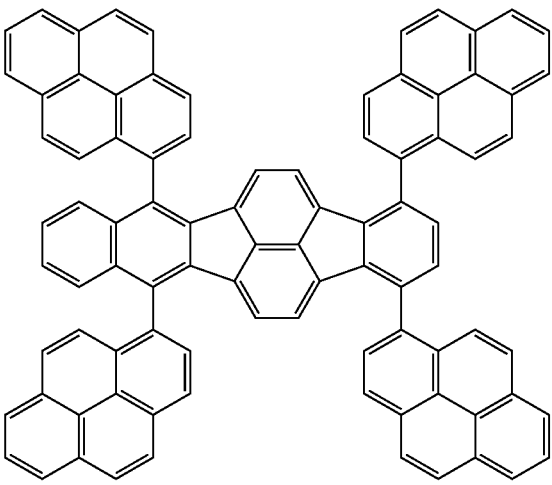
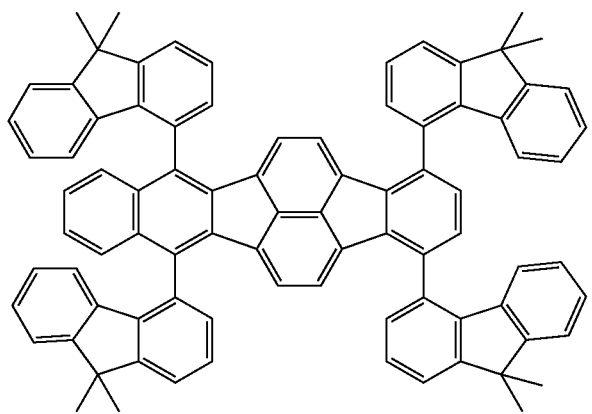

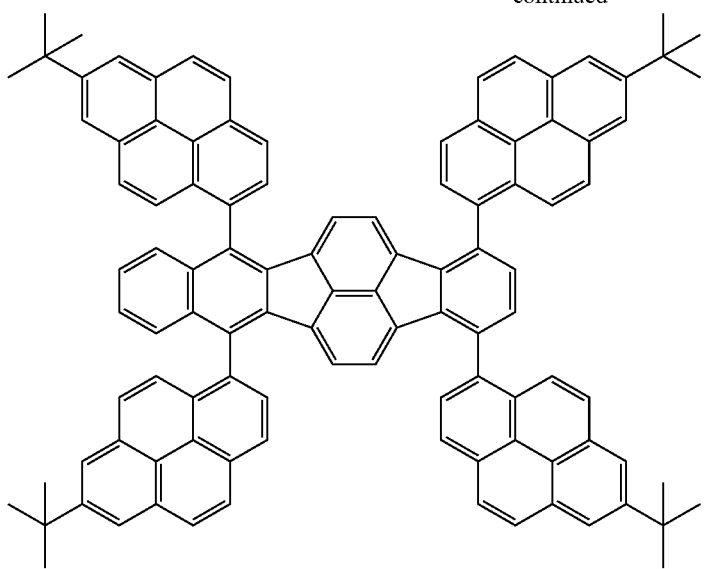
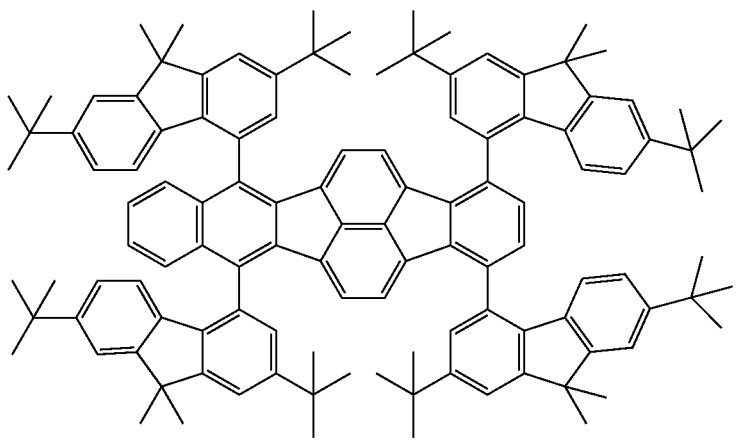
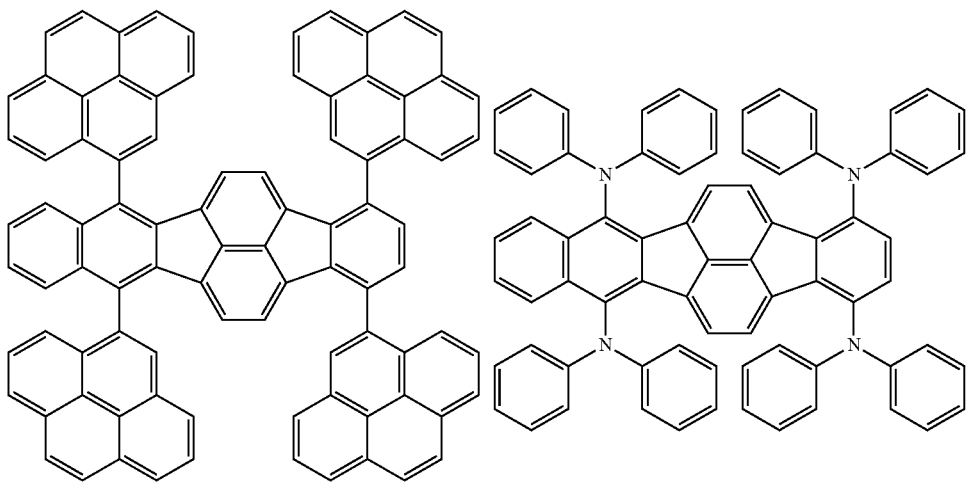

189 190
-continued
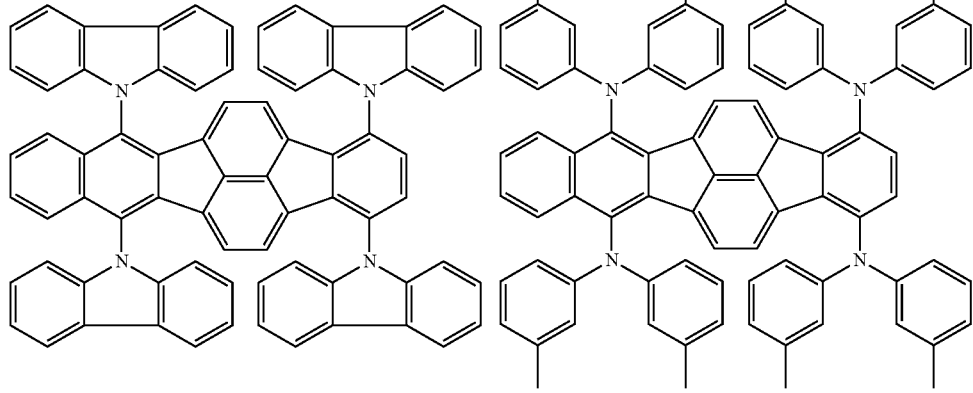
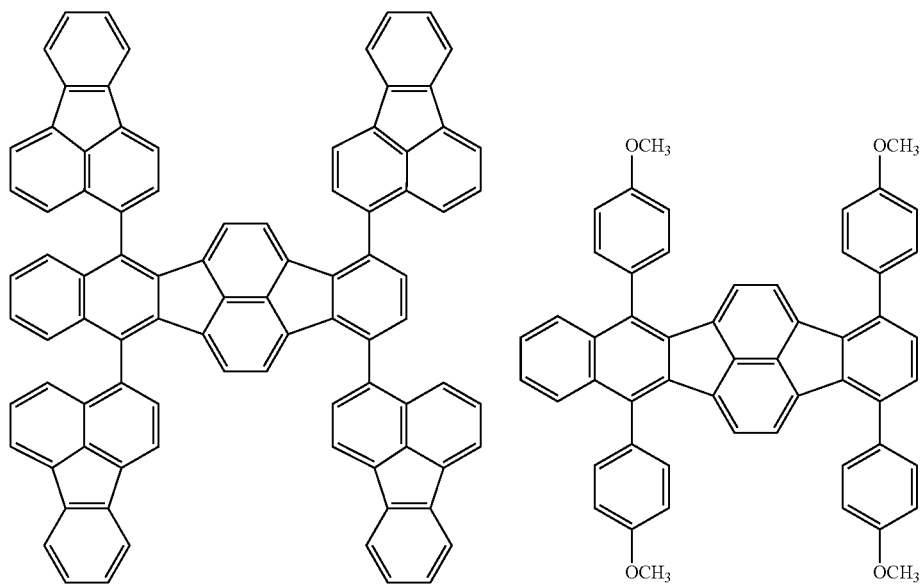

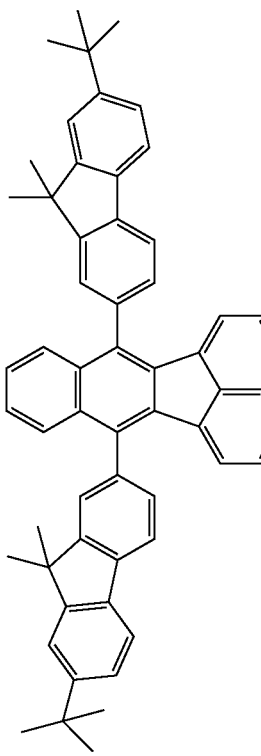 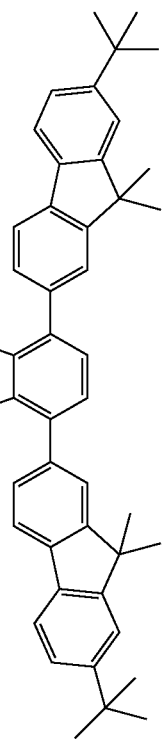 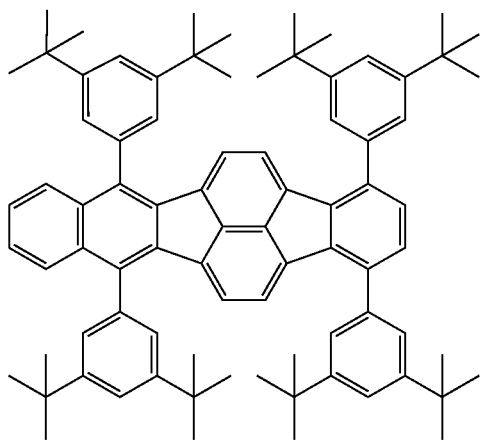
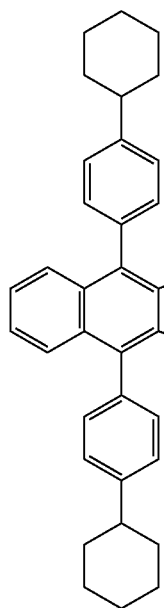 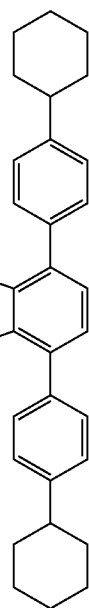 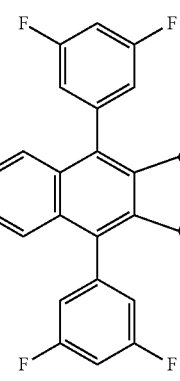 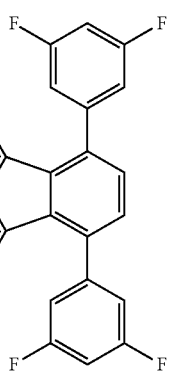

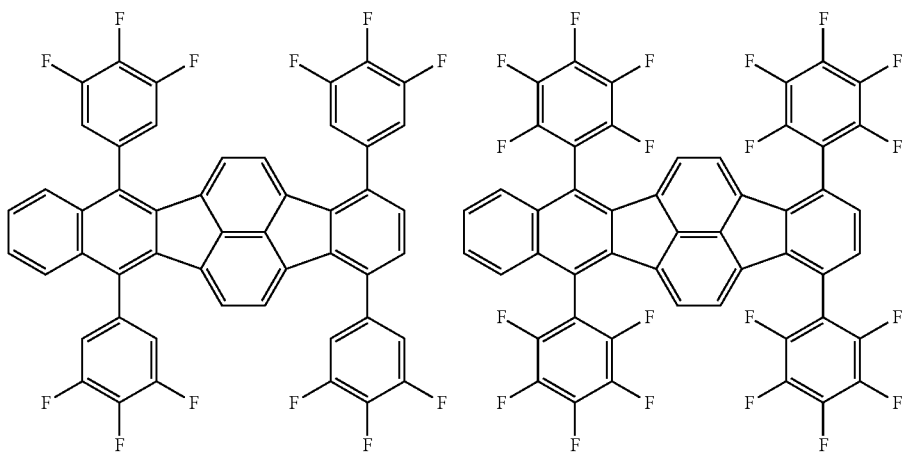
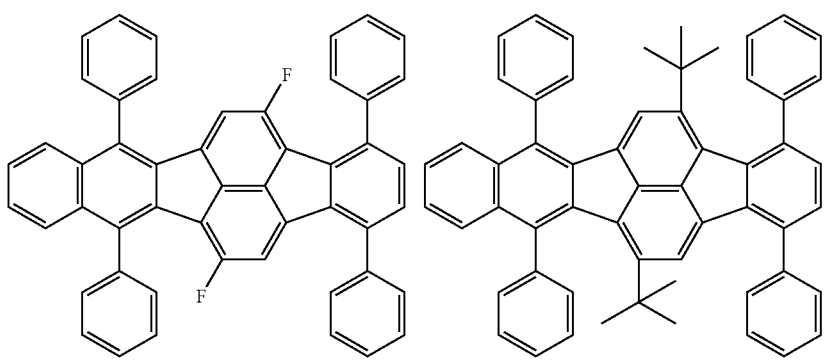
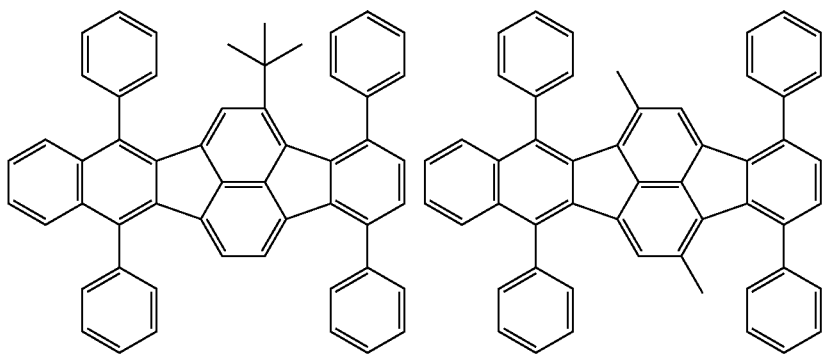
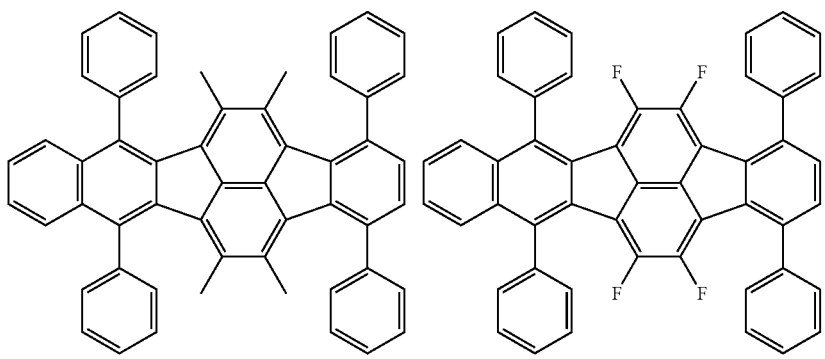

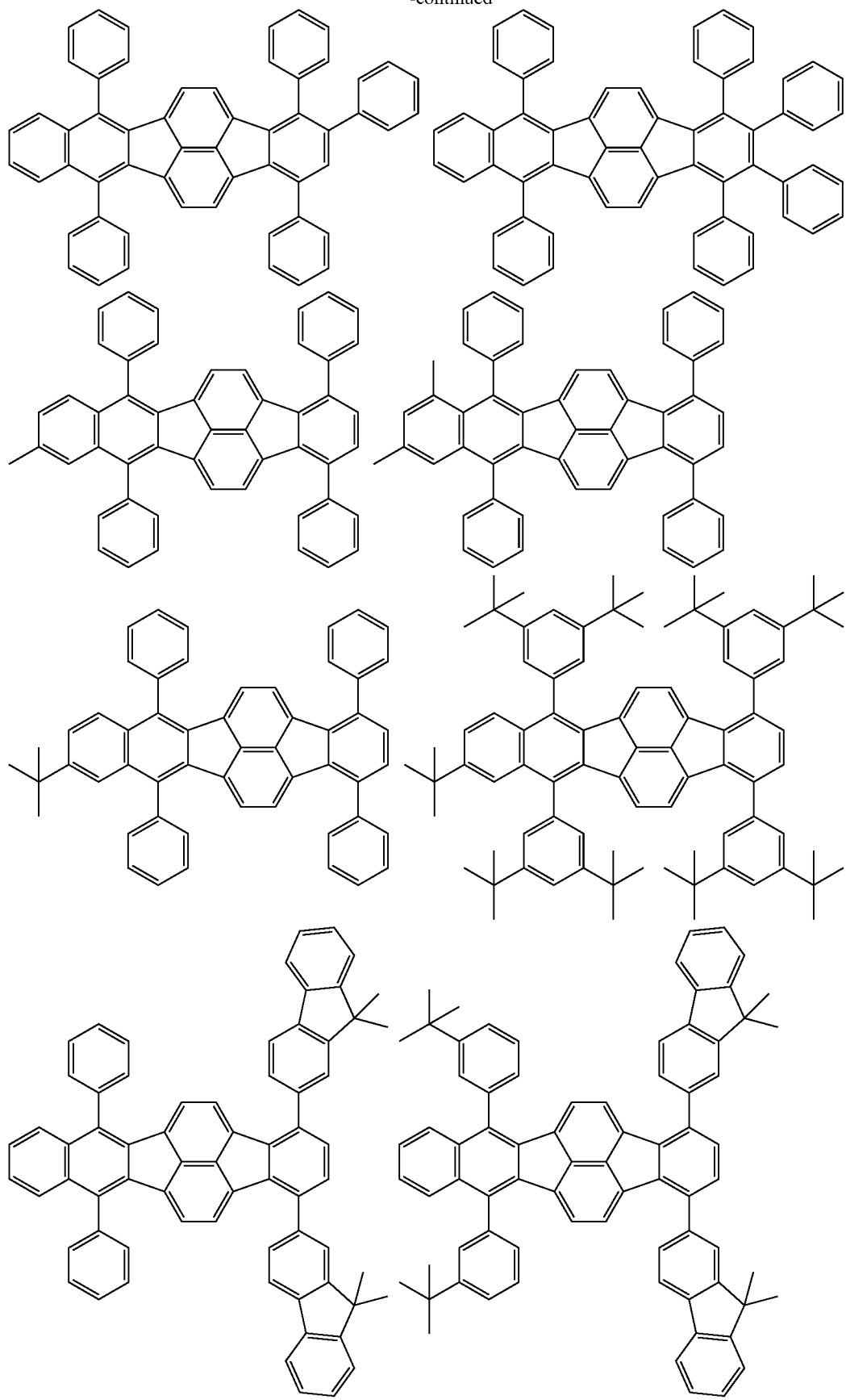

-continued
197 198
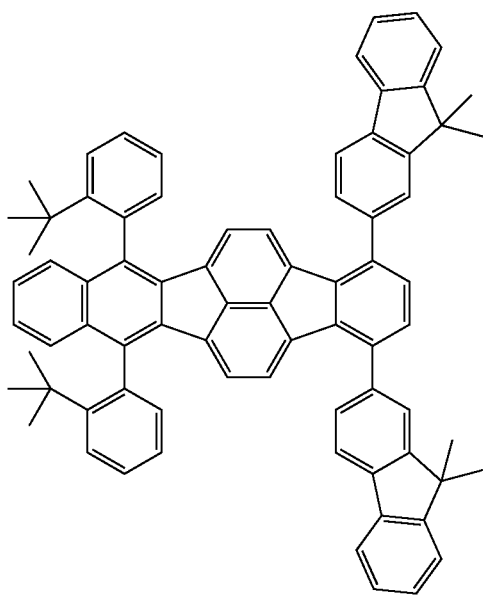
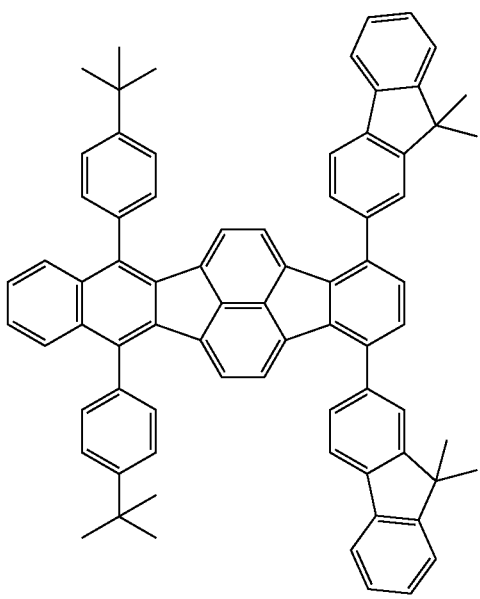
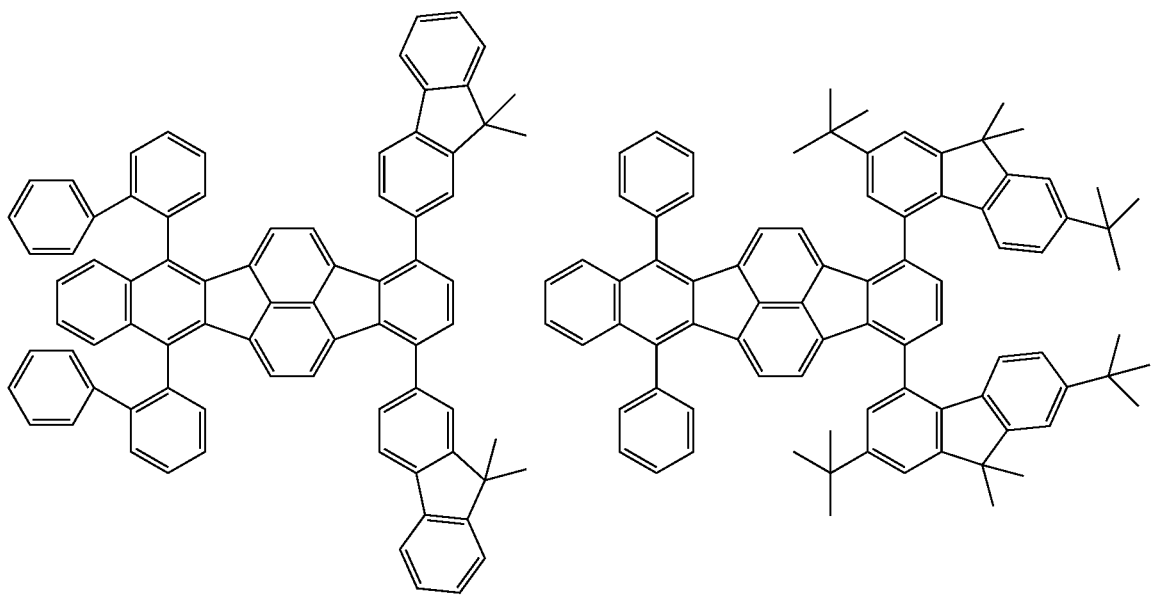

-continued
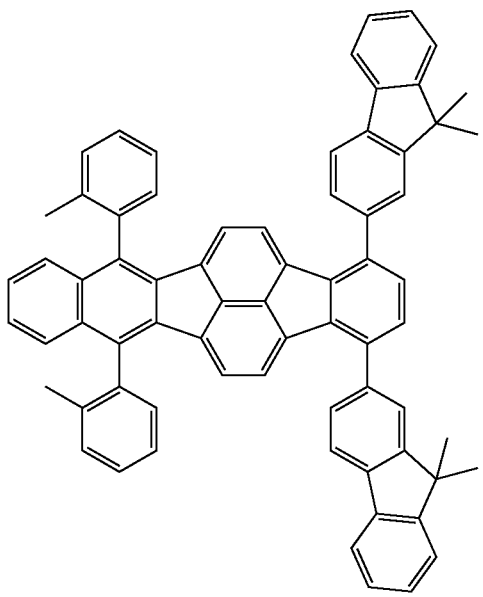
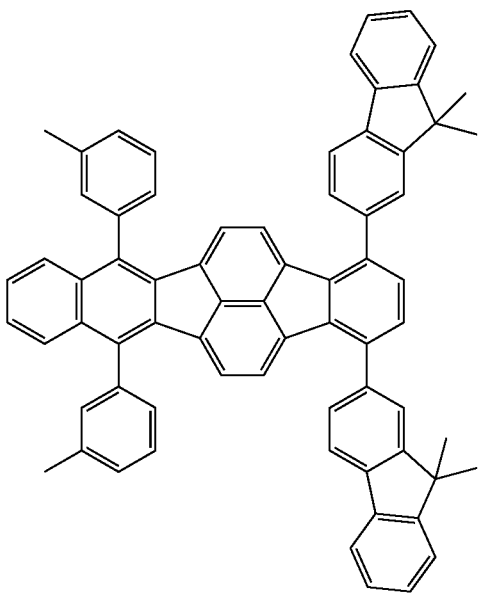
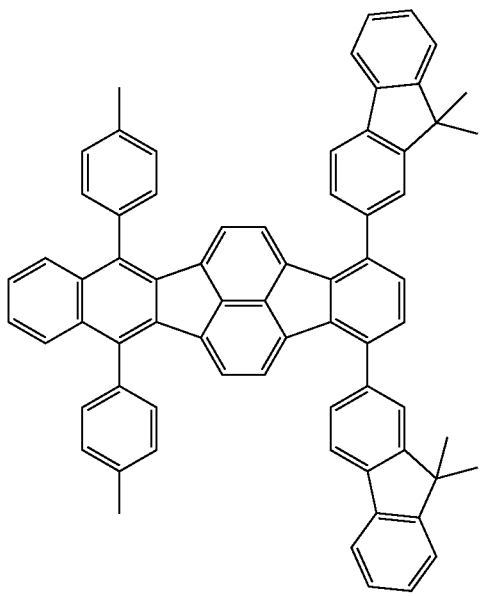
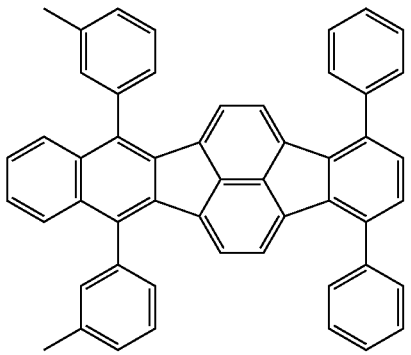
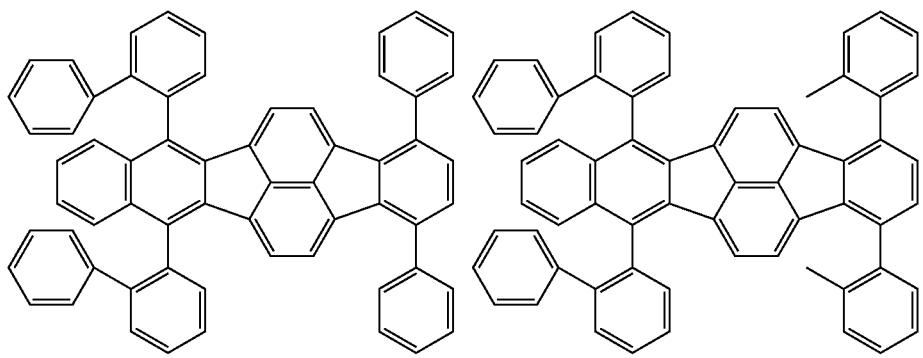

201
202
-continued
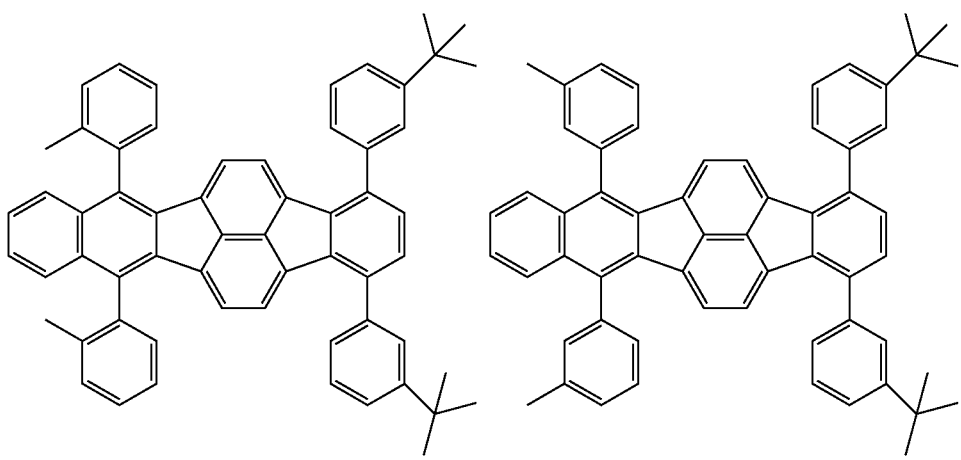
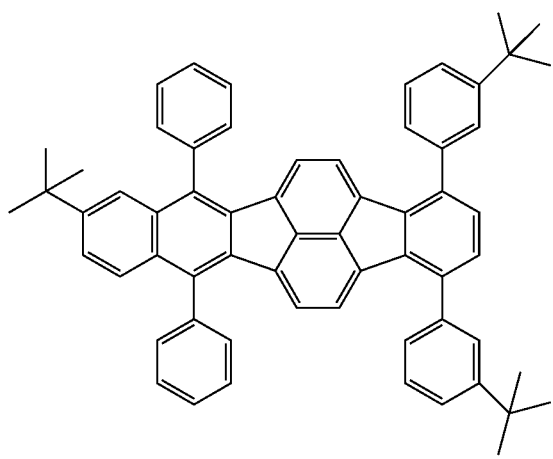
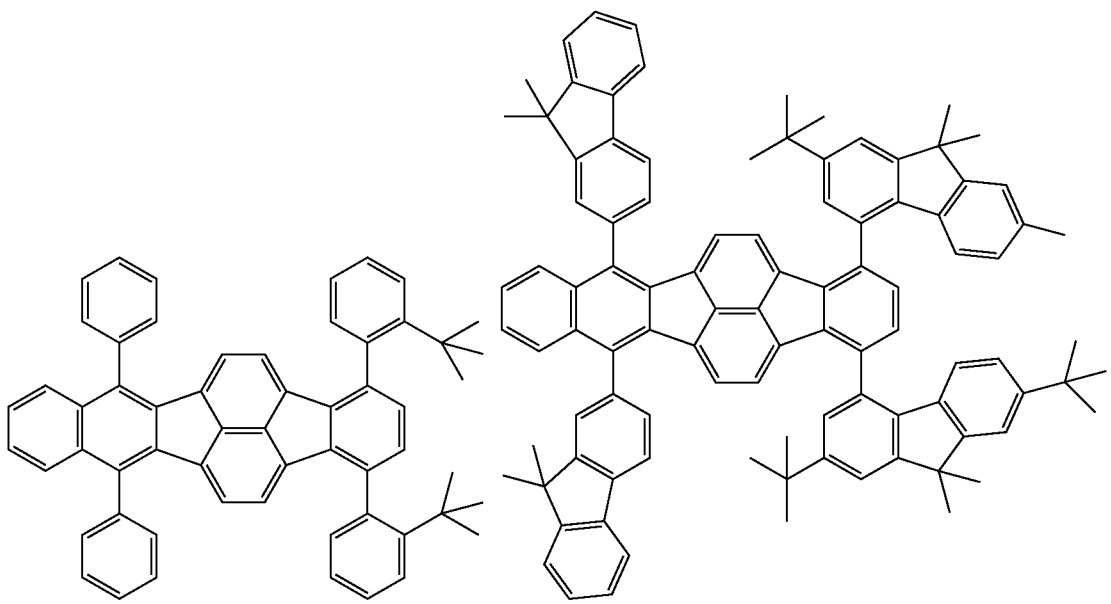

-continued
203
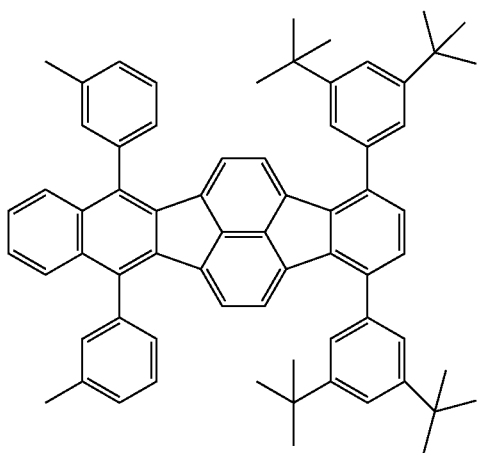
204
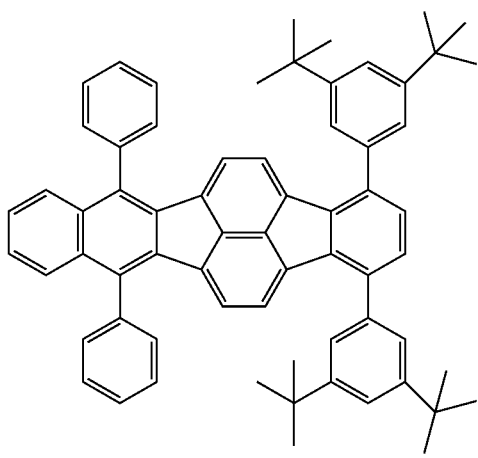
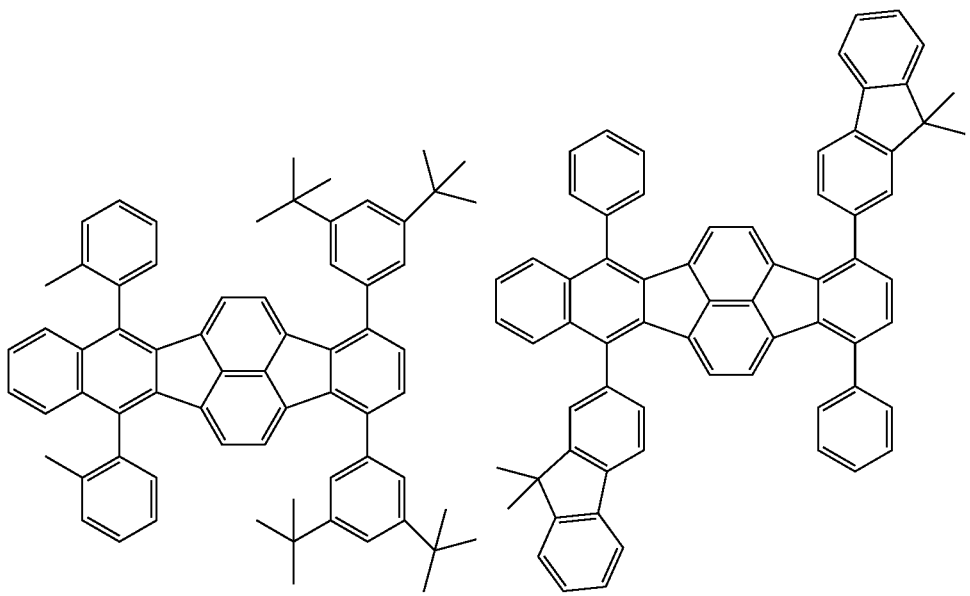
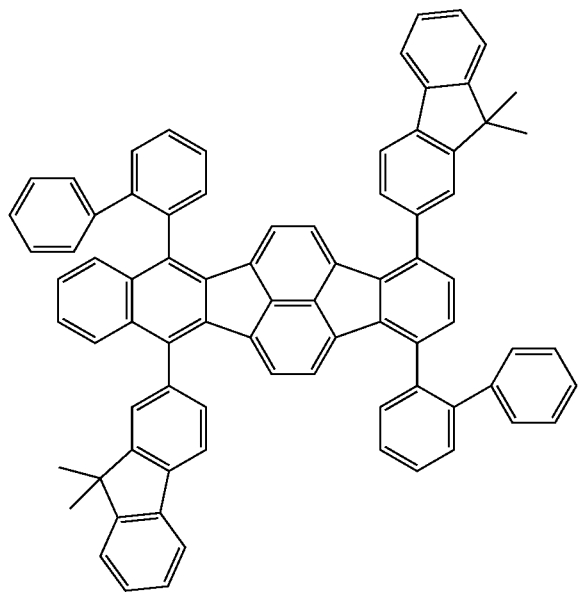

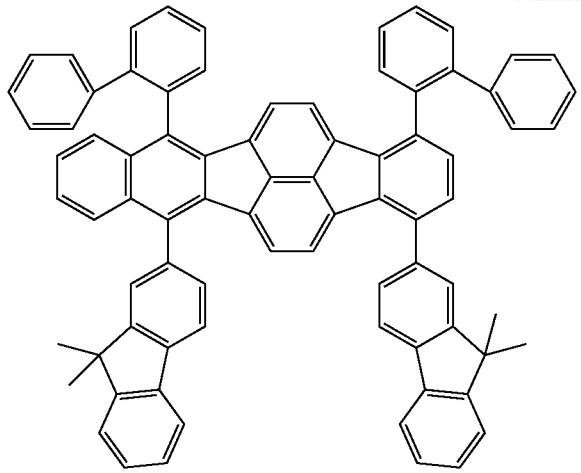
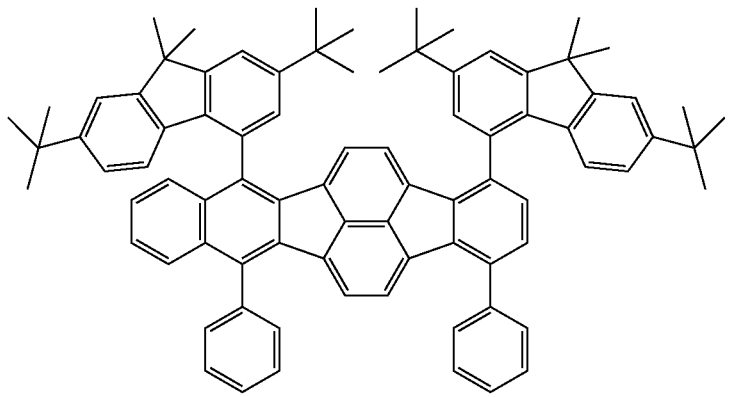
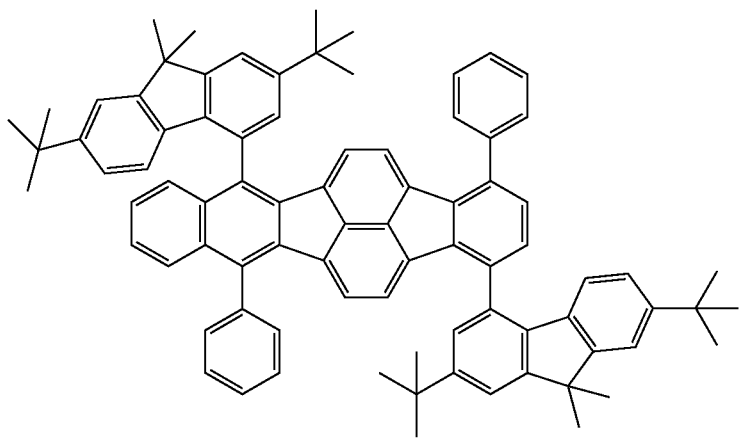
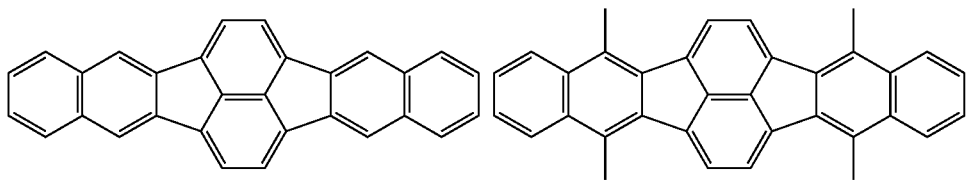

207
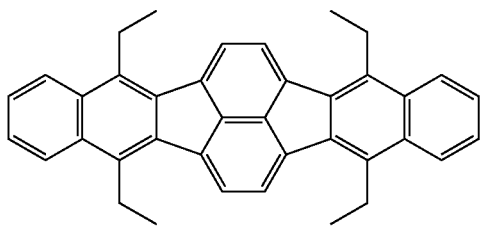
208
-continued
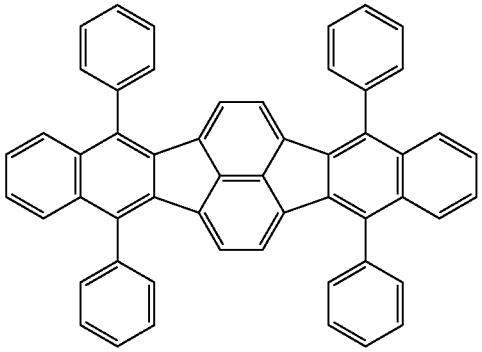
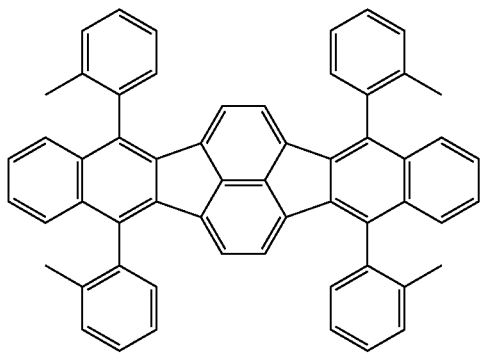
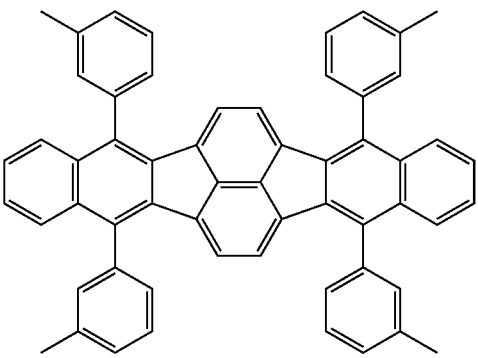
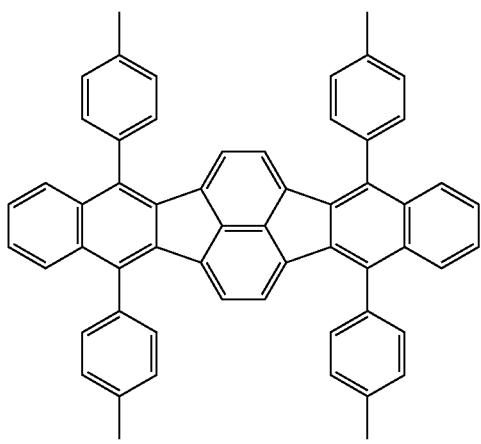
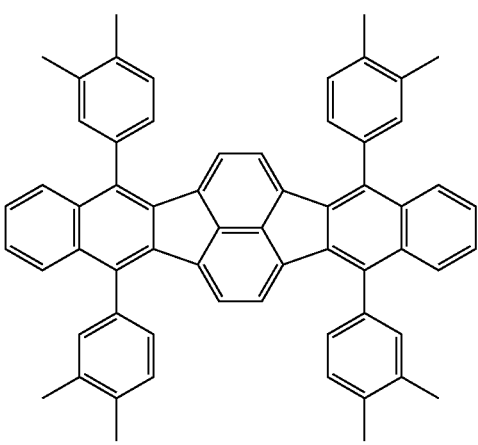
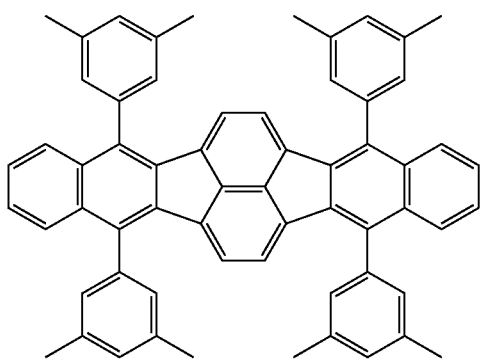
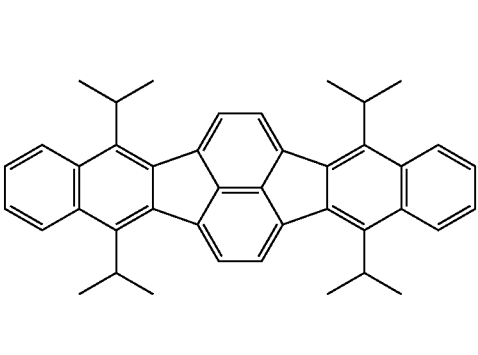

-continued
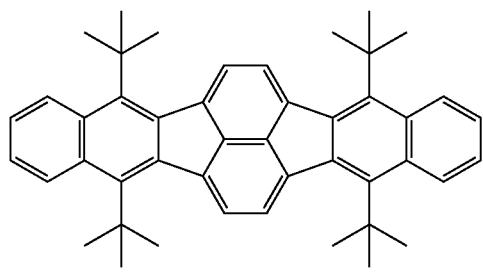
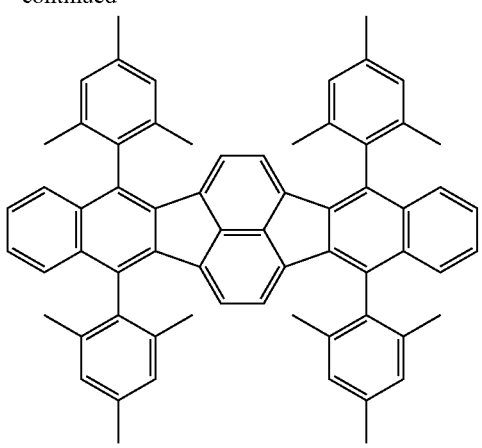
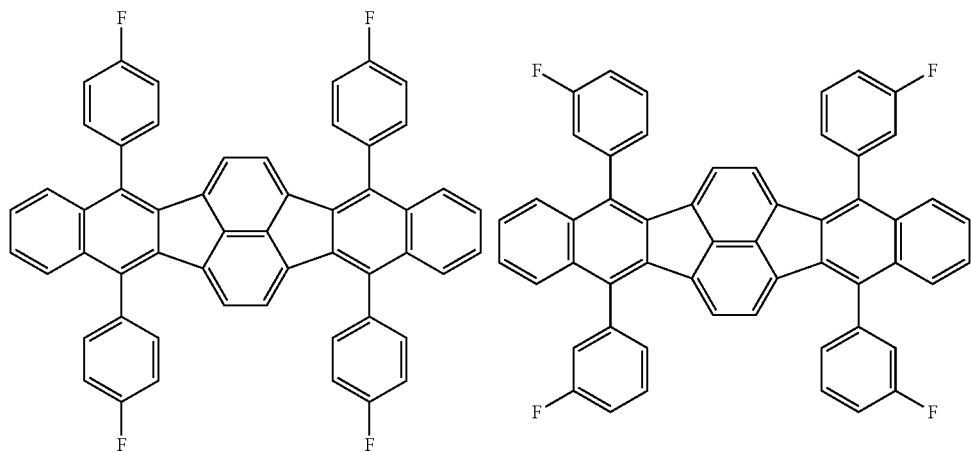
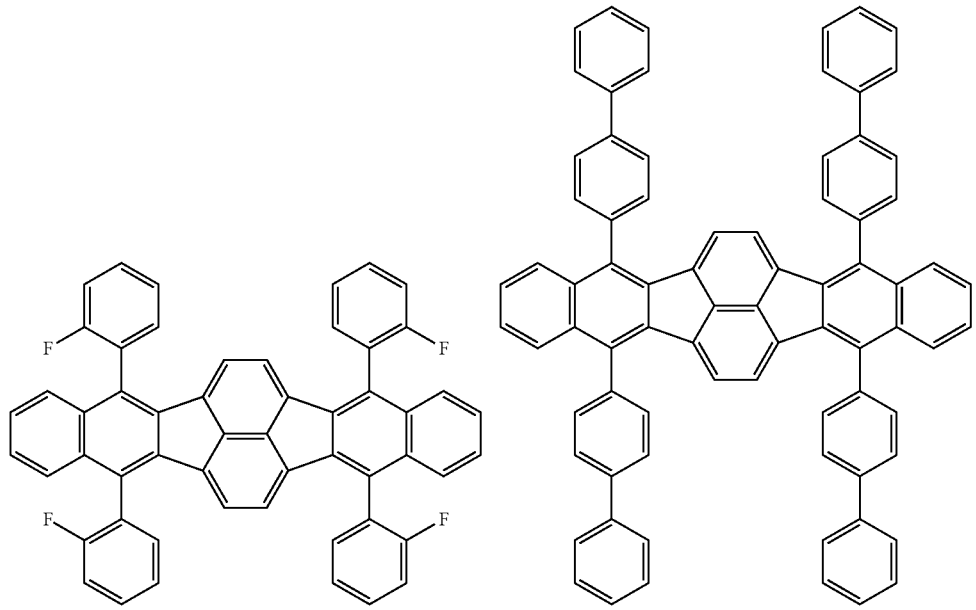

-continued
211    212
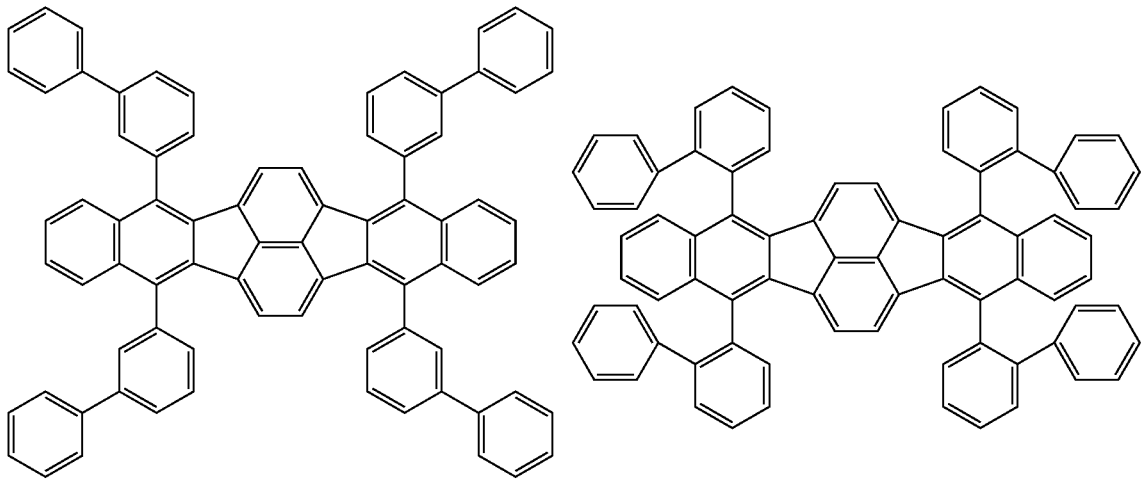
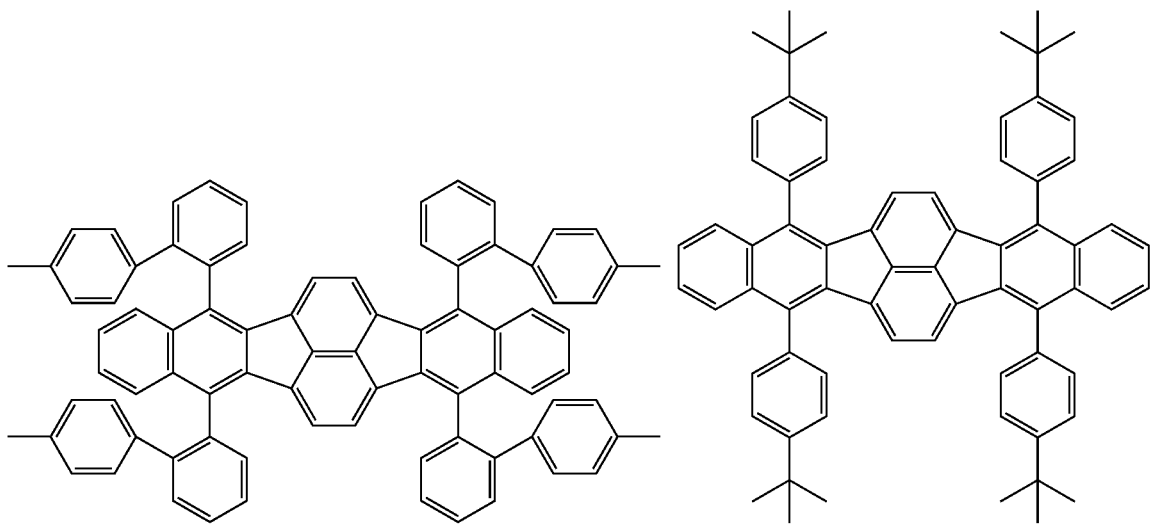
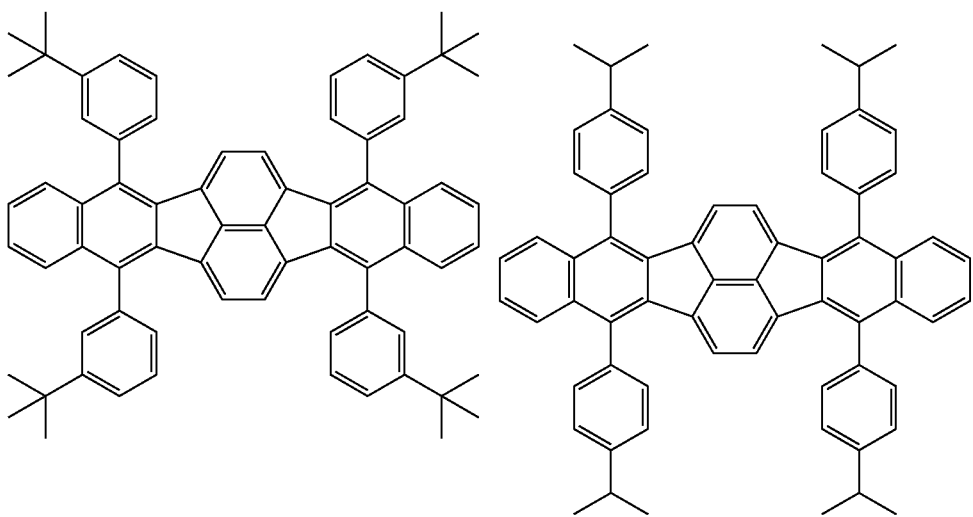

-continued
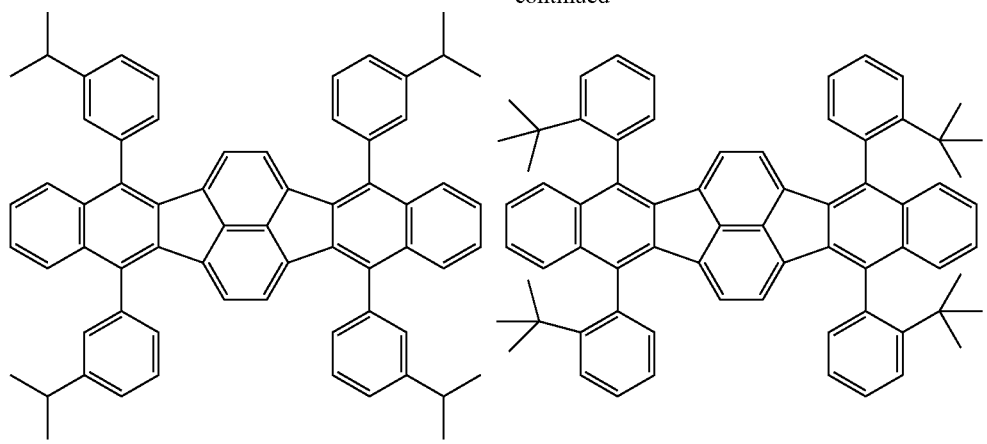
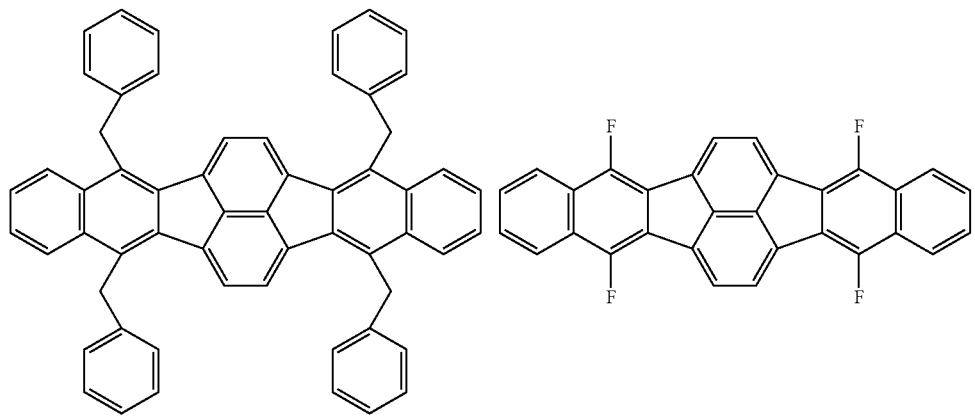
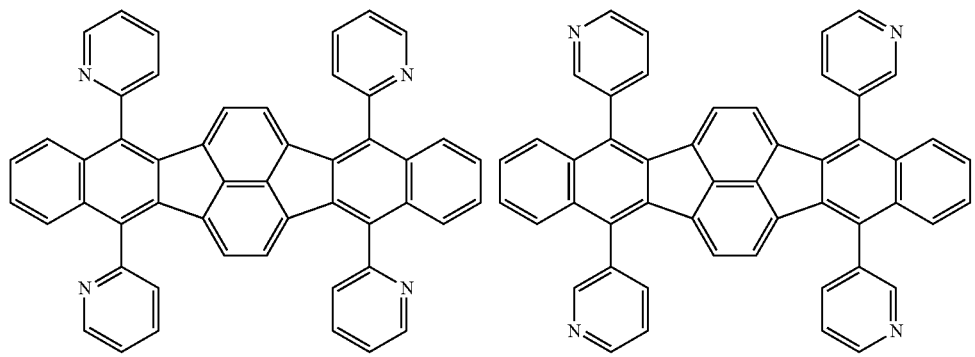
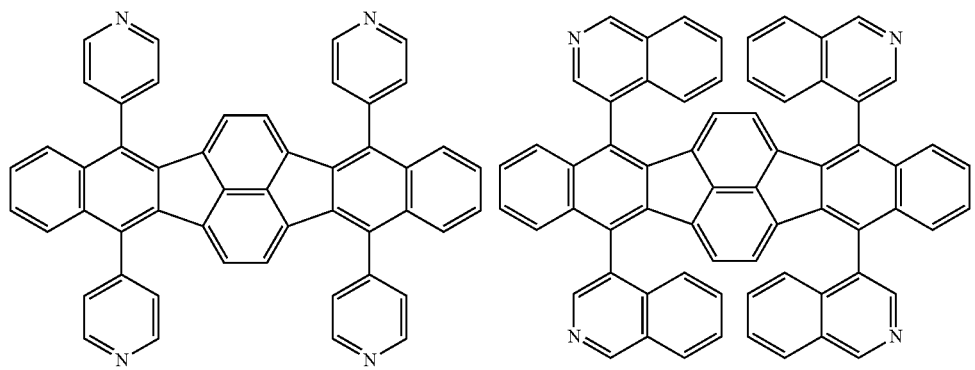

-continued
215
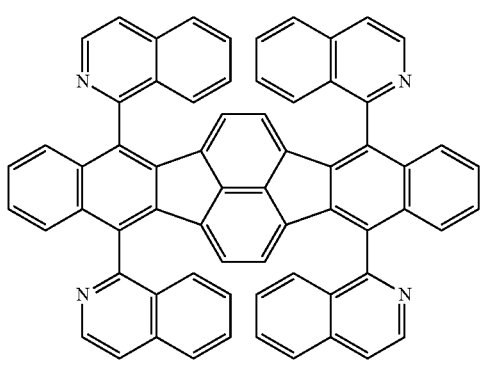
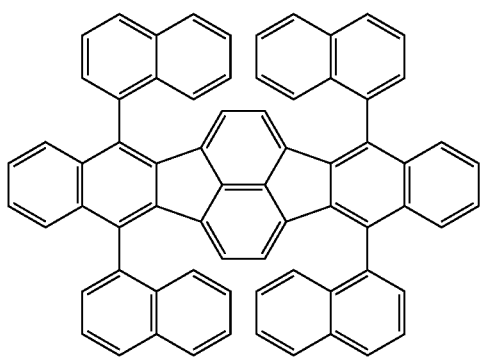
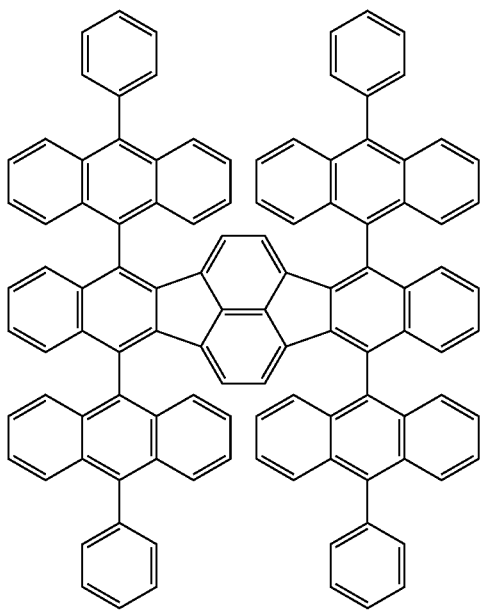
216
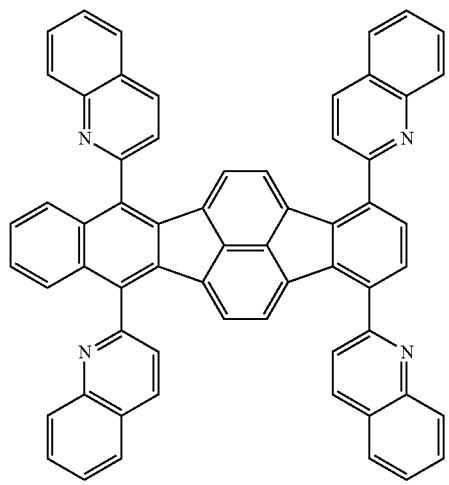
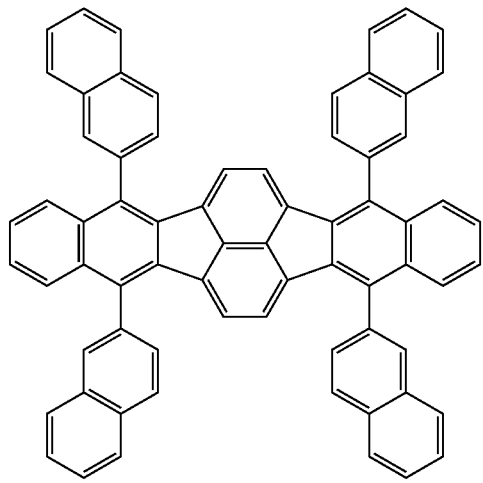
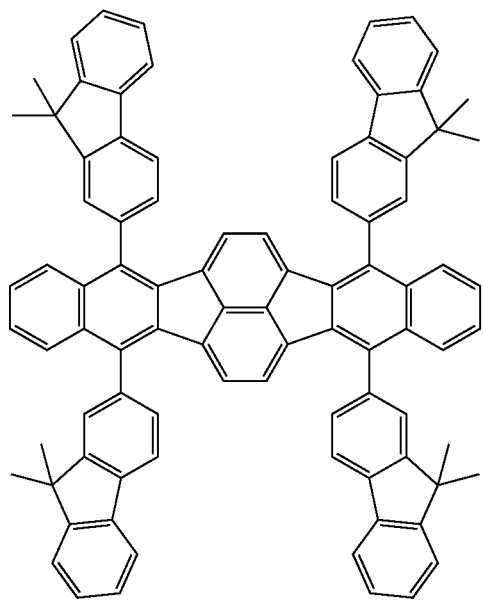

-continued
217
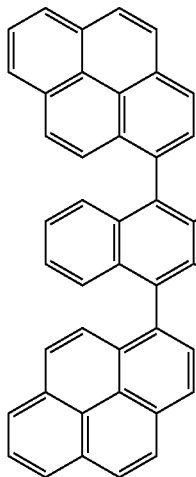 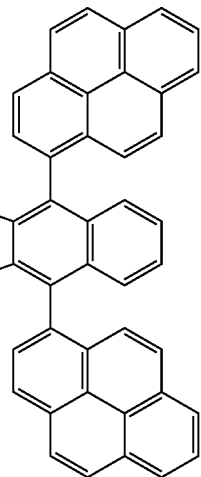
218
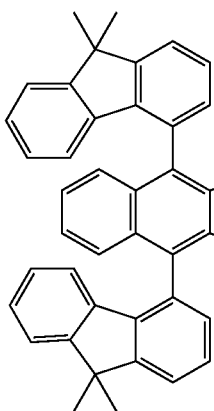 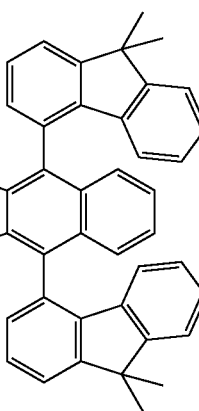
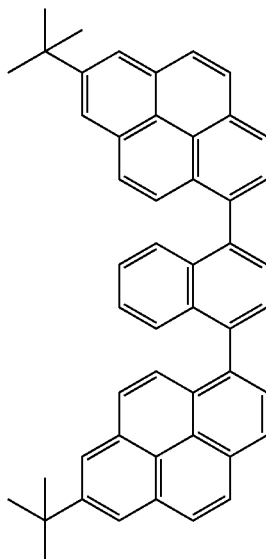 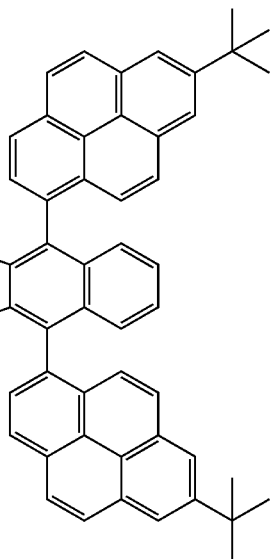
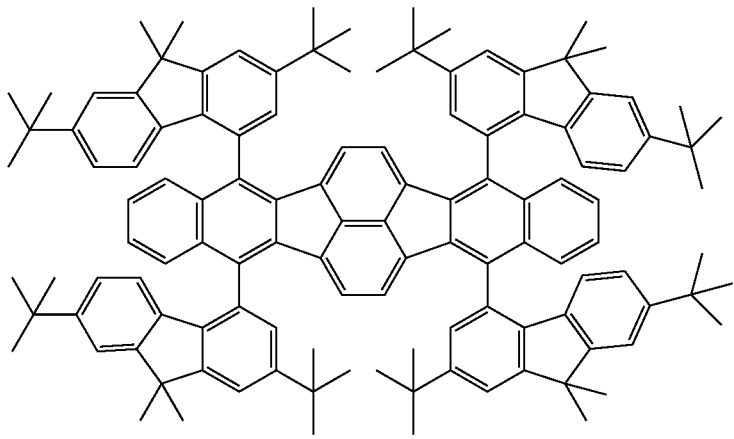

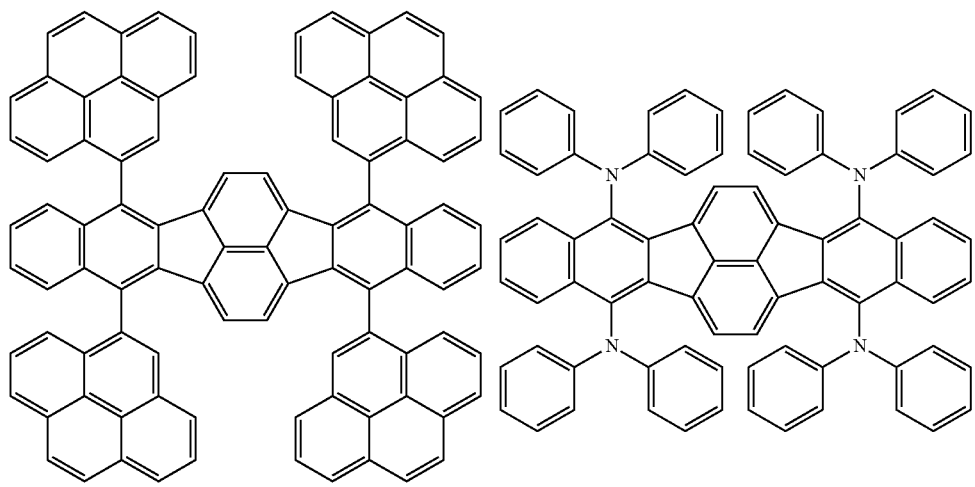
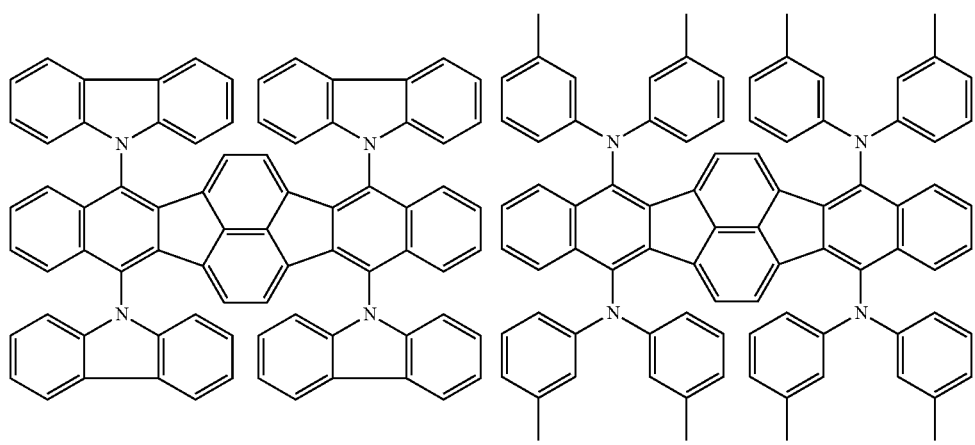
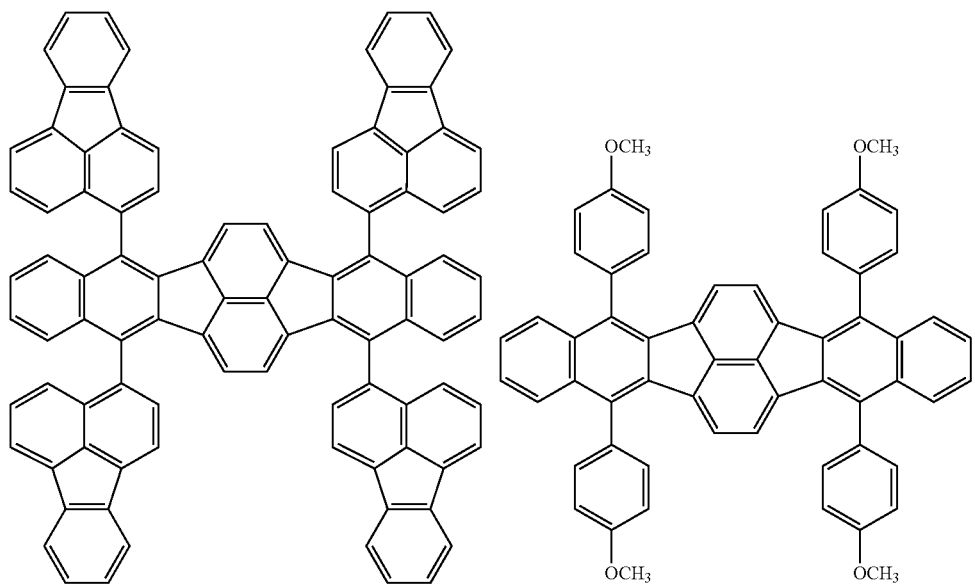

221 222
-continued
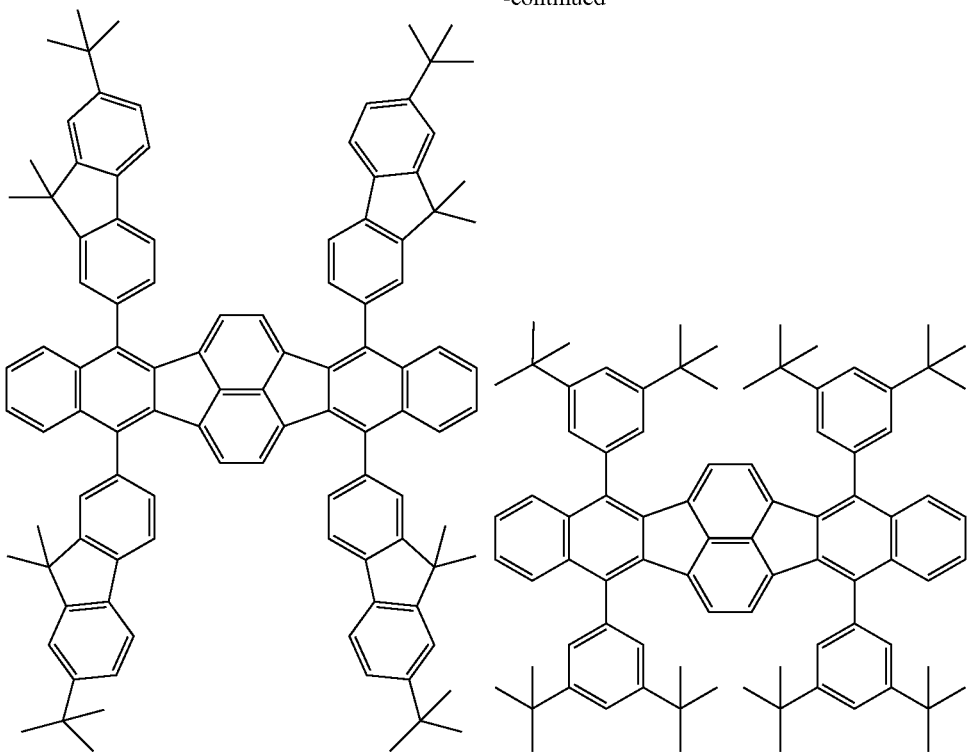
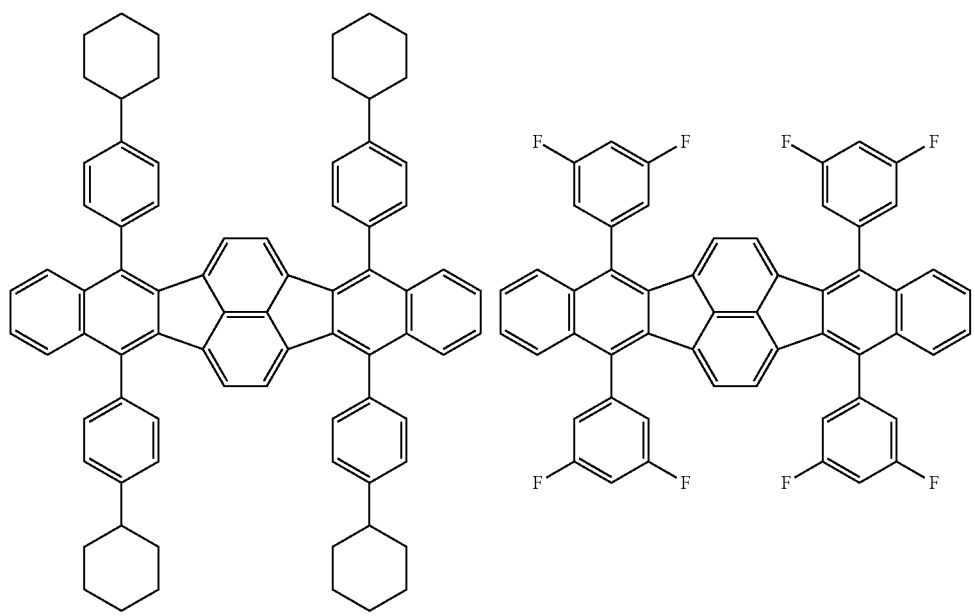

-continued
223 224
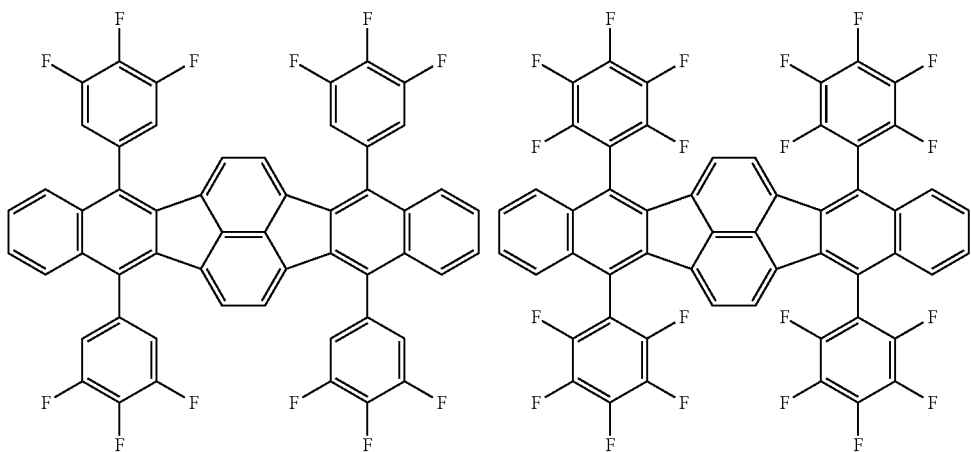
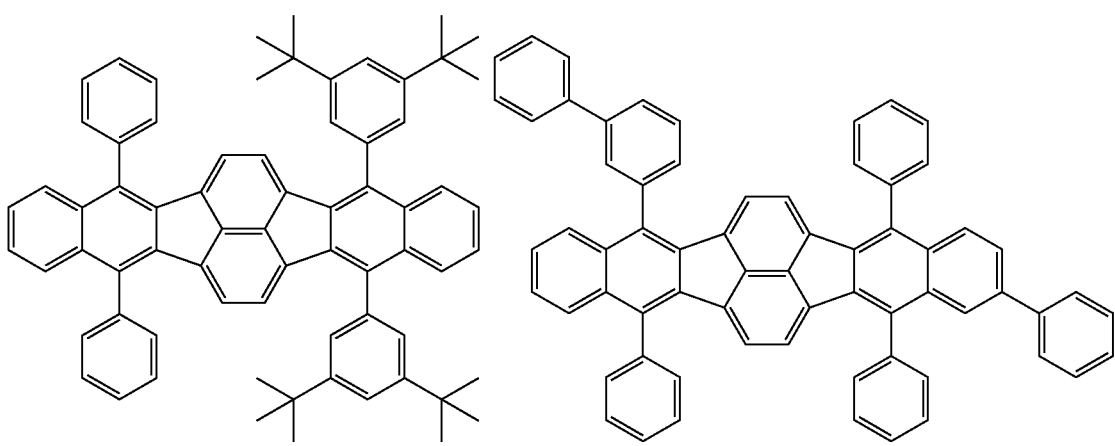
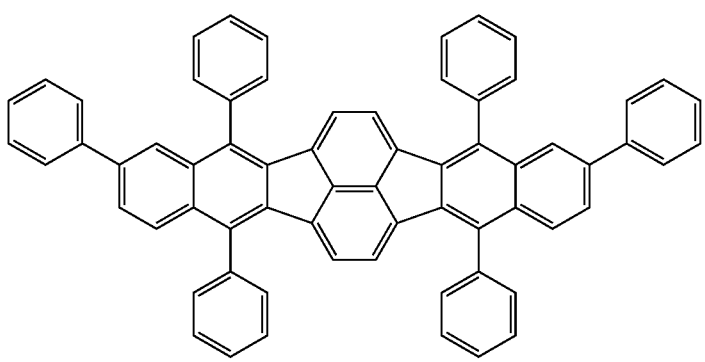
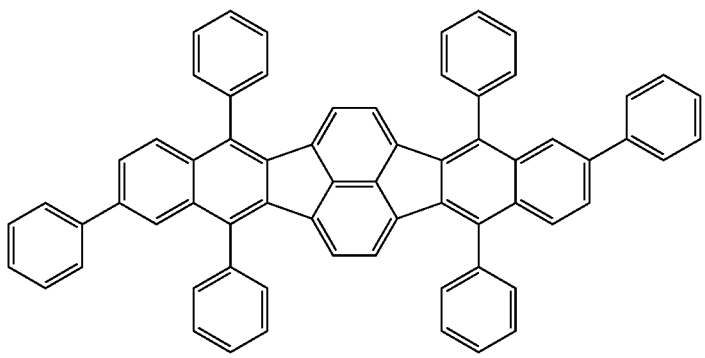

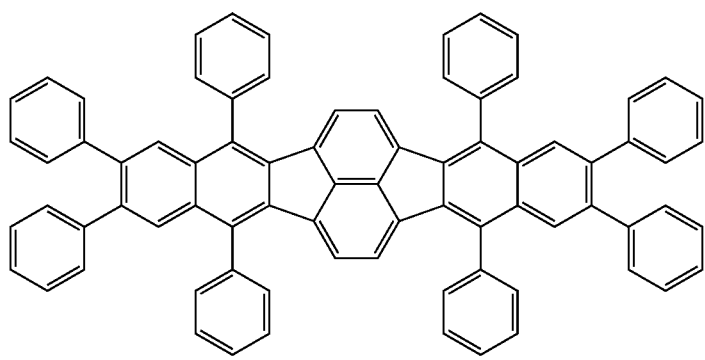
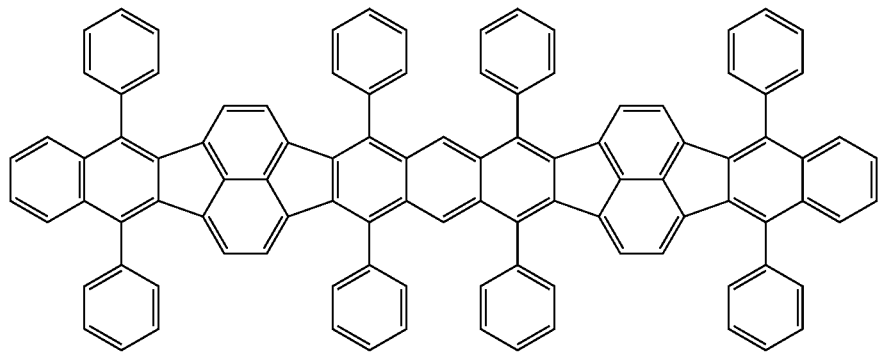
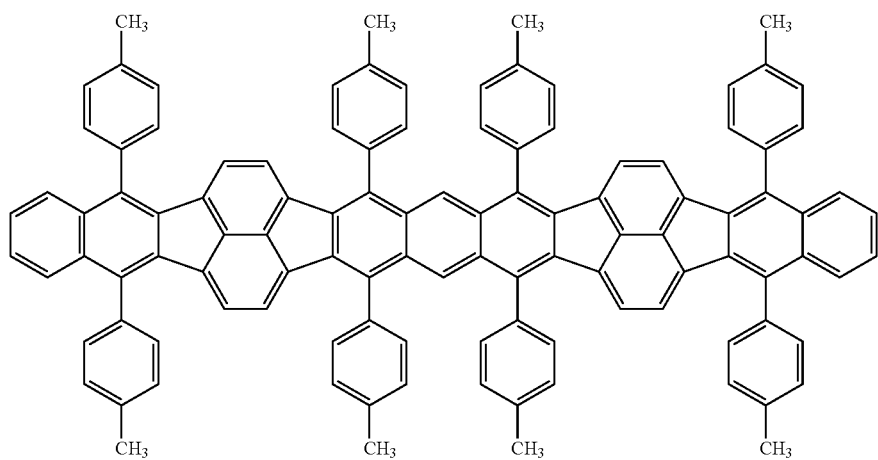
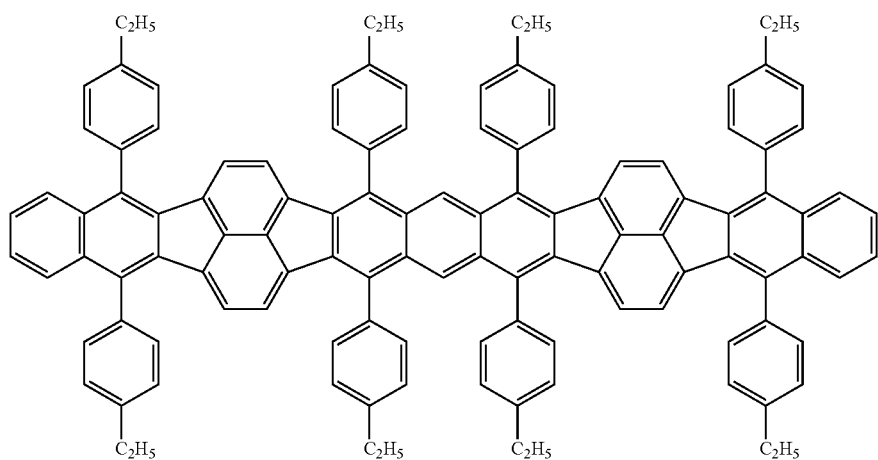

-continued
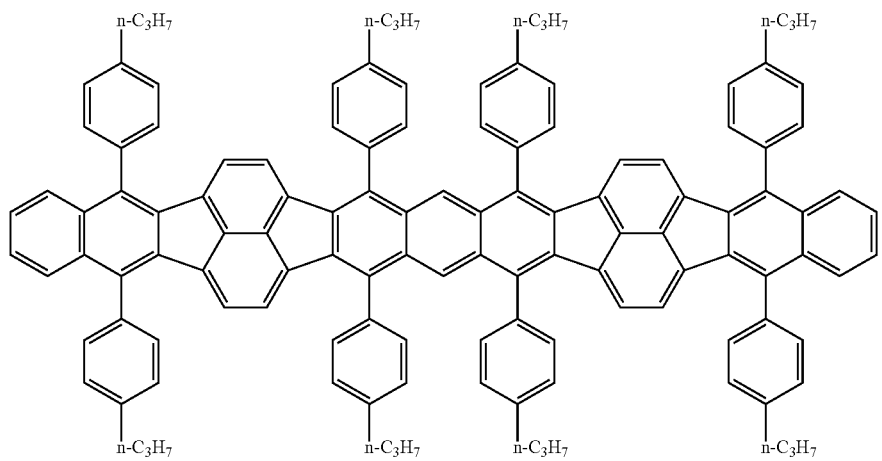
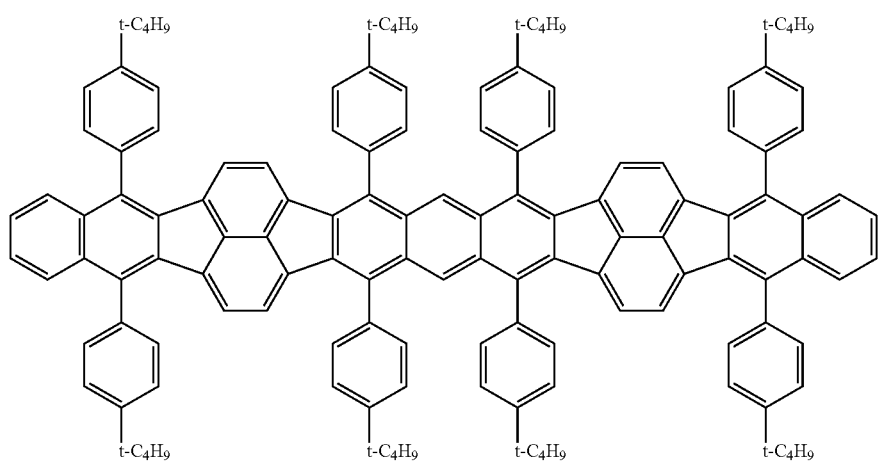
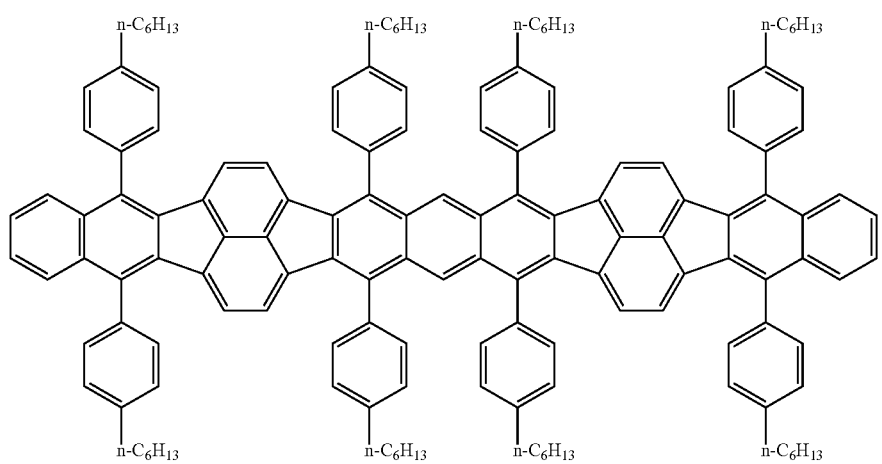

-continued
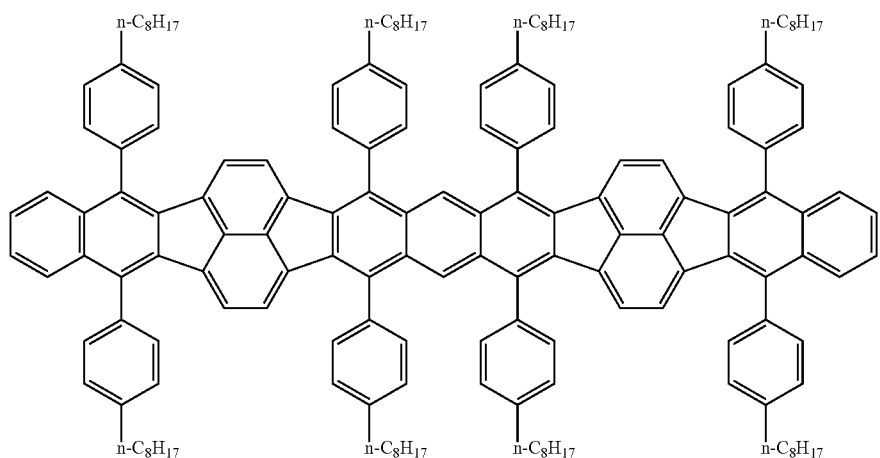
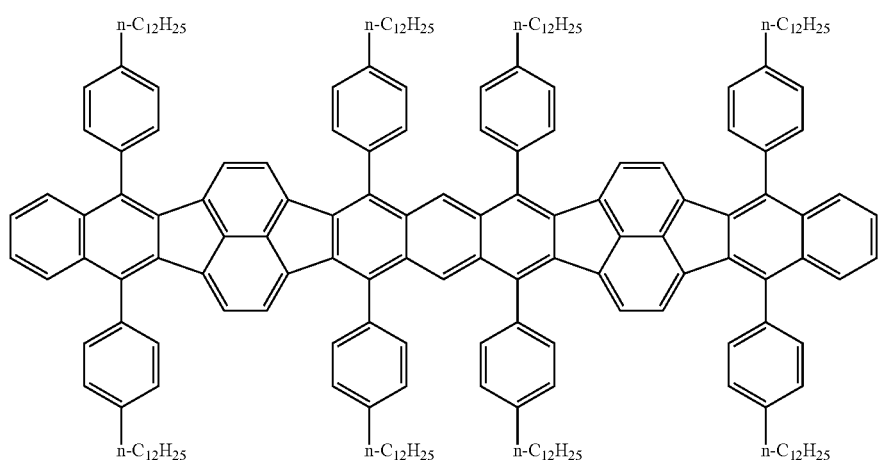
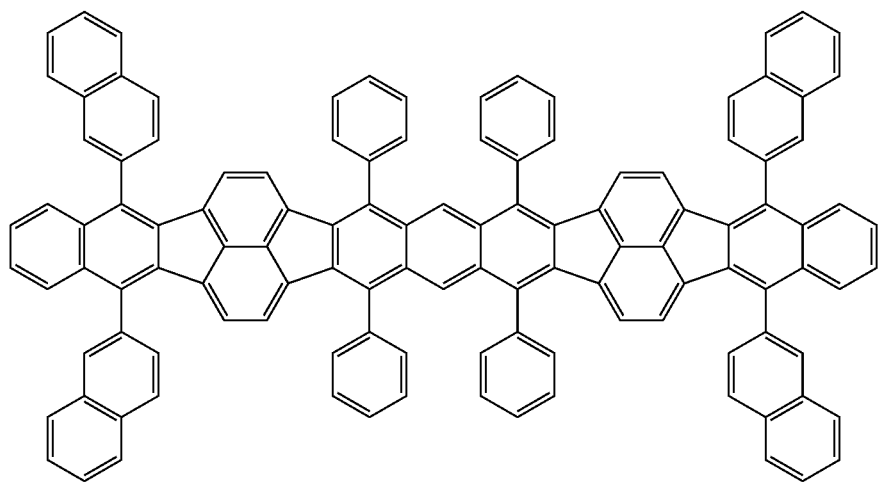

-continued
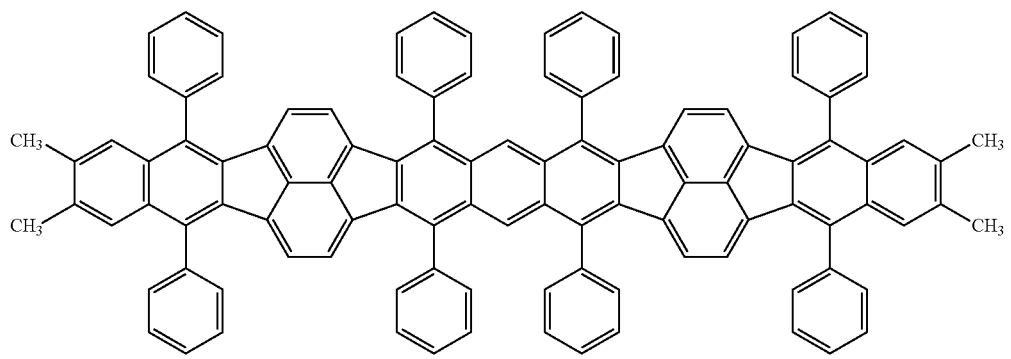
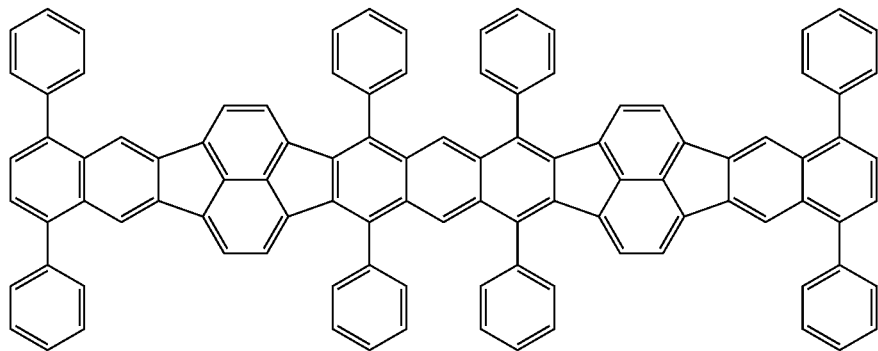
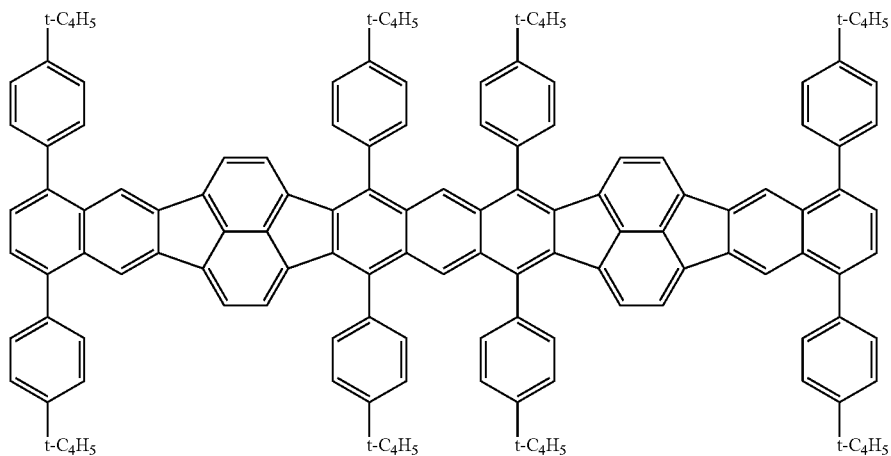
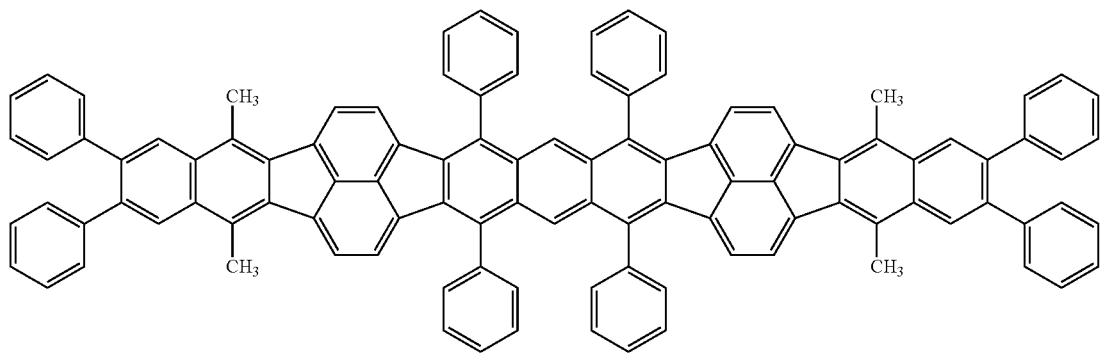

-continued
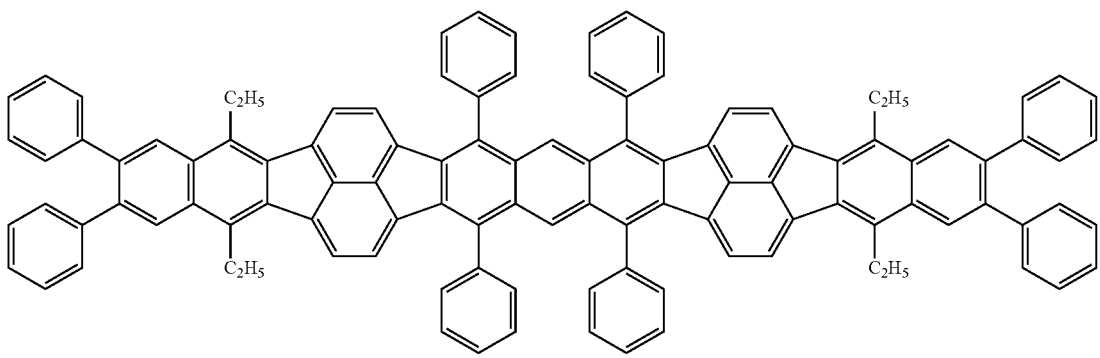
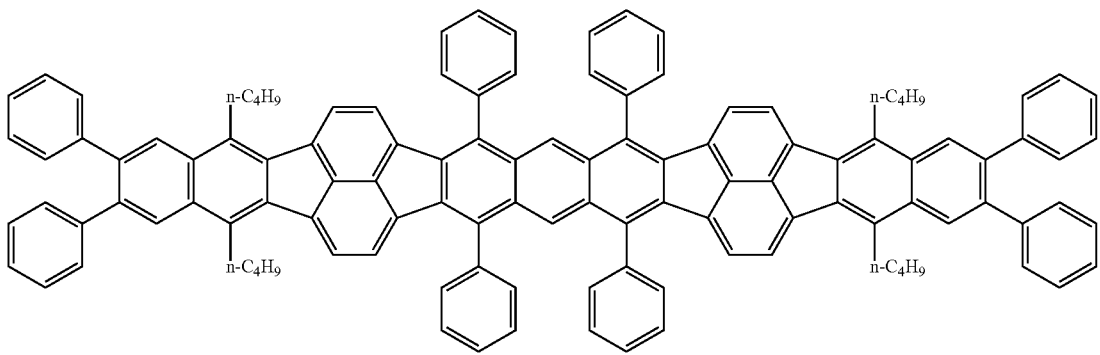
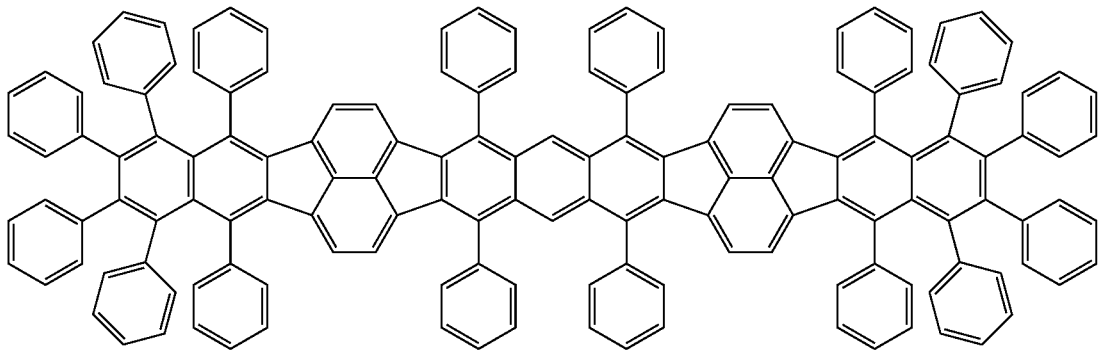
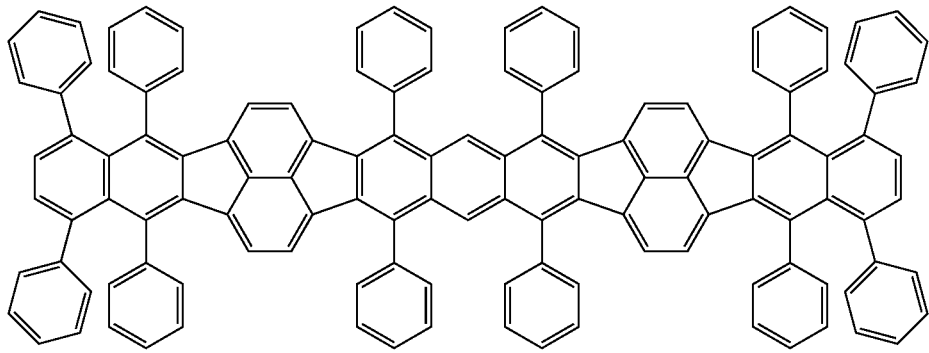

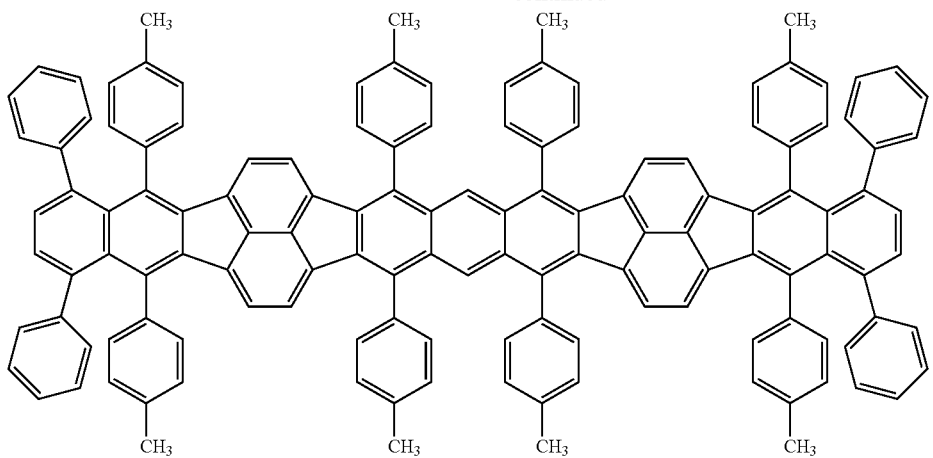
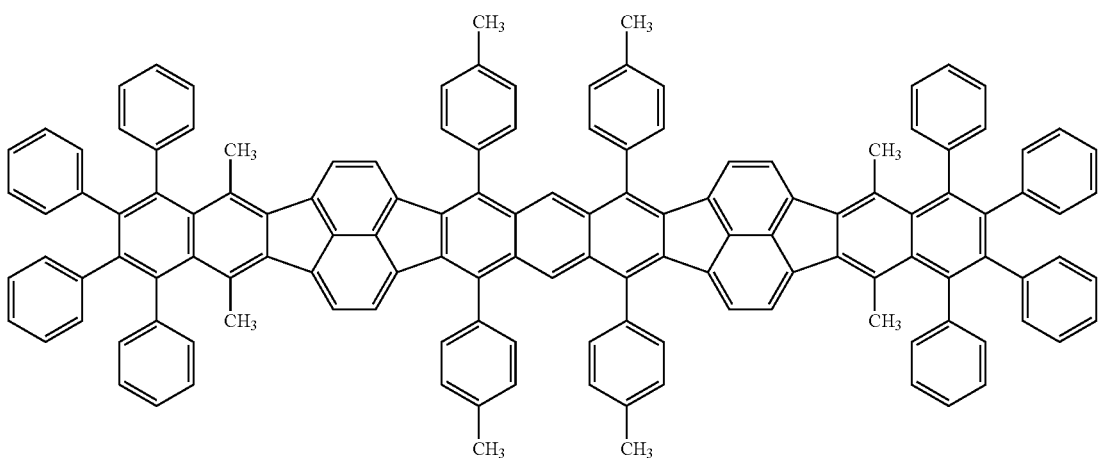
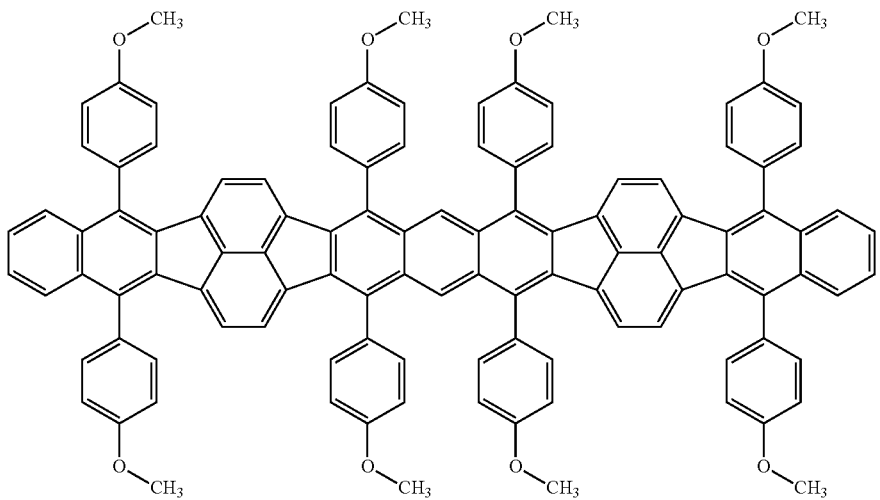

-continued
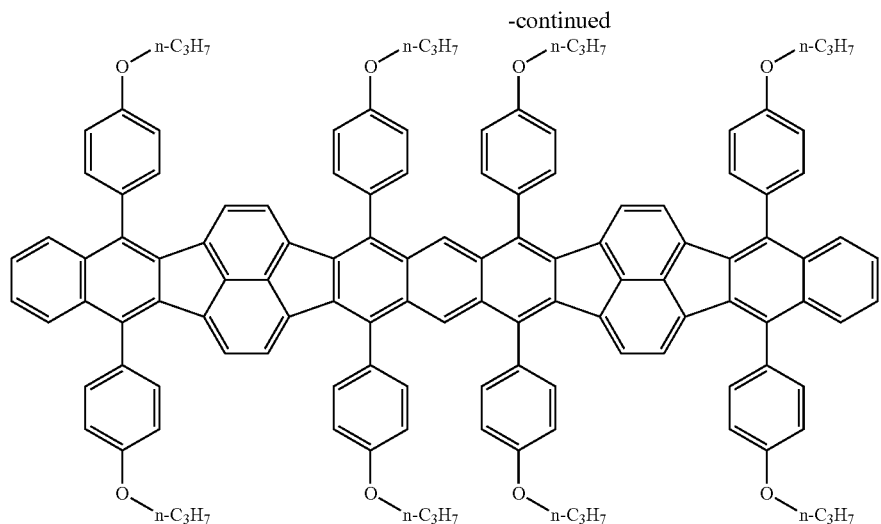
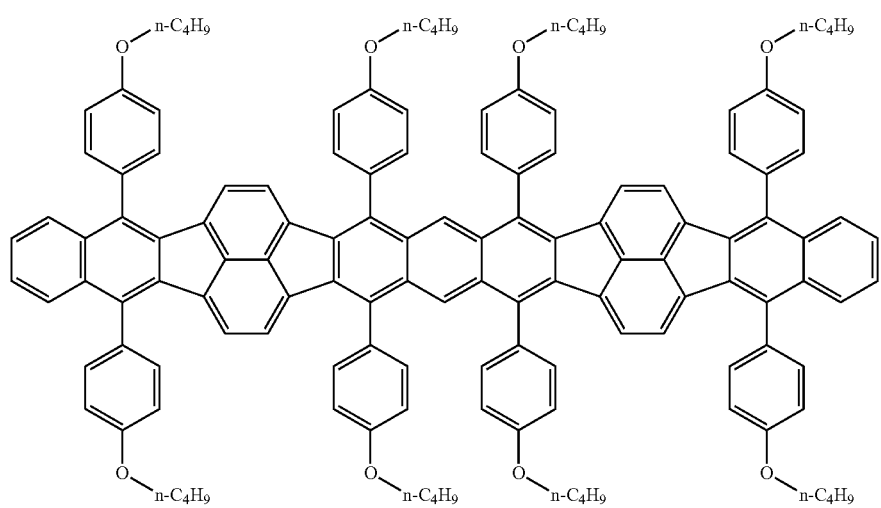
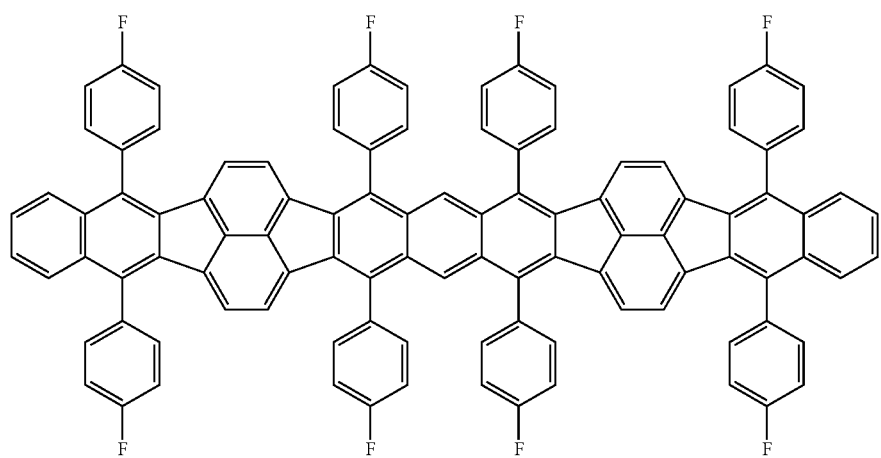

-continued
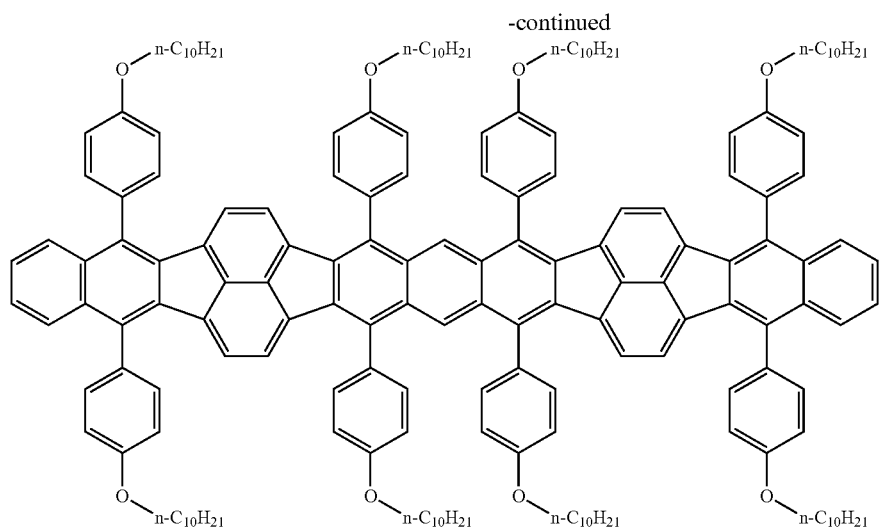
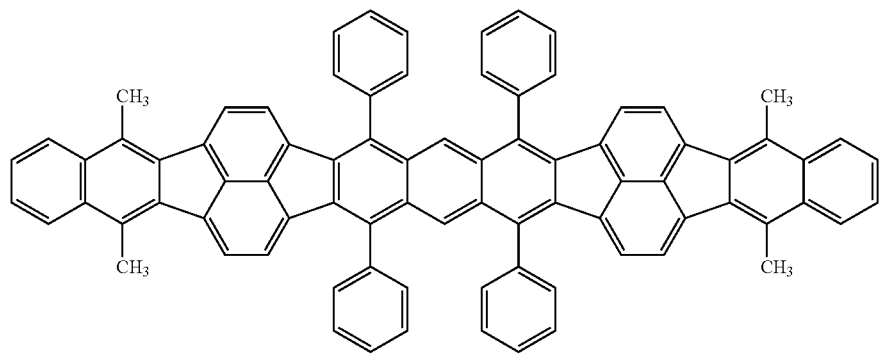
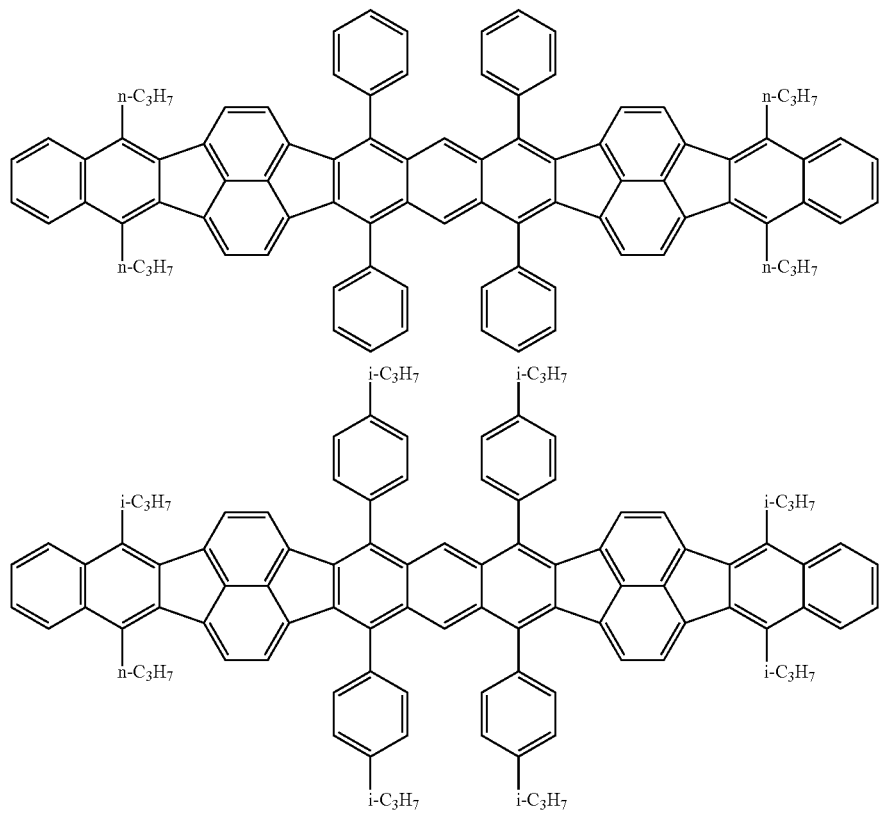

-continued
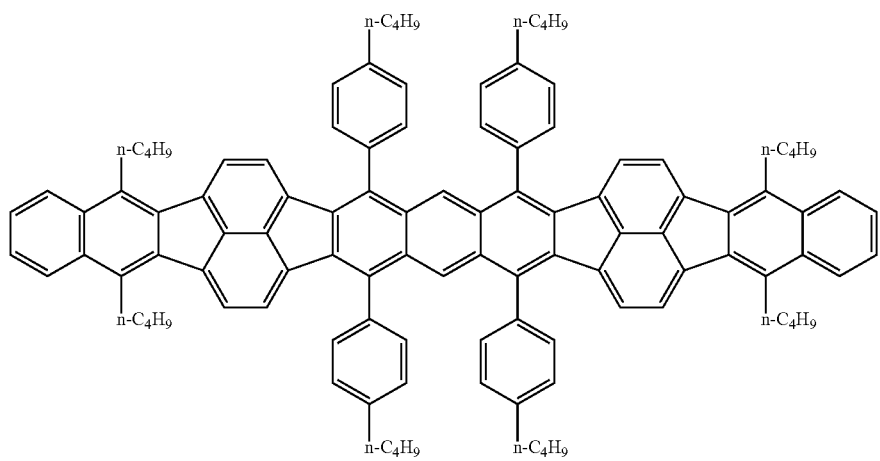
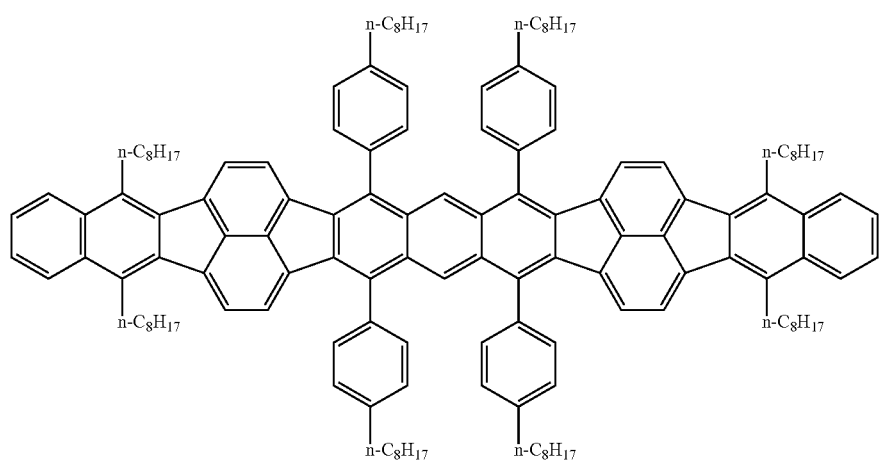
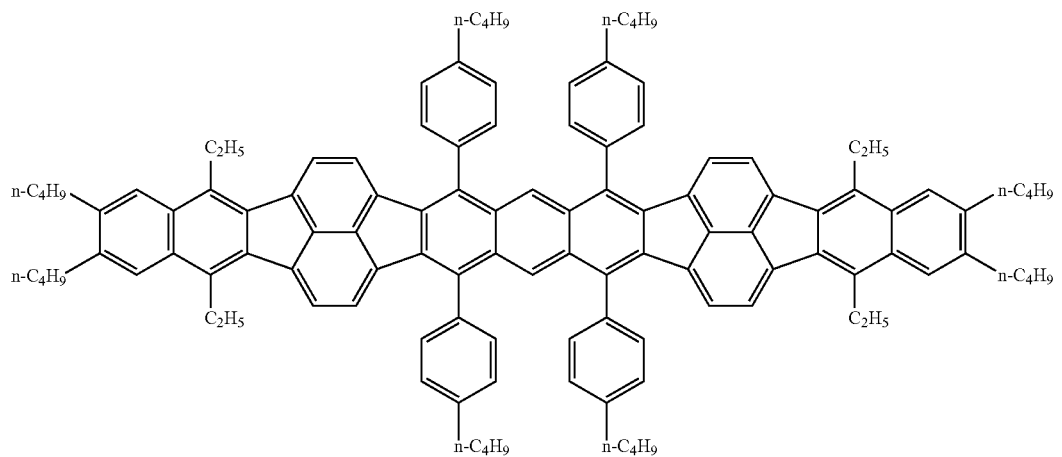

-continued
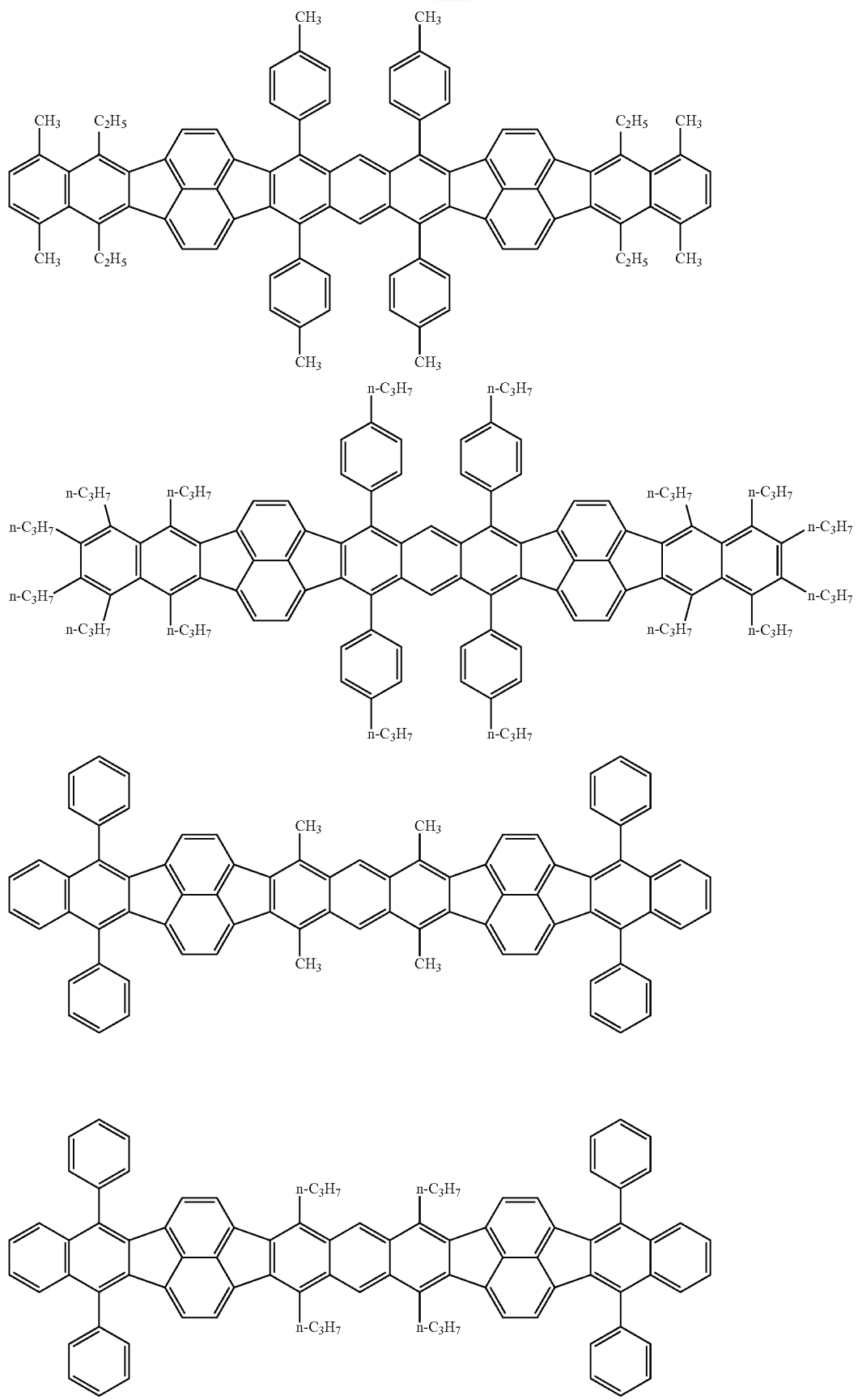

-continued
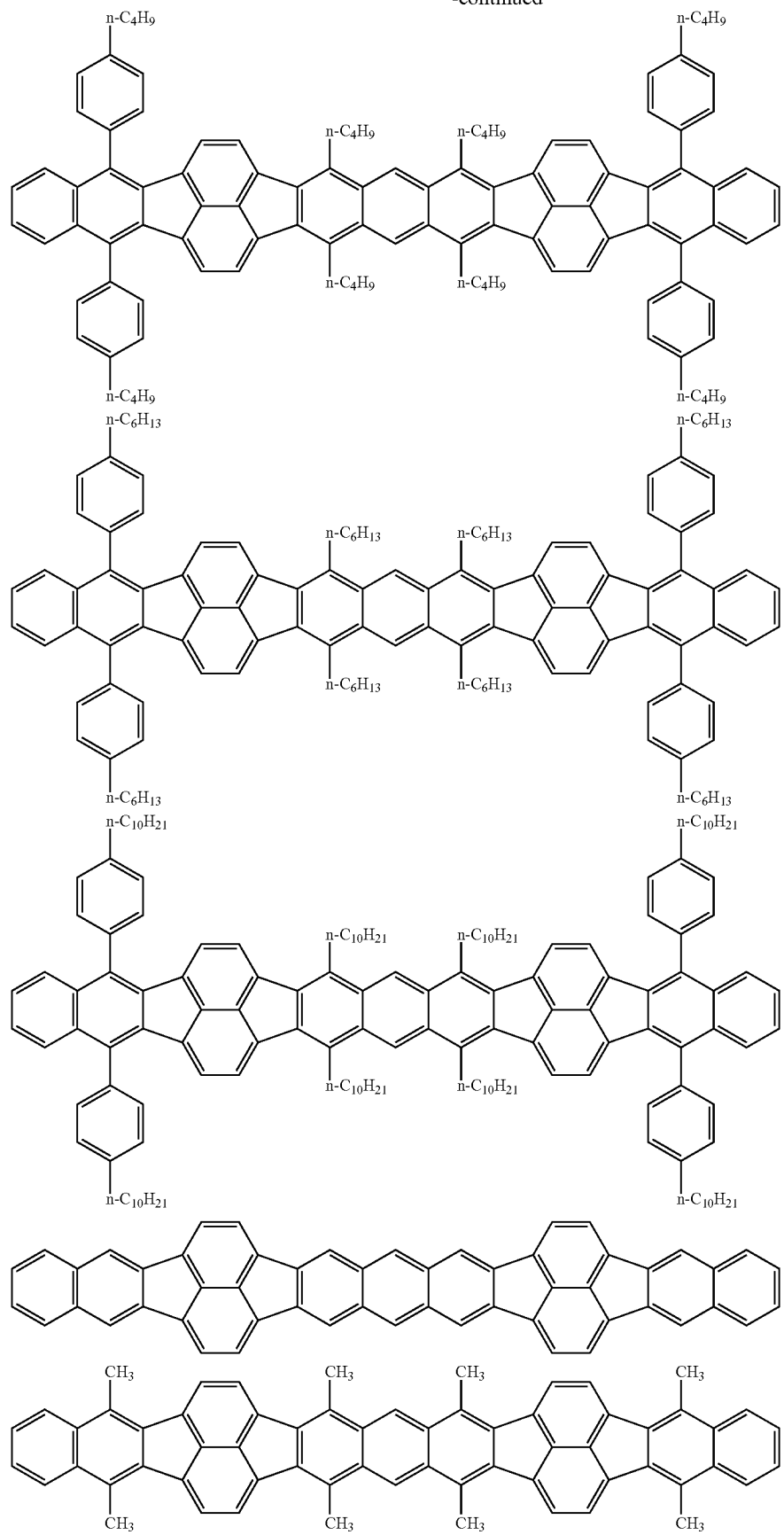

-continued
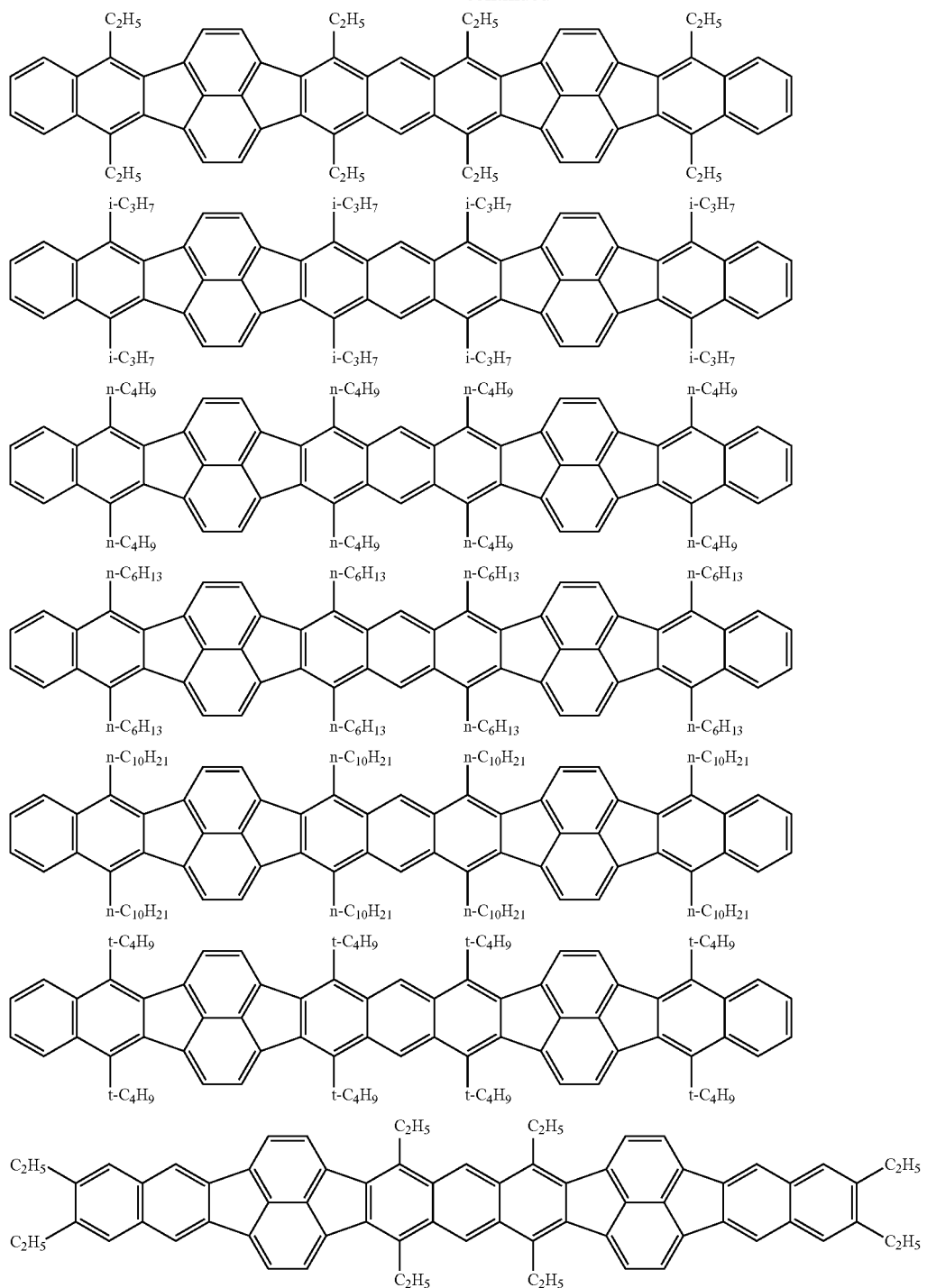
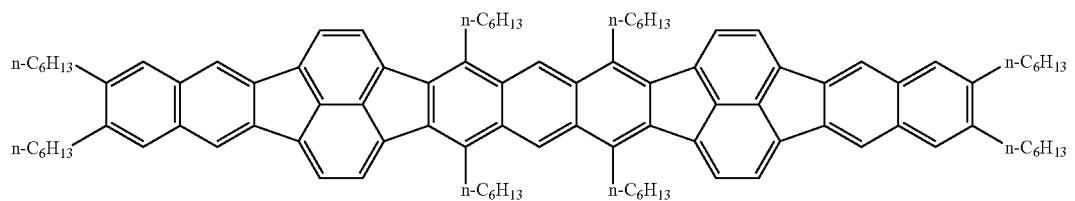

-continued
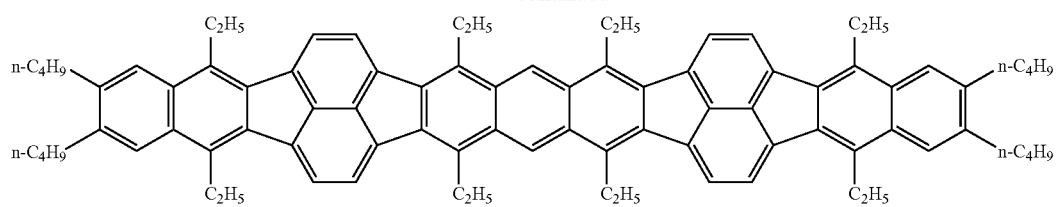
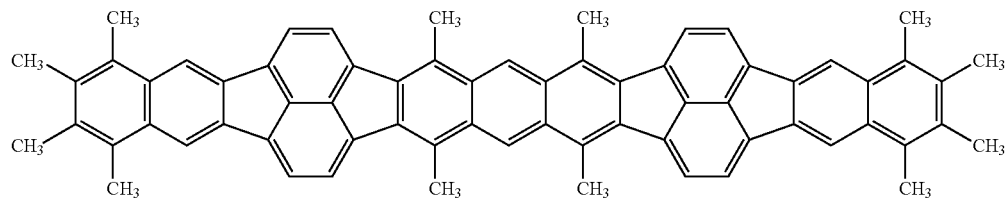
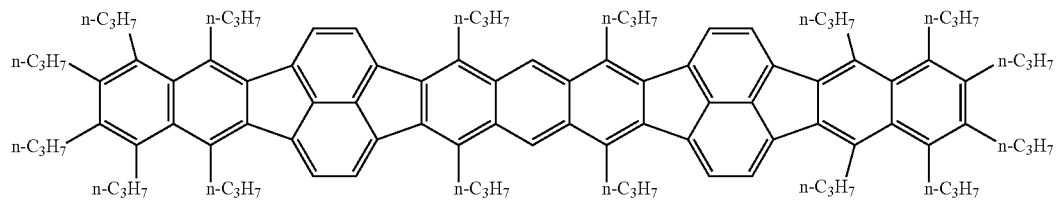
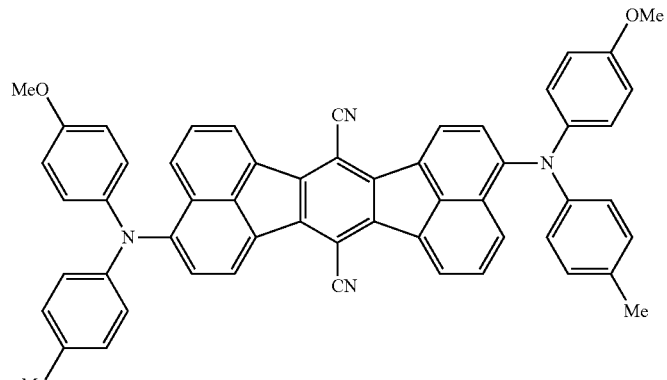
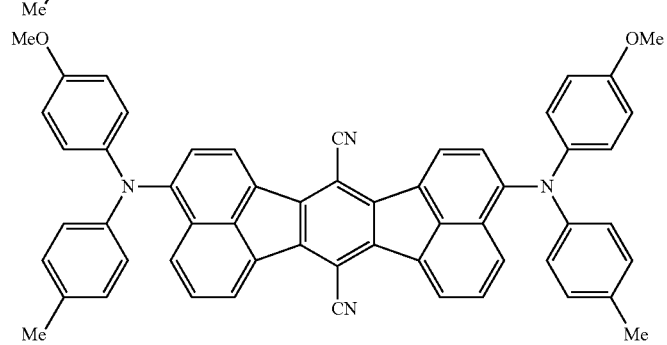
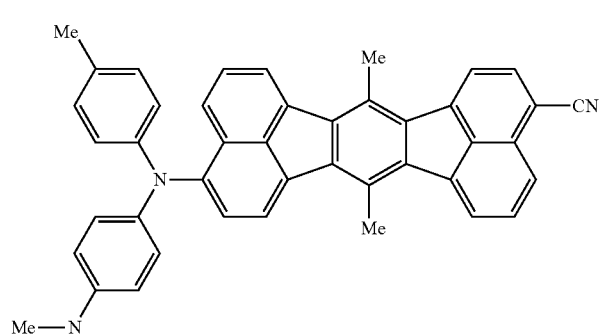

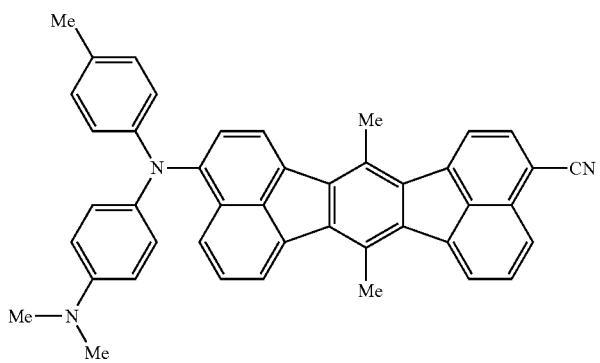
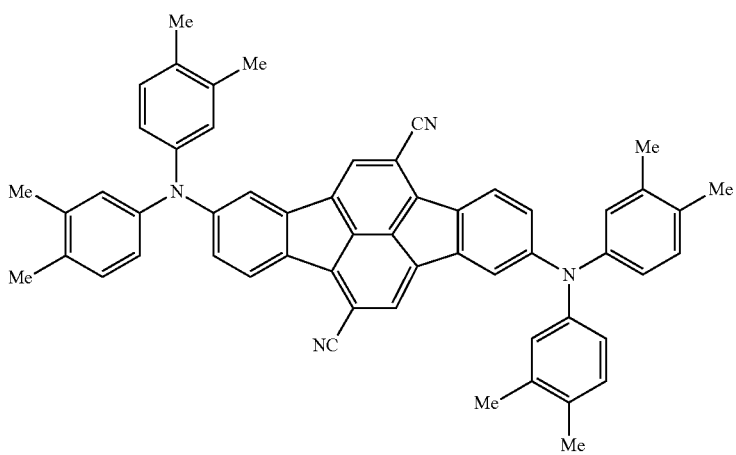
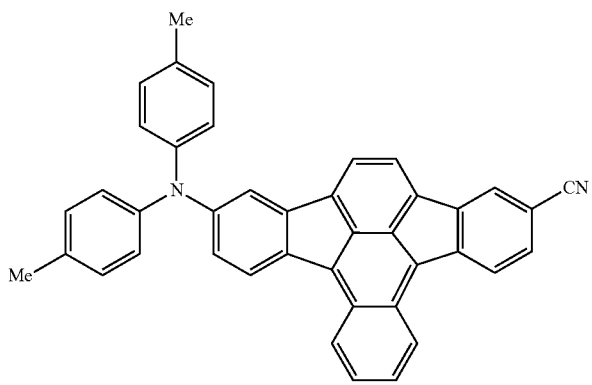
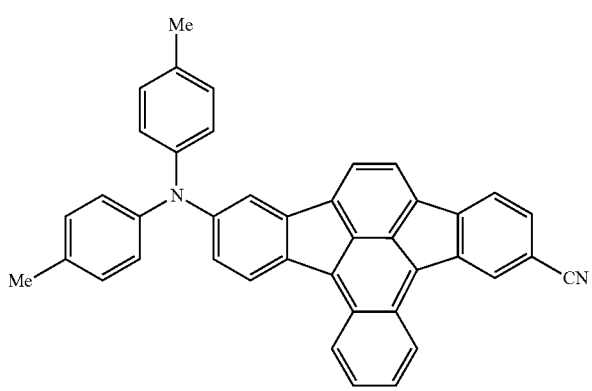

253
254
-continued
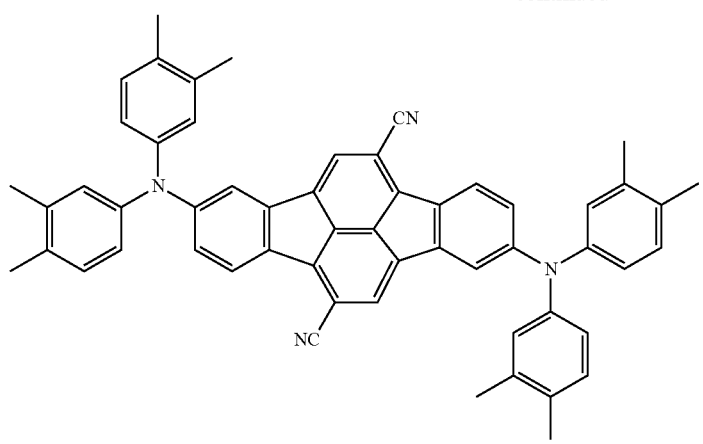
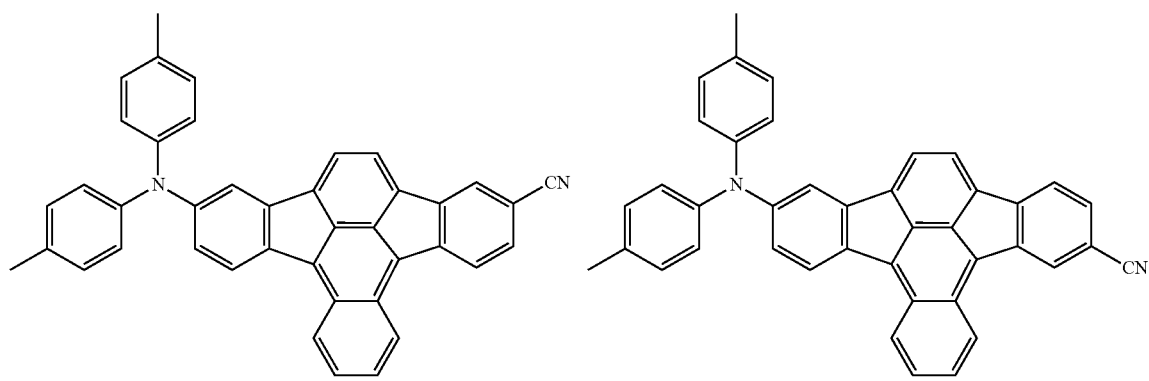
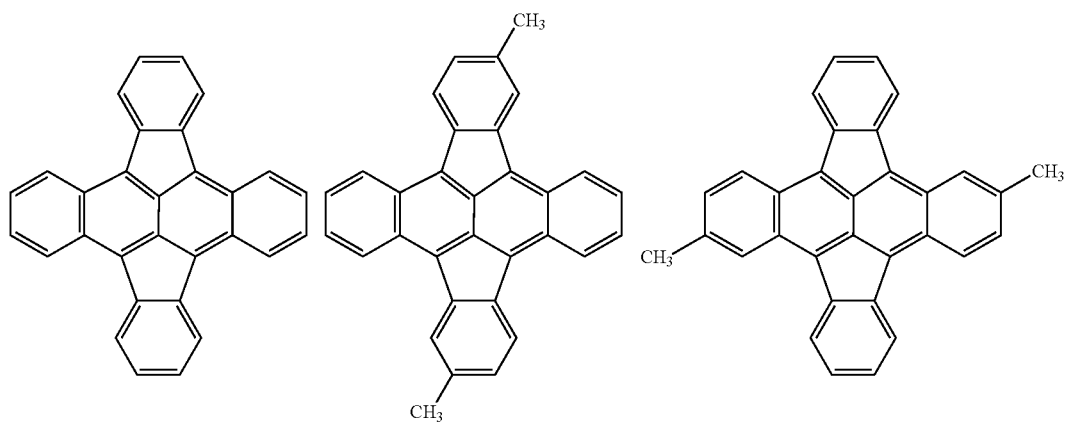
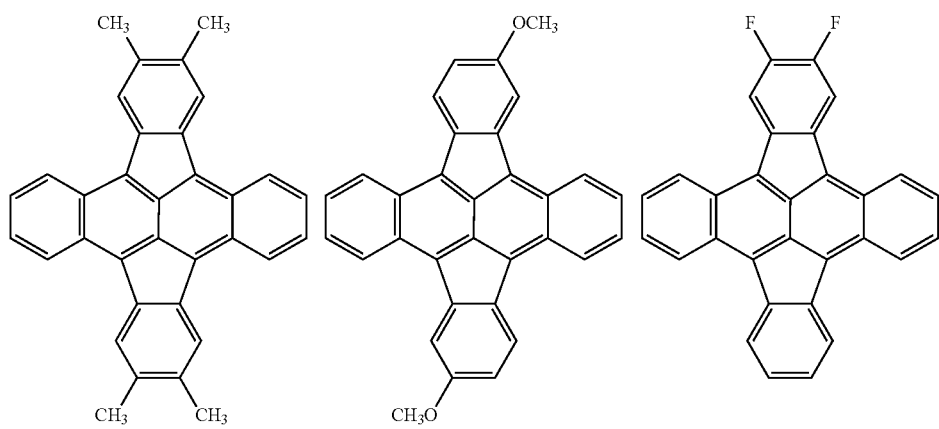

-continued
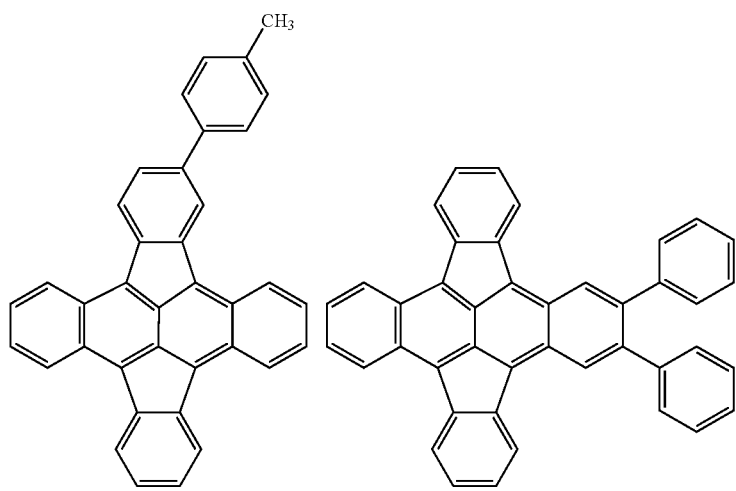
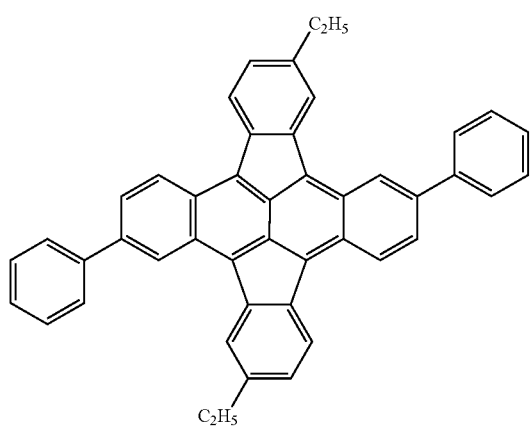
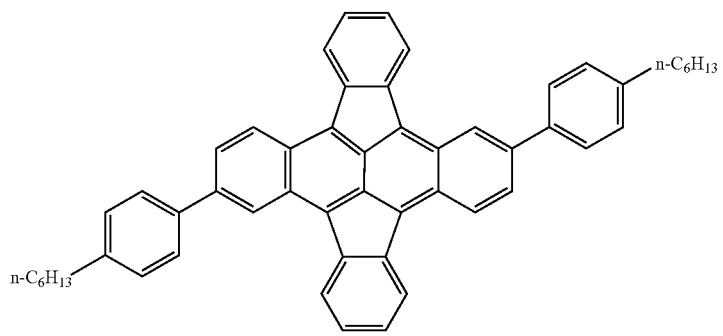

-continued
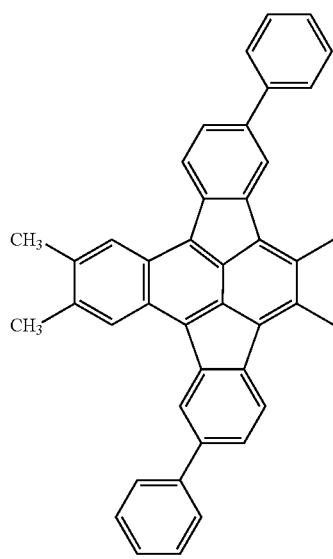
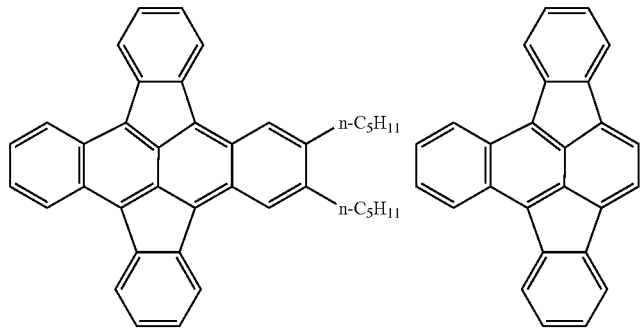
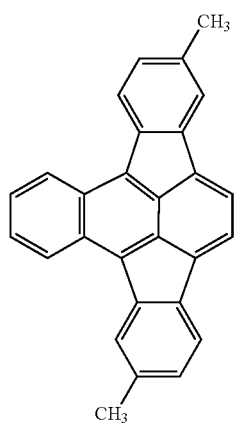
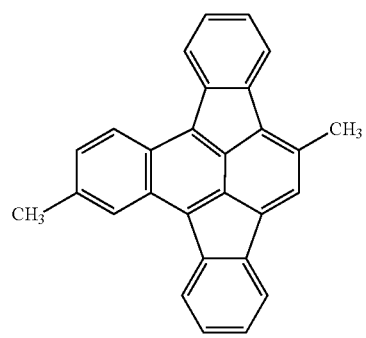
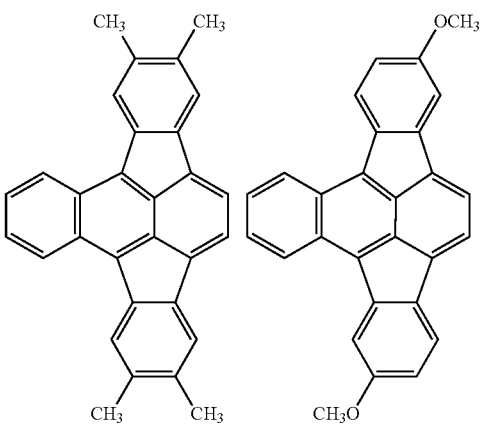
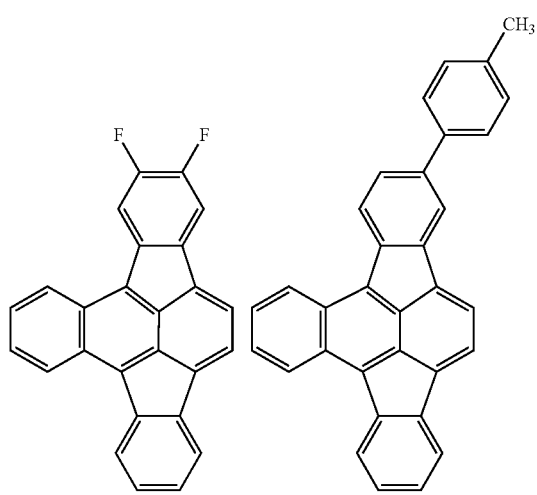
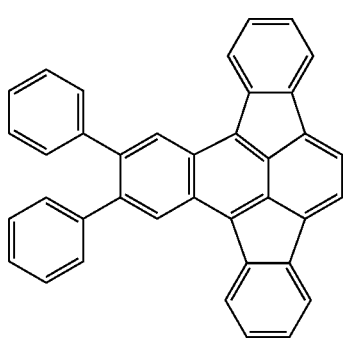

-continued
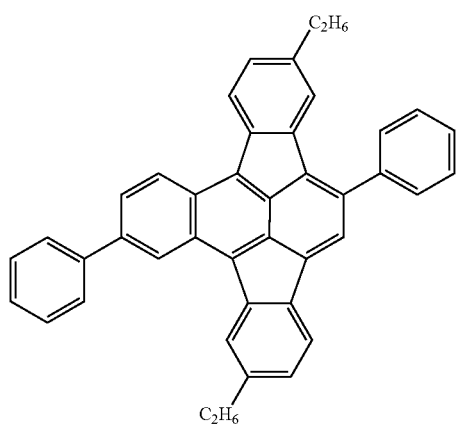
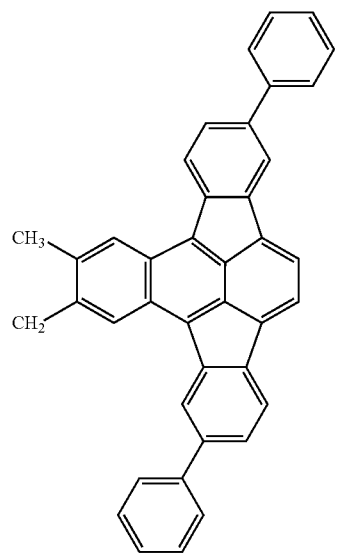
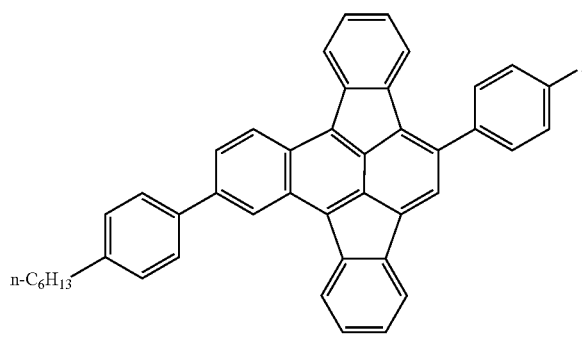
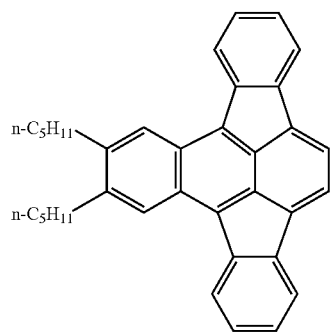
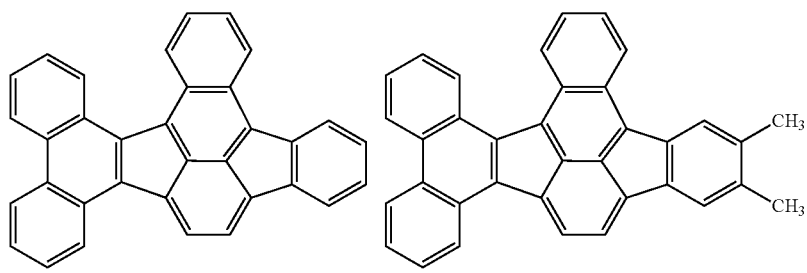
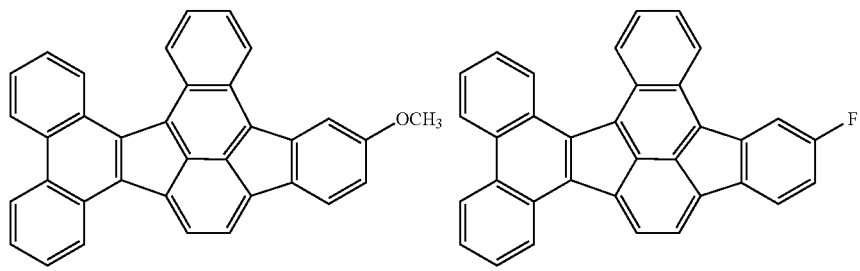
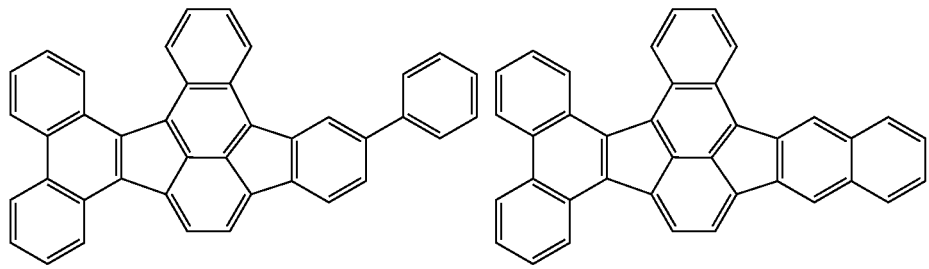

-continued
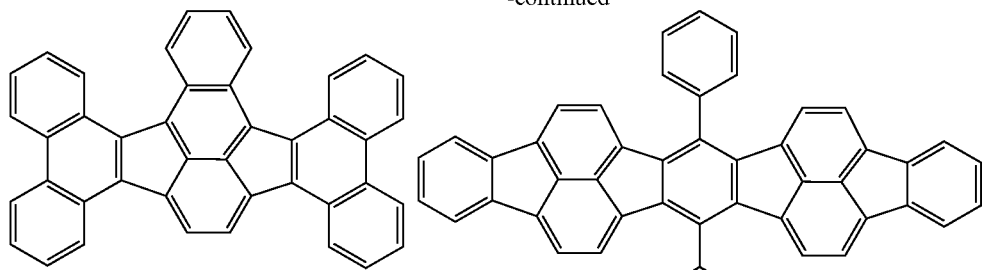
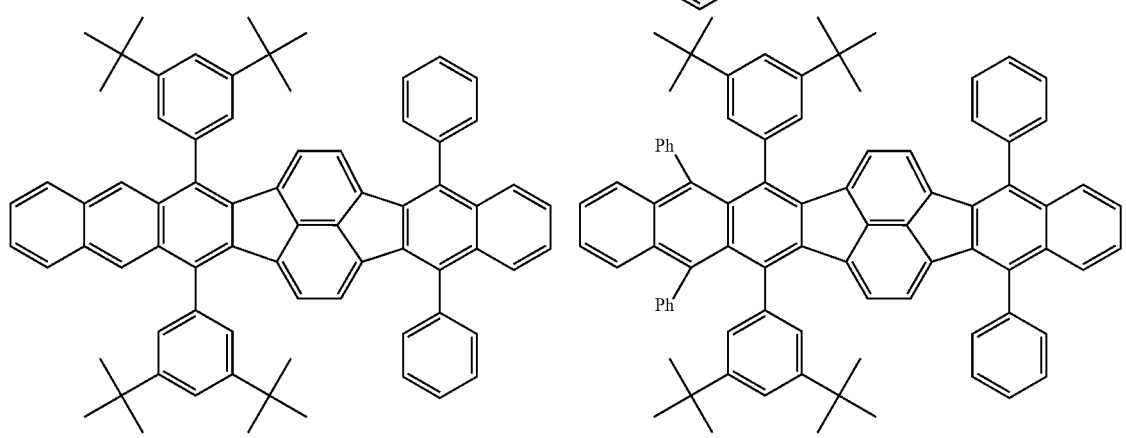
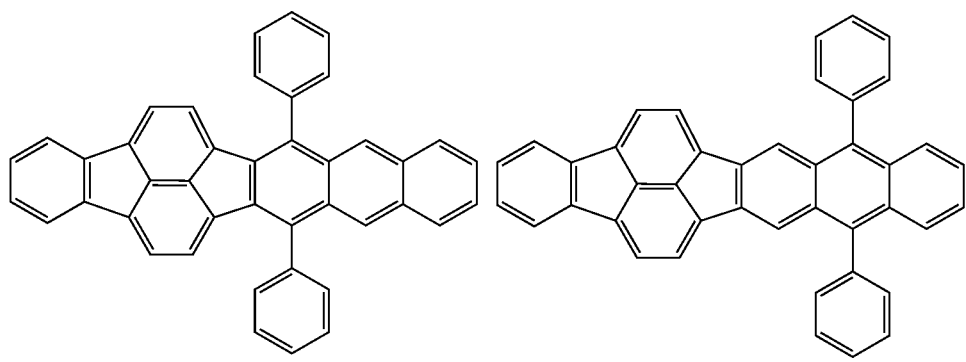
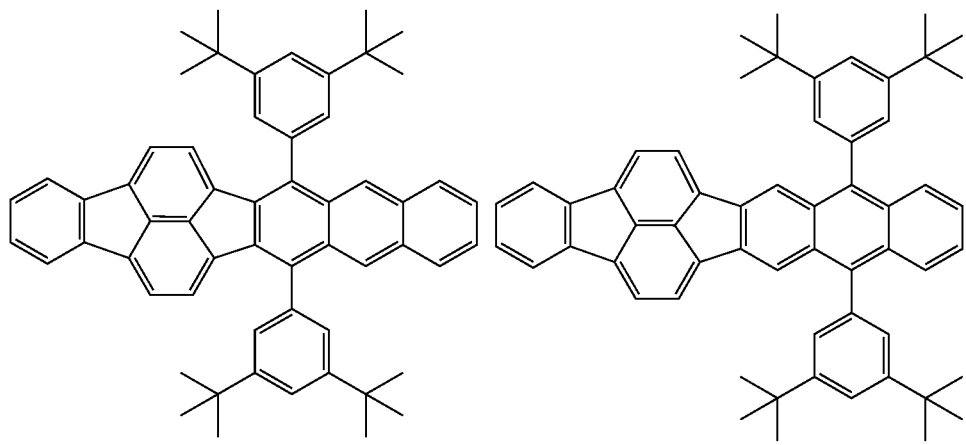

263 264
-continued
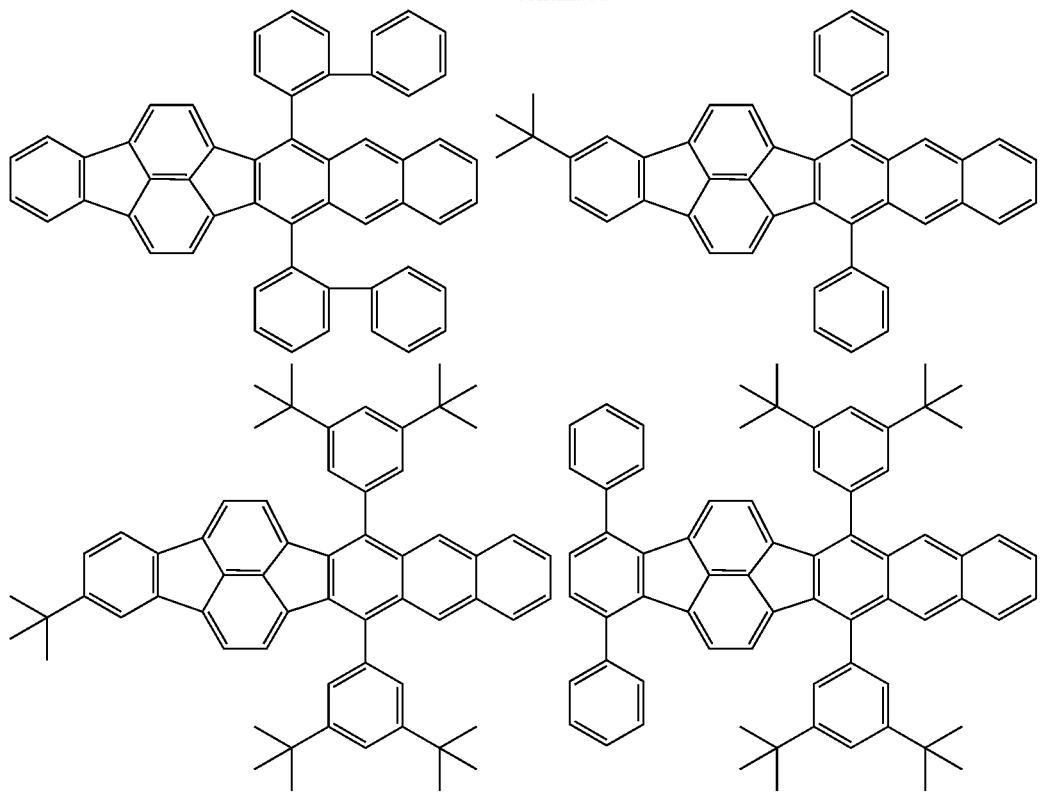
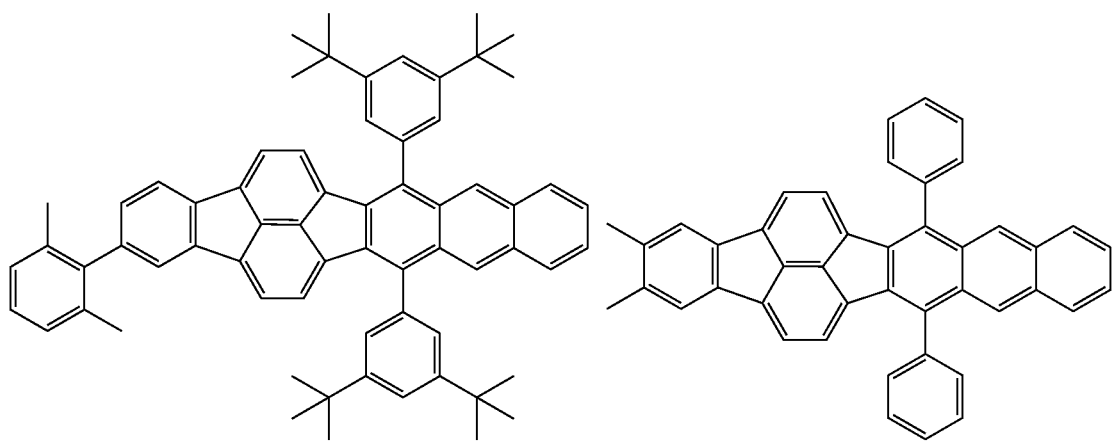
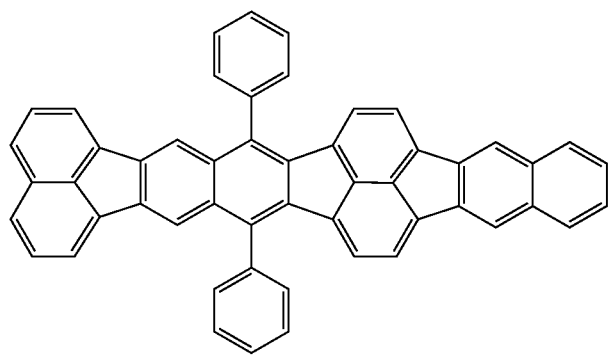

-continued
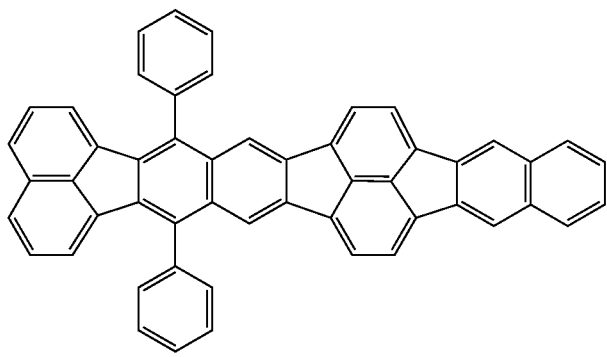
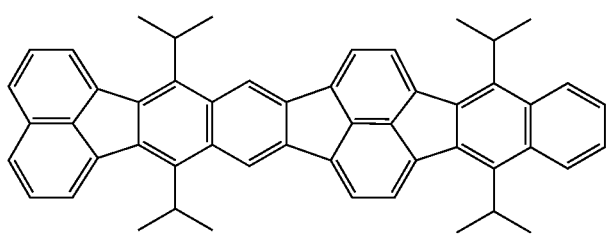
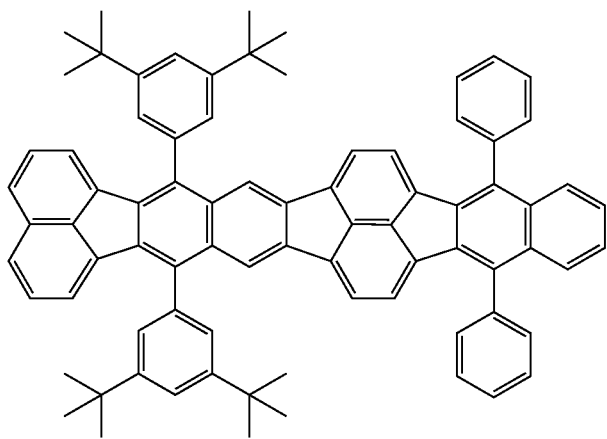
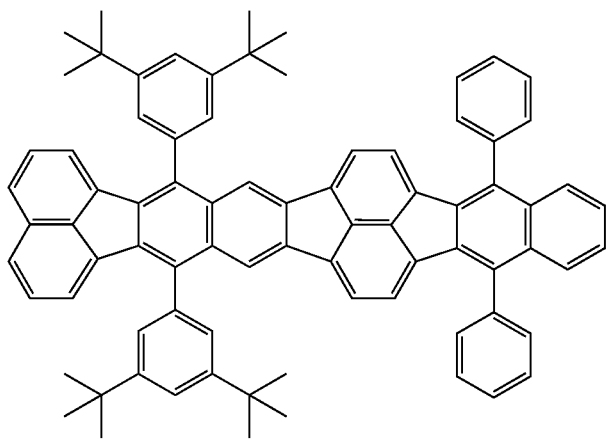

-continued
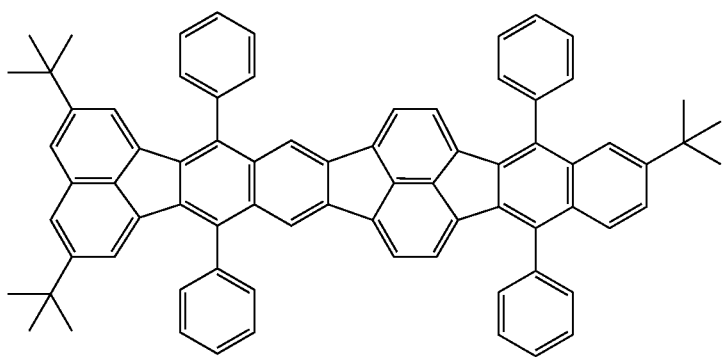
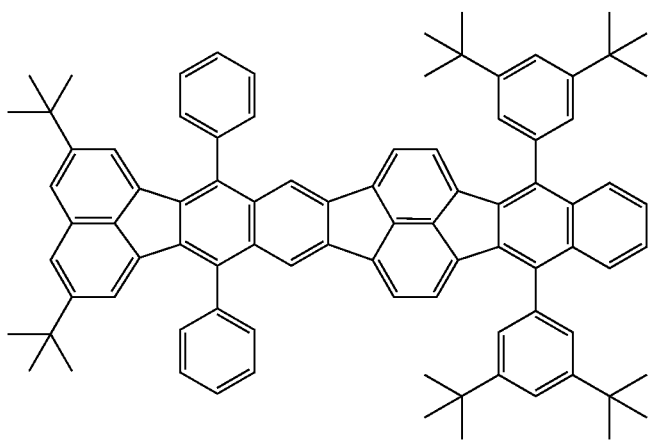
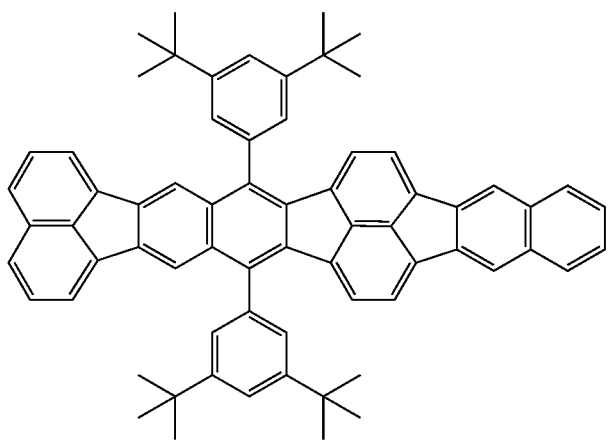
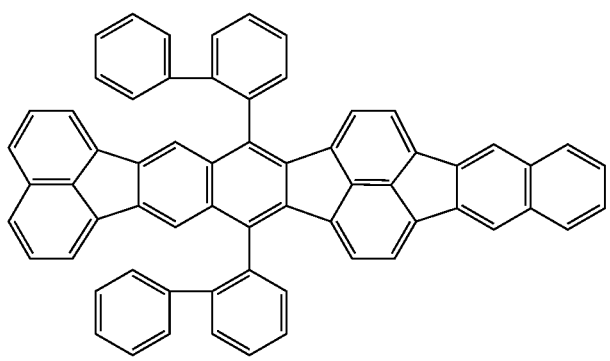

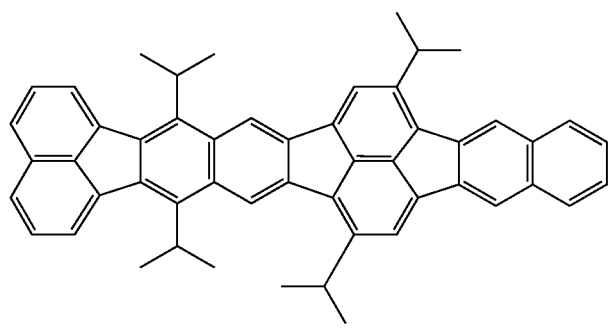
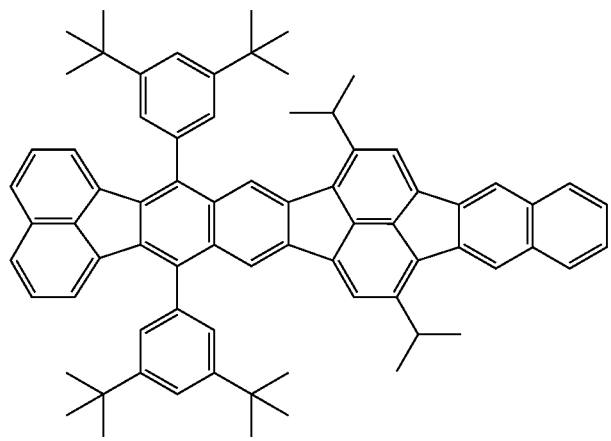
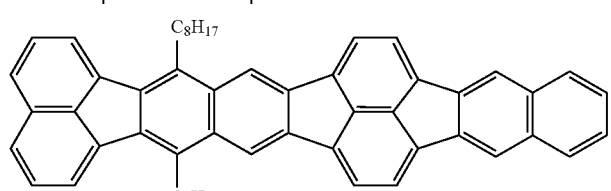
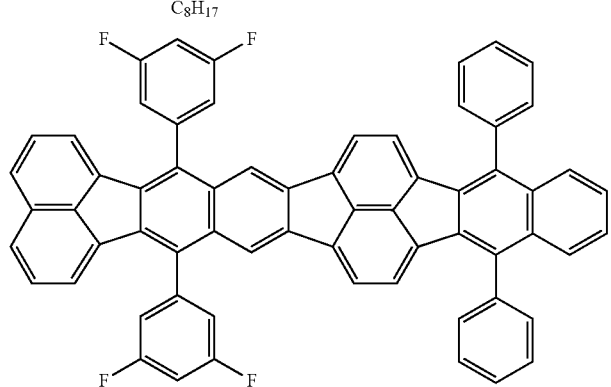
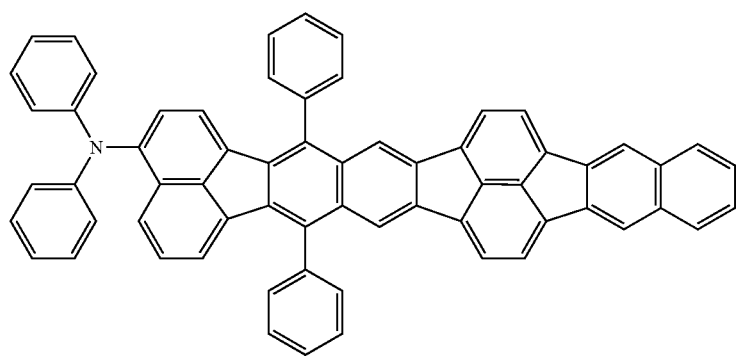

-continued

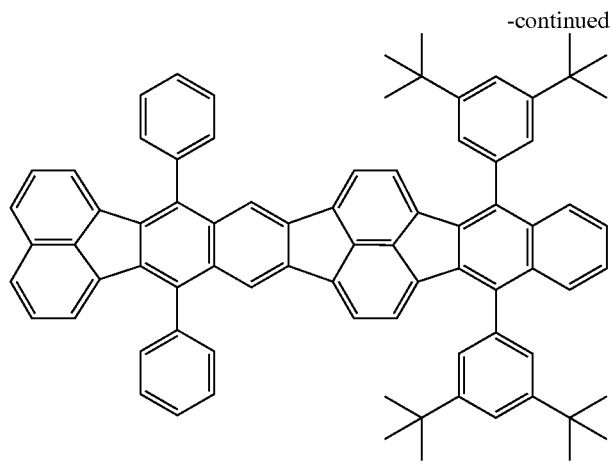

7,10,17,20-tetramethylacenaphtho[1,2-k]naphtho[1',8':5,6,7]-s-inadceno[1,2,3-cd]fluoranthene
7,10,17,20-tetraisopropylacenaphtho[1,2-k]naphtho[1',8':5,6,7]-s-inadceno[1,2,3-cd]fluoranthene
10,17-diethyl-7,20-di-n-butylacenaphtho[1,2-k]naphtho[1',8':5,6,7]-s-inadceno[1,2,3-cd]fluoranthene
7,10,17,20-tetraphenylacenaphtho[1,2-k]naphtho[1',8':5,6,7]-s-inadceno[1,2,3-cd]fluoranthene
10,17-di(4'-methoxyphenyl)-7,20-di(4'-ethylphenyl)acenaphtho[1,2-k]naphtho[1',8':5,6,7]-s-inadceno[1,2,3-cd]fluoranthene
10,17-diphenyl-7,20-dimethylacenaphtho[1,2-k]naphtho[1',8':5,6,7]-s-inadceno[1,2,3-cd]fluoranthene
10,17-di(4'-ethylphenyl)-7,20-di-n-butylacenaphtho[1,2-k]naphtho [1',8':5,6,7]-s-inadceno[1,2,3-cd]
acenaphtho [1,2-k]naphtho [1',8':5,6,7]-s-inadceno [1,2,3-cd]fluoranthene-7,10,17,20-tetracarboxylic acid-tetramethylesterfluoranthene
acenaphtho [1,2-k]naphtho [1',8':5,6,7]-s-inadceno [1,2,3-cd]fluoranthene-7,10,17,20-tetracarboxylic acid-tetra-n-octylester
acenaphtho [1,2-k]naphtho[1',8':5,6,7]-s-inadceno[1,2,3-cd]fluoranthene-7,10,17,20-tetracarboxylic acid-tetra-n-dodecylester
7,20-diethylacenaphtho[1,2-k]naphtho[1',8':5,6,7]-s-inadceno[1,2,3-cd]fluoranthene-10,17-dicarboxylic acid-diethylester
7,10,17,20-tetraethylacenaphtho[1,2-k]naphtho[1',8':5,6,7]-s-inadceno[1,2,3-cd]fluoranthene
10,17-diphenyl-7,20-di(4'-methoxyphenyl)acenaphtho[1,2-k]naphtho[1',8':5,6,7]-s-inadceno[1,2,3-cd]fluoranthene
acenaphtho[1,2-k]naphtho[1',8':5,6,7]-s-inadceno[1,2,3-cd]fluoranthene-7,10,17,20-tetracarboxylic acid-tetraisopropylester
10,17-diethyl-7,20-di-n-butylacenaphtho[1,2-k]naphtho[1',8':5,6,7]-s-inadceno[1,2,3-cd]fluoranthene
10,17-diphenyl-7,20-di(4'-chlorophenyl)acenaphtho[1,2-k]naphtho[1',8':5,6,7]-s-inadceno[1,2,3-cd]fluoranthene
7,10,17,20-tetra-n-hexylacenaphtho[1,2-k]naphtho[1',8':5,6,7]-s-inadceno[1,2,3-cd]fluoranthene
acenaphtho[1,2-k]naphth [1',8':5,6,7]-s-inadceno[1,2,3-cd]fluoranthene-7,10,17,20-tetracarboxylic acid-tetracyclohexylester
10,17-di(3'-methylphenyl)-7,20-di(4'-tert-butylphenyl)acenaphtho[1,2-k]naphtho[1',8':5,6,7]-s-inadceno[1,2,3-cd]fluoranthene According to the organic EL device in the exemplary embodiment, a more high-performance organic EL device can be provided as compared with a conventional art. According to the exemplary embodiment, an organic EL device with a long lifetime can be provided. It is considered that the stability of the compound contained in the emitting layer is a significantly influential factor to the lifetime of the organic EL device. The first compound contained in the emitting layer in the exemplary embodiment is a delayed fluorescent compound. Since the delayed fluorescent compound has a donor (electron-donating) moiety and an acceptor (electron-accepting) moiety in a molecule structure, charges are localized in the molecule of the delayed fluorescent compound when the compound is excited (i.e., charge-localized state). Since various side reactions possibly occur under such a charge-localized state, the delayed fluorescent compound having a long excitation lifetime tends to particularly show a low stability in the excited state.

The emitting layer in the exemplary embodiment contains the first compound and the second compound. Energy is quickly transferred from the first compound (delayed fluorescent compound) in the excited state to the second compound, so that the first compound returns to the ground state and the second compound turns into the excited state. When the second compound in the excited state returns to the ground state, the second compound emits light. Accordingly, it is considered that the stability of the second compound in the excited state also significantly influences the lifetime of the organic EL device.

The inventors studied based on the assumption that the deterioration of the emitting layer was preventable by using a compound with a relatively high excitation stability as the second compound and found that a highly efficient organic EL device with a long lifetime is obtainable when the emitting layer contains the second compound having the above-described structure and the first delayed fluorescent compound.

The compound used in the emitting layer together with the first delayed fluorescent compound is exemplified by an aromatic hydrocarbon compound. This is because charges are less localized in the excited state in the aromatic hydrocarbon compound than in the first delayed fluorescent compound. Further, the aromatic hydrocarbon compound has a shorter excitation lifetime than that of the first compound. Accordingly, the aromatic hydrocarbon compound has a higher excitation stability than that of the first compound.

Moreover, in the case of the aromatic hydrocarbon compound having a fused ring structure, since the aromatic hydrocarbon compound has a rigid skeleton in the molecule, a structural change in various states is small, and a chemical stability is also high.

Consequently, the inventors found the second compound having a structure suitable for prolonging the lifetime of the organic EL device among the aromatic hydrocarbon compound having the fused ring structure.

The organic EL device in the exemplary embodiment preferably emits light having the emission peak in a wavelength range from 480 nm to 560 nm. Specifically, a main peak wavelength of the light emitted from the organic EL device is preferably in a range from 480 nm to 560 nm. When the organic EL device of the exemplary embodiment emits light, it is preferable that the second compound in the emitting layer 5 mainly emits light. The wavelength range of the light emitted from the organic EL device is preferably in a range from 500 nm to 550 nm.

The organic EL device in the exemplary embodiment also preferably emits green fluorescence.

TADF Mechanism

In the organic EL device of the exemplary embodiment, the first compound is preferably a compound having a small $\Delta ST(M1)$ so that inverse intersystem crossing from the triplet energy level of the first compound to the singlet energy level thereof is easily caused by a heat energy given from the outside. An energy state conversion mechanism to perform spin exchange from the triplet state of electrically excited excitons within the organic EL device to the singlet state by inverse intersystem crossing is referred to as TADF Mechanism.

Figure 4:
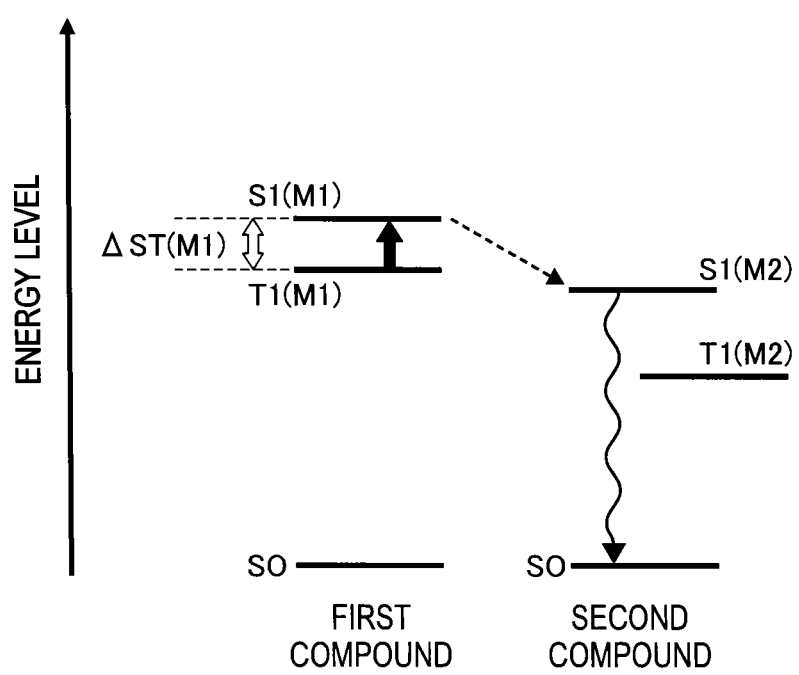
FIG. 4 shows a relationship between energy levels and energy transfer of compounds contained in en emitting layer in the first exemplary embodiment.

FIG. 4 shows an example of the relationship between energy levels of the first compound and the second compound in the emitting layer. In FIG. 4, S0 represents a ground state, S1(M1) represents a lowest singlet state of the first compound, T1(M1) represents a lowest triplet state of the first compound, S1(M2) represents a lowest singlet state of the second compound, T1(M2) represents a lowest triplet state of the second compound. A dashed arrow directed from S1(M1) to S1(M2) in FIG. 4 represents Förster energy transfer from the lowest singlet state of the first compound to the lowest singlet state of the second compound. A difference between the lowest singlet state Si and the lowest triplet state T1 is defined as $\Delta ST$.

As shown in FIG. 4, when a compound having a small $\Delta ST(M1)$ is used as the first compound, inverse intersystem crossing from the lowest triplet state T1(M1) to the lowest singlet state S1(M1) can be caused by a heat energy. Consequently, Förster energy transfer from the lowest singlet state S1(M1) of the first compound to the lowest singlet state S1(M2) of the second compound is caused. Consequently, fluorescence from the lowest singlet state S1(M2) of the second compound can be observed. It is inferred that the internal quantum efficiency can be theoretically raised up to 100% also by using delayed fluorescence by the TADF mechanism.

In the exemplary embodiment, a singlet energy S(M1) of the first compound is preferably larger than a singlet energy S(M2) of the second compound.

In the exemplary embodiment, an energy gap $T_{77K}(M1)$ at 77 [K] of the first compound is preferably larger than an energy gap $T_{77K}(M2)$ at 77 [K] of the second compound. $T_{77K}(M1)$ is preferably 2.0 eV or more, more preferably 2.2 eV or more.

Relationship Between Triplet Energy and Energy Gap at 77K

Description will be made on a relationship between a triplet energy and an energy gap at 77K. In the exemplary embodiment, the energy gap at 77 [K] is different from a typical triplet energy in some aspects.

Triplet energy is measured as follows. Firstly, a measurement target compound is deposited on a quartz substrate to prepare a sample, or dissolved in an appropriate solvent to prepare a solution and the solution is encapsulated in a quartz glass pipe to prepare a sample. A phosphorescent spectrum (ordinate axis: phosphorescent luminous intensity, abscissa axis: wavelength) of each of the samples was measured at a low temperature (77K). A tangent was drawn to the rise of the phosphorescent spectrum on the short-wavelength side. Triplet energy was calculated according to a predetermined conversion equation based on a wavelength value at an intersection of the tangent and the abscissa axis.

Herein, the first compound used in the exemplary embodiment is preferably a compound having a small $\Delta ST$. When $\Delta ST$ is small, intersystem crossing and inverse intersystem crossing easily occur even in a low temperature (77 [K]) condition, so that a singlet state and a triplet state are present in a mixed manner. As a result, spectrum measured in the same manner as the above includes emission from both of the singlet state and the triplet state and it is difficult to distinguish the emission from the singlet state from the emission from the triplet state. However, it is considered that the triplet energy is basically dominant.

Accordingly, in order to distinguish the triplet energy measured in the exemplary embodiment from a typical triplet energy T in a strict meaning although the measurement method is the same, a value measured as follows is referred to as an energy gap $T_{77K}$. In the measurement using a thin film, a measurement target compound is deposited on a quartz substrate to prepare a 100-nm thick sample. A phosphorescent spectrum (ordinate axis: phosphorescent luminous intensity, abscissa axis: wavelength) of the sample is measured at a low temperature (77K). A tangent is drawn to the rise of the phosphorescent spectrum on the short-wavelength side. An energy amount is calculated as the energy gap $T_{77K}$ according to a conversion equation 1 below based on a wavelength value $\lambda_{edge}$ (nm) at an intersection of the tangent and the abscissa axis.

$$T_{77K}[eV]=1239.85/\lambda_{edge} \quad \text{Conversion Equation 1:}$$

The tangent to the rise of the phosphorescence spectrum on the short-wavelength side is drawn as follows. While moving on a curve of the phosphorescence spectrum from the short-wavelength side to the maximum spectral value closest to the short-wavelength side among the maximum spectral values, a tangent is checked at each point on the curve toward the long-wavelength of the phosphorescence spectrum. An inclination of the tangent is increased as the curve rises (i.e., a value of the ordinate axis is increased). A tangent drawn at a point of the maximum inclination (i.e., a tangent at an inflection point) is defined as the tangent to the rise of the phosphorescence spectrum on the short-wavelength side.

The maximum with peak intensity being 15% or less of the maximum peak intensity of the spectrum is not included in the above-mentioned maximum closest to the short-wavelength side of the spectrum. The tangent drawn at a point of the maximum spectral value being closest to the short-wavelength side and having the maximum inclination is defined as a tangent to the rise of the phosphorescence spectrum on the short-wavelength side.

For phosphorescence measurement, a spectrophotofluorometer body F-4500 (manufactured by Hitachi High-Technologies Corporation) is usable. The measurement instrument is not limited to this arrangement. A combination of a cooling unit, a low temperature container, an excitation light source and a light-receiving unit may be used for measurement.

Film Thickness of Emitting Layer

A film thickness of the emitting layer 5 of the organic EL device of the exemplary embodiment is preferably in a range from 5 nm to 50 nm, more preferably in a range from 7 nm to 50 nm, and further preferably in a range from 10 nm to 50 nm. The thickness of less than 5 nm may cause difficulty in forming the emitting layer 5 and in controlling chromaticity, while the thickness of more than 50 nm may raise drive voltage.

Content Ratio of Compounds in Emitting Layer

In the organic EL device 1 of the exemplary embodiment, a content ratio of the first compound in the emitting layer 5 is preferably 5 mass % or more, more preferably in a range from 10 mass % to 80 mass %, further preferably in a range from 40 mass % to 60 mass %. A content of the second compound is preferably in a range from 1 mass % to 10 mass %. An upper limit of the total of the respective content ratios of the first and second compounds in the emitting layer 5 is 100 mass %. It should be noted that the emitting layer 5 of the exemplary embodiment may further contain another material in addition to the first and second compounds.

Substrate

A substrate 2 is used as a support for the organic EL device 1. For instance, glass, quartz, plastics and the like are usable for the substrate 2. A flexible substrate is also usable. The flexible substrate is a bendable substrate. The flexible substrate is exemplified by a plastic substrate made of polycarbonate, polyarylate, polyethersulfone, polypropylene, polyester, polyvinyl fluoride, polyvinyl chloride, polyimide, and polyethylene naphthalate. Moreover, an inorganic vapor deposition film is also usable as the substrate 2.

Anode

Metal, alloy, an electrically conductive compound and a mixture thereof, which have a large work function, specifically, of 4.0 eV or more, is preferably usable as the anode 3 formed on the substrate 2. Specific examples of the material for the anode include indium tin oxide (ITO), indium tin oxide containing silicon or silicon oxide, indium zinc oxide, tungsten oxide, indium oxide containing zinc oxide and graphene. In addition, gold (Au), platinum (Pt), nickel (Ni), tungsten (W), chrome (Cr), molybdenum (Mo), iron (Fe), cobalt (Co), copper (Cu), palladium (Pd), titanium (Ti), or nitrides of a metal material (e.g., titanium nitride) are usable.

The above materials are typically deposited as a film by sputtering. For instance, indium zinc oxide can be deposited as a film by sputtering using a target that is obtained by adding zinc oxide in a range from 1 mass % to 10 mass % to indium oxide. Moreover, for instance, indium oxide containing tungsten oxide and zinc oxide can be deposited as a film by sputtering using a target that is obtained by adding tungsten oxide in a range from 0.5 mass % to 5 mass % and zinc oxide in a range from 0.1 mass % to 1 mass % to indium oxide. In addition, vapor deposition, coating, ink jet printing, spin coating and the like may be used for forming the anode 3.

Among the organic layers formed on the anode 3, a hole injecting layer 6 formed adjacent to the anode 3 is formed of a composite material that facilitates injection of holes irrespective of the work function of the anode 3. Accordingly, a material usable as an electrode material (e.g., metal, alloy, an electrically conductive compound, a mixture thereof, and elements belonging to Groups 1 and 2 of the periodic table of the elements) is usable as the material for the anode 3.

The elements belonging to Groups 1 and 2 of the periodic table of the elements, which are materials having a small work function, namely, an alkali metal such as lithium (Li) and cesium (Cs) and an alkaline earth metal such as magnesium (Mg), calcium (Ca) and strontium (Sr), alloy thereof (e.g., MgAg, AlLi), a rare earth metal such as europium (Eu) and ytterbium (Yb), and alloy thereof are also usable as the material for the anode. When the anode 3 is formed of the alkali metal, alkaline earth metal and alloy thereof, vapor deposition and sputtering are usable. Further, when the anode is formed of silver paste and the like, coating, ink jet printing and the like are usable.

Hole Injecting Layer

A hole injecting layer 6 is a layer containing a highly hole-injectable substance. Examples of the highly hole-injectable substance include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

In addition, the examples of the highly hole-injectable substance further include: an aromatic amine compound, which is a low-molecule compound, such that 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl(abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1); and dipyrazino[2,3-f:20,30-h]quinoxaline-2,3,6,7,10,11-hexacarbonitrile (HAT-CN).

Moreover, a high-molecule compound (e.g., an oligomer, dendrimer and polymer) is also usable as the highly hole-injectable substance. Examples of the high-molecule compound include poly(N-vinylcarbazole) (abbreviation: PVK), poly(4-vinyltriphenylamine) (abbreviation: PVTPA), poly [N-(4-{N'-[4-(4-diphenylamino)phenyl]phenyl-N'-phenylamino}phenyl)methacrylamido] (abbreviation: PTPDMA), and poly[N,N'-bis(4-butylphenyl)-N,N'-bis(phenyl)benzidine] (abbreviation: Poly-TPD). Furthermore, the examples of the high-molecule compound include a high-molecule compound added with an acid such as poly(3,4-ethylene dioxythiophene)/poly(styrene sulfonic acid) (PEDOT/PSS), and polyaniline/poly(styrene sulfonic acid) (PAni/PSS).

Hole Transporting Layer

A hole transporting layer 7 is a layer containing a highly hole-transportable substance. An aromatic amine compound, carbazole derivative, anthracene derivative and the like are usable for the hole transporting layer 7. Specific examples of a material for the hole transporting layer include 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluorene-9-yl)triphenylamine (abbreviation: BAFLP), 4,4'-bis [N-(9,9-dimethylfluorene-2-yl)-N-phenylamino]biphenyl (abbreviation: DFLDPBi), 4,4',4''-tris(N,N-diphenylamino)triphenylamine (abbreviation: TDATA), 4,4',4''-tris[N-(3- methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The above-described substances mostly have a hole mobility of $10^{-6}$ cm$^2$/(V·s) or more.

A carbazole derivative (e.g., CBP, 9-[4-(N-carbazolyl)]phenyl-10-phenylanthracene (CzPA), and 9-phenyl-3-[4-(10-phenyl-9-anthryl)phenyl]-9H-carbazole (PCzPA)) and an anthracene derivative (e.g., t-BuDNA, DNA, and DPAnth) may be used for the hole transporting layer 7. A high polymer compound such as poly(N-vinylcarbazole) (abbreviation: PVK) and poly(4-vinyltriphenylamine) (abbreviation: PVTPA) is also usable.

However, any substance having a hole transporting performance higher than an electron transporting performance may be used in addition to the above substances. A highly hole-transportable substance may be provided in the form of a single layer or a laminated layer of two or more layers of the above substance.

When the hole transporting layer includes two or more layers, one of the layers with a larger energy gap is preferably provided closer to the emitting layer 5.

In the exemplary embodiment, the hole transporting layer 7 preferably has a function of preventing triplet excitons generated in the emitting layer 5 from dispersing to the hole transporting layer to trap the triplet excitons in the emitting layer 5.

Electron Transporting Layer An electron transporting layer 8 is a layer containing a highly electron-transportable substance. As the electron transporting layer, 1) a metal complex such as an aluminum complex, beryllium complex and zinc complex, 2) heteroaromatic compound such as an imidazole derivative, benzimidazole derivative, azine derivative, carbazole derivative, and phenanthroline derivative, and 3) a high-molecule compound are usable. Specifically, as a low-molecule organic compound, a metal complex such as Alq, tris(4-methyl-8-quinolinato)aluminum (abbreviation: Almq3), bis(10-hydroxybenzo[h]quinolinato)beryllium (abbreviation: BeBq2), BAlq, Znq, ZnPBO and ZnBTZ are usable. In addition to the metal complex, a heteroaromatic compound such as 2-(4-biphenyl)-5-(4-tert-butylphenyl)-1,3,4-oxadiazole (abbreviation: PBD), 1,3-bis[5-(ptert-butylphenyl)-1,3,4-oxadiazole-2-yl]benzene (abbreviation: OXD-7), 3-(4-tert-butylphenyl)-4-phenyl-5-(4-biphenyl)-1,2,4-triazole (abbreviation: TAZ), 3-(4-tert-butylphenyl)-4-(4-ethylphenyl)-5-(4-biphenyl)-1,2,4-triazole (abbreviation: p-EtTAZ), bathophenanthroline (abbreviation: BPhen), bathocuproine (abbreviation: BCP), and 4,4'-bis(5-methylbenzoxazole-2-yl)stilbene (abbreviation: BzOs) are usable. In the exemplary embodiment, a benzimidazole compound is suitably usable. The above-described substances mostly have an electron mobility of $10^{-6}$ cm$^2$/(V·s) or more. However, any substance having an electron transporting performance higher than a hole transporting performance may be used for the electron transporting layer 8 in addition to the above substances. The electron transporting layer 8 may be provided in the form of a single layer or a laminated layer of two or more layers of the above substance(s).

Moreover, a high-molecule compound is also usable for the electron transporting layer 8. For instance, poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)](abbreviation: PF-BPy) and the like are usable.

In the exemplary embodiment, the electron transporting layer 8 preferably has a function of preventing triplet excitons generated in the emitting layer 5 from dispersing to the electron transporting layer 8 and the electron injecting layer 9 to trap the triplet excitons in the emitting layer 5.

Electron Injecting Layer

An electron injecting layer 9 is a layer containing a highly electron-injectable substance. Examples of a material for the electron injecting layer include an alkali metal, alkaline earth metal and a compound thereof, examples of which include lithium (Li), cesium (Cs), calcium (Ca), lithium fluoride (LiF), cesium fluoride (CsF), calcium fluoride (CaF2), and lithium oxide (LiOx). In addition, a compound containing an alkali metal, alkaline earth metal and a compound thereof in the electron transportable substance, specifically, a compound containing magnesium (Mg) in Alq and the like may be used. With this compound, electrons can be more efficiently injected from the cathode.

Alternatively, a composite material provided by mixing an organic compound with an electron donor may be used for the electron injecting layer 9. The composite material exhibits excellent electron injecting performance and electron transporting performance since the electron donor generates electron in the organic compound. In this arrangement, the organic compound is preferably a material exhibiting an excellent transforming performance of the generated electrons. Specifically, for instance, the above-described substance for the electron transporting layer 8 (e.g., the metal complex and heteroaromatic compound) is usable. The electron donor may be any substance exhibiting an electron donating performance to the organic compound. Specifically, an alkali metal, alkaline earth metal and a rare earth metal are preferable, examples of which include lithium, cesium, magnesium, calcium, erbium and ytterbium. Moreover, an alkali metal oxide and alkaline earth metal oxide are preferable, examples of which include lithium oxide, calcium oxide, and barium oxide. Further, Lewis base such as magnesium oxide is also usable. Furthermore, tetrathiafulvalene (abbreviation: TTF) is also usable.

Cathode

Metal, alloy, an electrically conductive compound, a mixture thereof and the like, which have a small work function, specifically, of 3.8 eV or less, is preferably usable as a material for the cathode 4. Specific examples of the material for the cathode include: the elements belonging to Groups 1 and 2 of the periodic table of the elements, namely, an alkali metal such as lithium (Li) and cesium (Cs) and an alkaline earth metal such as magnesium (Mg), calcium (Ca) and strontium (Sr); alloy thereof (e.g., MgAg, AlLi); a rare earth metal such as europium (Eu) and ytterbium (Yb); and alloy thereof.

When the cathode 4 is formed of the alkali metal, alkaline earth metal and alloy thereof, vapor deposition and sputtering are usable. Moreover, when the anode is formed of silver paste and the like, coating, ink jet printing and the like are usable.

By providing the electron injecting layer 9, various conductive materials such as Al, Ag, ITO, graphene and indium tin oxide containing silicon or silicon oxide are usable for forming the cathode 4 irrespective of the magnitude of the work function. The conductive materials can be deposited as a film by sputtering, ink jet printing, spin coating and the like.

Layer Formation Method(s)

A method for forming each layer of the organic EL device 1 in the exemplary embodiment is subject to no limitation except for the above particular description. However, known methods of dry film-forming and wet film-forming are applicable. Examples of the dry film-forming include vacuum deposition, sputtering, plasma and ion plating. Examples of the wet film-forming include spin coating, dipping, flow coating and ink-jet.

Film Thickness

A film thickness of each of the organic layers of the organic EL device 1 according to the exemplary embodiment is subject to no limitation except for the above particular description. The thickness is generally preferably in a range from several nanometers to 1 μm, since too small thickness are likely to cause defects such as a pin hole while too large thickness requires high voltage to be applied and lowers efficiency.

Herein, the number of carbon atoms forming a ring (also referred to as ring carbon atoms) means the number of carbon atoms included in atoms forming the ring itself of a compound in which the atoms are bonded to form the ring (e.g., a monocyclic compound, a fused ring compound, a cross-linked compound, a carbocyclic compound, and a heterocyclic compound). When the ring is substituted by a substituent, carbon atom(s) included in the substituent is not counted as the ring carbon atoms. The same applies to the "ring carbon atoms" described below, unless particularly noted. For instance, a benzene ring has 6 ring carbon atoms, a naphthalene ring has 10 ring carbon atoms, a pyridinyl group has 5 ring carbon atoms, and a furanyl group has 4 ring carbon atoms. When a benzene ring or a naphthalene ring is substituted, for instance, by an alkyl group, the carbon atoms of the alkyl group are not counted as the ring carbon atoms. For instance, when a fluorene ring (inclusive of a spirofluorene ring) is bonded as a substituent to a fluorene ring, the carbon atoms of the fluorene ring as a substituent are not counted as the ring carbon atoms.

Herein, the number of atoms forming a ring (also referred to as ring atoms) means the number of atoms forming the ring itself of a compound in which the atoms are bonded to form the ring (e.g., a monocyclic compound, a fused ring compound, a cross-linked compound, a carbocyclic compound, and a heterocyclic compound). Atom(s) not forming the ring (e.g., hydrogen atom(s) for saturating the valence of the atom which forms the ring) and atom(s) in a substituent by which the ring is substituted are not counted as the ring atoms. The same applies to the "ring atoms" described below, unless particularly noted. For instance, a pyridine ring has 6 ring atoms, a quinazoline ring has 10 ring atoms, and a furan ring has 5 ring atoms. Hydrogen atoms respectively bonded to carbon atoms of the pyridine ring or the quinazoline ring and atoms forming a substituent are not counted as the ring atoms. For instance, when a fluorene ring (inclusive of a spirofluorene ring) is bonded as a substituent to a fluorene ring, the atoms of the fluorene ring as a substituent are not included in the ring atoms.

Next, each of substituents described in the above formulae will be described.

Examples of the aromatic hydrocarbon group (occasionally referred to as an aryl group) having 6 to 30 ring carbon atoms or having 6 to 40 ring carbon atoms in the exemplary embodiment are a phenyl group, biphenyl group, terphenyl group, naphthyl group, anthryl group, phenanthryl group, fluorenyl group, pyrenyl group, chrysenyl group, fluoranthenyl group, benz[a]anthryl group, benzo[c]phenanthryl group, triphenylenyl group, benzo[k]fluoranthenyl group, benzo[g]chrysenyl group, benzo[b]triphenylenyl group, picenyl group, and perylenyl group.

The aryl group in the exemplary embodiment preferably has 6 to 20 ring carbon atoms, more preferably 6 to 14 ring carbon atoms, further preferably 6 to 12 ring carbon atoms. Among the aryl group, a phenyl group, biphenyl group, naphthyl group, phenanthryl group, terphenyl group and fluorenyl group are particularly preferable. A carbon atom at a position 9 of each of 1-fluorenyl group, 2-fluorenyl group, 3-fluorenyl group and 4-fluorenyl group is preferably substituted by a substituted or unsubstituted alkyl group having 1 to 30 carbon atoms or a substituted or unsubstituted aryl group having 6 to 18 ring carbon atoms later described in the exemplary embodiment.

In the exemplary embodiment, the heterocyclic group (occasionally referred to as heteroaryl group, heteroaromatic ring group or aromatic heterocyclic group) having 5 to 30 ring atoms preferably contains at least one atom selected from the group consisting of nitrogen, sulfur, oxygen, silicon, selenium atom and germanium atom, and more preferably contains at least one atom selected from the group consisting of nitrogen, sulfur and oxygen.

Examples of the heterocyclic group (occasionally referred to as heteroaryl group, heteroaromatic ring group or aromatic heterocyclic group) having 5 to 30 ring atoms in the exemplary embodiment are a pyridyl group, pyrimidinyl group, pyrazinyl group, pyridazynyl group, triazinyl group, quinolyl group, isoquinolinyl group, naphthyridinyl group, phthalazinyl group, quinoxalinyl group, quinazolinyl group, phenanthridinyl group, acridinyl group, phenanthrolinyl group, pyrrolyl group, imidazolyl group, pyrazolyl group, triazolyl group, tetrazolyl group, indolyl group, benzimidazolyl group, indazolyl group, imidazopyridinyl group, benzotriazolyl group, carbazolyl group, furyl group, thienyl group, oxazolyl group, thiazolyl group, isoxazolyl group, isothiazolyl group, oxadiazolyl group, thiadiazolyl group, benzofuranyl group, benzothiophenyl group, benzoxazolyl group, benzothiazolyl group, benzisoxazolyl group, benzisothiazolyl group, benzoxadiazolyl group, benzothiadiazolyl group, dibenzofuranyl group, dibenzothiophenyl group, piperidinyl group, pyrrolidinyl group, piperazinyl group, morpholyl group, phenazinyl group, phenothiazinyl group, and phenoxazinyl group.

The heterocyclic group in the exemplary embodiment preferably has 5 to 20 ring atoms, more preferably 5 to 14 ring atoms. Among the above, a 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-carbazolyl group, 2-carbazolyl group, 3-carbazolyl group, 4-carbazolyl group, and 9-carbazolyl group are particularly preferable. A nitrogen atom at a position 9 of each of 1-carbazolyl group, 2-carbazolyl group, 3-carbazolyl group and 4-carbazolyl group is preferably substituted by a substituted or unsubstituted aryl group having 6 to 30 ring carbon atoms or a substituted or unsubstituted heterocyclic group having 5 to 30 ring atoms in the exemplary embodiment.

In the exemplary embodiment, the heterocyclic group may be a group derived from any one of moieties represented by formulae (XY-1) to (XY-18).

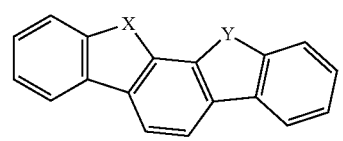

(XY-1)

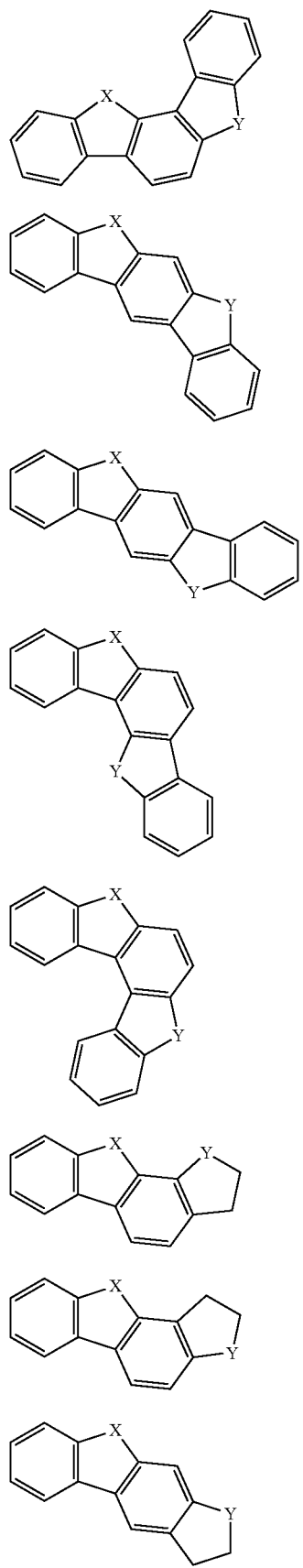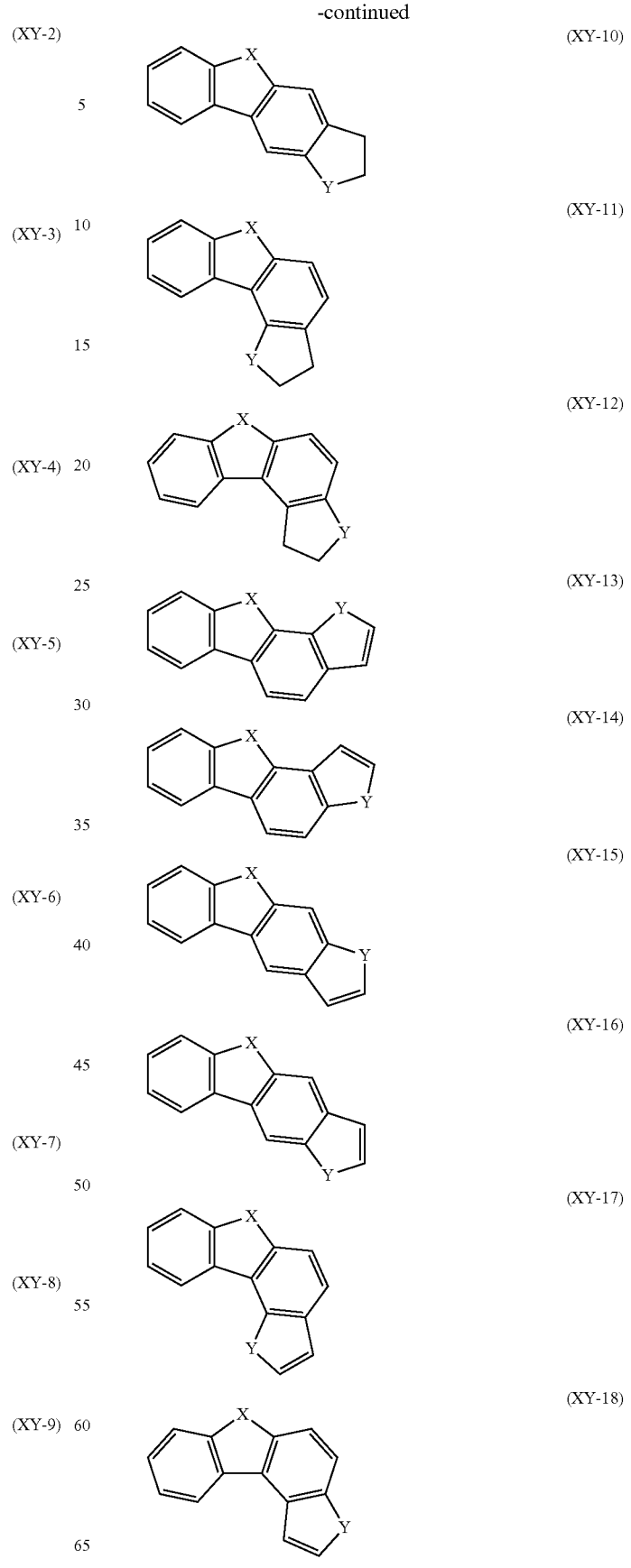

In the formulae (XY-1) to (XY-18), X and Y are each independently a hetero atom, and are preferably an oxygen atom, sulfur atom, selenium atom, silicon atom or germanium atom. The moieties represented by the formulae (XY-1) to (XY-18) may each be bonded in any position to be a heterocyclic group, which may be substituted.

In the exemplary embodiment, examples of the substituted or unsubstituted carbazolyl group may include a group in which a carbazole ring is further fused with a ring(s) as shown in the following formulae. Such a group may be substituted. The group may be bonded in any position as desired.

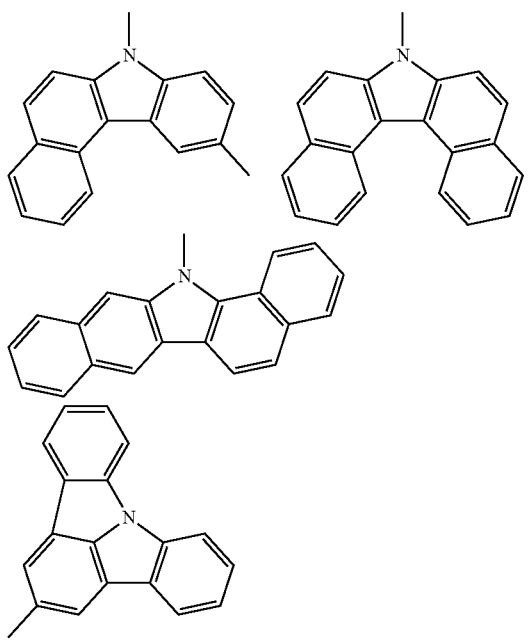

The alkyl group having 1 to 30 carbon atoms in the exemplary embodiment may be linear, branched or cyclic. Examples of the linear or branched alkyl group are a methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neo-pentyl group, amyl group, isoamyl group, 1-methylpentyl group, 2-methylpentyl group, 1-pentylhexyl group, 1-butylpentyl group, 1-heptyloctyl group and 3-methylpentyl group.

The linear or branched alkyl group in the exemplary embodiment preferably has 1 to 10 carbon atoms, more preferably 1 to 6 carbon atoms. Among the linear or branched alkyl group, a methyl group, ethyl group, propyl group, isopropyl group, n-butyl group, s-butyl group, isobutyl group, t-butyl group, n-pentyl group, n-hexyl group, amyl group, isoamyl group and neopentyl group are particularly preferable.

Examples of the cycloalkyl group having 3 to 30 in the exemplary embodiment are a cyclopropyl group, cyclobutyl group, cyclopentyl group, cyclohexyl group, 4-metylcyclohexyl group, adamantyl group and norbornyl group. The cycloalkyl group preferably has 3 to 10 ring carbon atoms, more preferably 5 to 8 ring carbon atoms. Among the cycloalkyl group, a cyclopentyl group and a cyclohexyl group are particularly preferable.

A halogenated alkyl group provided by substituting an alkyl group with a halogen atom is exemplified by one provided by substituting an alkyl group having 1 to 30 carbon atoms with one or more halogen atoms. Specific examples of the above halogenated alkyl group are a fluoromethyl group, difluoromethyl group, trifluoromethyl group, fluoroethyl group, trifluoromethylmethyl group, trifluoroethyl group and pentafluoroethyl group.

The alkoxy group having 1 to 30 carbon atoms in the exemplary embodiment is represented by —$OZ_1$. $Z_1$ is exemplified by the above alkyl group having 1 to 30 carbon atoms. Examples of the alkoxy group are a methoxy group, ethoxy group, propoxy group, butoxy group, pentyloxy group and hexyloxy group. The alkoxy group preferably has 1 to 20 carbon atoms.

A halogenated alkoxy group provided by substituting an alkoxy group with a halogen atom is exemplified by one provided by substituting an alkoxy group having 1 to 30 carbon atoms with one or more fluorine atoms.

The aryloxy group having 6 to 30 ring carbon atoms in the exemplary embodiment is represented by —$OZ_2$. $Z_2$ is exemplified by the above aryl group having 6 to 30 ring carbon atoms. The aryloxy group preferably has 6 to 20 ring carbon atoms. The aryloxy group is exemplified by a phenoxy group.

Examples of the substituted amino group in the exemplary embodiment are an alkylamino group having 2 to 30 carbon atoms and an arylamino group having 6 to 60 ring carbon atoms.

The alkylamino group having 2 to 30 carbon atoms is represented by —$NHR_V$ or —$N(R_V)_2$. $R_V$ is exemplified by the alkyl group having 1 to 30 carbon atoms.

The arylamino group having 6 to 60 ring carbon atoms is represented by —$NHR_W$ or —$N(R_W)_2$. $R_W$ is exemplified by the above aryl group having 6 to 30 ring carbon atoms.

Examples of the halogen atom include a fluorine atom, chlorine atom, bromine tom and iodine atom, among which a fluorine atom is preferable.

The aralkyl group is preferably an aralkyl group having 6 to 30 ring carbon atoms and is represented by —$Z_3$—$Z_4$. $Z_3$ is exemplified by an alkylene group corresponding to the above alkyl group having 1 to 30 carbon atoms. $Z_4$ is exemplified by the above aryl group having 6 to 30 ring carbon atoms. This aralkyl group is preferably an aralkyl group having 7 to 30 carbon atoms, in which an aryl moiety has 6 to 30 carbon atoms, preferably 6 to 20 carbon atoms, more preferably 6 to 12 carbon atoms and an alkyl moiety has 1 to 30 carbon atoms, preferably 1 to 20 carbon atoms, more preferably 1 to 10 carbon atoms, further preferably 1 to 6 carbon atoms. Examples of the aralkyl group are a benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, and 2-β-naphthylisopropyl group.

An aldehyde group, carbonyl group, ester group, carbamoyl group, and amino group may be substituted by an aliphatic hydrocarbon, alicyclic hydrocarbon, aromatic hydrocarbon, heterocyclic ring and the like. The aliphatic hydrocarbon, alicyclic hydrocarbon, aromatic hydrocarbon and heterocyclic may further have a substituent. A siloxanyl group is a silicon compound group with an ether bond, which is exemplified by a trimethylsiloxanyl group.

Herein, "carbon atoms forming a ring (ring carbon atoms)" mean carbon atoms forming a saturated ring, unsaturated ring, or aromatic ring. "Atoms forming a ring (ring atoms)" mean carbon atoms and hetero atoms forming a hetero ring including a saturated ring, unsaturated ring, or aromatic ring.

Herein, a hydrogen atom includes isotope having different numbers of neutrons, specifically, protium, deuterium and tritium.

Herein, examples of the substituent meant by "substituted or unsubstituted" are an alkylsilyl group, arylsilyl group, alkenyl group, alkynyl group, alkylthio group, arylthio group, hydroxyl group, nitro group and carboxy group, in addition to the above-described aryl group, heterocyclic group, alkyl group (a linear or branched alkyl group, cycloalkyl group, haloalkyl group), aralkyl group, substituted amino group, halogen atom, cyano group, alkoxy group and aryloxy group.

Among the above substituents, an aryl group, heterocyclic group, alkyl group, halogen atom, alkylsilyl group, arylsilyl group and cyano group are preferable. More preferable substituents are one listed as the preferable substituents described for each substituent.

The above substituents may be further substituted by an alkenyl group, alkynyl group, aralkyl group, halogen atom, cyano group, hydroxyl group, nitro group and carboxy group, in addition to the above-described aryl group, heterocyclic group, alkyl group, alkylsilyl group, arylsilyl group, alkoxy group, aryloxy group, alkylamino group, arylamino group, alkylthio group, and arylthio group. In addition, plural ones of these substituents may be mutually bonded to form a ring.

The alkenyl group is preferably an alkenyl group having 2 to 30 carbon atoms, which may be linear, branched or cyclic. Examples of the alkenyl group include a vinyl group, propenyl group, butenyl group, oleyl group, eicosapentaenyl group, docosahexaenyl group, styryl group, 2,2-diphenylvinyl group, 1,2,2-triphenylvinyl group, 2-phenyl-2-propenyl group, cyclopentadienyl group, cyclopentenyl group, cyclohexenyl group, and cyclohexadienyl group.

The alkynyl group is preferably an alkynyl group having 2 to 30 carbon atoms, which may be linear, branched or cyclic. Examples of the alkynyl group include ethynyl, propynyl, and 2-phenylethynyl.

The alkylthio group having 1 to 30 carbon atoms is represented by —$SR_V$. $R_V$ is exemplified by the alkyl group having 1 to 30 carbon atoms. The alkylthio group preferably has 1 to 20 carbon atoms.

The arylthio group having 6 to 30 ring carbon atoms is represented by —$SR_W$. $R_W$ is exemplified by the above aryl group having 6 to 30 ring carbon atoms. The arylthio group preferably has 6 to 20 ring carbon atoms.

Examples of the substituted silyl group in the exemplary embodiment are an alkylsilyl group having 3 to 30 carbon atoms and an arylsilyl group having 6 to 30 ring carbon atoms.

The alkylsilyl group having 3 to 30 carbon atoms in the exemplary embodiment is exemplified by a trialkylsilyl group having the above examples of the alkyl group having 1 to 30 carbon atoms. Specific examples of the alkylsilyl group are a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyl dimethylsilyl group, propyldimethylsilyl group, and triisopropylsilyl group. Three alkyl groups in the trialkylsilyl group may be the same or different.

Examples of the arylsilyl group having 6 to 30 ring carbon atoms in the exemplary embodiment are a dialkylarylsilyl group, alkyldiarylsilyl group and triarylsilyl group.

The dialkylarylsilyl group is exemplified by a dialkylarylsilyl group including two of the alkyl group listed as the examples of the alkyl group having 1 to 30 carbon atoms and one of the aryl group listed as the examples of the aryl group having 6 to 30 ring carbon atoms. The dialkylarylsilyl group preferably has 8 to 30 carbon atoms.

The alkyldiarylsilyl group is exemplified by an alkyldiarylsilyl group including one of the alkyl group listed as the examples of the alkyl group having 1 to 30 carbon atoms and two of the aryl group listed as the examples of the aryl group having 6 to 30 ring carbon atoms. The alkyldiarylsilyl group preferably has 13 to 30 carbon atoms.

The triarylsilyl group is exemplified by a triarylsilyl group including three of the aryl group listed as the examples of the aryl group having 6 to 30 ring carbon atoms. The triarylsilyl group preferably has 18 to 30 carbon atoms.

Herein, "unsubstituted" in "substituted or unsubstituted" means that a group is not substituted by the above-described substituents but bonded with a hydrogen atom.

Herein, "XX to YY carbon atoms" in the description of "substituted or unsubstituted ZZ group having XX to YY carbon atoms" represent carbon atoms of an unsubstituted ZZ group and do not include carbon atoms of a substituent(s) of a substituted ZZ group. "YY" is larger than "XX" and each of "XX" and "YY" represents an integer of 1 or more.

Herein, "XX to YY atoms" in the description of "substituted or unsubstituted ZZ group having XX to YY atoms" represent atoms of an unsubstituted ZZ group and does not include atoms of a substituent(s) of a substituted ZZ group. "YY" is larger than "XX" and each of "XX" and "YY" represents an integer of 1 or more.

Herein, when substituents are mutually bonded to form a cyclic structure, the cyclic structure is a saturated ring, unsaturated ring, aromatic hydrocarbon ring, or a heterocyclic ring. Moreover, the cyclic structure formed by bonding the substituents may have a substituent.

Herein, examples of the aromatic hydrocarbon group and the heterocyclic group for the linking group include a divalent or multivalent group obtained by removing at least one atom from the above-described monovalent groups.

Moreover, in the exemplary embodiment, examples of the aromatic hydrocarbon group and the heterocyclic group include cyclic structures from which the above-described monovalent groups are derived.

Electronic Device

The organic EL device 1 of the exemplary embodiment is usable in an electronic device such as a display device and a light-emitting device. Examples of the display unit include display components such as en organic EL panel module, TV, mobile phone, tablet, and personal computer. Examples of the light-emitting unit include an illuminator and a vehicle light.

Second Exemplary Embodiment

An arrangement of an organic EL device according to a second exemplary embodiment will be described below. In the description of the second exemplary embodiment, the same components as those in the first exemplary embodiment are denoted by the same reference signs and names to simplify or omit an explanation of the components. In the second exemplary embodiment, the same materials and compounds as described in the first exemplary embodiment are usable, unless otherwise specified.

The organic EL device according to the second exemplary embodiment is different from the organic EL device according to the first exemplary embodiment in that the emitting layer further contains the third compound. Except for the above difference, the organic EL device according to the second exemplary embodiment is the same as in the first exemplary embodiment.

Third Compound

The third compound has a larger singlet energy than a singlet energy of the first compound.

Figure 5:
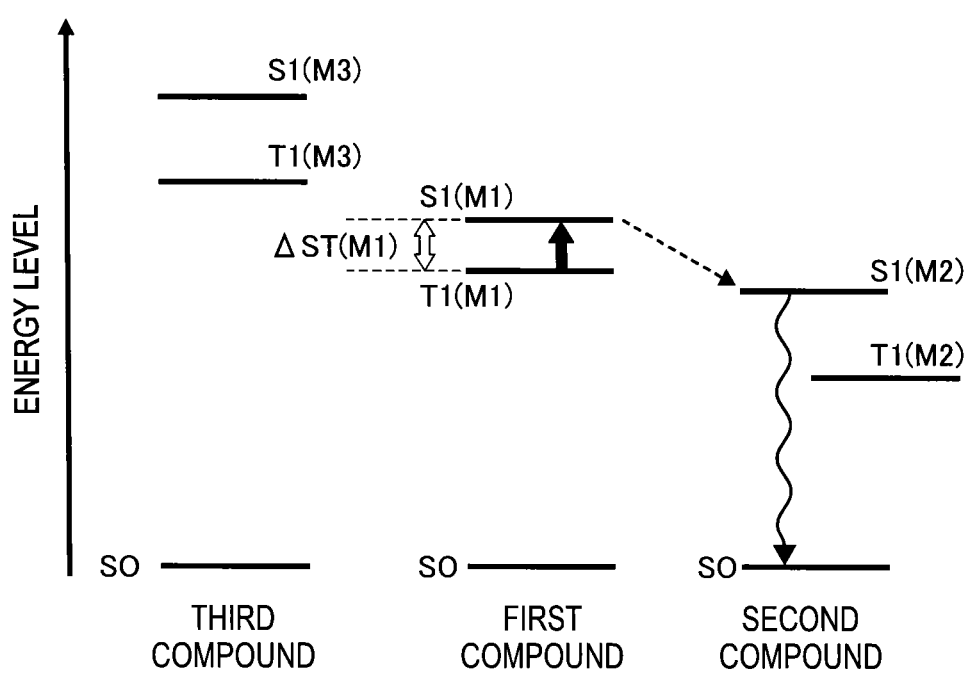
FIG. 5 shows a relationship between energy levels and energy transfer of compounds contained in en emitting layer in a second exemplary embodiment.

FIG. 5 shows an example of a relationship among energy levels of the first compound, the second compound and the third compound in the emitting layer. In FIG. 5, S0 represents a ground state, S1(M1) represents a lowest singlet state of the first compound, T1(M1) represents a lowest triplet state of the first compound, S1(M2) represents a lowest singlet state of the second compound, T1(M2) represents a lowest triplet state of the second compound, S1(M3) represents a lowest singlet state of the third compound, and T1(M3) represents a lowest triplet state of the third compound. A dashed arrow directed from S1(M1) to S1(M2) in FIG. 5 represents Förster energy transfer from the lowest singlet state of the first compound to the lowest singlet state of the second compound.

As shown in FIG. 5, when a compound having a small ΔST(M1) is used as the first compound, inverse intersystem crossing from the lowest triplet state T1(M1) to the lowest singlet state S1(M1) can be caused by a heat energy. Consequently, Förster energy transfer from the lowest singlet state S1(M1) of the first compound to the lowest singlet state S1(M2) of the second compound is caused. Consequently, fluorescence from the lowest singlet state S1(M2) of the second compound can be observed. It is considered that the internal quantum efficiency can be theoretically raised up to 100% also by using delayed fluorescence by the TADF mechanism.

Ratio of Three Components

In the emitting layer of the exemplary embodiment, it is preferable that the content ratio of the first compound is in a range from 10 mass % to 80 mass %, the content ratio of the second compound is in a range from 1 mass % to 10 mass %, and the content ratio of the third compound is in a range from 10 mass % to 80 mass %. The content ratio of the first compound is more preferably in a range from 20 mass % to 80 mass %, further preferably in a range from 40 mass % to 60 mass %. An upper limit of the total of the respective content ratios of the first, second and third compounds in the emitting layer is 100 mass %. It should be noted that the emitting layer of the exemplary embodiment may further contain another material in addition to the first, second and third compounds.

The third compound is not particularly limited, but preferably a compound other than an amine compound. Examples of the third compound include a carbazole derivative, dibenzofuran derivative and dibenzothiophene derivative, but not limited to the examples.

It is also preferable that the third compound has at least one of a partial structure represented by a formula (31) below and a partial structure represented by a formula (32) below in one molecule.

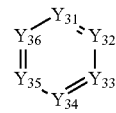
(31)

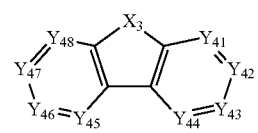
(32)

In the formula (31): $Y_{31}$ to $Y_{36}$ are each independently a nitrogen atom or a carbon atom bonded to another atom in the molecule of the third compound.

However, at least one of $Y_{31}$ to $Y_{36}$ is a carbon atom bonded to another atom in the molecule of the third compound.

In the formula (32): $Y_{41}$ to $Y_{48}$ are each independently a nitrogen atom or a carbon atom bonded to another atom in the molecule of the third compound.

However, at least one of $Y_{41}$ to $Y_{48}$ is a carbon atom bonded to another atom in the molecule of the third compound.

$X_3$ is a nitrogen atom, an oxygen atom or a sulfur atom.

In the formula (32), at least two of $Y_{41}$ to $Y_{48}$ are carbon atoms bonded to other atoms in the molecule of the third compound. A cyclic structure including the above carbon atoms is also preferably formed.

The partial structure represented by the formula (32) is preferably any one selected from the group consisting of partial structures group represented by formulae (321), (322), (323), (324), (325) and (326) below.

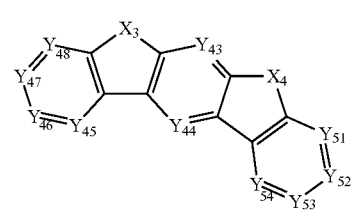
(321)

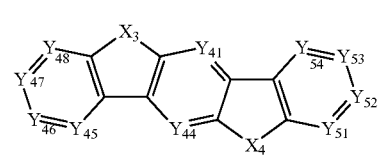
(322)

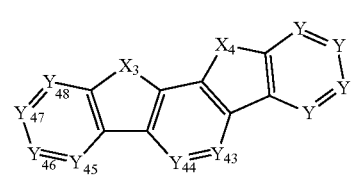
(323)

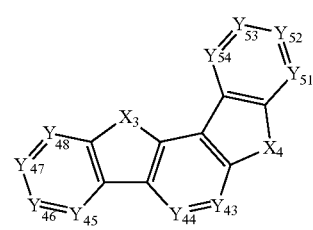
(324)

(325)
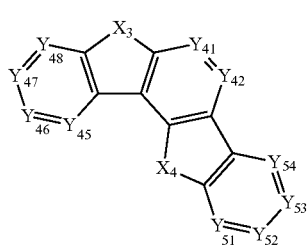

(326)
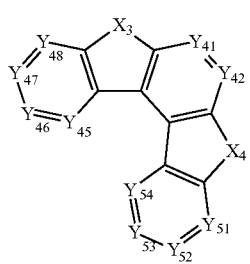

In the above formulae (321) to (326), $X_3$ is a nitrogen atom, an oxygen atom or a sulfur atom.

$Y_{41}$ to $Y_{48}$ are each independently a nitrogen atom or a carbon atom bonded to another atom in the molecule of the third compound.

$X_4$ is a nitrogen atom, an oxygen atom, a sulfur atom or a carbon atom.

$Y_{51}$ to $Y_{54}$ are each independently a nitrogen atom or a carbon atom bonded to another atom in the molecule of the third compound.

In the exemplary embodiment, the third compound also preferably has the partial structure represented by the formula (323) among the formulae (321) to (326).

The partial structure represented by the formula (31) is preferably in a form of at least one group selected from the group consisting of groups represented by formulae (33) and (34) below and preferably contained in the third compound.

For the third compound, bonding positions are preferably both situated in meta positions as shown in formulae (33) and (34) below to keep an energy gap $T_{77K}(M3)$ at 77 [K] high.

(33)
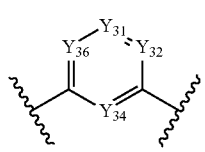

(34)
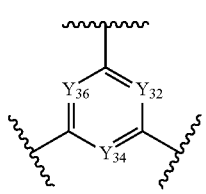

In the formulae (33) and (34), $Y_{31}$, $Y_{32}$, $Y_{34}$ and $Y_{36}$ are each independently a nitrogen atom or $CR_{31}$, in which $R_{31}$ is a hydrogen atom or a substituent. When $R_{31}$ is a substituent, the substituent is selected from the group consisting of a substituted or unsubstituted aromatic hydrocarbon group having 6 to 30 ring carbon atoms, substituted or unsubstituted heterocyclic group having 5 to 30 ring atoms, substituted or unsubstituted alkyl group having 1 to 30 carbon atoms, substituted or unsubstituted fluoroalkyl group having 1 to 30 carbon atoms, substituted or unsubstituted cycloalkyl group having 3 to 30 carbon atoms, substituted or unsubstituted aralkyl group having 7 to 30 carbon atoms, substituted silyl group, substituted germanium group, substituted phosphine oxide group, halogen atom, cyano group, nitro group, and carboxy group. The substituted or unsubstituted aromatic hydrocarbon group having 6 to 30 ring carbon atoms for $R_{31}$ is preferably a non-fused ring.

Wavy lines in the formulae (33) and (34) each show a bonding position with another atom or another structure in the molecule of the third compound.

$Y_{31}$, $Y_{32}$, $Y_{34}$ and $Y_{36}$ in the formula (33) are preferably each independently $CR_{31}$. A plurality of $R_{31}$ may be the same or different.

$Y_{32}$, $Y_{34}$ and $Y_{36}$ in the formula (34) are preferably each independently $CR_{31}$. A plurality of $R_{31}$ may be the same or different.

The substituted germanium group is preferably represented by $—Ge(R_{101})_3$. $R_{101}$ is each independently a substituent. The substituent $R_{101}$ is preferably a substituted or unsubstituted alkyl group having 1 to 30 carbon atoms or a substituted or unsubstituted aromatic hydrocarbon group having 6 to 30 ring carbon atoms. A plurality of $R_{101}$ are optionally mutually the same or different.

The partial structure represented by the formula (32) is preferably in a form of at least one group selected from the group consisting of a group represented by a formula (35) below, a group represented by a formula (36) below, a group represented by a formula (37) below, a group represented by a formula (38) below, a group represented by a formula (39) below and a group represented by a formula (30a) below, and preferably contained in the third compound.

(35)
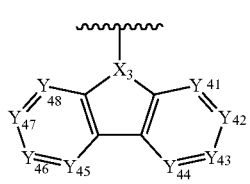

936)
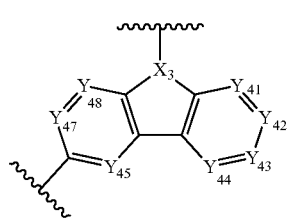

937)
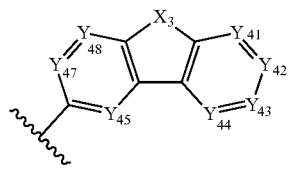

(38)
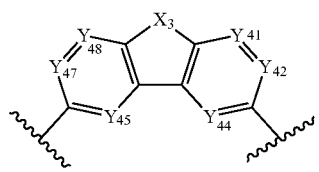

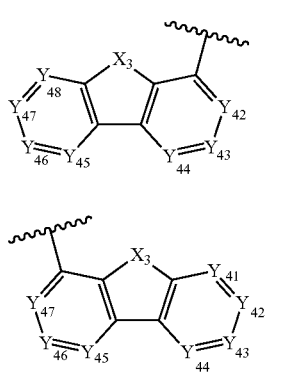

(39)

(30a)

In the above formulae (35) to (39) and (30a), $Y_{41}$, $Y_{42}$, $Y_{43}$, $Y_{44}$, $Y_{45}$, $Y_{46}$, $Y_{47}$ and $Y_{48}$ are each independently a nitrogen atom or $CR_{32}$, in which $R_{32}$ is a hydrogen atom or a substituent. When $R_{32}$ is a substituent, the substituent is selected from the group consisting of a substituted or unsubstituted aromatic hydrocarbon group having 6 to 30 ring carbon atoms, substituted or unsubstituted heterocyclic group having 5 to 30 ring atoms, substituted or unsubstituted alkyl group having 1 to 30 carbon atoms, substituted or unsubstituted fluoroalkyl group having 1 to 30 carbon atoms, substituted or unsubstituted cycloalkyl group having 3 to 30 carbon atoms, substituted or unsubstituted aralkyl group having 7 to 30 carbon atoms, substituted silyl group, substituted germanium group, substituted phosphine oxide group, halogen atom, cyano group, nitro group, and carboxy group. The substituted or unsubstituted aromatic hydrocarbon group having 6 to 30 ring carbon atoms for $R_{32}$ is preferably a non-fused ring.

$X_3$ in the formulae (35) and (36) is a nitrogen atom.

$X_3$ in the formulae (37) to (39) and (30a) is $NR_{33}$, an oxygen atom or a sulfur atom, in which $R_{33}$ is a substituent selected from the group consisting of a substituted or unsubstituted aromatic hydrocarbon group having 6 to 30 ring carbon atoms, substituted or unsubstituted heterocyclic group having 5 to 30 ring atoms, substituted or unsubstituted alkyl group having 1 to 30 carbon atoms, substituted or unsubstituted fluoroalkyl group having 1 to 30 carbon atoms, substituted or unsubstituted cycloalkyl group having 3 to 30 carbon atoms, substituted or unsubstituted aralkyl group having 7 to 30 carbon atoms, substituted silyl group, substituted germanium group, substituted phosphine oxide group, fluorine atom, cyano group, nitro group, and carboxy group. The substituted or unsubstituted aromatic hydrocarbon group having 6 to 30 ring carbon atoms for $R_{33}$ is preferably a non-fused ring.

Wavy lines in the formulae (35) to (39) and (30a) each show a bonding position with another atom or another structure in the molecule of the third compound.

$Y_{41}$ to $Y_{48}$ in the formula (35) are preferably each independently $CR_{32}$. $Y_{41}$ to $Y_{45}$, $Y_{47}$ and $Y_{48}$ in the formulae (36) and (37) are preferably each independently $CR_{32}$. $Y_{41}$, $Y_{42}$, $Y_{44}$, $Y_{45}$, $Y_{47}$ and $Y_{48}$ in the formula (38) are preferably each independently $CR_{32}$. $Y_{42}$ to $Y_{48}$ in the formula (39) are preferably each independently $CR_{32}$. $Y_{42}$ to $Y_{47}$ in the formula (30a) are preferably each independently $CR_{32}$. A plurality of $R_{32}$ are optionally mutually the same or different.

In the third compound, $X_3$ is preferably an oxygen atom or a sulfur atom, more preferably an oxygen atom.

In the third compound, $R_{31}$ and $R_{32}$ are each independently a hydrogen atom or a substituent. The substituent in $R_{31}$ and $R_{32}$ is preferably selected from the group consisting of a fluorine atom, a cyano group, a substituted or unsubstituted alkyl group having 1 to 30 carbon atoms, a substituted or unsubstituted aromatic hydrocarbon group having 6 to 30 ring carbon atoms, and substituted or unsubstituted heterocyclic group having 5 to 30 ring atoms. $R_{31}$ and $R_{32}$ are preferably a hydrogen atom, cyano group, substituted or unsubstituted aromatic hydrocarbon group having 6 to 30 ring carbon atoms, or substituted or unsubstituted aromatic heterocyclic group having 5 to 30 ring atoms. However, the substituted or unsubstituted aromatic hydrocarbon group having 6 to 30 ring carbon atoms in $R_{31}$ and $R_{32}$ is preferably a non-fused ring.

The third compound is also preferably an aromatic hydrocarbon compound or aromatic heterocyclic ring compound. Moreover, the third compound preferably has no fused aromatic hydrocarbon ring in the molecule.

Method of Preparing Third Compound

The third compound can be prepared by a method described in International Publication Nos. WO2012/153780 and WO2013/038650 and the like.

Examples of the substituent for the third compound are shown below, but the invention is not limited thereto.

Specific examples of the aromatic hydrocarbon group (occasionally referred to as an aryl group) include a phenyl group, tolyl group, xylyl group, naphthyl group, phenanthryl group, pyrenyl group, chrysenyl group, benzo[c]phenanthryl group, benzo[g]chrysenyl group, benzoanthryl group, triphenylenyl group, fluorenyl group, 9,9-dimethylfluorenyl group, benzofluorenyl group, dibenzofluorenyl group, biphenyl group, terphenyl group, quarterphenyl group and fluoranthenyl group, among which a phenyl group, biphenyl group, terphenyl group, quarterphenyl group, naphthyl group, triphenylenyl group and fluorenyl group may be preferable.

Specific examples of the substituted aromatic hydrocarbon group include a tolyl group, xylyl group and 9,9-dimethylfluorenyl group.

As is understood from the specific examples, the aryl group includes both fused aryl group and non-fused aryl group.

Preferable examples of the aromatic hydrocarbon group include a phenyl group, biphenyl group, terphenyl group, quarterphenyl group, naphthyl group, triphenylenyl group and fluorenyl group.

Specific examples of the aromatic heterocyclic group (occasionally referred to as a heteroaryl group, heteroaromatic ring group and heterocyclic group) include a pyrrolyl group, pyrazolyl group, pyrazinyl group, pyrimidinyl group, pyridazynyl group, pyridyl group, triazinyl group, indolyl group, isoindolyl group, imidazolyl group, benzimidazolyl group, indazolyl group, imidazo[1,2-a]pyridinyl group, furyl group, benzofuranyl group, isobenzofuranyl group, dibenzofuranyl group, azadibenzofuranyl group, thiophenyl group, benzothiophenyl group, dibenzothiophenyl group, azadibenzothiophenyl group, quinolyl group, isoquinolyl group, quinoxalinyl group, quinazolinyl group, naphthyridinyl group, carbazolyl group, azacarbazolyl group, phenanthridinyl group, acridinyl group, phenanthrolinyl group, phenazinyl group, phenothiazinyl group, phenoxazinyl group, oxazolyl group, oxadiazolyl group, furazanyl group, benzoxazolyl group, thienyl group, thiazolyl group, thiadiazolyl group, benzothiazolyl group, triazolyl group and tetrazolyl group, among which a dibenzofuranyl group, dibenzothiophenyl group, carbazolyl group, pyridyl group, pyrimidinyl group, triazinyl group, azadibenzofuranyl group and azadibenzothiophenyl group may be preferable.

The aromatic heterocyclic group is preferably any one of a dibenzofuranyl group, dibenzothiophenyl group, carbazolyl group, pyridyl group, pyrimidinyl group, triazinyl group, azadibenzofuranyl group and azadibenzothiophenyl group, and further preferably any one of a dibenzofuranyl group, dibenzothiophenyl group, azadibenzofuranyl group and azadibenzothiophenyl group.

In the third compound, the substituted silyl group is also preferably a substituted or unsubstituted trialkylsilyl group, a substituted or unsubstituted arylalkylsilyl group, or a substituted or unsubstituted triarylsilyl group.

Specific examples of the substituted or unsubstituted trialkylsilyl group include trimethylsilyl group and triethylsilyl group.

Specific examples of the substituted or unsubstituted arylalkylsilyl group include diphenylmethylsilyl group, ditolylmethylsilyl group, and phenyldimethylsilyl group.

Specific examples of the substituted or unsubstituted triarylsilyl group include triphenylsilyl group and tritolylsilyl group.

In the third compound of the exemplary embodiment, the substituted phosphine oxide is also preferably a substituted or unsubstituted diaryl phosphine oxide group.

Specific examples of the substituted or unsubstituted diaryl phosphine oxide group include a diphenyl phosphine oxide group and ditolyl phosphine oxide group.

According to the organic EL device in the second exemplary embodiment, a highly efficient organic EL device with a long lifetime can be provided.

The emitting layer of the organic EL device in the second exemplary embodiment contains the first delayed fluorescent compound, the second compound having a specific structure represented by the formula (2) or the like, and the third compound having a larger singlet energy than that of the first compound, so that the luminous efficiency of the organic EL device is improved. It is considered that the luminous efficiency of the organic EL device is improved because the carrier balance of the emitting layer is improved by containing the third compound in the emitting layer.

Modification of Embodiments

The invention is not limited to the above exemplary embodiments. The invention may include any modification and improvement as long as such modification and improvement are compatible with the invention.

For instance, the emitting layer is not limited to a single layer, but may be provided by laminating a plurality of emitting layers. When the organic EL device has the plurality of emitting layers, it is only required that at least one of the emitting layers contains the first and second compounds. For instance, the rest of the emitting layers may be a fluorescent emitting layer or a phosphorescent emitting layer using emission by electronic transition from the triplet state directly to the ground state.

When the organic EL device includes the plurality of emitting layers, the plurality of emitting layers may be adjacent to each other, or provide a so-called tandem-type organic EL device in which a plurality of emitting units are layered through an intermediate layer.

For instance, a blocking layer may be provided in contact with an anode-side or a cathode-side of the emitting layer. It is preferable that the blocking layer is adjacent to the emitting layer and blocks at least one of holes, electrons and excitons.

For instance, when the blocking layer is provided in contact with the cathode-side of the emitting layer, the blocking layer permits transport of electrons, but prevents holes from reaching a layer provided near the cathode (e.g., the electron transporting layer) beyond the blocking layer. When the organic EL device includes an electron transporting layer, the blocking layer is preferably interposed between the emitting layer and the electron transporting layer.

When the blocking layer is provided in contact with the emitting layer near the anode, the blocking layer permits transport of holes, but prevents electrons from reaching a layer provided near the anode (e.g., the hole transporting layer) beyond the blocking layer. When the organic EL device includes a hole transporting layer, the blocking layer is preferably interposed between the emitting layer and the hole transporting layer.

Further, a blocking layer may be provided in contact with the emitting layer to prevent an excitation energy from leaking from the emitting layer into a layer in the vicinity thereof. Excitons generated in the emitting layer are prevented from moving into a layer provided near the electrode (e.g., an electron transporting layer and a hole transporting layer) beyond the blocking layer.

The emitting layer and the blocking layer are preferably bonded to each other.

Further, the materials and treatments for practicing the invention may be altered to other arrangements and treatments as long as such other arrangements and treatments are compatible with the invention.

EXAMPLES

Examples of the invention will be described. However, the invention is not limited to the Examples.

Compounds used for preparing the organic EL device are shown below.

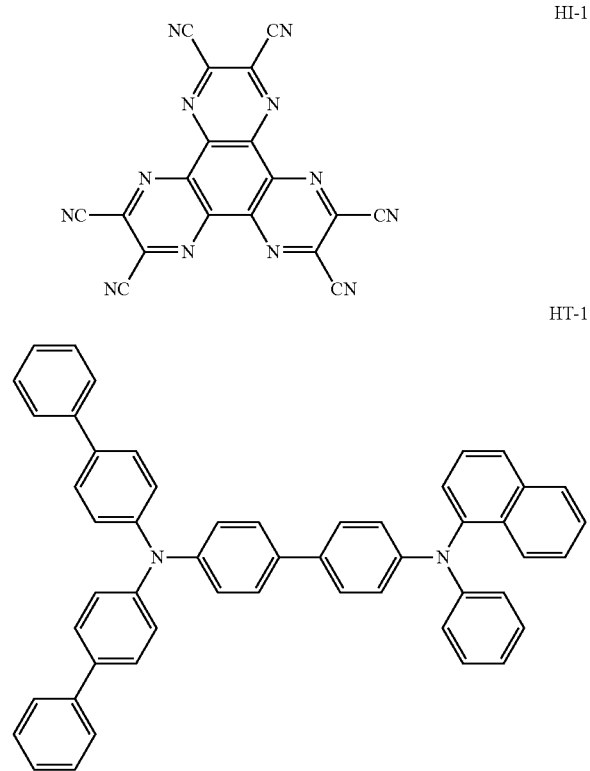

HT-2
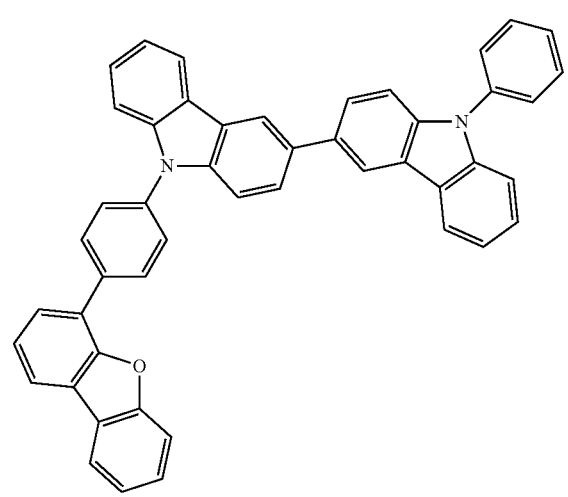
HB
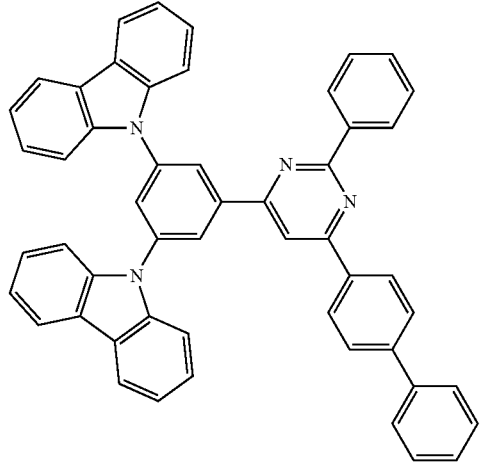
H-1
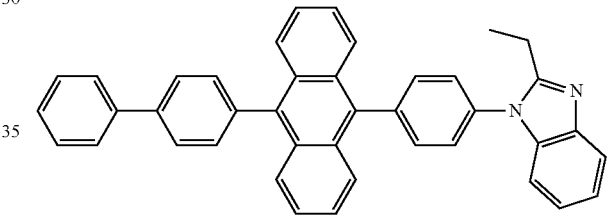
ET-1
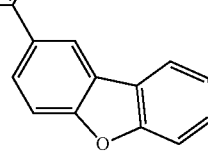
CH-1
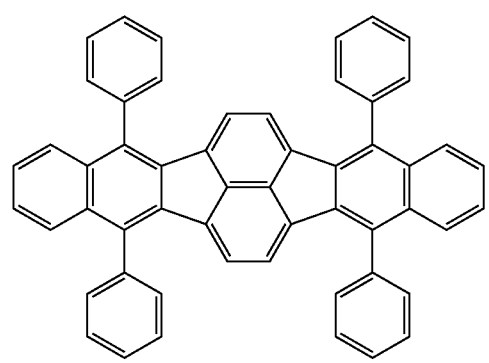
H-2
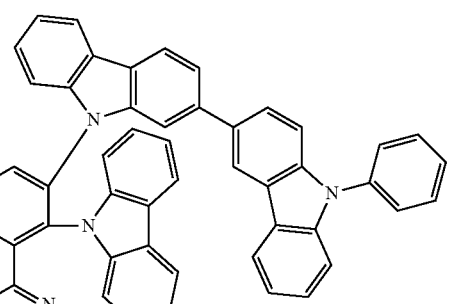
D1

H-3

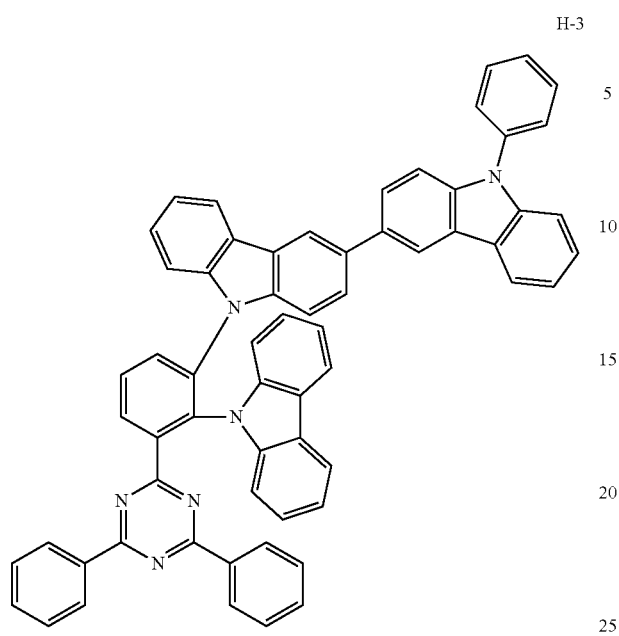

H-4

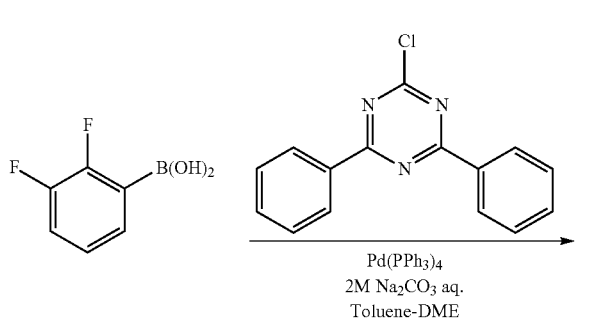

Synthesis of Compound(s)

Synthesis of Compound H-2

(1) Synthesis of Intermediate A

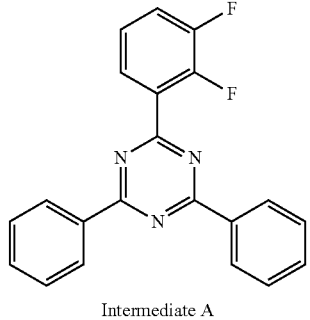

To a three-necked flask, 2,3-difluorophenyl boronic acid (2.27 g, 14.4 mmmol), 2-chloro-4,6-diphenyltriazine (3.50 g, 13.1 mmol), an aqueous solution of 2M sodium carbonate (16 mL), 1,2-dimethoxyethane (DME) (100 mL) and toluene (100 mL) were added. Next, tetrakis(triphenylphosphine)palladium (0.45 g, 0.39 mmol) was added thereto and heated to reflux with stirring for eight hours under an argon gas atmosphere. An organic layer was separated. The residue obtained by concentrating the separated organic layer was refined under reduced pressure by silica-gel column chromatography (using toluene as an eluent). The obtained solid was suspended and washed with ethanol, so that a white solid was obtained as an intermediate A.

A yield of the intermediate A was 4.2 g and a yield rate thereof was 92%.

(2) Synthesis of Intermediate B

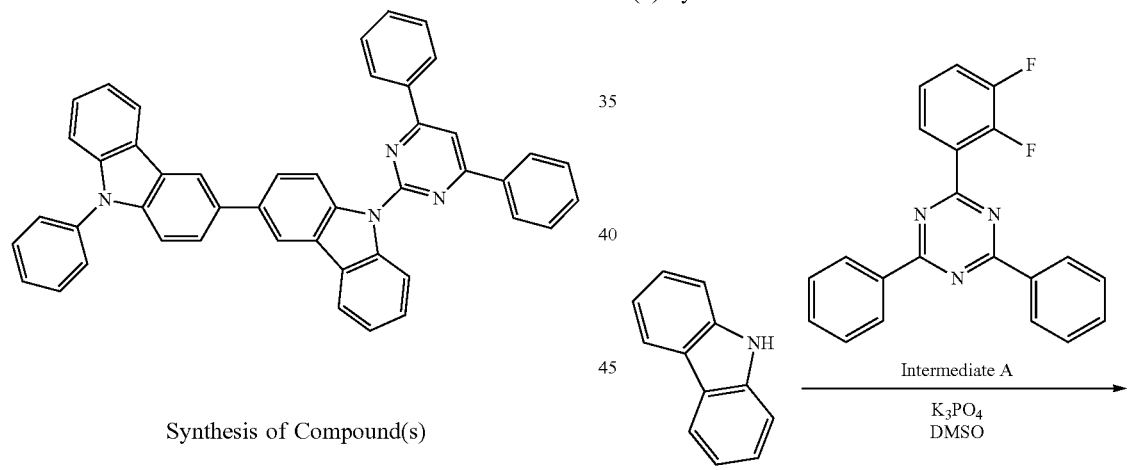

To a three-necked flask, carbazole (0.97 g, 5.80 mmol), the intermediate A (1.67 g, 4.84 mmol), tripotassium phosphate (1.23 g, 5.80 mmol), and dimethylsulfoxide (DMSO)

(20 mL) were added and heated with stirring at 85 degrees C. for 40 hours under an argon gas atmosphere. The reaction solution was put into a mixture liquid of methanol (100 mL) and water (100 mL). The precipitated solid was collected by filtration. Next, the obtained solid was suspended and washed in ethanol, so that the target was obtained as a white solid.

A yield of the intermediate B was 2.06 g and a yield rate thereof was 86%.

(3) Synthesis of Compound H-2

A yield of the compound H-2 was 2.1 g and a yield rate thereof was 56%.

FD-MS analysis consequently showed that m/e was equal to 881 while a calculated molecular weight was 881.

Evaluation of Compounds

Next, delayed fluorescence and a singlet energy of the compounds were measured. A measurement method and a calculation method are shown below.

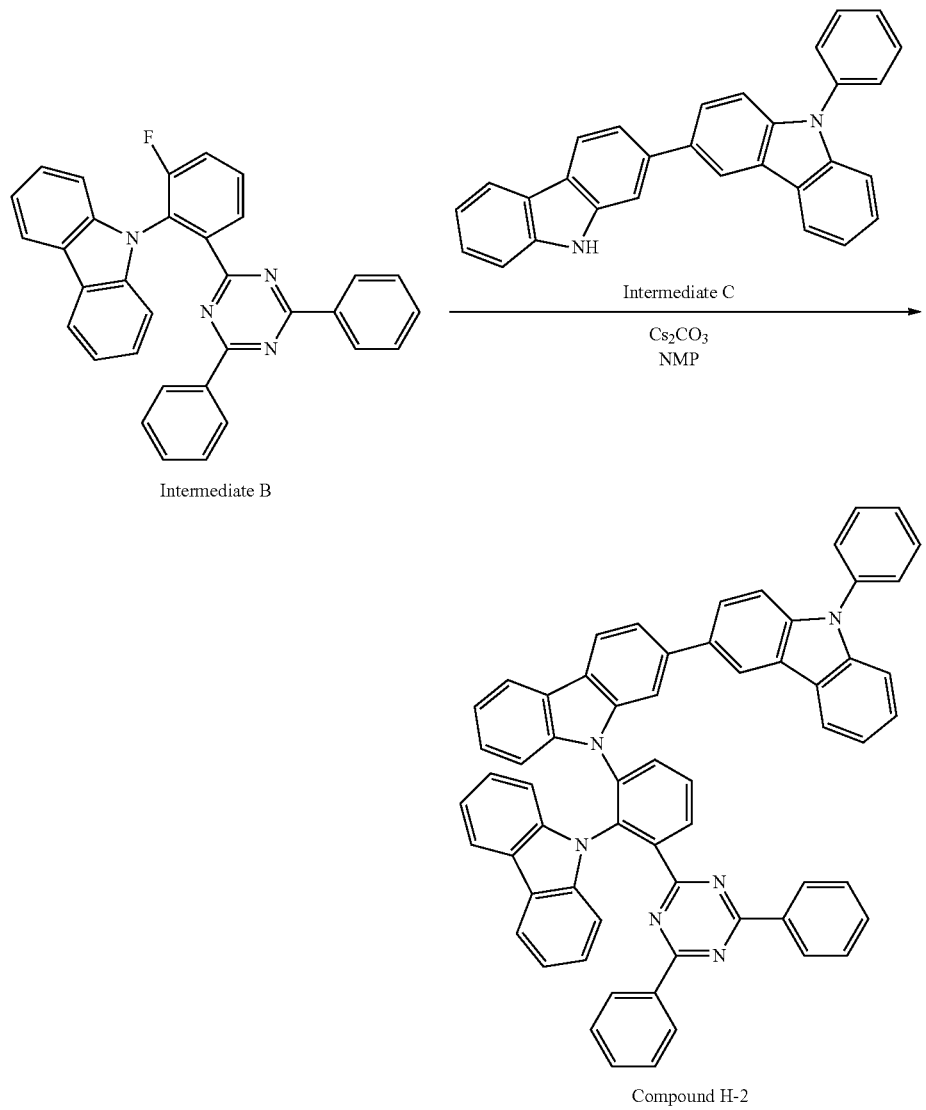

To a three-necked flask, the intermediate B (2.06 g, 4.2 mmol), an intermediate C (1.88 g, 4.6 mmol), which was synthesized by the method described in WO2011-132684, cesium carbonate (2.05 g, 6.3 mmol), and N-methyl-2-pyrrolidone (NMP) (20 mL) were added and heated at 140 degrees C. with stirring for 35 hours. The reaction solution was put into a mixture liquid of methanol (100 mL) and water (100 mL). The precipitated solid was collected by filtration. Next, the obtained solid was repeatedly suspended and washed in each of ethanol, acetone and ethyl acetate in this order, so that the target was obtained as a white solid.

Delayed Fluorescence

Delayed fluorescence was checked by measuring transient PL using the device shown in FIG. 2. A sample was prepared by co-depositing the compounds H-1 and TH-2 on a quartz substrate at a ratio of the compound H-1 of 12 mass % to form a 100-nm-thick thin film. There are two types of emission: Prompt emission observed immediately when the excited state is achieved by exciting the compound H-1 with a pulse beam (i.e., a beam emitted from a pulse laser) having an absorbable wavelength; and Delay emission observed not immediately when but after the excited state is achieved. The delayed fluorescence in the exemplary embodiment means that an amount of Delay Emission is 5% or more based on an amount of Prompt Emission.

It was found that the amount of Delay Emission was 5% or more based on the amount of Prompt Emission in the compound H-1.

With respect to the compounds H-2, H-3 and H-4, the transient PL was measured for delayed fluorescence in the same manner as with respect to the compound H-1, so that the compounds H-2, H-3 and H-4 were determined as delayed fluorescent compounds.

The amount of Prompt Emission and the amount of Delay Emission can be obtained according to the method as a method described in "Nature 492, 234-238, 2012." A device used for calculating the amounts of Prompt Emission and Delay Emission is not limited to the device of FIG. 2 and a device described in the above document.

Singlet Energy S

A singlet energy S was measured as follows. A 10 μmol/L toluene solution of a measurement target compound was prepared as a sample and put in a quartz cell. A luminescence spectrum (ordinate axis: luminous intensity, abscissa axis: wavelength) of the sample was measured at a normal temperature (300K). A tangent was drawn to the fall of the absorption spectrum on the long-wavelength side, and a wavelength value λedge (nm) at an intersection of the tangent and the abscissa axis was assigned to a conversion equation 2 below to calculate a singlet energy.

$S[eV] = 1239.85/\lambda edge$     Conversion Equation 2:

In Example, the absorption spectrum was measured using a spectrophotometer manufactured by Hitachi, Ltd. (device name: U3310). It should be noted that the absorption spectrum measuring device may be different from the above device.

The calculated singlet energies S are shown below.
H-1: 2.89 eV
H-2: 2.91 eV
H-3: 2.86 eV
H-4: 3.09 eV
CH-1: 3.55 eV Preparation and Evaluation of Organic EL Device The organic EL devices were prepared in the following manner and evaluated.

Example 1

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes. After the ultrasonic-cleaning, the glass substrate was UV/ozone-cleaned for 30 minutes A film of ITO was 130 nm thick.

The cleaned glass substrate was mounted on a substrate holder of a vacuum evaporation apparatus. Initially, a compound HI-1 was deposited on a surface of the glass substrate where the transparent electrode line was provided in a manner to cover the transparent electrode, thereby forming a 5-nm-thick hole injecting layer.

Next, the compound HT-1 was deposited on the hole injecting layer to form a 110-nm-thick first hole transporting layer on the HI-1 film.

Next, the compound HT-2 was deposited on the first hole transporting layer to form a 15-nm-thick second hole transporting layer.

Further, the compound H-1 (the first compound) and the compound D1 (the second compound) were co-deposited on the second hole transporting layer to form a 25-nm-thick emitting layer. A concentration of the compound D1 in the emitting layer was 1 mass %.

Next, a compound HB was deposited on the emitting layer to form a 5-nm-thick blocking layer.

Next, a compound ET-1 was deposited on the blocking layer to form a 35-nm-thick electron transporting layer.

Lithium fluoride (LiF) was then deposited on the electron transporting layer to form a 1-nm-thick electron injecting electrode (cathode).

A metal aluminum (Al) was then deposited on the electron injecting electrode to form an 80-nm-thick metal Al cathode.

A device arrangement of the organic EL device in Example 1 is schematically shown as follows.

ITO(130)/HI-1(5)/HT-1(110)/HT-2(15)/H-1: D1 (25, 1%)/HB(5)/ET-1(35)/LiF(1)/Al(80)

Numerals in parentheses represent a film thickness (unit: nm). The numerals in the form of percentage in parentheses indicate ratio (mass %) of the second compound in the emitting layer.

Example 2

An organic EL device of Example 2 was prepared in the same manner as the organic EL device of Example 1 except that the formation process of the emitting layer was changed as follows. In Example 2, the compound H-1 (the first compound), the compound D1 (the second compound) and a compound CH-1 (the third compound) were co-deposited on the second hole transporting layer to form a 25-nm-thick emitting layer. A concentration of the compound D1 was 1 mass % and a concentration of the compound H-1 was 50 mass % in the emitting layer.

A device arrangement of the organic EL device in Example 2 is schematically shown as follows.

ITO(130)/HI-1(5)/HT-1(110)/HT-2(15)/CH-1: H-1:D1 (25, 50%, 1%)/HB(5)/ET-1(35)/LiF(1)/Al(80)

Numerals in parentheses represent a film thickness (unit: nm). The numerals in the form of percentage in parentheses indicate ratios (mass %) of the first and second compounds in the emitting layer.

Evaluation of Organic EL Devices

The prepared organic EL devices were evaluated as below. The evaluation results are shown in Table 2.

CIE1931 Chromaticity, Main Peak Wavelength $\lambda_p$, Current Efficiency L/J

Voltage was applied on each of the organic EL devices such that a current density was 10 mA/cm², where coordinates (x, y) of CIE1931 chromaticity were measured by a spectroradiometer (CS-1000 manufactured by Konica Minolta, Inc.). A main peak wavelength $\lambda_p$ was calculated based on the obtained spectral-radiance spectra. A current efficiency (unit: cd/A) was calculated from the obtained spectral radiance spectra.

Lifetime LT80

A continuous direct-current test was conducted on the organic EL devices at an initial current density of 50 mA/cm², where a time elapsed before a luminance intensity was reduced to 80% of the initial luminance intensity was defined as lifetime (LT80).

TABLE 2

|  | CIE Chromaticity | | L/J | $\lambda_p$ | LT80 |
|---|---|---|---|---|---|
|  | x | y | (cd/A) | (nm) | (h) |
| Example 1 | 0.296 | 0.619 | 25.3 | 506 | 47 |
| Example 2 | 0.262 | 0.614 | 26.6 | 504 | 54 |

The organic EL devices in Examples 1 and 2 exhibited a high efficiency and a long lifetime.

Example 3

An organic EL device of Example 3 was prepared in the same manner as the organic EL device of Example 1 except that the concentration of the compound D1 in the emitting layer in Example 1 was 0.5 mass %.

A device arrangement of the organic EL device in Example 3 is schematically shown as follows.

ITO(130)/HI-1(5)/HT-1(110)/HT-2(15)/H-1:D1 (25, 0.5%)/HB(5)/ET-1(35)/LiF(1)/Al(80)

Example 4

An organic EL device of Example 4 was prepared in the same manner as the organic EL device of Example 1 except that the compound H-2 was used as the first compound in place of the compound H-1 in the emitting layer of Example 1.

A device arrangement of the organic EL device in Example 4 is schematically shown as follows.

ITO(130)/HI-1(5)/HT-1(110)/HT-2(15)/H-2:D1 (25, 1%)/HB(5)/ET-1(35)/LiF(1)/Al(80)

(実施例 5)

An organic EL device of Example 5 was prepared in the same manner as the organic EL device of Example 1 except that the compound H-3 was used as the first compound in place of the compound H-1 in the emitting layer of Example 1.

A device arrangement of the organic EL device in Example 5 is schematically shown as follows.

ITO(130)/HI-1(5)/HT-1(110)/HT-2(15)/H-3:D1 (25, 1%)/HB(5)/ET-1(35)/LiF(1)/Al(80)

The prepared organic EL devices were evaluated by the same method as described above. The evaluation results are shown in Table 3.

TABLE 3

| | Emitting Layer | | CIE Chromaticity | | L/J | $\lambda_p$ | LT80 |
|---|---|---|---|---|---|---|---|
| | First Compound | Second Compound/ Concentration (mass %) | x | y | (cd/A) | (nm) | (h) |
| Example 3 | H-1 | D1/0.5 | 0.276 | 0.611 | 24.4 | 504 | 38 |
| Example 4 | H-2 | D1/1 | 0.242 | 0.601 | 14.7 | 503 | 14 |
| Example 5 | H-3 | D1/1 | 0.251 | 0.605 | 20.4 | 504 | 14 |

Example 6

An organic EL device of Example 6 was prepared in the same manner as the organic EL device of Example 1 except that the compound H-4 was used as the first compound in place of the compound H-1 in the emitting layer of Example 1.

A device arrangement of the organic EL device in Example 6 is schematically shown as follows.

ITO(130)/HI-1(5)/HT-1(110)/HT-2(15)/H-4:D1 (25, 1%)/HB(5)/ET-1(35)/LiF(1)/Al(80)

Example 7

An organic EL device of Example 7 was prepared in the same manner as the organic EL device of Example 6 except that the concentration of the compound D1 in the emitting layer in Example 6 was 0.5 mass %.

A device arrangement of the organic EL device in Example 7 is schematically shown as follows.

ITO(130)/HI-1(5)/HT-1(110)/HT-2(15)/H-4:D1 (25, 0.5%)/HB(5)/ET-1(35)/LiF(1)/Al(80)

The prepared organic EL devices were evaluated by the same method as described above. The evaluation results are shown in Table 4.

TABLE 4

| | Emitting Layer | | CIE Chromaticity | | $\lambda_p$ | LT80 |
|---|---|---|---|---|---|---|
| | First Compound | Second Compound/ Concentration (mass %) | x | y | (nm) | (h) |
| Example 6 | H-4 | D1/1 | 0.244 | 0.619 | 503 | 26 |
| Example 7 | H-4 | D1/0.5 | 0.245 | 0.604 | 502 | 17 |

Example 8

An organic EL device of Example 8 was prepared in the same manner as the organic EL device of Example 2 except that the compound H-4 was used as the first compound in place of the compound H-1 in the emitting layer of Example 2.

A device arrangement of the organic EL device in Example 8 is schematically shown as follows.

ITO(130)/HI-1(5)/HT-1(110)/HT-2(15)/CH-1:H-4:D1 (25, 50%, 1%)/HB(5)/ET-1(35)/LiF(1)/Al(80)

Example 9

An organic EL device of Example 9 was prepared in the same manner as the organic EL device of Example 8 except that the concentration of the compound D1 in the emitting layer in Example 8 was 0.5 mass %.

A device arrangement of the organic EL device in Example 9 is schematically shown as follows.

ITO(130)/HI-1(5)/HT-1(110)/HT-2(15)/CH-1:H-4:D1 (25, 50%, 0.5%)/HB(5)/ET-1(35)/LiF(1)/Al(80)

The prepared organic EL devices were evaluated by the same method as described above. The evaluation results are shown in Table 5.

TABLE 5

| | Emitting Layer | | | CIE Chromaticity | | λp | LT80 |
|---|---|---|---|---|---|---|---|
| | First Compound | Second Compound/ Concentration (mass %) | Third Compound | x | y | (nm) | (h) |
| Example 8 | H-4 | D1/1 | CH-1 | 0.234 | 0.591 | 502 | 23 |
| Example 9 | H-4 | D1/0.5 | CH-1 | 0.234 | 0.573 | 502 | 14 |

What is claimed is:

1. An organic electroluminescence device, comprising:
an anode;
a cathode; and
an emitting layer,
wherein:
the emitting layer comprises a first compound and a second compound;
the first compound is a delayed fluorescent compound; and
the second compound is represented by formula (2):

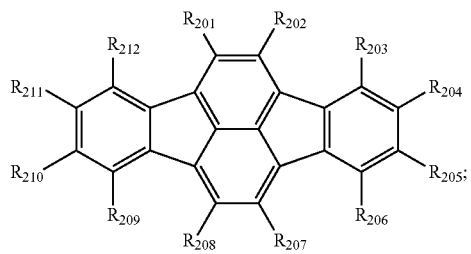

(2)

$R_{201}$ to $R_{212}$ are each independently a hydrogen atom or a substituent;
when $R_{201}$ to $R_{212}$ each are a substituent, the substituent is selected from the group consisting of a substituted or unsubstituted alkyl group having 1 to 30 carbon atoms, a substituted or unsubstituted aryl group having 6 to 30 ring carbon atoms, a substituted or unsubstituted heterocyclic group having 5 to 30 ring atoms, a substituted or unsubstituted alkoxy group having 1 to 30 carbon atoms, a substituted or unsubstituted aryloxy group having 6 to 30 ring carbon atoms, a substituted or unsubstituted aralkyl group having 6 to 30 ring carbon atoms, a substituted amino group, a cyano group, and a halogen atom; and
the substituents of $R_{201}$ to $R_{212}$ are optionally mutually bonded to form a cyclic structure.

2. The organic electroluminescence device according to claim 1, wherein:
the emitting layer further comprises a third compound; and
the third compound has a larger singlet energy than a singlet energy of the first compound.

3. The organic electroluminescence device according to claim 2, wherein the first compound is contained in a range from 10 mass % to 80 mass % in the emitting layer.

4. The organic electroluminescence device according to claim 1, wherein:

the second compound is represented by formula (21):

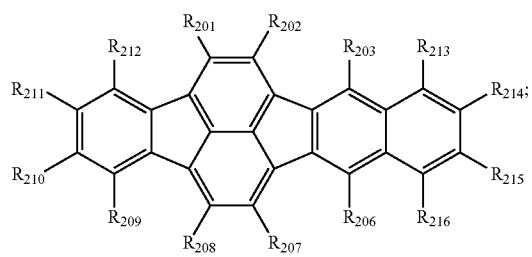

(21)

$R_{201}$ to $R_{203}$ and $R_{206}$ to $R_{216}$ are each independently a hydrogen atom or a substituent;
when $R_{201}$ to $R_{203}$ and $R_{206}$ to $R_{216}$ each are a substituent, the substituent is selected from the group consisting of a substituted or unsubstituted alkyl group having 1 to 30 carbon atoms, a substituted or unsubstituted aryl group having 6 to 30 ring carbon atoms, a substituted or unsubstituted heterocyclic group having 5 to 30 ring atoms, a substituted or unsubstituted alkoxy group having 1 to 30 carbon atoms, a substituted or unsubstituted aryloxy group having 6 to 30 ring carbon atoms, a substituted or unsubstituted aralkyl group having 6 to 30 ring carbon atoms, a substituted amino group, a cyano group, and a halogen atom; and
the substituents of $R_{201}$ to $R_{203}$ and $R_{206}$ to $R_{216}$ are optionally mutually bonded to form a cyclic structure.

5. The organic electroluminescence device according to claim 1, wherein:
the second compound is represented by formula (211):

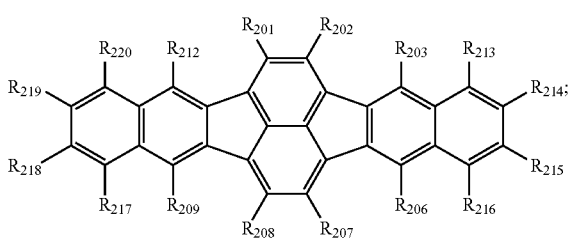

(211)

$R_{201}$ to $R_{203}$, $R_{206}$ to $R_{209}$ and $R_{212}$ to $R_{220}$ are each independently a hydrogen atom or a substituent;
when $R_{201}$ to $R_{203}$, $R_{206}$ to $R_{209}$ and $R_{212}$ to $R_{220}$ each are a substituent, the substituent is selected from the group consisting of a substituted or unsubstituted alkyl group having 1 to 30 carbon atoms, a substituted or unsubstituted aryl group having 6 to 30 ring carbon atoms, a substituted or unsubstituted heterocyclic group having 5 to 30 ring atoms, a substituted or unsubstituted alkoxy group having 1 to 30 carbon atoms, a substituted or unsubstituted aryloxy group having 6 to 30 ring carbon atoms, a substituted or unsubstituted aralkyl group having 6 to 30 ring carbon atoms, a substituted amino group, a cyano group, and a halogen atom; and the substituents of $R_{201}$ to $R_{203}$, $R_{206}$ to $R_{209}$ and $R_{212}$ to $R_{220}$ are optionally mutually bonded to form a cyclic structure.

6. The organic electroluminescence device according to claim 5, wherein $R_{201}$ and $R_{207}$ are the same, $R_{202}$ and $R_{208}$ are the same, $R_{203}$ and $R_{209}$ are the same, $R_{213}$ and $R_{217}$ are the same, $R_{214}$ and $R_{218}$ are the same, $R_{215}$ and $R_{219}$ are the same, $R_{216}$ and $R_{220}$ are the same, and $R_{206}$ and $R_{212}$ are the same.

7. The organic electroluminescence device according to claim 5, wherein at least one of a combination of $R_{201}$ and $R_{207}$, a combination of $R_{202}$ and $R_{208}$, a combination of $R_{203}$ and $R_{209}$, a combination of $R_{213}$ and $R_{217}$, a combination of $R_{214}$ and $R_{218}$, a combination of $R_{215}$ and $R_{219}$, a combination of $R_{216}$ and $R_{220}$, and a combination of $R_{206}$ and $R_{212}$ comprises mutually different groups.

8. The organic electroluminescence device according to claim 5, wherein $R_{203}$, $R_{206}$, $R_{209}$ and $R_{212}$ are each independently a substituted or unsubstituted aryl group having 6 to 30 ring carbon atoms in the formula (211).

9. The organic electroluminescence device according to claim 5, wherein $R_{203}$, $R_{206}$, $R_{209}$ and $R_{212}$ are each independently selected from the group consisting of a phenyl group, biphenyl group, terphenyl group, naphthyl group, fluorenyl group, phenanthrenyl group, fluoranthenyl group, anthryl group, pyrenyl group, and chrysenyl group in the formula (211).

10. The organic electroluminescence device according to claim 5, wherein $R_{203}$, $R_{206}$, $R_{209}$ and $R_{212}$ are each independently selected from the group consisting of a phenyl group, biphenyl group, terphenyl group, naphthyl group, and fluorenyl group in the formula (211).

11. The organic electroluminescence device according to claim 1, wherein:

the second compound is represented by formula (214):

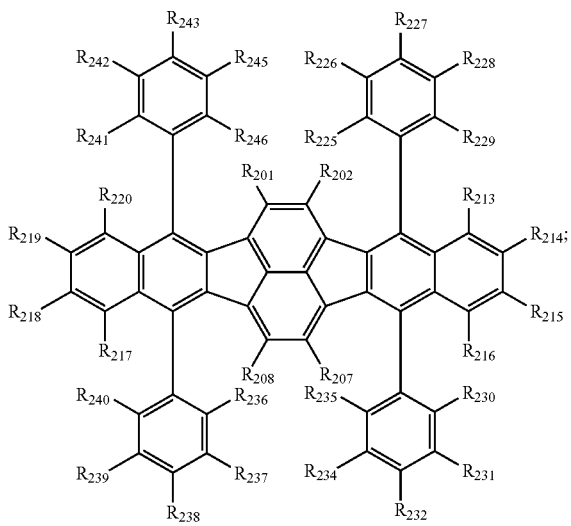

(214)

$R_{201}$, $R_{202}$, $R_{207}$, $R_{208}$, $R_{213}$ to $R_{220}$ and $R_{225}$ to $R_{246}$ are each independently a hydrogen atom or a substituent;

when $R_{201}$, $R_{202}$, $R_{207}$, $R_{208}$, $R_{213}$ to $R_{220}$ and $R_{225}$ to $R_{246}$ each are a substituent, the substituent is selected from the group consisting of a substituted or unsubstituted alkyl group having 1 to 30 carbon atoms, a substituted or unsubstituted aryl group having 6 to 30 ring carbon atoms, a substituted or unsubstituted heterocyclic group having 5 to 30 ring atoms, a substituted or unsubstituted alkoxy group having 1 to 30 carbon atoms, a substituted or unsubstituted aryloxy group having 6 to 30 ring carbon atoms, a substituted or unsubstituted aralkyl group having 6 to 30 ring carbon atoms, a substituted amino group, a cyano group, and a halogen atom; and the substituents of $R_{201}$, $R_{202}$, $R_{207}$, $R_{208}$ and $R_{213}$ to $R_{220}$ are optionally mutually bonded to form a cyclic structure.

12. The organic electroluminescence device according to claim 1, wherein the first compound has 2.0 eV or more of an energy gap at 77K.

13. The organic electroluminescence device according to claim 1, wherein the second compound is a fluorescent compound having an emission peak in a wavelength range from 480 nm to 560 nm.

14. The organic electroluminescence device according to claim 1, wherein the second compound is a green fluorescent compound.

15. The organic electroluminescence device according to claim 1, wherein:

the first compound is represented by formula (1):

(1)

A is an acceptor moiety that is a group having a partial structure selected from partial structures represented by formulae (a-1) to (a-7) below;

when a plurality of A are present, the plurality of A are mutually the same or different and the plurality of A are optionally mutually bonded to form a saturated or unsaturated ring;

B is a donor moiety that is a group having a partial structure selected from partial structures represented by formulae (b-1) to (b-6) below;

when a plurality of B are present, the plurality of B are mutually the same or different and the plurality of B are optionally mutually bonded to form a saturated or unsaturated ring;

a, b and d are each independently an integer of 1 to 5;

c is an integer of 0 to 5;

when c is 0, A is bonded to B by a single bond or a spiro bond;

when c is an integer of 1 to 5, L is a linking group selected from the group consisting of a substituted or unsubstituted aromatic hydrocarbon group having 6 to 30 ring carbon atoms and a substituted or unsubstituted heterocyclic group having 5 to 30 ring atoms;

when a plurality of L are present, the plurality of L are mutually the same or different and are optionally mutually bonded to form a saturated or unsaturated ring,

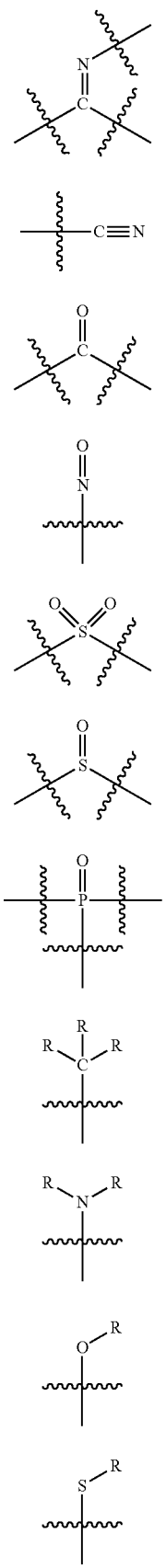

(a-1)

(a-2)

(a-3)

(a-4)

(a-5)

(a-6)

(a-7)

(b-1)

(b-2)

(b-3)

(b-4)

-continued

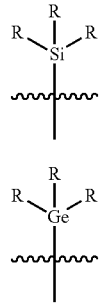 (b-5)

(b-6)

where, in the formulae (b-1) to (b-6):
R is each independently a hydrogen atom or a substituent;
when R is a substituent, the substituent is selected from the group consisting of a substituted or unsubstituted aromatic hydrocarbon group having 6 to 30 ring carbon atoms, a substituted or unsubstituted heterocyclic group having 5 to 30 ring atoms, and a substituted or unsubstituted alkyl group having 1 to 30 carbon atoms; and
when a plurality of R are present, the plurality of R are mutually the same or different and are optionally mutually bonded to form a saturated or unsaturated ring.

16. The organic electroluminescence device according to claim 1, wherein:
the first compound is represented by formula (1A):

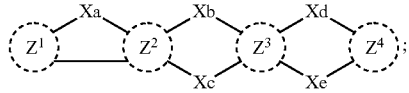

(1A)

Xa is an oxygen atom, a sulfur atom, $NR^1$ or $CR^3R^4$;
Xb, Xc, Xd and Xe are each independently a single bond, an oxygen atom, a sulfur atom, $NR^1$ or $CR^3R^4$;
at least one of Xa, Xb, Xc, Xd, and Xe is $NR^1$;
Xb and Xc are not single bonds at the same time; Xd and Xe are not single bonds at the same time;
$R^1$ is a hydrogen atom or a substituent;
$R^1$ as the substituent is selected from the group consisting of a substituted or unsubstituted alkyl group having 1 to 30 carbon atoms, a substituted or unsubstituted cycloalkyl group having 3 to 30 ring carbon atoms, a substituted or unsubstituted aromatic hydrocarbon group having 6 to 30 ring carbon atoms, a substituted or unsubstituted heterocyclic group having 5 to 30 ring atoms, and a group represented by $-L^1-R^2$;
$L^1$ is a single bond or a linking group;
$L^1$ as the linking group is selected from the group consisting of a substituted or unsubstituted aromatic hydrocarbon group having 6 to 30 ring carbon atoms and a substituted or unsubstituted heterocyclic group having 5 to 30 ring atoms;
$R^2$ to $R^4$ are each independently a hydrogen atom or a substituent;
$R^2$ to $R^4$ as the substituent are each independently selected from the group consisting of a substituted or unsubstituted alkyl group having 1 to 30 carbon atoms, a substituted or unsubstituted cycloalkyl group having 3 to 30 ring carbon atoms, a substituted or unsubstituted aromatic hydrocarbon group having 6 to 30 ring carbon atoms, and a substituted or unsubstituted heterocyclic group having 5 to 30 ring atoms; and $Z^1$, $Z^2$, $Z^3$ and $Z^4$ each independently represent a ring structure selected from the group consisting of a substituted or unsubstituted aromatic hydrocarbon ring having 6 to 30 ring carbon atoms and a substituted or unsubstituted heterocyclic ring having 5 to 30 ring atoms.

17. The organic electroluminescence device according to claim 16, wherein:

the first compound is represented by formula (10):

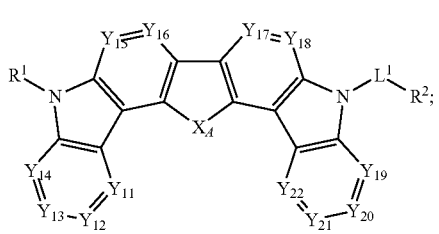

(10)

$R^1$, $R^2$ and $L^1$ represent the same as $R^1$, $R^2$ and $L^1$ in the formula (1A);

$X_A$ is an oxygen atom, a sulfur atom, $NR_{10}$ or $CR_{11}R_{12}$;

$Y_{11}$ to $Y_{22}$ are each independently a nitrogen atom or $CR_{13}$;

$R_{10}$ to $R_{13}$ are each independently a hydrogen atom or a substituent;

$R_{10}$ to $R_{13}$ as the substituent are each independently selected from the group consisting of a substituted or unsubstituted alkyl group having 1 to 30 carbon atoms, a substituted or unsubstituted cycloalkyl group having 3 to 30 carbon atoms, a substituted or unsubstituted aromatic hydrocarbon group having 6 to 30 ring carbon atoms, and a substituted or unsubstituted heterocyclic group having 5 to 30 ring atoms; and a plurality of $R_{13}$ are optionally mutually the same or different; and, when at least two of the plurality of $R_{13}$ are substituents, the substituents $R_{13}$ are optionally mutually bonded to form a cyclic structure.

18. The organic electroluminescence device according to claim 17, wherein $X_A$ is an oxygen atom or a sulfur atom.

19. The organic electroluminescence device according to claim 17, wherein $Y_{11}$ to $Y_{22}$ are each independently $CR_{13}$, in which $R_{13}$ is a hydrogen atom.

20. The organic electroluminescence device according to claim 16, wherein:

$R^2$ is a group represented by formula (11):

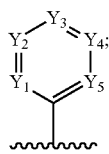

(11)

$Y_1$ to $Y_5$ are each independently a nitrogen atom or $CR_{14}$;

$R_{14}$ is a hydrogen atom or a substituent;

$R_{14}$ as the substituent is selected from the group consisting of a fluorine atom, a cyano group, a substituted or unsubstituted alkyl group having 1 to 30 carbon atoms, a substituted or unsubstituted cycloalkyl group having 3 to 30 carbon atoms, a substituted silyl group, a substituted phosphine oxide group, a substituted or unsubstituted aromatic hydrocarbon group having 6 to 30 ring carbon atoms, and a substituted or unsubstituted heterocyclic group having 5 to 30 ring atoms;

a plurality of $R_{14}$ are optionally mutually the same or different; and when at least two of the plurality of $R_{14}$ are substituents, the substituents $R_{14}$ are optionally mutually bonded to form a cyclic structure.

21. The organic electroluminescence device according to claim 20, wherein at least one of $Y_1$ to $Y_5$ is a nitrogen atom.

22. The organic electroluminescence device according to claim 1, wherein:

the first compound is represented by formula (100):

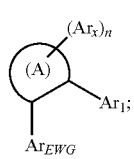

(100)

$Ar_1$ is any group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group and groups represented by formulae (12a) to (12j) below;

$Ar_{EWG}$ is a substituted or unsubstituted heteroaryl group having 5 to 30 ring atoms including at least one nitrogen atom in the ring or a substituted or unsubstituted aryl group having 6 to 30 ring carbon atoms and substituted by at least one cyano group;

$Ar_X$ is each independently a hydrogen atom or a substituent, $Ar_X$ as the substituent is any group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group and groups represented by the formulae (12a) to (12j) below;

n is an integer of 0 to 5;

when n is 2 or more, a plurality of $Ar_X$ are optionally mutually the same or different;

a ring (A) is a five-membered ring, a six-membered ring, or a seven-membered ring; and at least one of $Ar_1$ and $Ar_X$ is any group selected from the group consisting of the groups represented by the formulae (12a) to (12j) below,

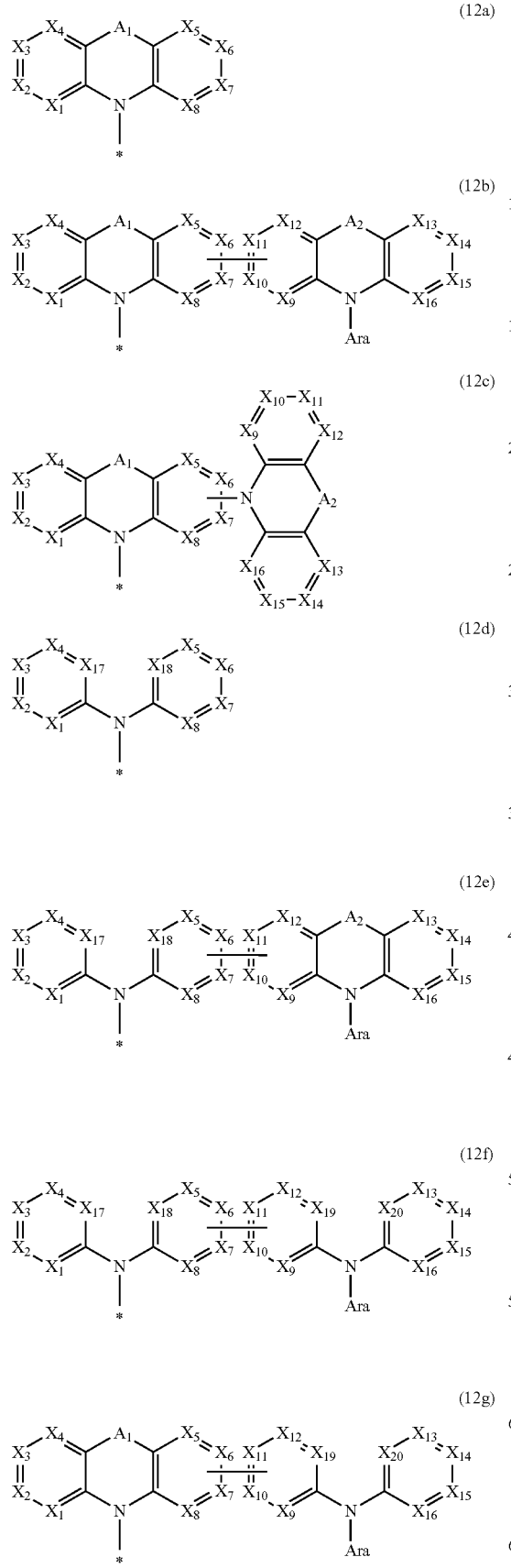

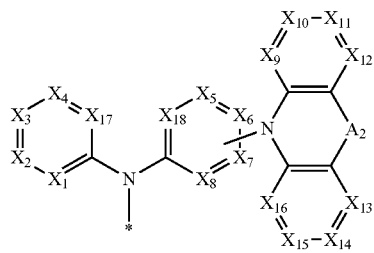

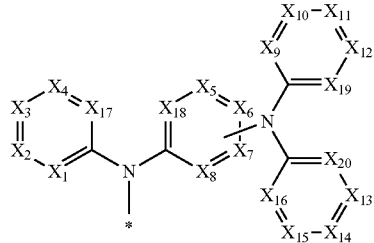

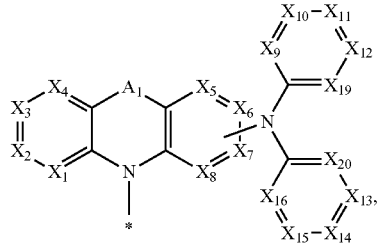

in the formulae (12a) to (12j): $X_1$ to $X_{20}$ are each independently N or C-Rx;

in the formula (12b), any one of $X_5$ to $X_8$ is a carbon atom to be bonded to any one of $X_9$ to $X_{12}$ and any one of $X_9$ to $X_{12}$ is a carbon atom to be bonded to any one of $X_5$ to $X_8$;

in the formula (12c), any one of $X_5$ to $X_8$ is a carbon atom bonded to a nitrogen atom of a five-membered ring in a fused ring including $X_9$ to $X_{12}$ and $X_{13}$ to $X_{16}$;

in the formula (12e), any one of $X_5$ to $X_8$ and $X_{18}$ is a carbon atom bonded to any one of $X_9$ to $X_{12}$ and any one of $X_9$ to $X_{12}$ is a carbon atom bonded to any one of $X_5$ to $X_8$ and $X_{18}$;

in the formula (12f), any one of $X_5$ to $X_8$ and $X_{18}$ is a carbon atom bonded to any one of $X_9$ to $X_{12}$ and $X_{19}$ and any one of $X_9$ to $X_{12}$ and $X_{19}$ is a carbon atom bonded to any one of $X_5$ to $X_8$ and $X_{18}$;

in the formula (12g), any one of $X_5$ to $X_8$ is a carbon atom bonded to any one of $X_9$ to $X_{12}$ and $X_{19}$ and any one of $X_9$ to $X_{12}$ and $X_{19}$ is a carbon atom bonded to any one of $X_5$ to $X_8$;

in the formula (12h), any one of $X_5$ to $X_8$ and $X_{18}$ is a carbon atom bonded to a nitrogen atom of a six-membered ring in a fused ring including $X_9$ to $X_{12}$, $X_{13}$ to $X_{16}$ and $A_2$;

in the formula (12i), any one of $X_5$ to $X_8$ and $X_{18}$ is a carbon atom bonded to a nitrogen atom linking a ring including $X_9$ to $X_{12}$ and $X_{19}$ to a ring including $X_{13}$ to $X_{16}$ and $X_{20}$;

in the formula (12j), any one of $X_5$ to $X_8$ is a carbon atom bonded to a nitrogen atom linking a ring including $X_9$ to $X_{12}$ and $X_{19}$ to a ring including $X_{13}$ to $X_{16}$ and $X_{20}$;

Rx is each independently a hydrogen atom or a substituent;

Rx as the substituent is any group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group;

a plurality of Rx as the substituent are optionally mutually the same or different;

the plurality of Rx as the substituent are optionally directly bonded to each other to form a ring, or are optionally bonded to each other by a hetero atom to form a ring;

$A_1$ and $A_2$ are each independently a single bond, O, S, $C(R_{101})(R_{102})$, $Si(R_{103})(R_{104})$, C(=O), S(=O), $SO_2$ or $N(R_{105})$;

$R_{101}$ to $R_{105}$ are each independently a hydrogen atom or a substituent;

$R_{101}$ to $R_{105}$ as the substituent is any group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group; and Ara is any group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, and a substituted silyl group.

23. The organic electroluminescence device according to claim 22, wherein:
the first compound is represented by formula (101):

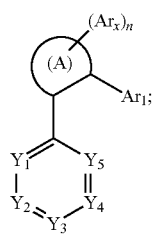

(101)

$Y_1$ to $Y_5$ are each independently N, C—CN or C-Ry;
at least one of $Y_1$ to $Y_5$ is N or C—CN;
Ry is each independently a hydrogen atom or a substituent;

Ry as the substituent is any group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group;

$Ar_1$ is any group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group and groups represented by the formulae (12a) to (12c);

$Ar_X$ is each independently a hydrogen atom or a substituent: $Ar_X$ as the substituent is any group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group and groups represented by the formulae (12a) to (12c);

n is an integer of 0 to 5;
when n is 2 or more, a plurality of $Ar_X$ are optionally mutually the same or different;
a ring (A) is a five-membered ring, a six-membered ring, or a seven-membered ring; and
at least one of $Ar_1$ and $Ar_X$ is any group selected from the group consisting of the groups represented by the formulae (12a) to (12c).

24. The organic electroluminescence device according to claim 22, wherein:
the first compound is represented by formula (102):

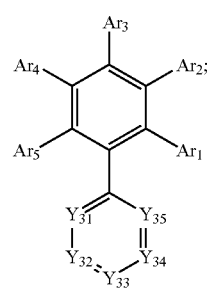

(102)

$Y_{31}$ to $Y_{35}$ are each independently N, C—CN or C-Ry;
at least one of $Y_{31}$ to $Y_{35}$ is N or C—CN;

Ry is each independently a hydrogen atom or a substituent;

Ry as the substituent is any group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group;

$Ar_1$ is any group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group and groups represented by the formulae (12a) to (12c);

$Ar_2$ to $Ar_5$ are each independently a hydrogen atom or a substituent; $Ar_2$ to $Ar_5$ as the substituent is any group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group and groups represented by the formulae (12a) to (12c); and at least one of $A_1$ and $Ar_5$ is any group selected from the group consisting of the groups represented by the formulae (12a) to (12c).

25. The organic electroluminescence device according to claim 24, wherein:

the first compound is a compound represented by formula (103), (104) or (105):

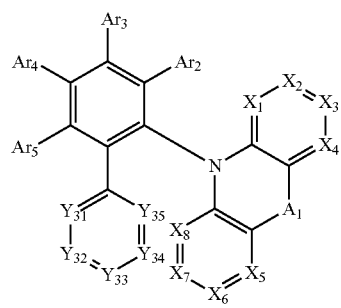

(103)

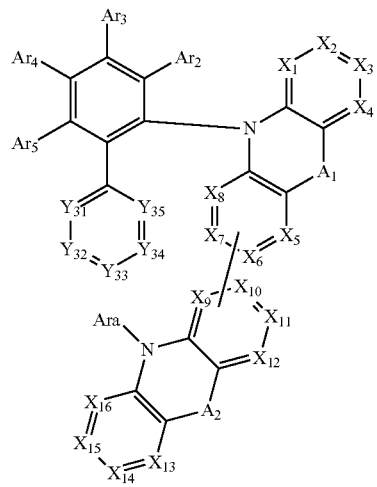

(104)

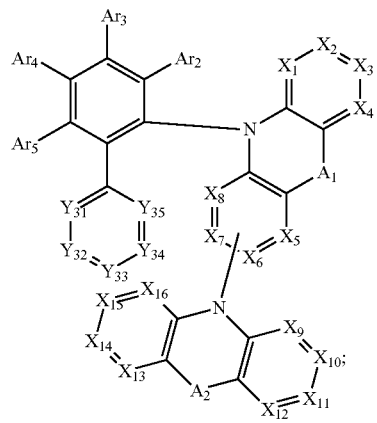

(105)

and $Y_{31}$ to $Y_{35}$, Ry, $Ar_2$ to $Ar_5$, $X_1$ to $X_{16}$, Rx, $A_1$, $A_2$, $R_{101}$ to $R_{105}$ and Ara represent the same as $Y_{31}$ to $Y_{35}$, Ry, $Ar_2$ to $Ar_5$, $X_1$ to $X_{16}$, Rx, $A_1$, $A_2$, $R_{101}$ to $R_{105}$ and Ara described above.

26. The organic electroluminescence device according to claim 24, wherein:

the first compound is a compound represented by formula (106), (107) or (108):

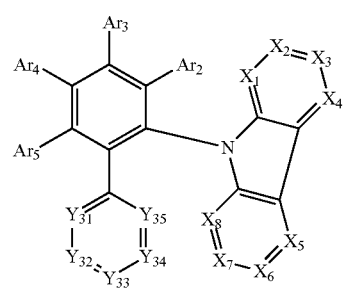

(106)

-continued

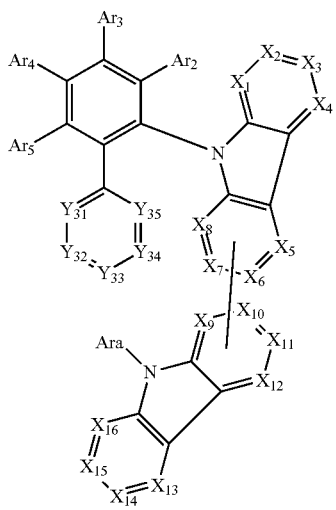

(107)

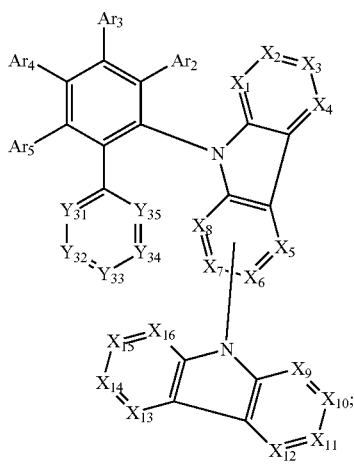

(108)

and

Y$_{31}$ to Y$_{35}$, Ry, Ar$_2$ to Ar$_5$, X$_1$ to X$_{16}$, Rx and Ara represent the same as Y$_{31}$ to Y$_{35}$, Ry, Ar$_2$ to Ar$_5$, X$_1$ to X$_{16}$, Rx and Ara described above.

27. The organic electroluminescence device according to claim 23, wherein at least one of Y$_1$, Y$_3$ and Y$_5$ is N.

28. The organic electroluminescence device according to claim 23, wherein:

Y$_1$, Y$_3$ and Y$_5$ are N; and

Y$_2$ and Y$_4$ are C-Ry.

29. The organic electroluminescence device according to claim 1, wherein:

the first compound is represented by formula (150):

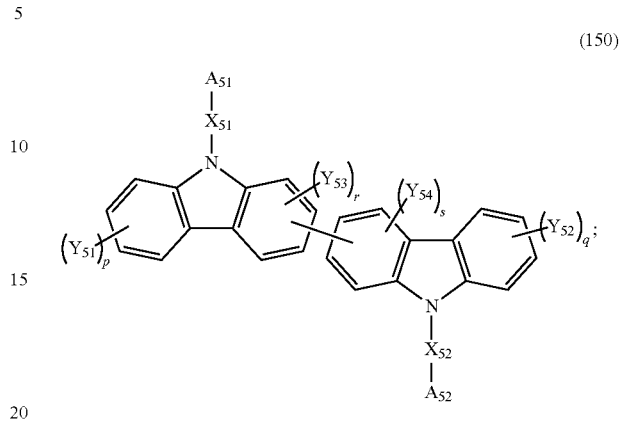

(150)

A$_{51}$ is a substituted or unsubstituted nitrogen-containing heterocyclic group having 1 to 30 ring carbon atoms;

A$_{52}$ is a substituted or unsubstituted aromatic hydrocarbon group having 6 to 30 ring carbon atoms or a substituted or unsubstituted nitrogen-containing heterocyclic group having 1 to 30 ring carbon atoms;

X$_{51}$ and X$_{52}$ are each independently a single bond or a linking group; X$_{51}$ and X$_{52}$ as the linking group are each independently selected from the group consisting of a substituted or unsubstituted aromatic hydrocarbon group having 6 to 30 ring carbon atoms, a substituted or unsubstituted fused aromatic hydrocarbon group having 10 to 30 ring carbon atoms, a substituted or unsubstituted aromatic heterocyclic group having 2 to 30 ring carbon atoms, and a substituted or unsubstituted fused aromatic heterocyclic group having 2 to 30 ring carbon atoms;

Y$_{51}$ to Y$_{54}$ are each independently a hydrogen atom or a substituent: Y$_{51}$ to Y$_{54}$ as the substituent is each independently selected from the group consisting of a fluorine atom, a cyano group, a substituted or unsubstituted alkyl group having 1 to 20 carbon atoms, a substituted or unsubstituted alkoxy group having 1 to 20 carbon atoms, a substituted or unsubstituted haloalkyl group having 1 to 20 carbon atoms, a substituted or unsubstituted haloalkoxy group having 1 to 20 carbon atoms, a substituted or unsubstituted alkylsilyl group having 1 to 10 carbon atoms, a substituted or unsubstituted arylsilyl group having 6 to 30 carbon atoms, a substituted or unsubstituted aromatic hydrocarbon group having 6 to 30 ring carbon atoms, and a substituted or unsubstituted heterocyclic group having 5 to 30 ring atoms;

p is an integer of 1 to 4;
q is an integer of 1 to 4;
r is an integer of 1 to 3;
s is an integer of 1 to 3;
a plurality of Y$_{51}$ are mutually the same or different and are optionally bonded to each other to form a cyclic structure;
a plurality of Y$_{52}$ are mutually the same or different and are optionally bonded to each other to form a cyclic structure;
a plurality of Y$_{53}$ are mutually the same or different and are optionally bonded to each other to form a cyclic structure; and a plurality of $Y_{54}$ are mutually the same or different and are optionally bonded to each other to form a cyclic structure.

30. The organic electroluminescence device according to claim 29, wherein:
the first compound is represented by formula (151):

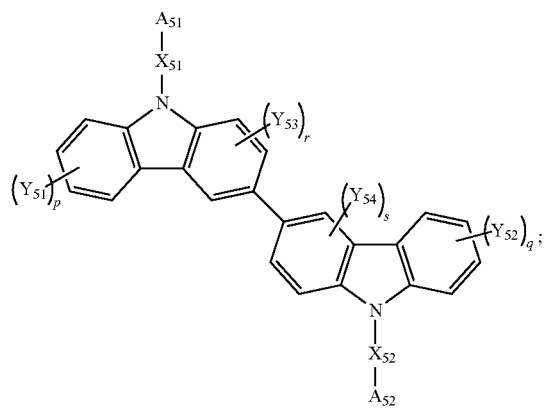

(151)

and
$A_{51}, A_{52}, X_{51}, X_{52}, Y_{51}$ to $Y_{54}$, p, q, r and s represent the same as $A_{51}, A_{52}, X_{51}, X_{52}, Y_{51}$ to $Y_{54}$, p, q, r and s in the formula (150).

31. The organic electroluminescence device according to claim 29, wherein $A_{51}$ is selected from the group consisting of a substituted or unsubstituted pyridine ring, substituted or unsubstituted pyrimidine ring and substituted or unsubstituted triazine ring.

32. The organic electroluminescence device according to claim 29, wherein $A_{51}$ is selected from the group consisting of a substituted or unsubstituted pyrimidine ring and substituted or unsubstituted triazine ring.

33. The organic electroluminescence device according to claim 29, wherein $A_{51}$ is a substituted or unsubstituted pyrimidine ring.

34. The organic electroluminescence device according to claim 30, wherein:
the first compound is represented by formula (152):

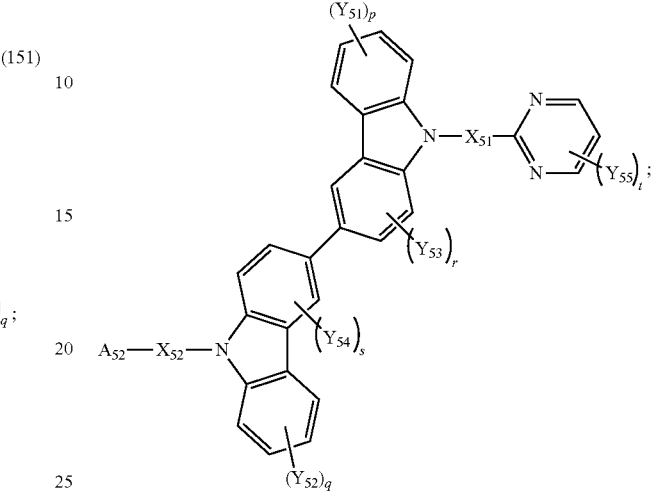

(152)

$A_{52}, X_{51}, Y_{51}$ to $Y_{54}$, p, q, r and s represent the same as $A_{52}, X_{51}, Y_{51}$ to $Y_{54}$, p, q, r and s in the formula (151);
$Y_{55}$ represents the same as $Y_{51}$ to $Y_{54}$ in the formula (151),
t is an integer of 1 to 3; and
a plurality of $Y_{55}$ are mutually the same or different.

35. The organic electroluminescence device according to claim 1, further comprising: a hole transporting layer between the anode and the emitting layer.

36. The organic electroluminescence device according to claim 1, further comprising:
an electron transporting layer between the emitting layer and the cathode.

37. An electronic device, comprising the organic electroluminescence device according to claim 1.

* * * * *